US010219948B2

(12) United States Patent
Sahler et al.

(10) Patent No.: US 10,219,948 B2
(45) Date of Patent: Mar. 5, 2019

(54) OPHTHALMIC LASER TREATMENT SYSTEM AND METHOD

(71) Applicant: PERFECT IP, LLC, Dallas, TX (US)

(72) Inventors: Ruth Sahler, Irvine, CA (US); Raymond Kenneth Alley, Irvine, CA (US); Josef F. Bille, Heidelberg (DE)

(73) Assignee: PERFECT IP, LLC, Dallas, TX (US)

( * ) Notice: Subject to any disclaimer, the term of this patent is extended or adjusted under 35 U.S.C. 154(b) by 0 days.

(21) Appl. No.: 15/439,768

(22) Filed: Feb. 22, 2017

(65) Prior Publication Data
US 2017/0239087 A1 Aug. 24, 2017

Related U.S. Application Data

(60) Provisional application No. 62/299,425, filed on Feb. 24, 2016.

(51) Int. Cl.
A61F 9/009 (2006.01)
A61F 9/008 (2006.01)

(52) U.S. Cl.
CPC .... A61F 9/009 (2013.01); A61F 2009/00865 (2013.01); A61F 2009/00872 (2013.01); A61F 2009/00897 (2013.01)

(58) Field of Classification Search
CPC .................. A61F 9/008; A61F 9/009
See application file for complete search history.

(56) References Cited

U.S. PATENT DOCUMENTS 1,375,445 A   4/1921  Crossley
3,308,810 A   3/1967  Galin
3,943,931 A   3/1976  Krasnov
4,549,539 A   10/1985 Donaldson
4,665,913 A   5/1987  L'Esperance, Jr.
4,732,148 A   3/1988  L'Esperance, Jr.
4,773,414 A   9/1988  L'Esperance, Jr.
4,798,204 A   1/1989  L'Esperance, Jr.
4,966,452 A   10/1990 Shields et al.
(Continued)

FOREIGN PATENT DOCUMENTS

EP    1099432 B1    4/2005
WO    02087451 A1   11/2002

Primary Examiner — Carl H Layno
Assistant Examiner — Dacheng Xie
(74) Attorney, Agent, or Firm — David W. Carstens; Jeffrey G. Degenfelder; Carstens & Cahoon, LLP

(57) ABSTRACT

An ophthalmic laser treatment system and method providing for a liquid optical interface (LOI) with a patient eye surface (PES) using an elliptical ocular suction ring (OSR) is disclosed. A disposable ocular patient interface (OPI) provides for simultaneous differential vacuum mating of the PES, OSR, OPI, and an optical window retainer (OWR). The PES, OSR, OPI, and OWR form an enclosed volume in which liquid may be interjected to cover the PES during laser treatment. A vacuum suction pump (VSP) provides controlled vacuum to the OPI ensuring proper differential vacuum mating (DVM) between the PES, OSR, OPI, and OWR during laser treatment. The OWR connects to a laser objective bracket (LOB) via an ocular force sensor (OFS) and an optical separator bracket (OSB). The OFS senses applied pressure to the PES and provides data to a computerized control device (CCD) that limits applied pressure to the PES during laser treatment.

30 Claims, 128 Drawing Sheets

(56) References Cited

U.S. PATENT DOCUMENTS

| | | |
|---|---|---|
| 4,994,058 A | 2/1991 | Raven et al. |
| 5,009,660 A | 4/1991 | Clapham |
| 5,098,438 A | 3/1992 | Siepser |
| 5,171,242 A | 12/1992 | Dewey et al. |
| 5,171,254 A | 12/1992 | Sher |
| 5,219,343 A | 6/1993 | L'Esperance, Jr. |
| 5,336,215 A | 8/1994 | Hsueh et al. |
| 5,372,595 A | 12/1994 | Gaasterland et al. |
| 5,505,723 A | 4/1996 | Muller |
| 5,548,352 A | 8/1996 | Dewey |
| 5,549,632 A | 8/1996 | Lai |
| 5,573,544 A | 11/1996 | Simon et al. |
| 5,645,550 A | 7/1997 | Hohla |
| 5,807,380 A | 9/1998 | Dishler |
| 6,019,472 A | 2/2000 | Koester et al. |
| 6,254,595 B1 | 7/2001 | Juhasz et al. |
| 6,325,792 B1 | 12/2001 | Swinger et al. |
| 6,373,571 B1 | 4/2002 | Juhasz et al. |
| 6,387,107 B1 | 5/2002 | Hellenkamp |
| 6,436,113 B1 | 8/2002 | Burba et al. |
| 6,458,141 B1 | 10/2002 | Peyman |
| 6,497,700 B1 | 12/2002 | LaHaye |
| 6,623,476 B2 | 9/2003 | Juhasz et al. |
| 6,663,644 B1 | 12/2003 | Ross et al. |
| 6,676,653 B2 | 1/2004 | Juhasz et al. |
| 6,726,679 B1 | 4/2004 | Dick et al. |
| 6,730,074 B2 | 5/2004 | Bille et al. |
| 6,899,707 B2 | 5/2005 | Scholler et al. |
| 6,991,629 B1 | 1/2006 | Juhasz et al. |
| 7,018,376 B2 | 3/2006 | Webb et al. |
| 7,022,119 B2 | 4/2006 | Hohla |
| 7,182,759 B2 | 2/2007 | Kadziauskas et al. |
| 7,371,230 B2 | 5/2008 | Webb et al. |
| 7,390,089 B2 | 6/2008 | Loesel et al. |
| 7,402,159 B2 | 7/2008 | Loesel et al. |
| 7,458,380 B2 | 12/2008 | Jones et al. |
| 7,496,174 B2 | 2/2009 | Gertner et al. |
| 7,564,946 B2 | 7/2009 | Gertner |
| 7,611,507 B2 | 11/2009 | Raksi et al. |
| 7,655,002 B2 | 2/2010 | Myers |
| 7,665,467 B2 | 2/2010 | Jones et al. |
| 7,691,099 B2 | 4/2010 | Berry |
| 7,976,155 B2 | 7/2011 | Muhlhoff et al. |
| 7,997,279 B2 | 8/2011 | Jones et al. |
| 8,118,806 B2 | 2/2012 | Triebel et al. |
| 8,348,935 B2 | 1/2013 | Muller et al. |
| 8,363,783 B2 | 1/2013 | Gertner et al. |
| 8,398,236 B2 | 3/2013 | Juhasz et al. |
| 8,409,189 B2 | 4/2013 | Muller |
| 8,414,564 B2 | 4/2013 | Goldshleger et al. |
| 8,469,952 B2 | 6/2013 | Muller et al. |
| 8,500,723 B2 | 8/2013 | Gertner et al. |
| 8,506,558 B2 | 8/2013 | Frey et al. |
| 8,512,236 B2 | 8/2013 | Gertner et al. |
| 8,523,941 B2 | 9/2013 | Ichinohe et al. |
| 8,556,425 B2 | 10/2013 | Frey et al. |
| 8,568,394 B2 | 10/2013 | Lummis et al. |
| 8,585,686 B2 | 11/2013 | Bergt et al. |
| 8,630,388 B2 | 1/2014 | Gertner et al. |
| 8,652,131 B2 | 2/2014 | Muller et al. |
| 8,678,593 B2 | 3/2014 | Abt |
| 8,690,862 B2 | 4/2014 | Palanker et al. |
| 8,764,737 B2 | 7/2014 | Kurtz et al. |
| 8,784,406 B2 | 7/2014 | Rathjen |
| 8,845,624 B2 | 9/2014 | Raksi et al. |
| 8,863,749 B2 | 10/2014 | Gooding et al. |
| 8,920,406 B2 | 12/2014 | Gertner et al. |
| 8,920,408 B2 | 12/2014 | Rathjen |
| 8,923,479 B2 | 12/2014 | Gertner et al. |
| 8,939,967 B2 | 1/2015 | Raksi |
| 9,044,302 B2 | 1/2015 | Gooding et al. |
| 9,044,304 B2 | 6/2015 | Raksi et al. |
| 9,089,401 B2 | 7/2015 | Raksi et al. |
| 9,155,652 B2 | 10/2015 | Peyman |
| 9,173,771 B2 | 11/2015 | Keller |
| 9,237,967 B2 | 1/2016 | Gooding et al. |
| 2003/0153904 A1 | 8/2003 | Patel |
| 2004/0254568 A1 | 12/2004 | Rathjen |
| 2006/0287662 A1 | 12/2006 | Berry et al. |
| 2007/0093796 A1 | 4/2007 | Raksi et al. |
| 2007/0142828 A1 | 6/2007 | Peyman |
| 2007/0179478 A1 | 8/2007 | Dobschal et al. |
| 2008/0071254 A1 | 3/2008 | Lummis et al. |
| 2008/0287927 A1 | 11/2008 | Rathjen |
| 2009/0024117 A1 | 1/2009 | Muller |
| 2009/0069794 A1 | 3/2009 | Kurtz |
| 2009/0137989 A1 | 5/2009 | Kataoka |
| 2009/0137991 A1 | 5/2009 | Kurtz |
| 2010/0114109 A1 | 5/2010 | Peyman |
| 2010/0274228 A1* | 10/2010 | Mrochen ............... A61F 9/009 604/541 |
| 2011/0009851 A1 | 1/2011 | Donitzky et al. |
| 2011/0022035 A1 | 1/2011 | Porter et al. |
| 2011/0112519 A1 | 5/2011 | Donitzky et al. |
| 2011/0190739 A1 | 8/2011 | Frey et al. |
| 2011/0190741 A1 | 8/2011 | Deisinger et al. |
| 2011/0224657 A1 | 9/2011 | Stevens et al. |
| 2012/0016349 A1 | 1/2012 | Brownell |
| 2012/0078241 A1* | 3/2012 | Gooding ............... A61F 9/009 606/6 |
| 2012/0240939 A1 | 9/2012 | Kandulla |
| 2012/0271286 A1 | 10/2012 | Curatu et al. |
| 2013/0035674 A1 | 2/2013 | Lummis et al. |
| 2013/0041354 A1 | 2/2013 | Brownell et al. |
| 2013/0053837 A1 | 2/2013 | Kandulla et al. |
| 2013/0102895 A1 | 4/2013 | Gooding et al. |
| 2013/0102922 A1 | 4/2013 | Gooding |
| 2013/0237970 A1 | 9/2013 | Summers et al. |
| 2013/0345682 A1 | 12/2013 | Hailmann et al. |
| 2014/0128821 A1* | 5/2014 | Gooding ............ A61M 1/0052 604/290 |
| 2014/0128852 A1* | 5/2014 | Gooding ............... A61F 9/008 606/4 |
| 2014/0128853 A1 | 5/2014 | Angeley et al. |
| 2014/0142599 A1 | 5/2014 | Jeglorz et al. |
| 2014/0163534 A1 | 6/2014 | Angeley et al. |
| 2014/0257256 A1 | 9/2014 | Hohla et al. |
| 2014/0275751 A1 | 9/2014 | Heitel et al. |
| 2014/0276671 A1 | 9/2014 | Gooding |
| 2014/0276678 A1 | 9/2014 | Berry et al. |
| 2014/0364744 A1 | 12/2014 | Wellhoefer |
| 2015/0088175 A1 | 3/2015 | McWhirter et al. |
| 2015/0366551 A1 | 12/2015 | Blumenkranz et al. |

* cited by examiner

1100

3800

4200

5800

7600

8300

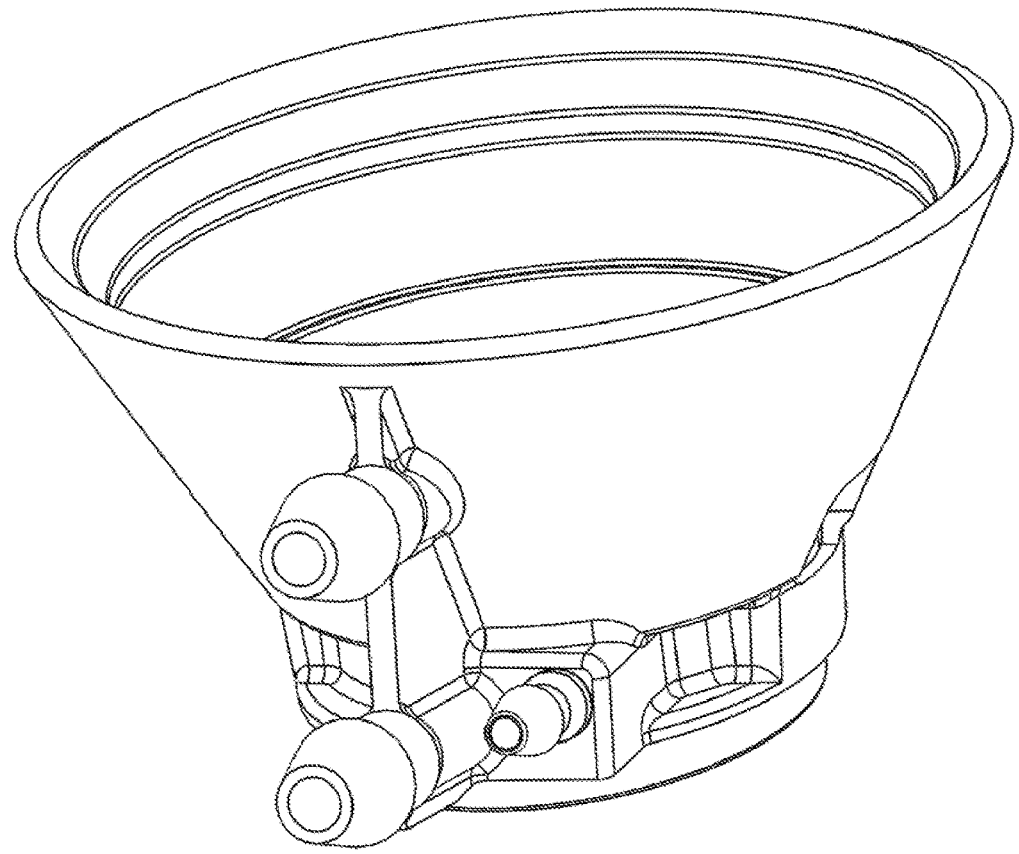
FIG. 104
10400

10700

12200

12300

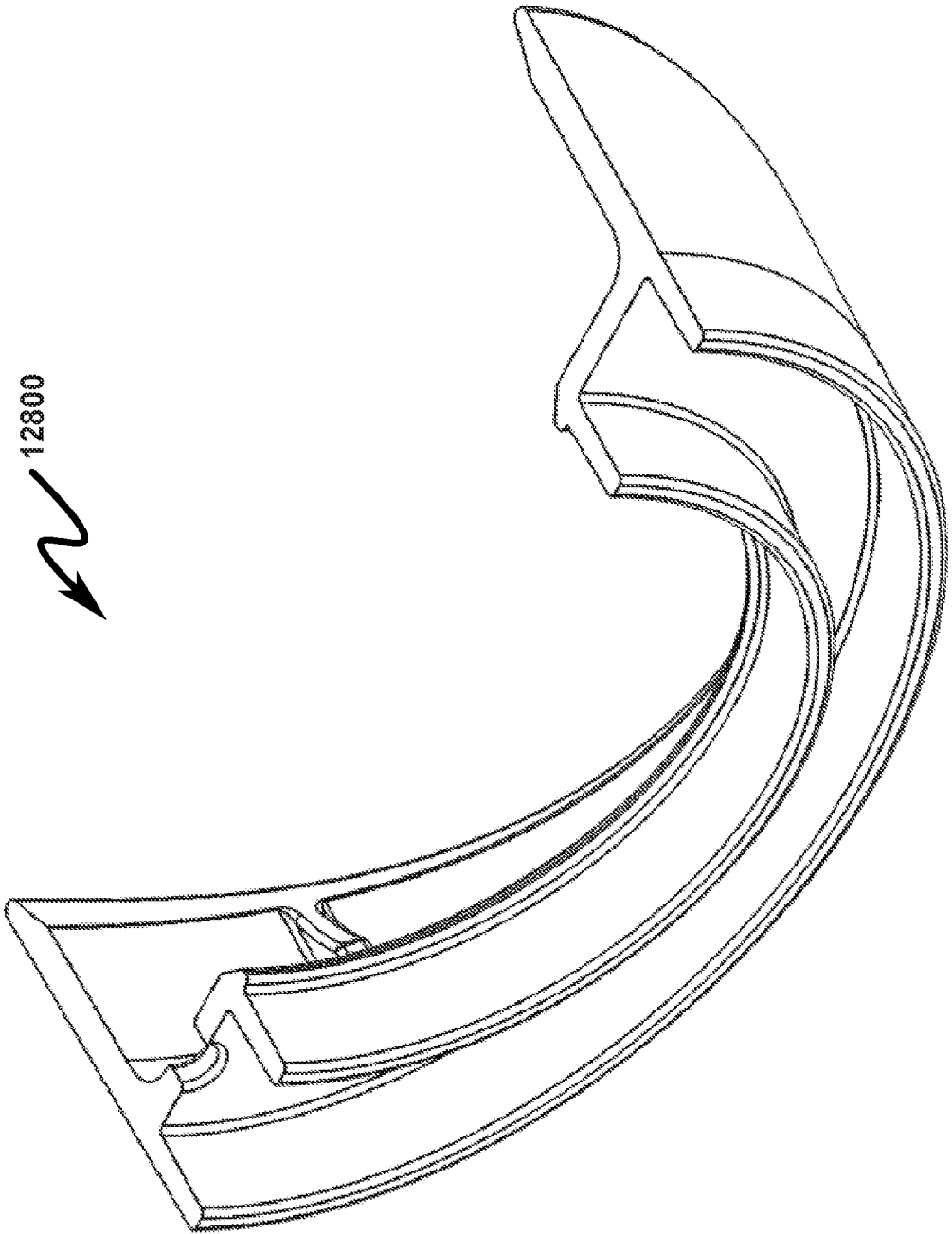
FIG. 128  12800

OPHTHALMIC LASER TREATMENT SYSTEM AND METHOD

CROSS REFERENCE TO RELATED APPLICATIONS

This application claims benefit under 35 U.S.C. § 119 and incorporates by reference U.S. Provisional Patent Application for OPHTHALMIC LASER TREATMENT SYSTEM AND METHOD by inventors Ruth (nmn) Sahler, Raymond Kenneth Alley, and Josef F. Bille, filed with the USPTO on Feb. 24, 2016, with Ser. No. 62/299,425.

PARTIAL WAIVER OF COPYRIGHT

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

STATEMENT REGARDING FEDERALLY SPONSORED RESEARCH OR DEVELOPMENT

Not Applicable

REFERENCE TO A MICROFICHE APPENDIX

Not Applicable

FIELD OF THE INVENTION

The present invention generally relates to systems and methods for performing laser ophthalmic surgery and specifically relates to the generation of a liquid optical interface (LOI) with a patient eye surface (PES) using an elliptical ocular suction ring (OSR).

PRIOR ART AND BACKGROUND OF THE INVENTION

Overview

Existing liquid patient interfaces (LPI) for use in ophthalmic laser surgery are designed with a circular end piece which connects to the patient eye surface (PES). The diameter of the circular attachment normally ranges between 18 mm to 24 mm. This design creates uneven pressure along a small attachment area on the PES. The circular design creates issues for patients having limited cornea exposure due to a small eyelid opening and require the application of an eyelid speculum during patient ophthalmic laser treatment.

For example, Patent Application Publication US20110022035 for a LIQUID HOLDING INTERFACE DEVICE FOR OPHTHALMIC LASER PROCEDURES discloses a ring shaped patient interface design. Neither reduction of eye movement nor patient comfort is a concern of existing liquid patient interfaces.

Deficiencies in the Prior Art

The prior art as detailed above suffers from the following deficiencies:

Prior art ophthalmic laser treatment systems and methods limit the LPI to a circular shaped end-piece connected to the PES, which excludes use for a large number of patients.

Prior art ophthalmic laser treatment systems and methods provide for PES motion stabilization but still allows saccadic eye movements to affect the target area on the PES. Saccadic eye movements constitute a quick, simultaneous movement of both eyes between two phases of fixation in the same direction.

Prior art ophthalmic laser treatment systems and methods provide for an interface in which the pressure is uneven along the edges of the attachment to the eye.

Prior art ophthalmic laser treatment systems and methods provide for a narrow band of attachment which creates discomfort for the patient during laser treatment.

Prior art ophthalmic laser treatment systems and methods provide for a PES interface in which suction is applied to only one area of the PES.

While some of the prior art may teach some solutions to several of these problems, the core issue of providing a comfortable and effective universal LPI for use in ophthalmic laser procedures has not been solved by the prior art.

OBJECTIVES OF THE INVENTION

Accordingly, the objectives of the present invention are (among others) to circumvent the deficiencies in the prior art and affect the following objectives in the context of an ophthalmic laser treatment system and method:

(1) Provide for an ophthalmic laser treatment system and method that allows greater patient comfort during ophthalmic laser treatment;
(2) Provide for an ophthalmic laser treatment system and method that reduces surface pressure to the PES during ophthalmic laser treatment;
(3) Provide for an ophthalmic laser treatment system and method that provides for greater PES stability during ophthalmic laser treatment;
(4) Provide for an ophthalmic laser treatment system and method that accommodates a wide variety of patient eye sizes;
(5) Provide for an ophthalmic laser treatment system and method that distributes contact pressure of the system over a wider area of the PES;
(6) Provide for an ophthalmic laser treatment system and method that provides for controlled liquid coverage of the PES during ophthalmic laser treatment;
(7) Provide for an ophthalmic laser treatment system and method that provides for application of controlled pressure to the PES during ophthalmic laser treatment to reduce the instances of PES damage due to corneal folds;
(8) Provide for an ophthalmic laser treatment system and method that minimizes the effect of saccadic eye movements during ophthalmic laser treatment;
(9) Provide for an ophthalmic laser treatment system and method that provides precise and stable docking to a wide range of PES surface forms;
(10) Provide for an ophthalmic laser treatment system and method that provides for reduced likelihood of hemorrhaging and corneal folds (edema) by controlled application of pressure to the PES during ophthalmic laser treatment.

While these objectives should not be understood to limit the teachings of the present invention, in general these objectives are achieved in part, or in whole, by the disclosed invention that is discussed in the following sections. One skilled in the art will no doubt be able to select aspects of the present invention as disclosed to affect any combination of the objectives described above.

BRIEF SUMMARY OF THE INVENTION

The present invention provides a liquid patient interface (LPI) for the use in ophthalmic laser surgery. The LPI attaches to the patient eye surface (PES) and allows the physician to perform procedures on various portions of the interior of the eye (e.g., cornea, lens, and retina). The benefits of the present invention LPI are as follows:
 (1) the LPI connects with a larger surface area of the PES by using a unique design of the inner and outer PES contacts in a novel optical suction ring (OSR);
 (2) the OSR is designed with an elliptical shape designed to optimally contact the PES for patients having narrow eyelids and smaller amounts of exposed eye surface;
 (3) the LPI minimizes PES force by using an interior suction region (ISR) between two OSR elliptical interface contacts;
 (4) radial ribs in the OSR connect the inner and outer rings of the OSR and are configured to contact the PES and evenly distribute suction pressure to the PES;
 (5) the consistent pressure throughout the entire OSR and the greater surface area reduce saccadic eye movement during laser treatment;
 (6) the elliptical shape, the lower pressure, and homogenous application of pressure provides for greater patient comfort during the ophthalmic laser procedure;
 (7) the LPI utilizes a disposable ocular patient interface (OPI) vacuum docking system to mate one-time-use components such as the OSR and multi-time-use components of the system such as the laser electronics, thus providing for the sterilization of instruments that contact the PES;
 (8) the OPI provides for differential vacuum mating (DVM) between the OPI and the OSR as well as between the OPI and multi-time-use portions of the system, thus providing for controlled vacuum force to be applied to the PES;
 (9) the OPI provides for a liquid injection port (LIP) that allows the PES to be covered with fluid and also provides for liquid overflow chambers (LOC) and liquid overflow ports (LOP) to regulate the fluid level covering the PES during the laser treatment procedure; and
 (10) the system supports an ocular force sensor (OFS) that permits pressure applied to the PES to be controlled during the laser treatment procedure, thus reducing the chance of damage to the PES and potential corneal folds.

The invention in some embodiments may also be augmented with a computing control device (CCD) to monitor ocular force/pressure, OSR suction vacuum, and position of the laser radiation source (LRS) during the ophthalmic laser treatment procedure.

BRIEF DESCRIPTION OF THE DRAWINGS

For a fuller understanding of the advantages provided by the invention, reference should be made to the following detailed description together with the accompanying drawings wherein:

FIG. 104 illustrates a bottom left front perspective view of a preferred exemplary ocular patient interface (OPI) embodiment useful in some invention configurations;

FIG. 119 illustrates a bottom left rear perspective view of a preferred exemplary ocular suction ring (OSR) embodiment useful in some invention configurations;

FIG. 120 illustrates a bottom left front perspective view of a preferred exemplary ocular suction ring (OSR) embodiment useful in some invention configurations;

FIG. 121 illustrates a front view of a preferred exemplary ocular suction ring (OSR) embodiment useful in some invention configurations;

FIG. 122 illustrates a rear view of a preferred exemplary ocular suction ring (OSR) embodiment useful in some invention configurations;

FIG. 123 illustrates a left view of a preferred exemplary ocular suction ring (OSR) embodiment useful in some invention configurations;

FIG. 124 illustrates a right view of a preferred exemplary ocular suction ring (OSR) embodiment useful in some invention configurations;

FIG. 125 illustrates a top view of a preferred exemplary ocular suction ring (OSR) embodiment useful in some invention configurations;

FIG. 126 illustrates a bottom view of a preferred exemplary ocular suction ring (OSR) embodiment useful in some invention configurations;

FIG. 127 illustrates a right section perspective view of a preferred exemplary ocular suction ring (OSR) embodiment useful in some invention configurations; and FIG. 128 illustrates a top section perspective view of a preferred exemplary ocular suction ring (OSR) embodiment useful in some invention configurations.

DESCRIPTION OF THE PRESENTLY PREFERRED EXEMPLARY EMBODIMENTS

Figure 1:
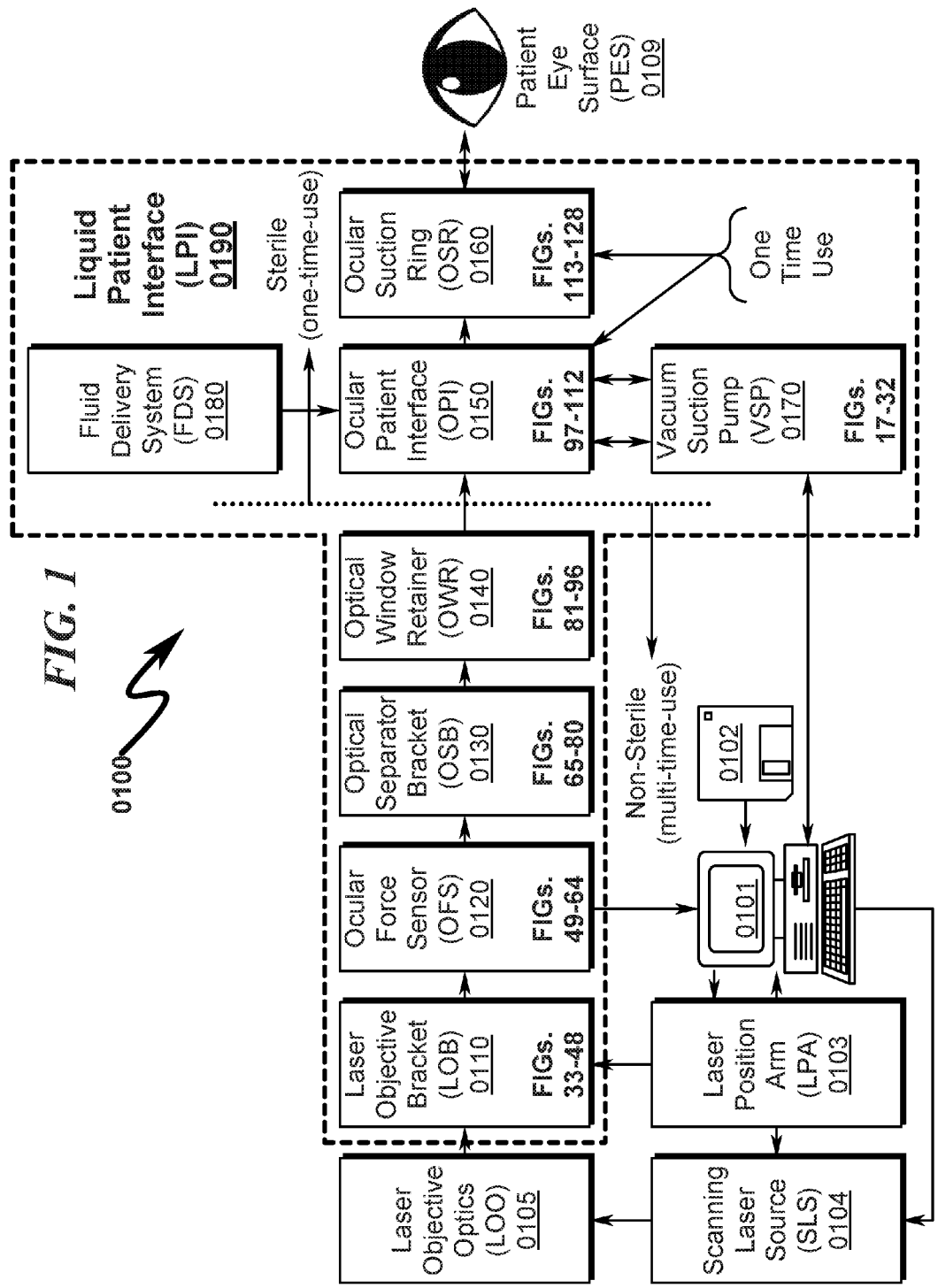
FIG. 1 illustrates a block diagram depicting a preferred exemplary system embodiment of the present invention.

While this invention is susceptible of embodiment in many different forms, there is shown in the drawings and will herein be described in detailed preferred embodiment of the invention with the understanding that the present disclosure is to be considered as an exemplification of the principles of the invention and is not intended to limit the broad aspect of the invention to the embodiment illustrated.

The numerous innovative teachings of the present application will be described with particular reference to the presently preferred embodiment, wherein these innovative teachings are advantageously applied to the particular problems of an OPHTHALMIC LASER TREATMENT SYSTEM AND METHOD. However, it should be understood that this embodiment is only one example of the many advantageous uses of the innovative teachings herein. In general, statements made in the specification of the present application do not necessarily limit any of the various claimed inventions. Moreover, some statements may apply to some inventive features but not to others.

Ellipse Definition

The present invention makes use of an elliptical ocular suction ring (OSR) to make contact with the patient eye surface (PES). The term "ellipse" has the following mathematical definition:

In mathematics, an ellipse is a curve on a plane that surrounds two focal points such that the sum of the distances to the two focal points is constant for every point on the curve. As such, it is a generalization of a circle, which is a special type of an ellipse that has both focal points at the same location. The shape of an ellipse (how 'elongated' it is) is represented by its eccentricity, which for an ellipse can be any number from 0 (the limiting case of a circle) to arbitrarily close to but less than 1.

Ellipses have two perpendicular axes about which the ellipse is symmetric. These axes intersect at the center of the ellipse due to this symmetry. The larger of these two axes, which corresponds to the larger distance between antipodal points on the ellipse, is called the major axis. The smaller of these two axes, and the smaller distance between antipodal points on the ellipse, is called the minor axis.

However, within the context of the present invention, the terms "ellipse" and "elliptical" shall be restricted to ellipses having an eccentricity greater than zero. In these situations the ellipse major axis has a greater length than the ellipse minor axis.

Mechanical Features Depicted are not Limiting

The present invention may incorporate a wide variety of mechanical features that may be implemented in a variety of different application contexts. The depictions provided herein are only exemplary of one preferred exemplary invention embodiment and do not limit the invention scope.

Overview

Figure 2:
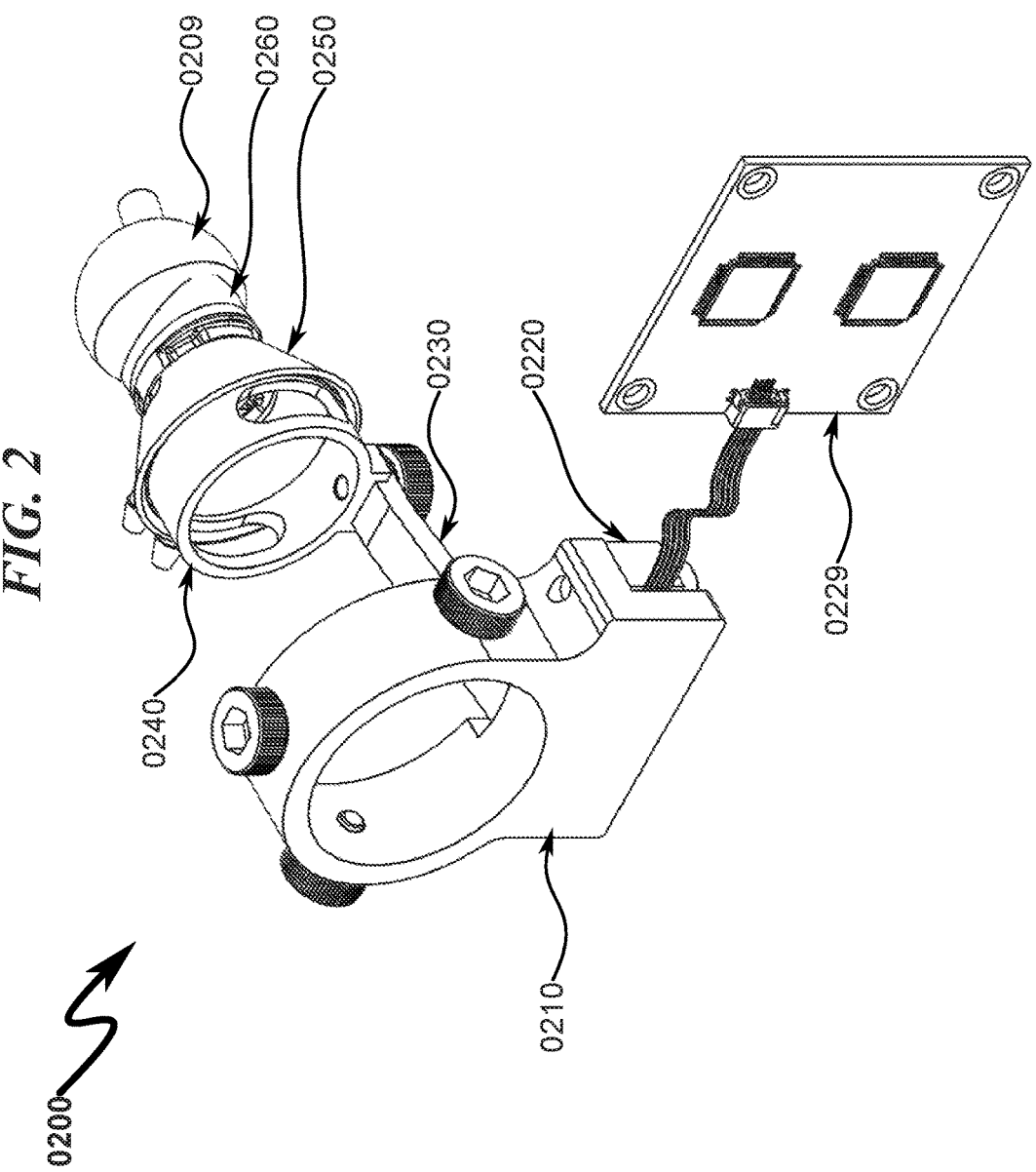
FIG. 2 illustrates a perspective view of several major components of a preferred exemplary invention LPI embodiment.

As generally depicted in FIG. 1 (0100) and FIG. 2 (0200) the present invention implements a liquid optical interface (LOI) useful in performing ocular laser treatment of a human eye. The LOI interface consists of assemblies that mate with a laser radiation source (LRS) and other assemblies that vacuum mate to a patient eye surface (PES).

One LRS assembly attaches to the laser's objective lens by use of a laser objective bracket (LOB). The LOB is connected to an optical force sensor (OFS) that is further connected to an optical window retainer (OWR) via an optical separator bracket (OSB). The OSB in conjunction with the OFS provides a mechanism to monitor pressure applied to the PES and thus prevent possible injury to the patient.

The OWR is configured to vacuum dock to an ocular patient interface (OPI) that mates with an ocular suction ring (OSR) that directly contacts the PES. Positive contact between the OSR and OPI is maintained by a secondary differential vacuum control supplied to the OPI and fed by the OPI to the OSR.

Once the OPI is vacuum docked to the OWR and PES, fluid may be injected into the OPI to cover the PES and provide a constant index of refraction by which ophthalmic laser treatment of the patient may be performed. A planar lens held in press-fit suspension by the OPI covers and makes contact with the injected liquid to provide a uniform plane by which laser radiation may enter the patient's eye.

The OSR and OPI may be mated using press-fit peripheral cylindrical ridges as shown herein or may be combined using any number of adhesives. Without adhesive, a light press fit and vacuum pressure holds the ring in place. The OSR and OPI are designed in this system to be disposable and therefore can be sterilized to prevent infection of the PES during the ophthalmic procedure.

The OPI comprises a number of vacuum and liquid chambers. A docking vacuum port (DVP) is connected to a vacuum source, which evacuates air from the periphery of the outer conical surface of the OPI and thus allow mating to the OWR to occur. A suction vacuum port (SVP) allows the ocular suction ring to firmly grip the PES. A liquid injection port provides a path for fluid which is used to fill a chamber between the cornea and lower surface of a liquid interface window (LIW). Once the fluid level reaches the underside of the LIW, additional fluid moves into reservoir channels contained in the OPI. In the very rare case of excess fluid injection, the fluid will exit drain windows in the OPI.

The system implements use of an elliptical shape in the ocular suction ring (OSR), which allows for greater suction area when compared to a purely circular suction ring. The OSR features two edges that come in direct contact with the eye and whose smoothness and geometry are critical for sealing. On the top surface of the OSR a mating surface is configured to affect mating to the OPI. In order to avoid using adhesive between the OSR and OPI, these mating surfaces must be accurate and smooth. Otherwise, adhesives such as silicone may be used to join the two components.

Other features of the OSR include one or more radial ribs that prevent the collapse of the suction ring chamber, distributes the pressure across a wider area of the PES and reduces sclera stress. Lastly, a vacuum channel in the OSR connects the OSR vacuum chamber to the OPI vacuum chamber SVP vacuum port.

Typical vacuum port nozzles in many preferred embodiments are designed for ⅛" diameter silicone tubing. A fluid delivery port in many embodiments may utilize a 1/16" fluid delivery nozzle. This may be designed for improved manufacturing of the OPI via the use of a press fit nozzle or an ultrasonically welded component made of a polymeric material.

Radial spacing of support ribs in the OSR is optimally placed in four circumferential locations. The OPI may be configured to allow a press fit of the LIW. The OPI may be configured with a cavity belonging to a series of overflow chambers that fill once the injected fluid reaches the underside of the LIW.

The OWR, OSB, and LOB are optimally constructed from aluminum and is used for docking and is designed to prevent movement of the OPI relative to the laser radiation source. Movement of the OPI may occur from patient eye movement or head movement.

Information on the dimensions of a typical human eye were used to create a 3D CAD model of the human eye, which in turn was utilized to create a Finite Element Model (FEM) for OSR contact analysis. An optimized elliptical suction ring design was obtained by performing a FEM simulation. The best design for the considered 23×19 mm eye interfacing ellipse was determined, which resulted in the lowest intraocular pressure (IOP) rise and the highest stiffness of the OSR. This optimized design reduces the chances of increased sclera stress that can lead to a higher likelihood of hemorrhaging and also decreases the chances of corneal compressive stress that may lead to corneal folds.

System Overview (0100)

The present invention may be summarized as depicted in the application context system block diagram of FIG. 1 (0100). Here the system is configured using a computing control device (CCD) (0101) executing machine instructions read from a tangible computer readable medium (0102). The system as depicted provides for a laser position arm (LPA) (0103) that positions a scanning laser source (SLS) (0104) and laser objective optics (LOO) (0105). The laser radiation source (LRS) comprising the major laser provisioning components (0103, 0104, 0105) interface to the remainder of components in the system (termed the liquid patient interface (LPI) (0190)) that will now be further described.

The laser objective bracket (LOB) (0110) mates with the laser provisioning components (0103, 0104, 0105) and is connected to an ocular force sensor (OFS) (0120) that measures pressure applied to the patient eye surface (PES) (0109) by the LPI (0190). The OFS (0120) is actuated by an optical separator bracket (OSB) (0130) that provides a leverage action between the OFS (0120) and an optical window retainer (OWR) (0140) that merges components associated with the PES (0109) interface. This leverage action permits pressure applied to the PES (0109) by the LPI (0190) to be reflected back to the OFS (0120) for reporting to the physician via the CCD (0101).

The OWR (0140) component is responsible for providing an interface between the sterile one-time-use environment interfacing with the PES (0109) and the multi-time-use environment of the laser provisioning components and ocular force sensing apparatus. The OWR (0140) provides for a conical mating interface to the disposable ocular patient interface (OPI) (0150). The OPI (0150) provides mechanical support to retain a liquid interface window (LIW) that faces an ocular suction ring (OSR) (0160) that makes physical contact with the patient eye surface (PES) (0109).

The OPI (0150) provides for a docking vacuum port (DVP), a suction vacuum port (SVP), and a liquid injection port (LIP). The DVP is connected to a void in the conical mating interface between the OWR (0140) and the OPI (0150) such that vacuum applied to the DVP forces a dynamic physical mate between the OWR (0140) and the OPI (0150). This allows the OPI (0150) and the OSR (0160) to mate with the PES (0109) and then subsequently dock with the OWR (0140). The suction vacuum port (SVP) on the OPI (0150) allows vacuum applied to the SVP to mate the OSR (0160) to the PES (0109). Vacuum sourced to the OPI (0150) may be supplied from a vacuum suction pump (VSP) (0170) controlled either manually or automatically by the CCD (0101).

The LIP on the OPI (0150) allows liquid to be inserted in the OPI to the surface of the LIW and thus provide a constant refractive index between the LRS and the PES (0109). This LIP on the OPI (0150) may include a variety of fluid delivery system (FDS) (0180) components including syringes, hoses, and automated fluid delivery systems under operational control of the CCD (0101).

Exemplary LPI Configuration (0200)

A perspective view of a preferred exemplary embodiment of optical components within the liquid patient interface (LPI) (0190) from FIG. 1 (0100) is generally depicted in FIG. 2 (0200). Here the laser objective bracket (LOB) (0210) is illustrated as mated to the ocular force sensor (OFS) (0220) along with force sensing electronics (0229) associated with the OFS (0220). The optical separator bracket (OSB) (0230) is illustrated connecting the OFS (0220) and the optical window retainer (OWR) (0240). The OWR (0240) is shown mated to the ocular patient interface (OPI) (0250). The OPI (0250) is illustrated mated to the ocular suction ring (OSR) (0260) which is contacting the patient eye surface (0209).

Method Overview (0300)-(0400)

Figure 3:
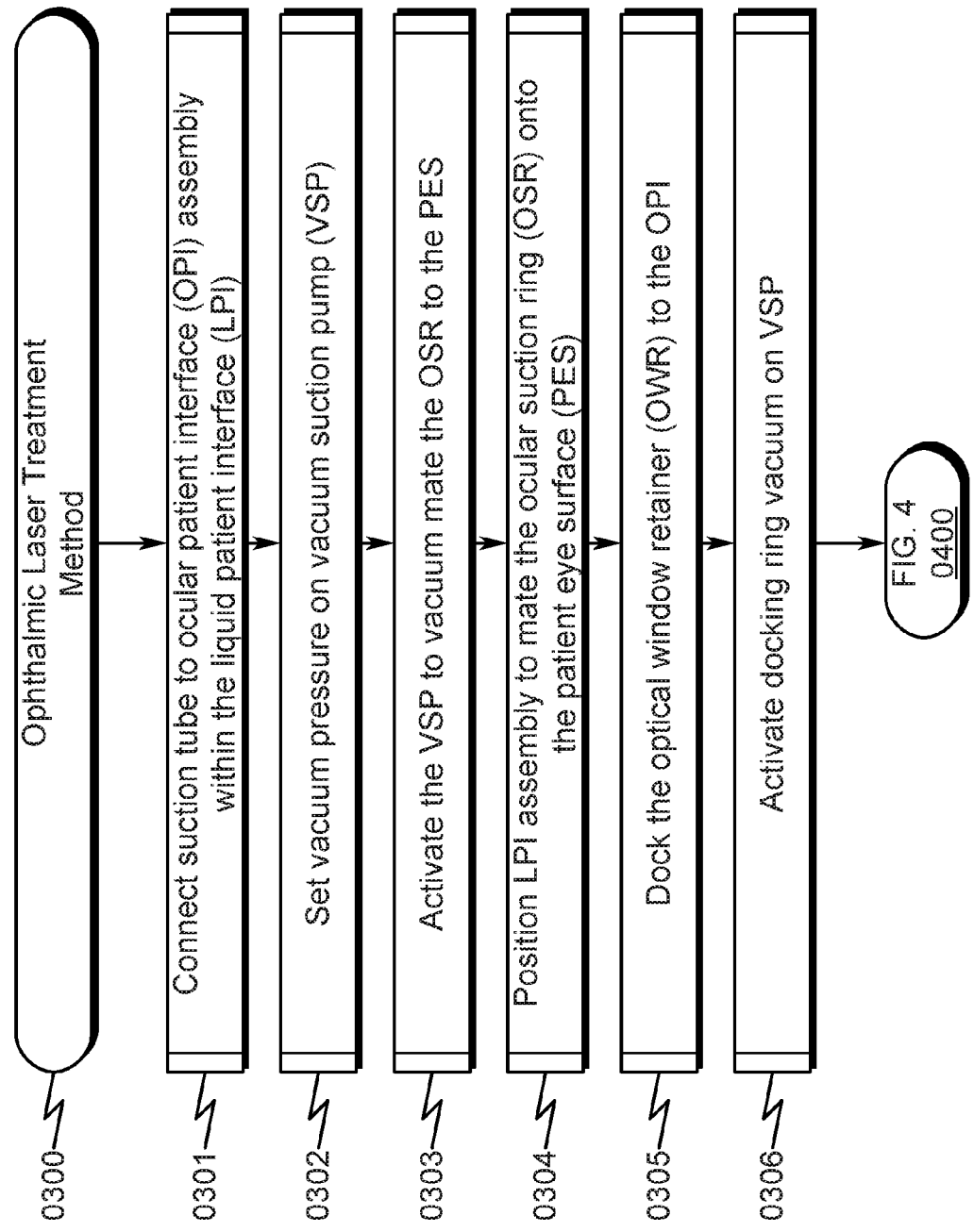
FIG. 3 illustrates a flowchart depicting a preferred exemplary invention method embodiment (page 1/2)
Figure 4:
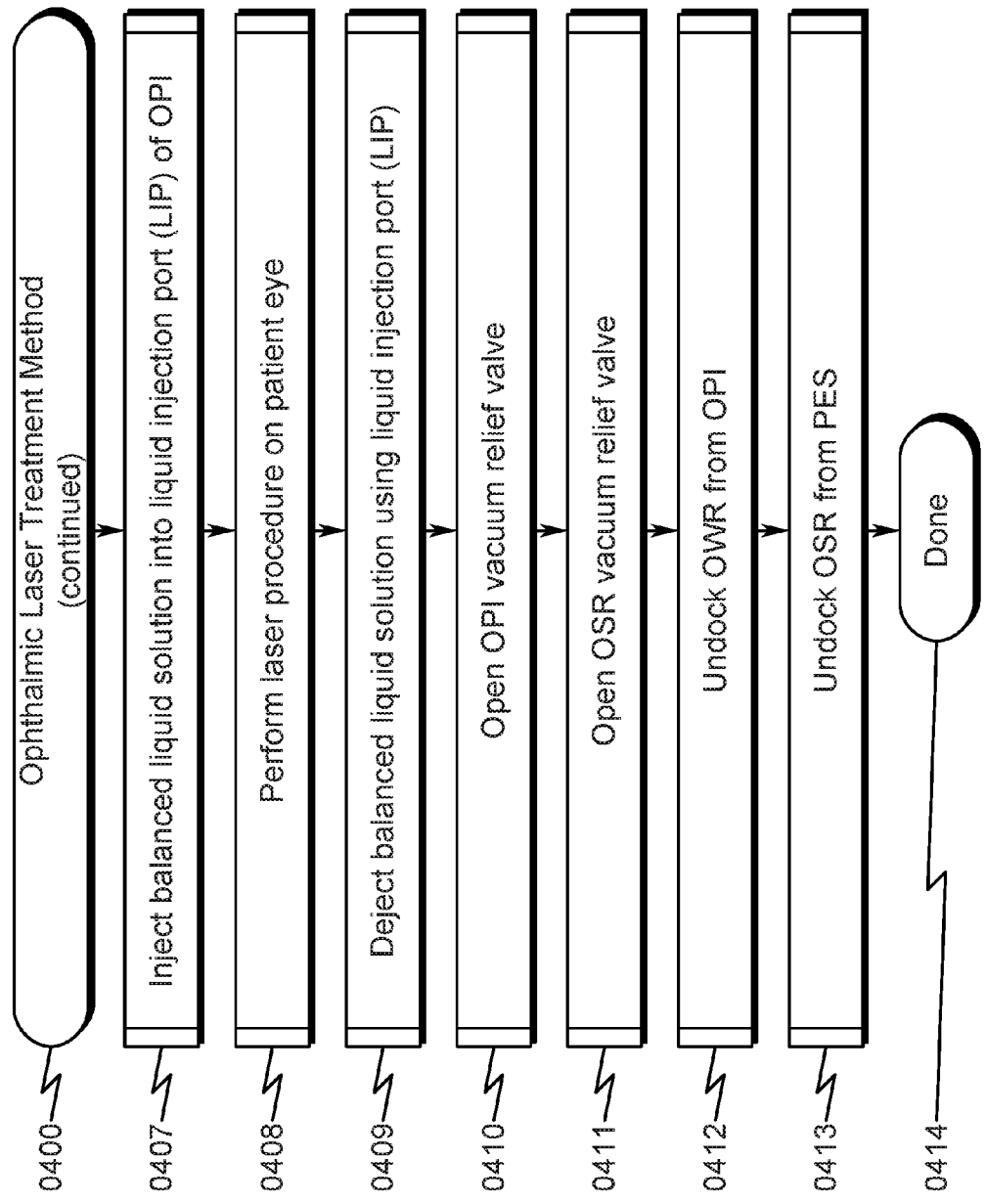
FIG. 4 illustrates a flowchart depicting a preferred exemplary invention method embodiment (page 2/2)

Associated with the exemplary system overview described in FIG. 1 (0100)-FIG. 2 (0200) is an ophthalmic laser treatment method as depicted in FIG. 3 (0300)-FIG. 4 (0400) that comprises the following steps:

(1) Connecting a suction tube to the ocular patient interface (OPI) assembly within the liquid patient interface (LPI) (0301);
(2) Setting vacuum pressure on a vacuum suction pump (VSP) (0302);
(3) Activating the vacuum suction pump (VSP) to vacuum mate the OSR to the PES (0303);
(4) Positioning the LPI assembly to mate the ocular suction ring (OSR) onto the patient eye surface (PES) (0304);
(5) Docking the optical window retainer (OWR) to the OPI (0305);
(6) Activate the docking ring vacuum with the VSP (0306);
(7) Injecting a balanced liquid solution (BLS) into the liquid injection port (LIP) of the OPI (0407);
(8) Performing laser surgery on the patient eye with the laser positioned within the laser objective bracket (LOB) (0408);
(9) Dejecting the balanced liquid solution (BLS) using the liquid injection port (LIP) of the OPI (0409);
(10) Opening the OPI vacuum relief valve (VRV) to disengage the OWR from the OPI (0410);
(11) Opening the OSR vacuum relief valve (VRV) to disengage the OSR from the PES (0411);
(12) Undocking the OWR from the OPI (0412); and
(13) Undocking the OSR from the PES (0413).

One skilled in the art will recognize that these method steps may be augmented or rearranged without limiting the teachings of the present invention. This general method summary may be augmented by the various elements described herein to produce a wide variety of invention embodiments consistent with this overall design description.

Exemplary LPI System Configuration Views (0500)-(1600)

Figure 5:
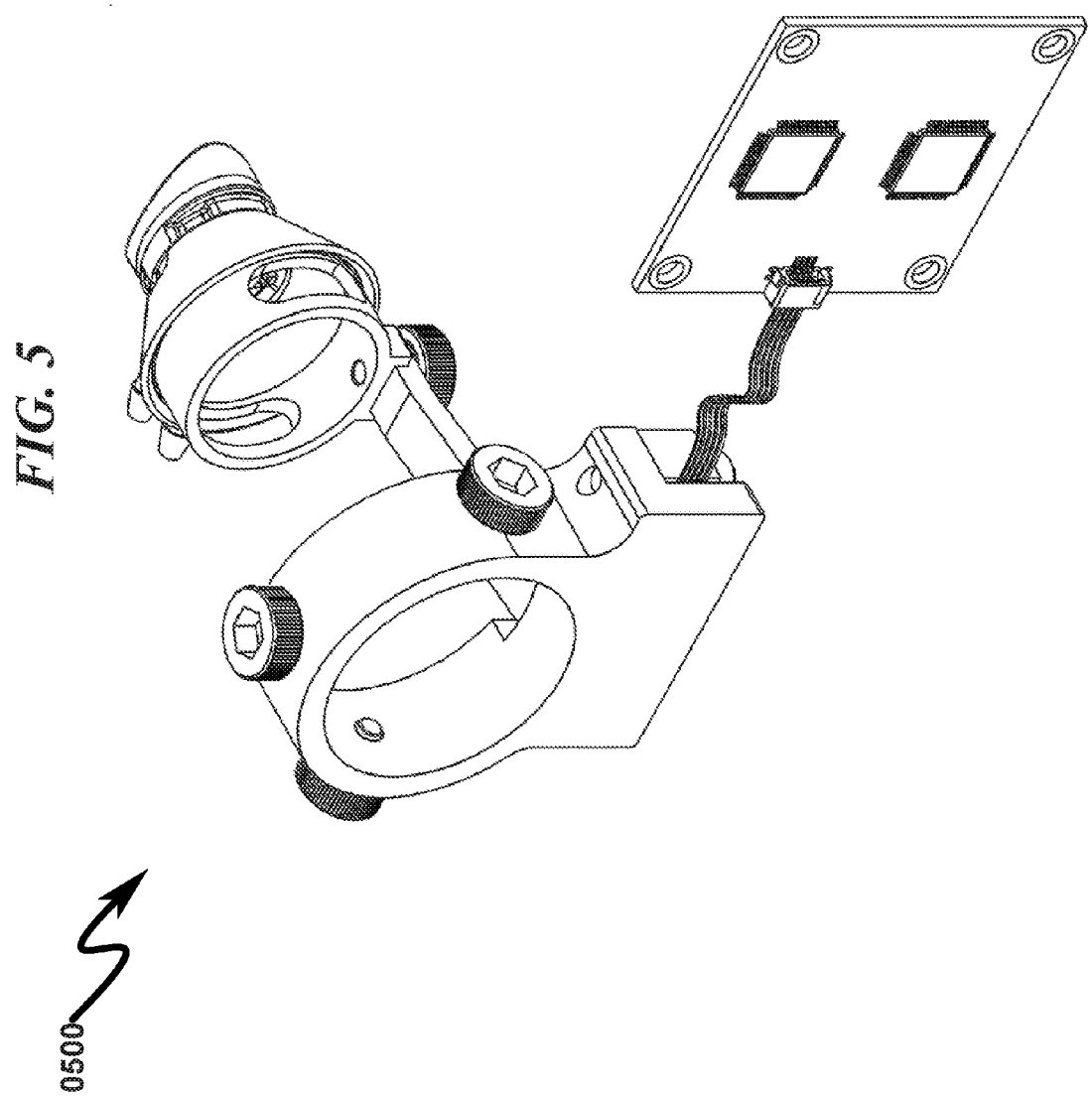
FIG. 5 illustrates a top right front perspective view of a preferred exemplary invention LPI system embodiment.
Figure 6:
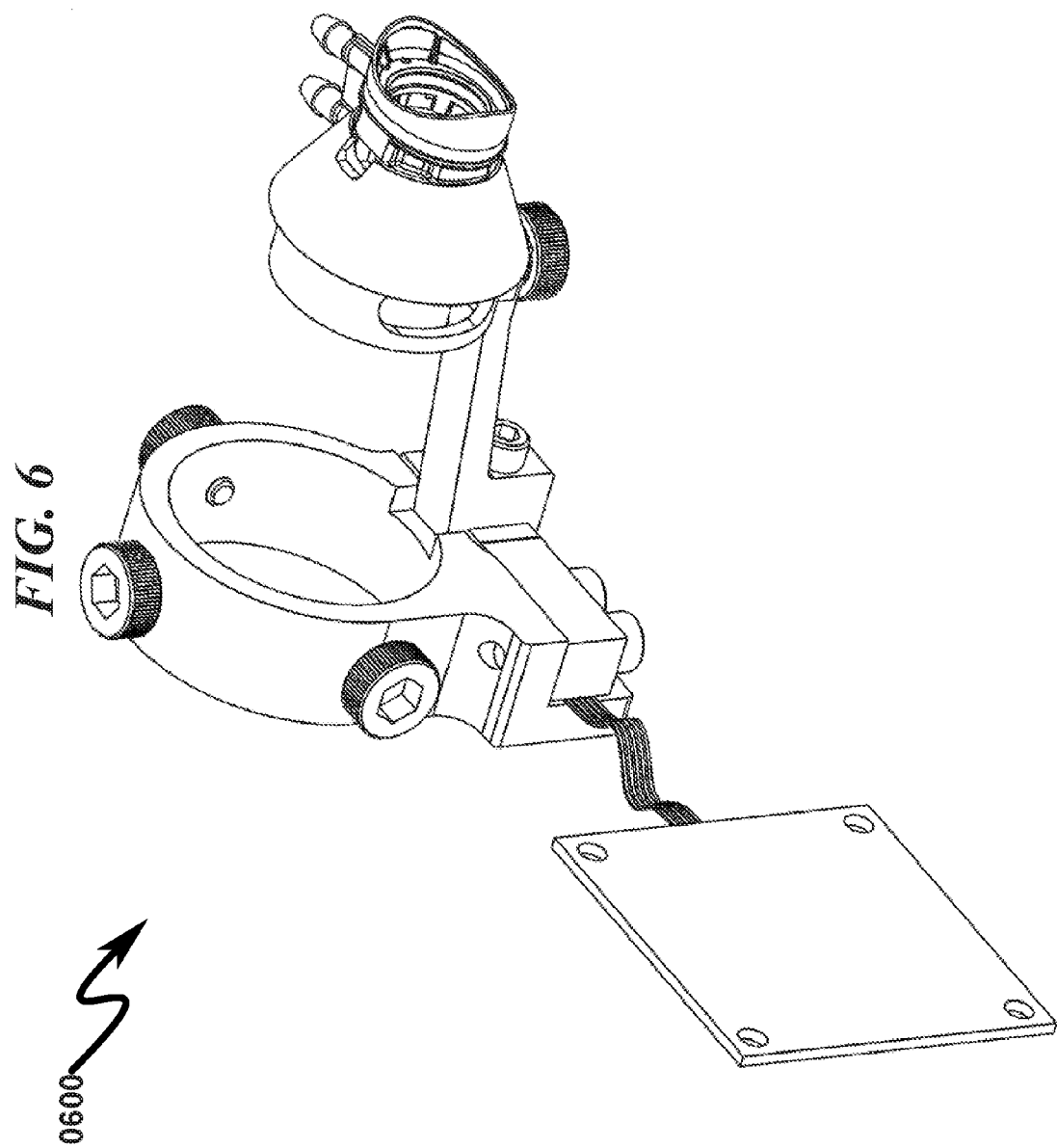
FIG. 6 illustrates a top right rear perspective view of a preferred exemplary invention LPI system embodiment.
Figure 7:
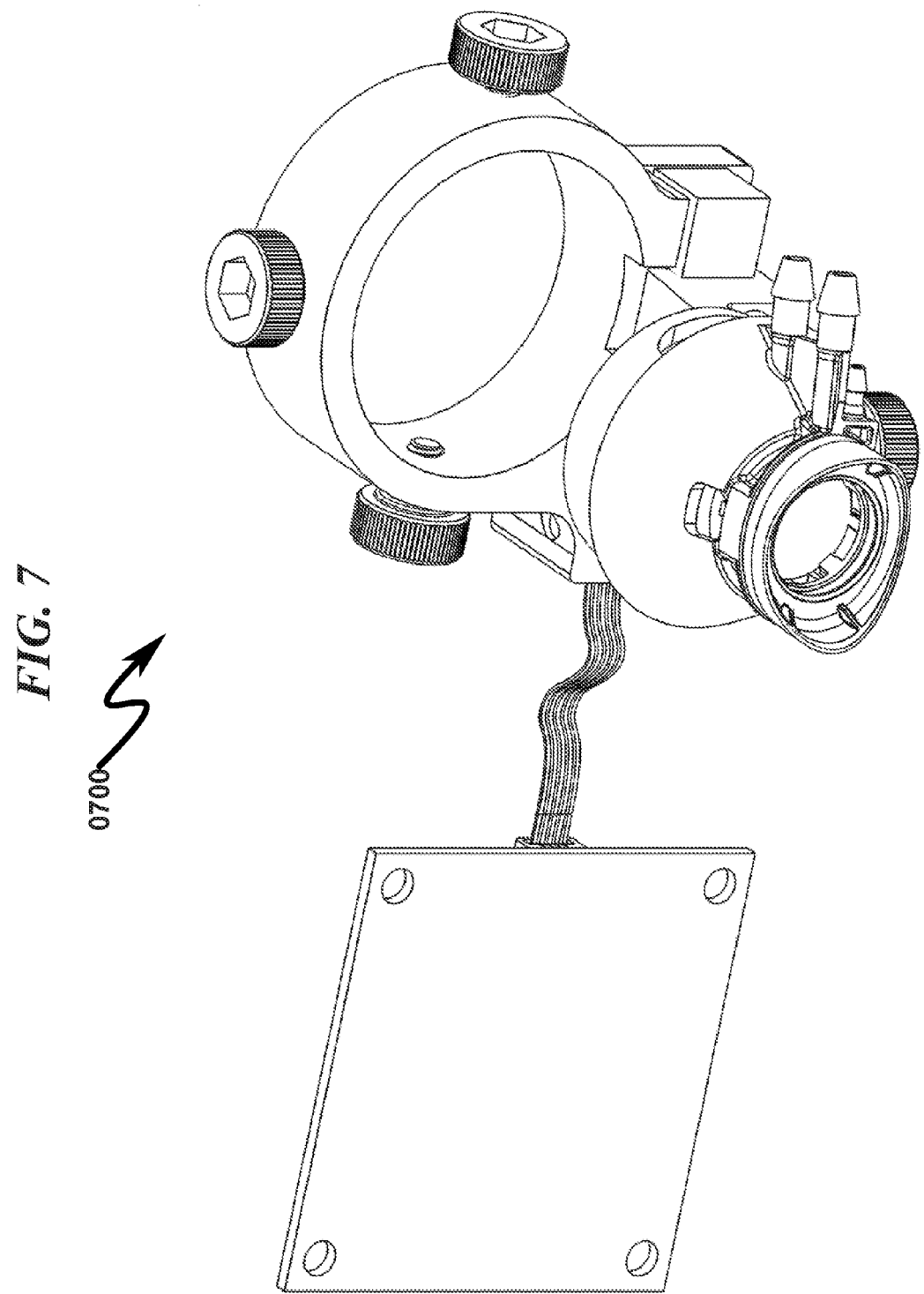
FIG. 7 illustrates a top left rear perspective view of a preferred exemplary invention LPI system embodiment.
Figure 8:
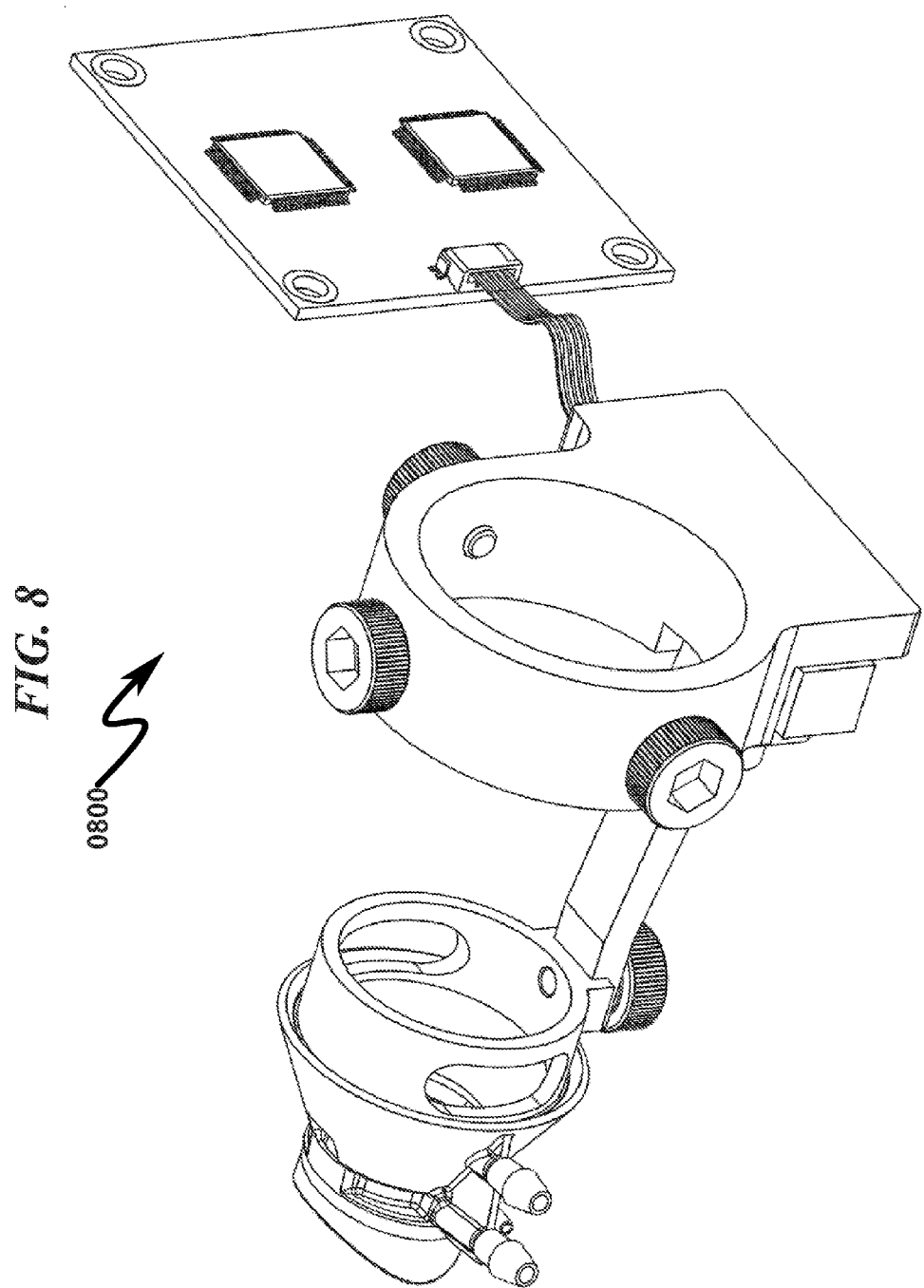
FIG. 8 illustrates a top left front perspective view of a preferred exemplary invention LPI system embodiment.
Figure 9:
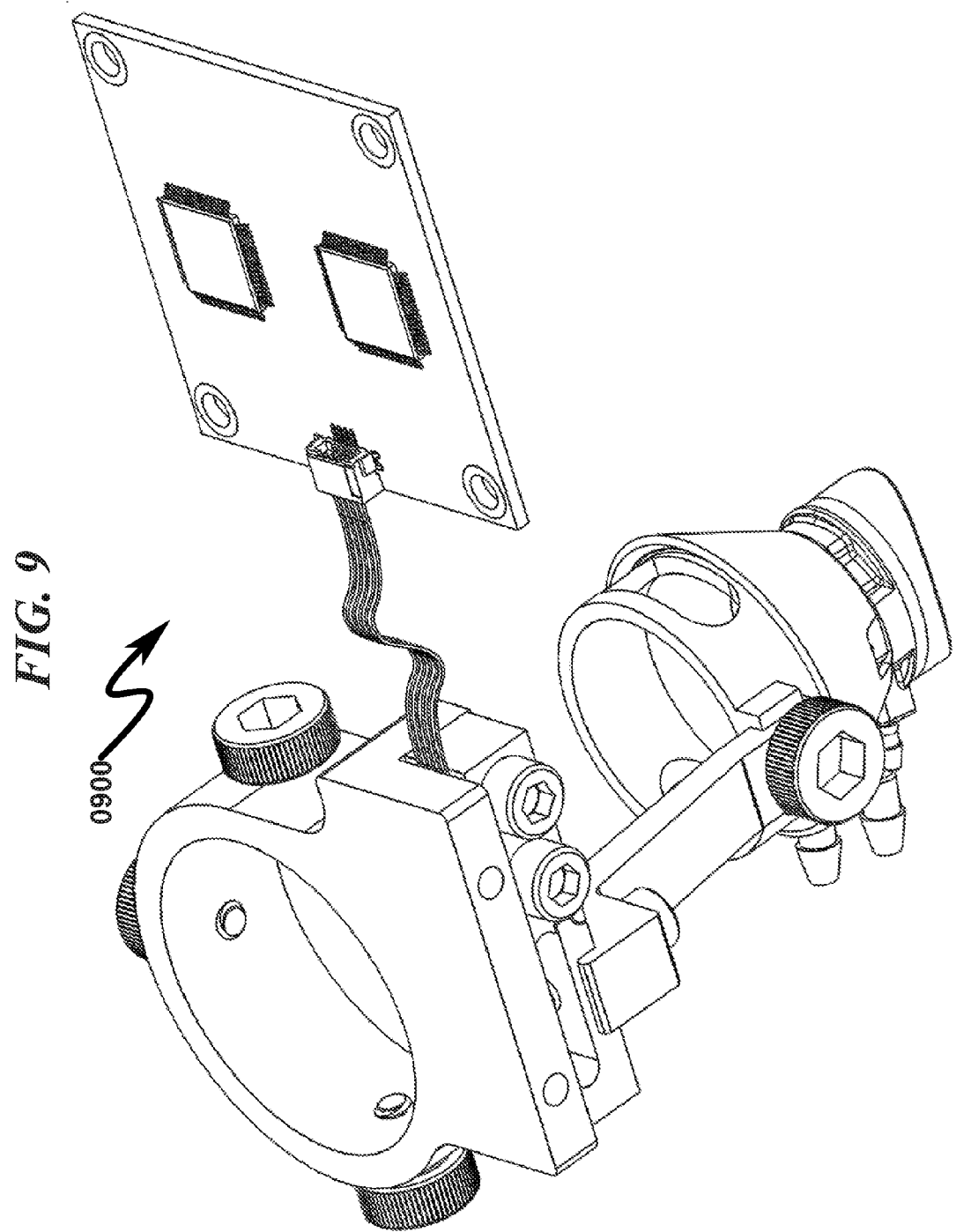
FIG. 9 illustrates a bottom right front perspective view of a preferred exemplary invention LPI system embodiment.
Figure 10:
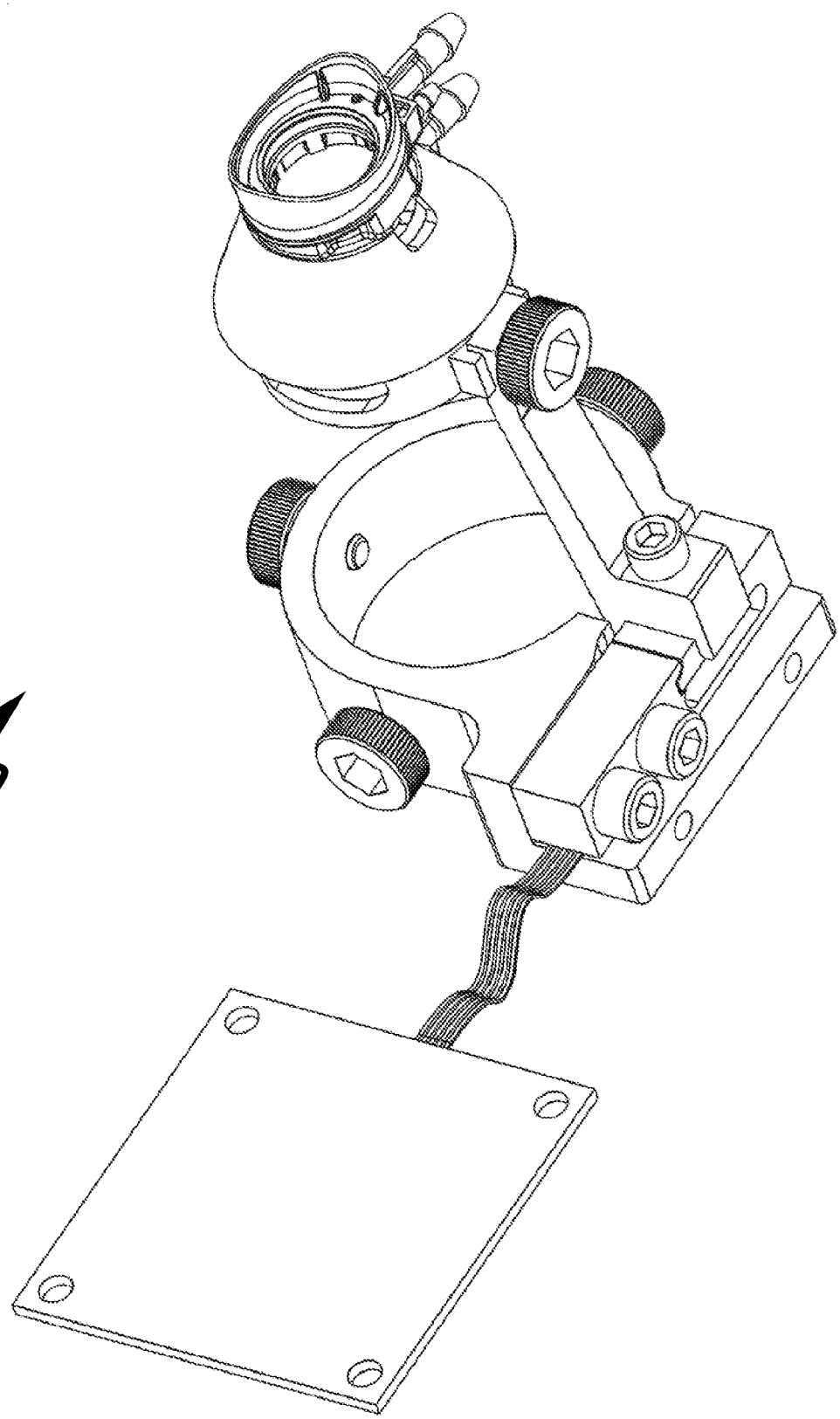
FIG. 10 illustrates a bottom right rear perspective view of a preferred exemplary invention LPI system embodiment.
Figure 11:
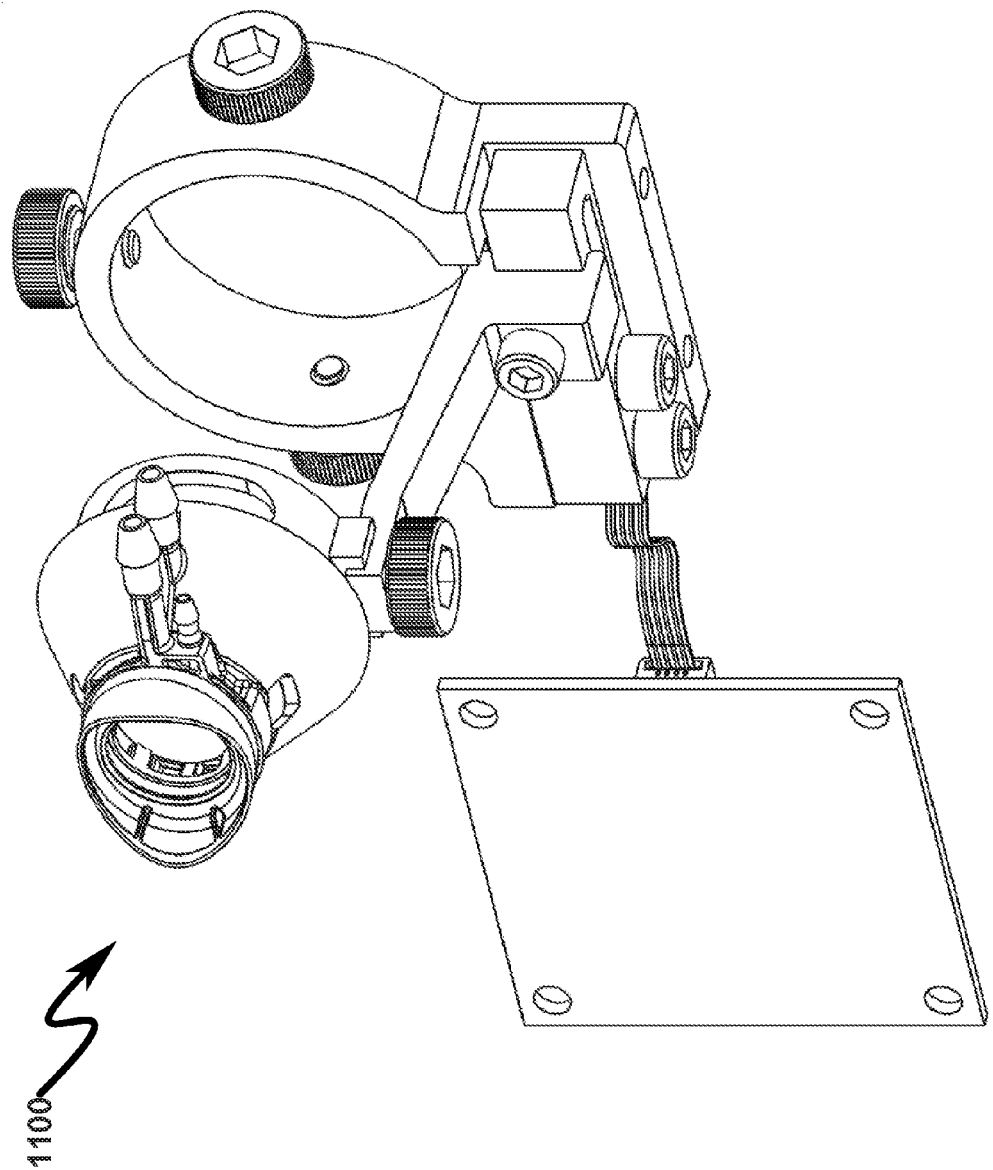
FIG. 11 illustrates a bottom left rear perspective view of a preferred exemplary invention LPI system embodiment.
Figure 12:
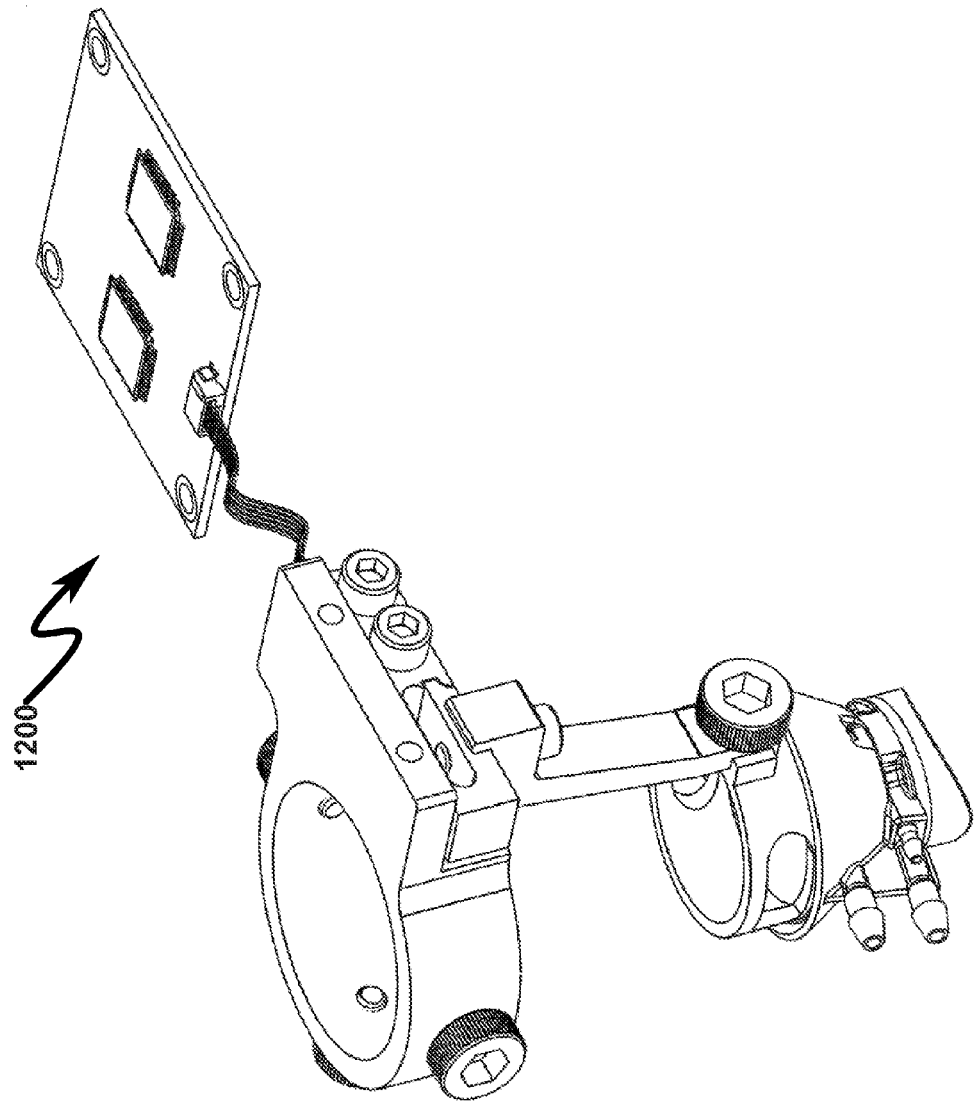
FIG. 12 illustrates a bottom left front perspective view of a preferred exemplary invention LPI system embodiment.
Figure 13:
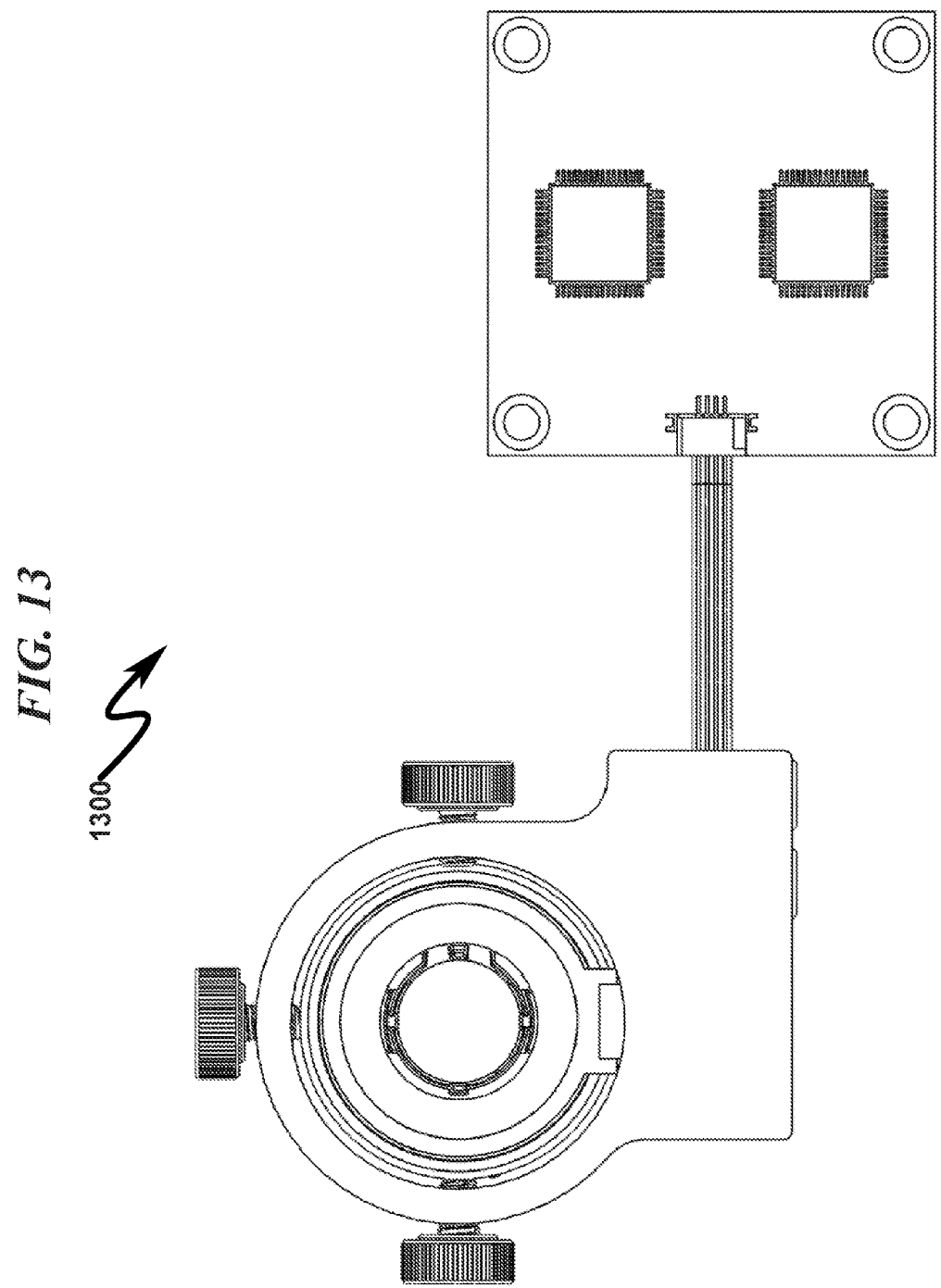
FIG. 13 illustrates a front view of a preferred exemplary invention LPI system embodiment with OFS electronics depicted.
Figure 14:
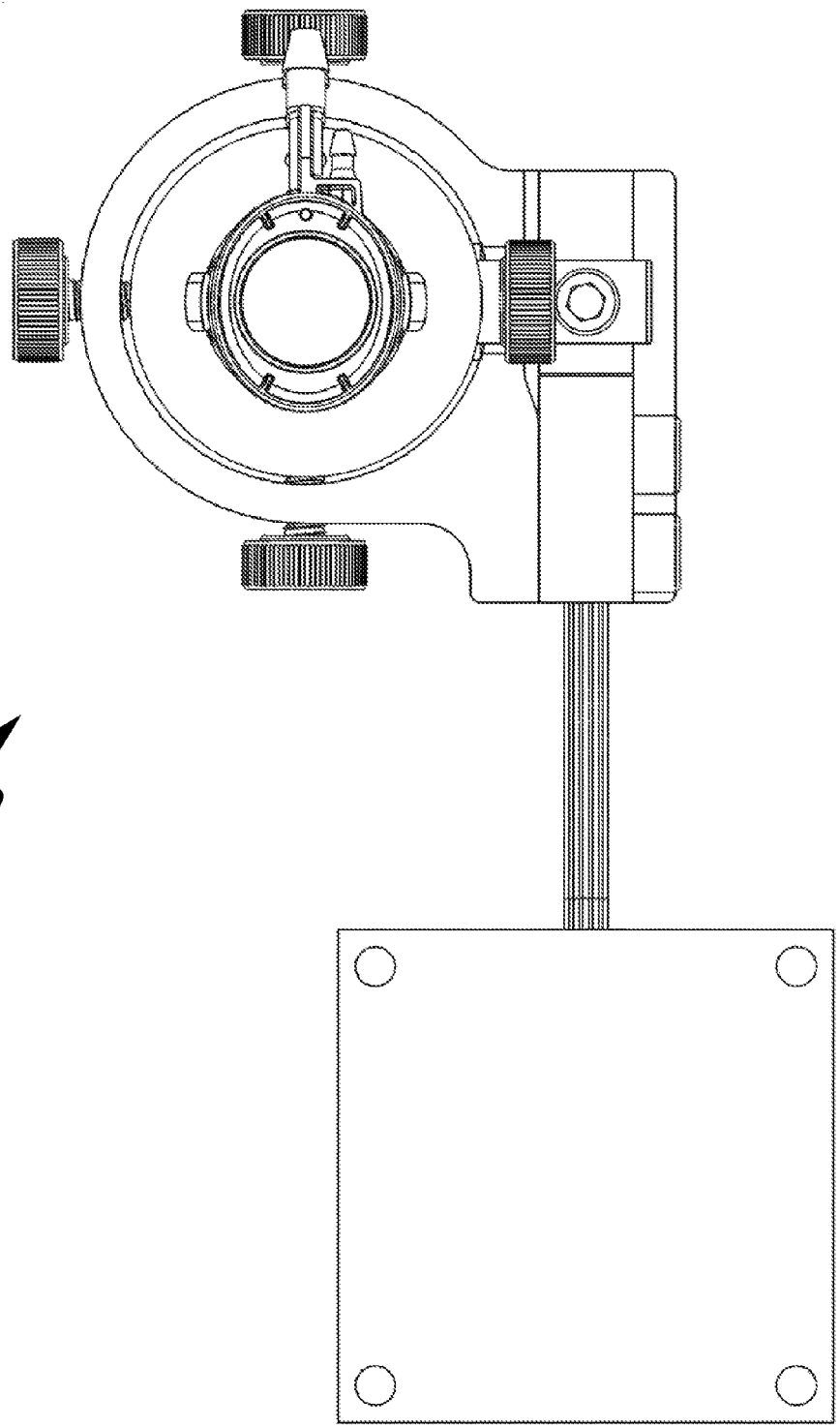
FIG. 14 illustrates a rear view of a preferred exemplary invention LPI system embodiment with OFS electronics depicted.
Figure 15:
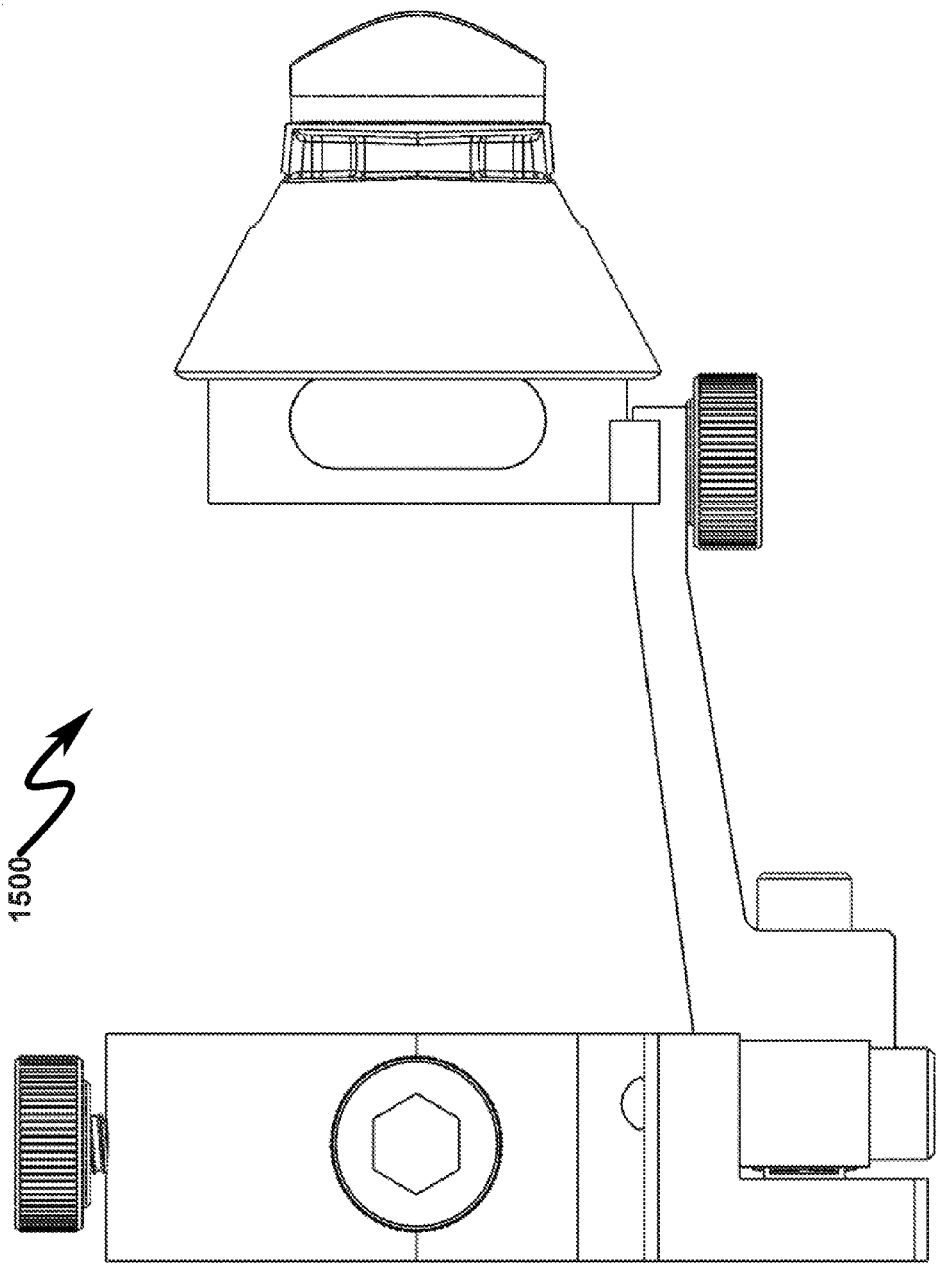
FIG. 15 illustrates a right side view of a preferred exemplary invention LPI system embodiment with OFS electronics omitted.
Figure 16:
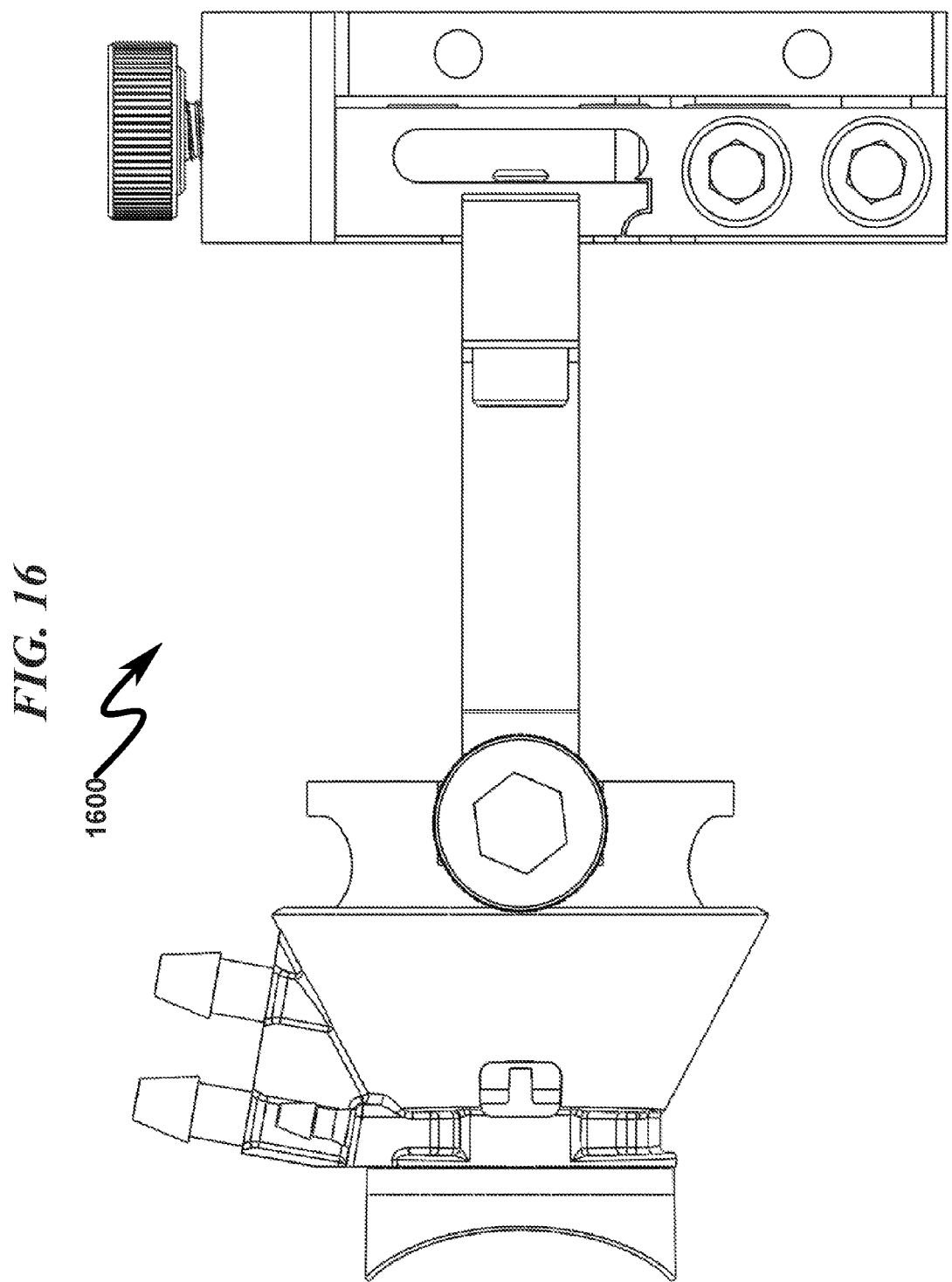
FIG. 16 illustrates a bottom view of a preferred exemplary invention LPI system embodiment with OFS electronics omitted.

Various views of a preferred exemplary system configuration are depicted in FIG. 5 (0500)-FIG. 16 (1600) without the patient eye surface (PES) depicted in FIG. 2 (0200). Not shown in these LPI drawing views are details of the computing control device (CCD), laser objective optics (LOO), scanning laser source (SLS), laser position arm (LPA), vacuum suction pump (VSP), and fluid delivery system (FDS).

Exemplary LPI Optical Path (1700)-(2400)

Figure 17:
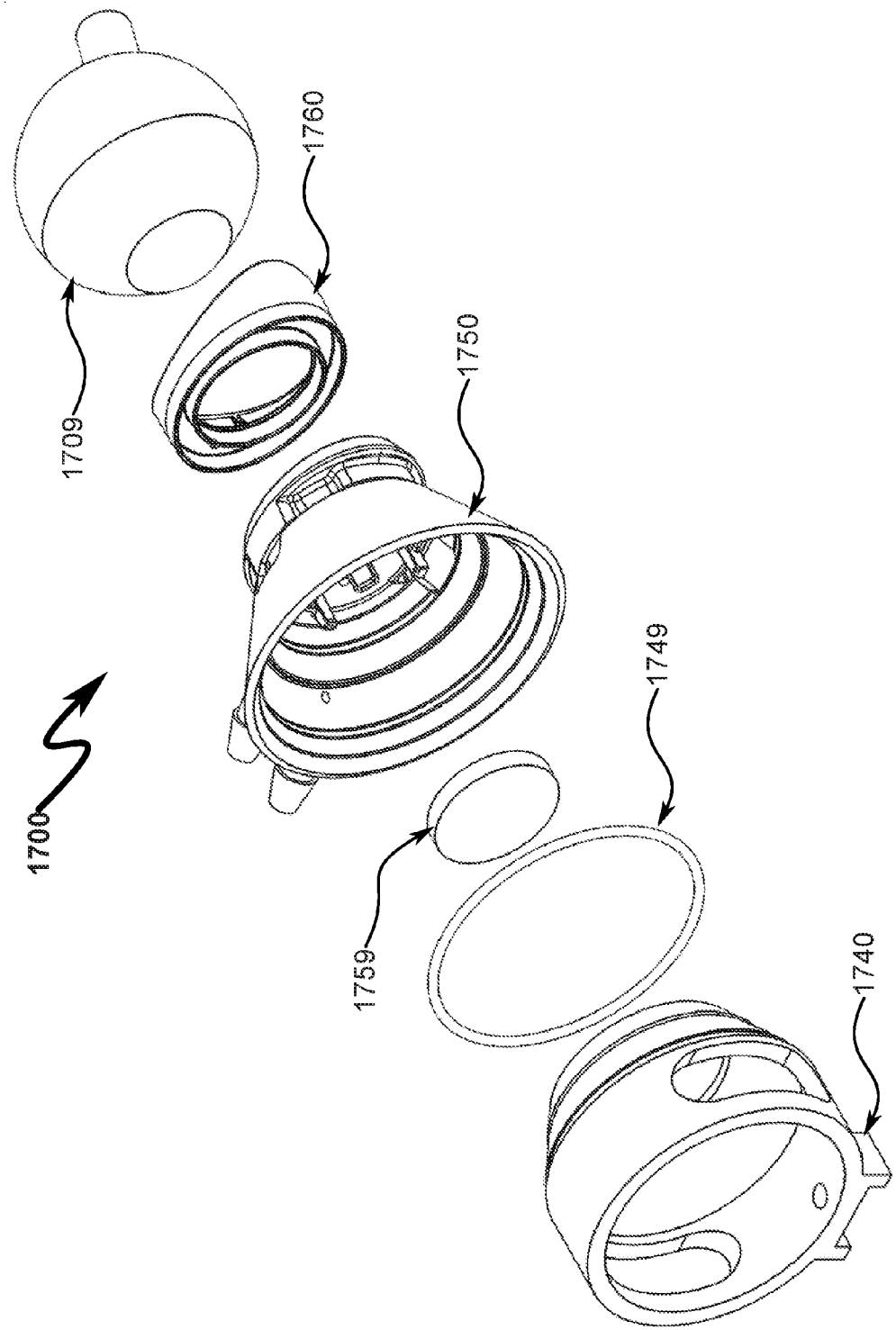
FIG. 17 illustrates a top right front perspective assembly view of a preferred exemplary invention optical path LPI embodiment.
Figure 18:
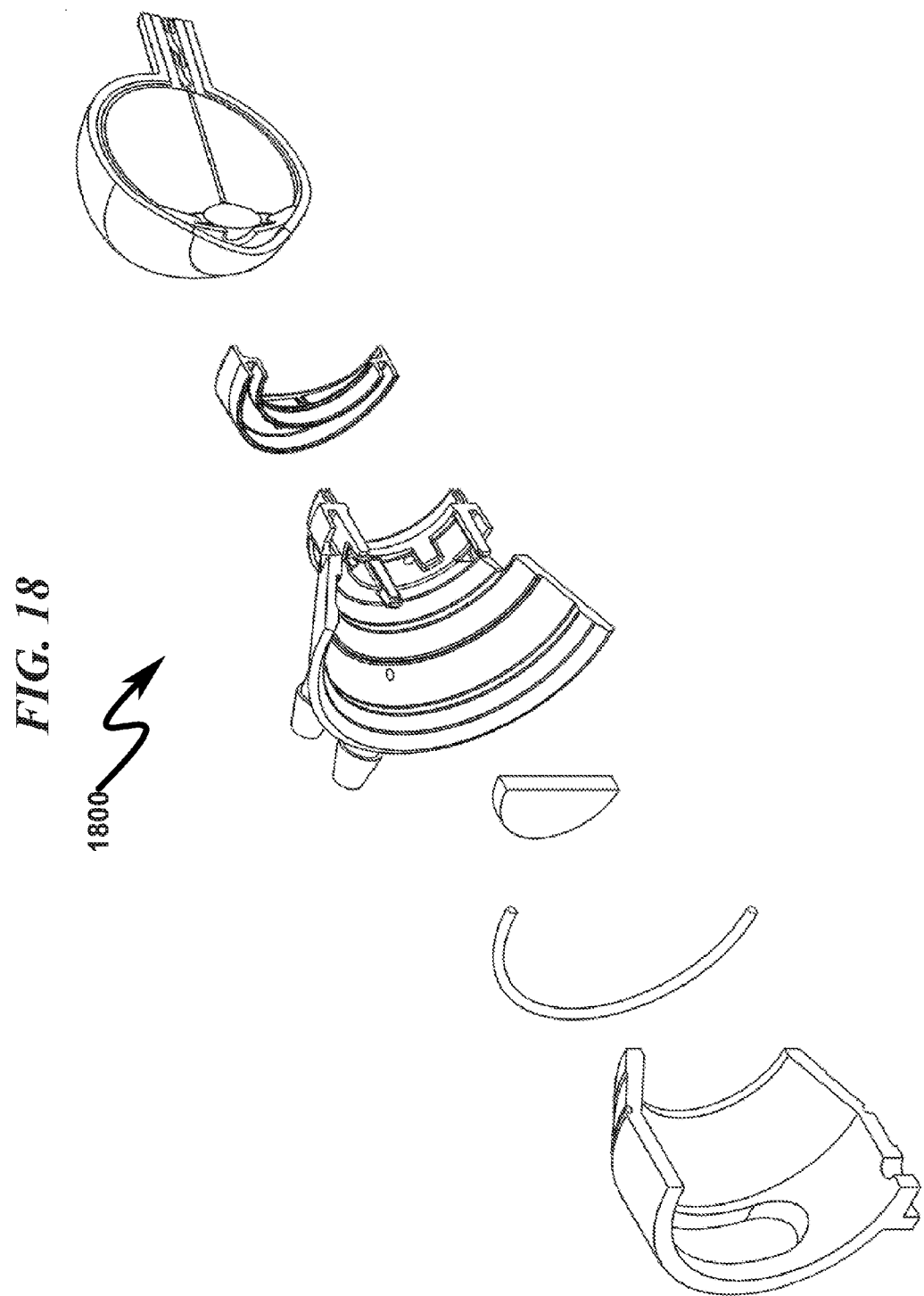
FIG. 18 illustrates a top right front perspective right section assembly view of a preferred exemplary invention optical path LPI embodiment.
Figure 19:
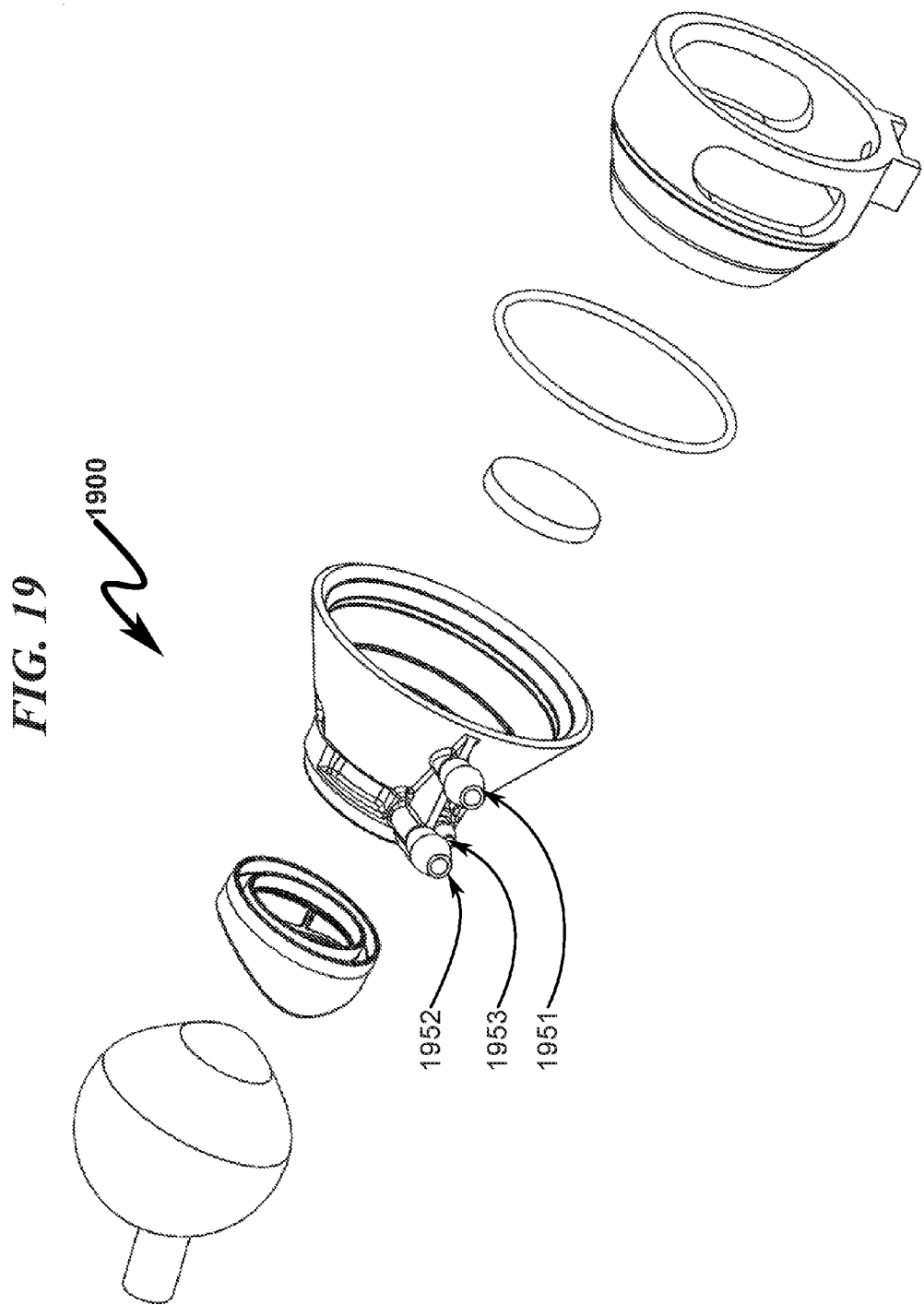
FIG. 19 illustrates a top left front perspective assembly view of a preferred exemplary invention optical path LPI embodiment.
Figure 20:
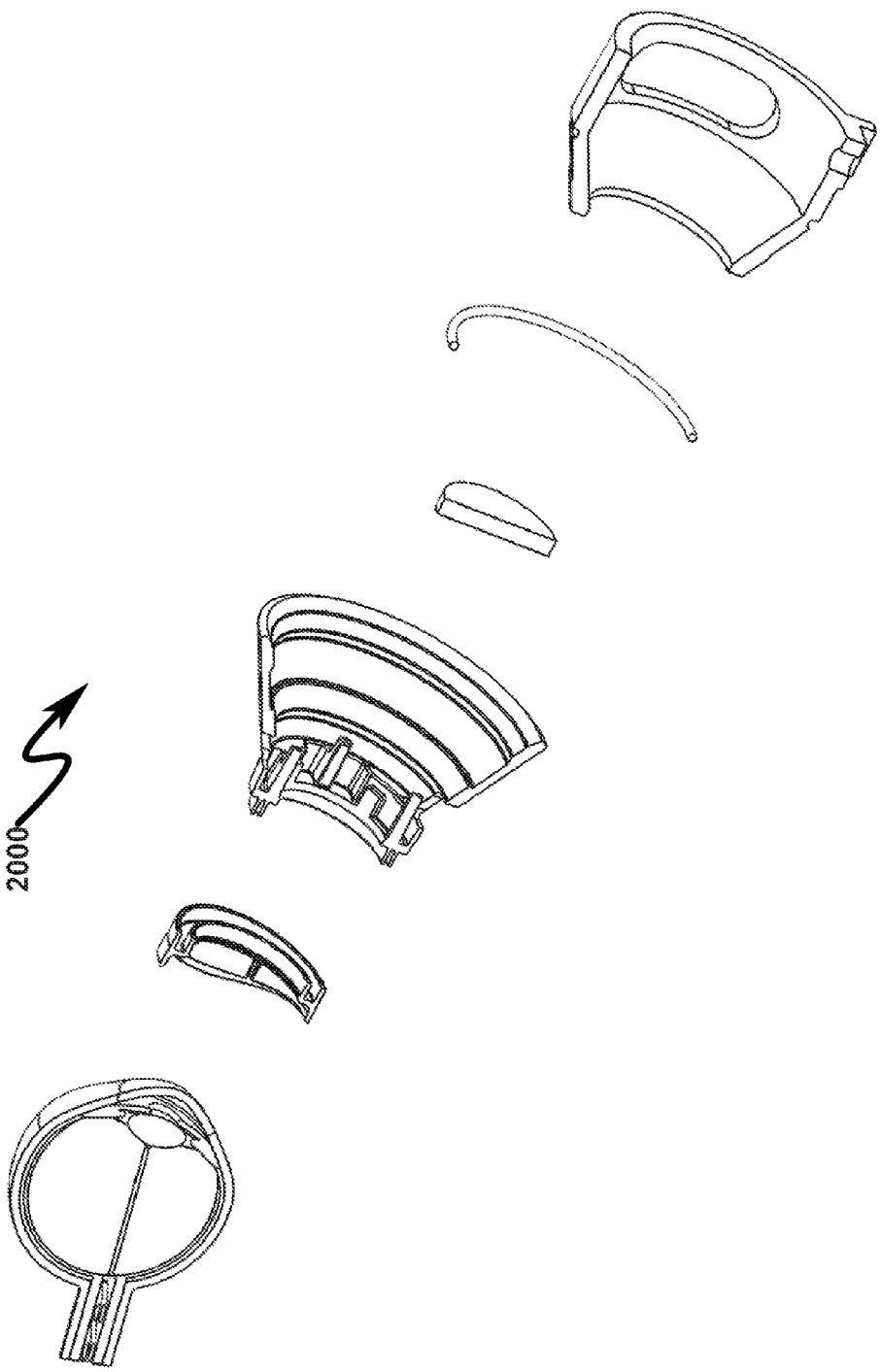
FIG. 20 illustrates a top left front perspective left section assembly view of a preferred exemplary invention optical path LPI embodiment.
Figure 21:
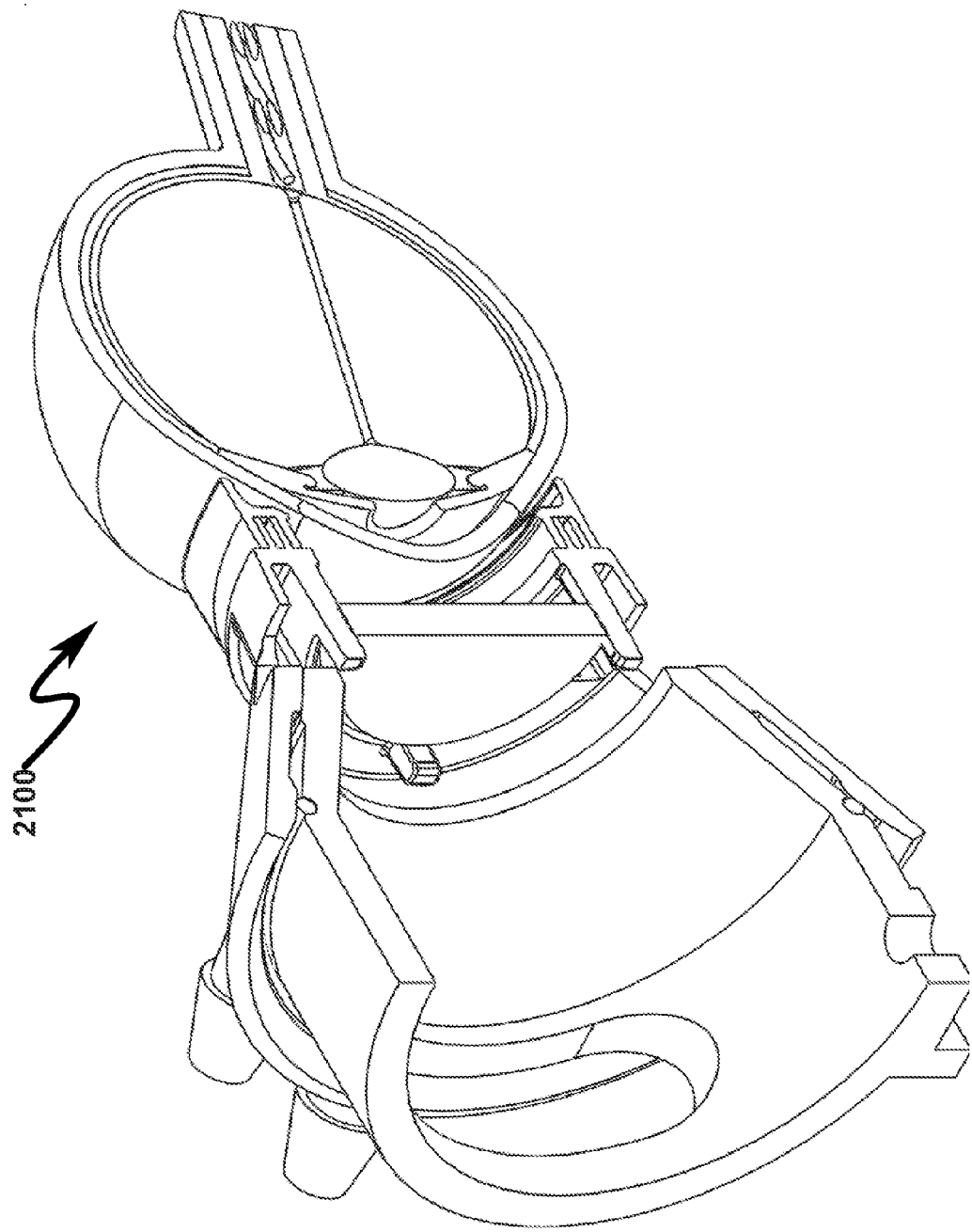
FIG. 21 illustrates a top right front perspective right section detail view of a preferred exemplary invention embodiment depicting typical mating between OWR, OPI, OSR, and PES.
Figure 22:
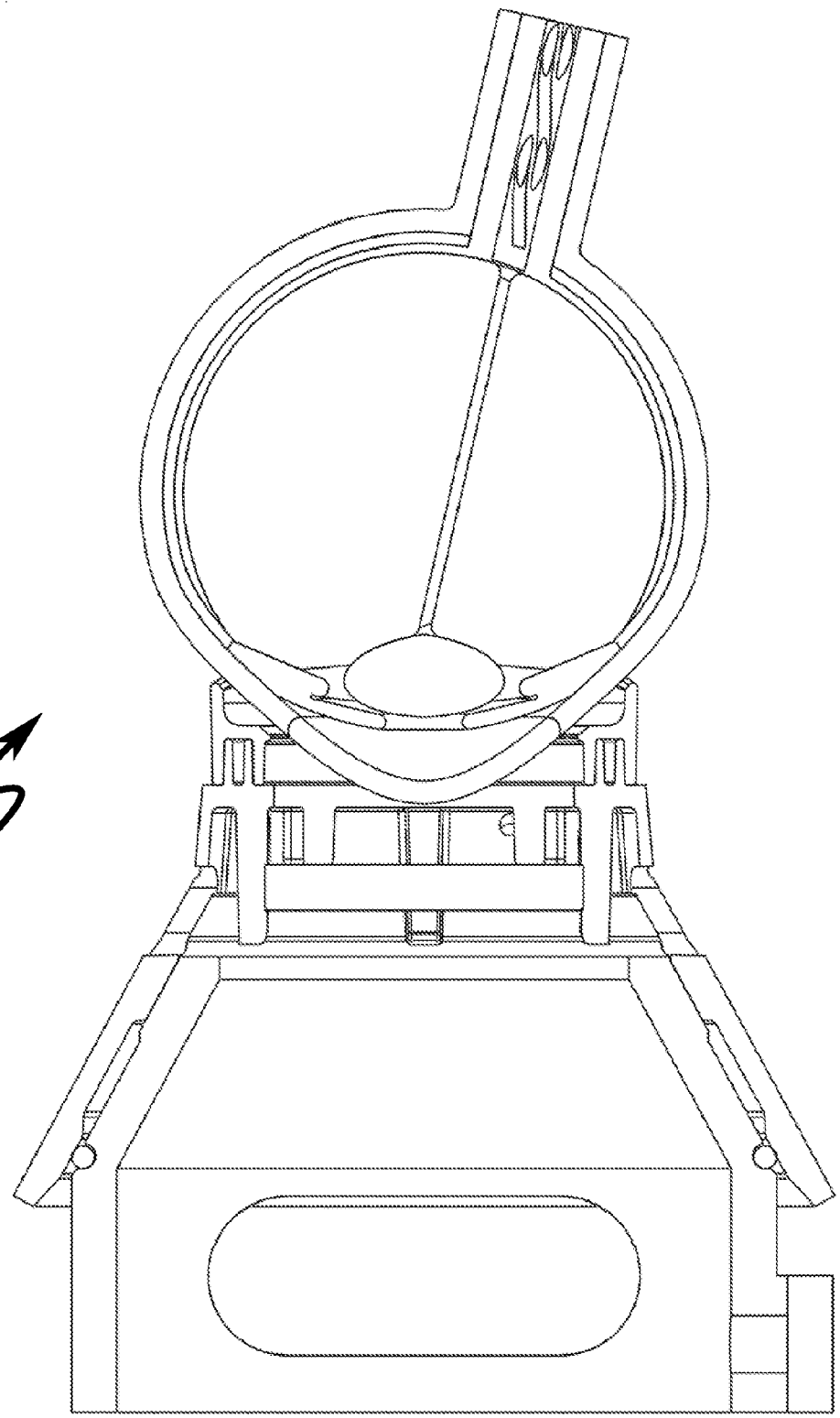
FIG. 22 illustrates a right section detail view of a preferred exemplary invention embodiment depicting typical mating between OWR, OPI, OSR, and PES.
Figure 23:
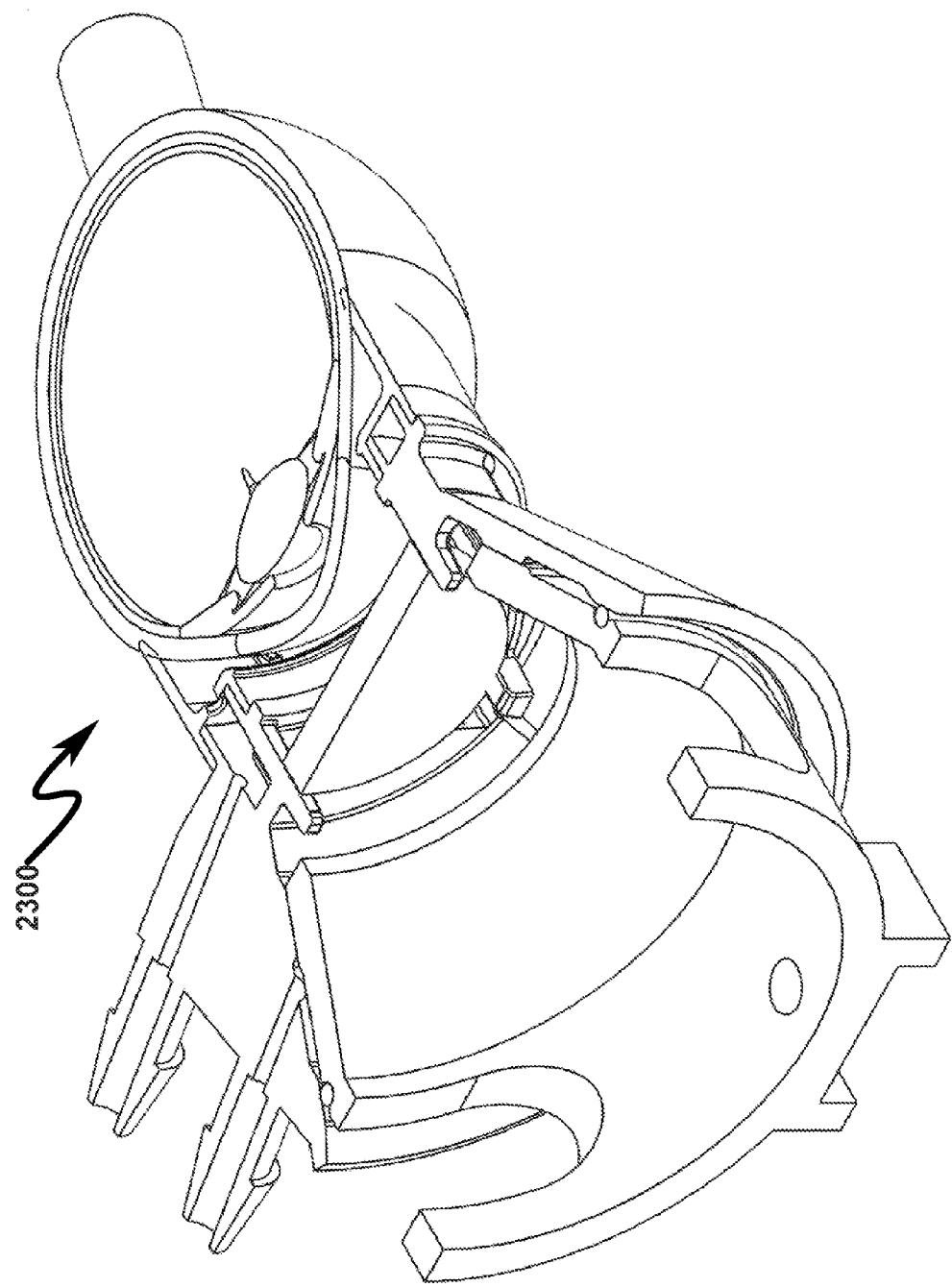
FIG. 23 illustrates a top right front perspective top section detail view of a preferred exemplary invention embodiment depicting typical mating between OWR, OPI, OSR, and PES.
Figure 24:
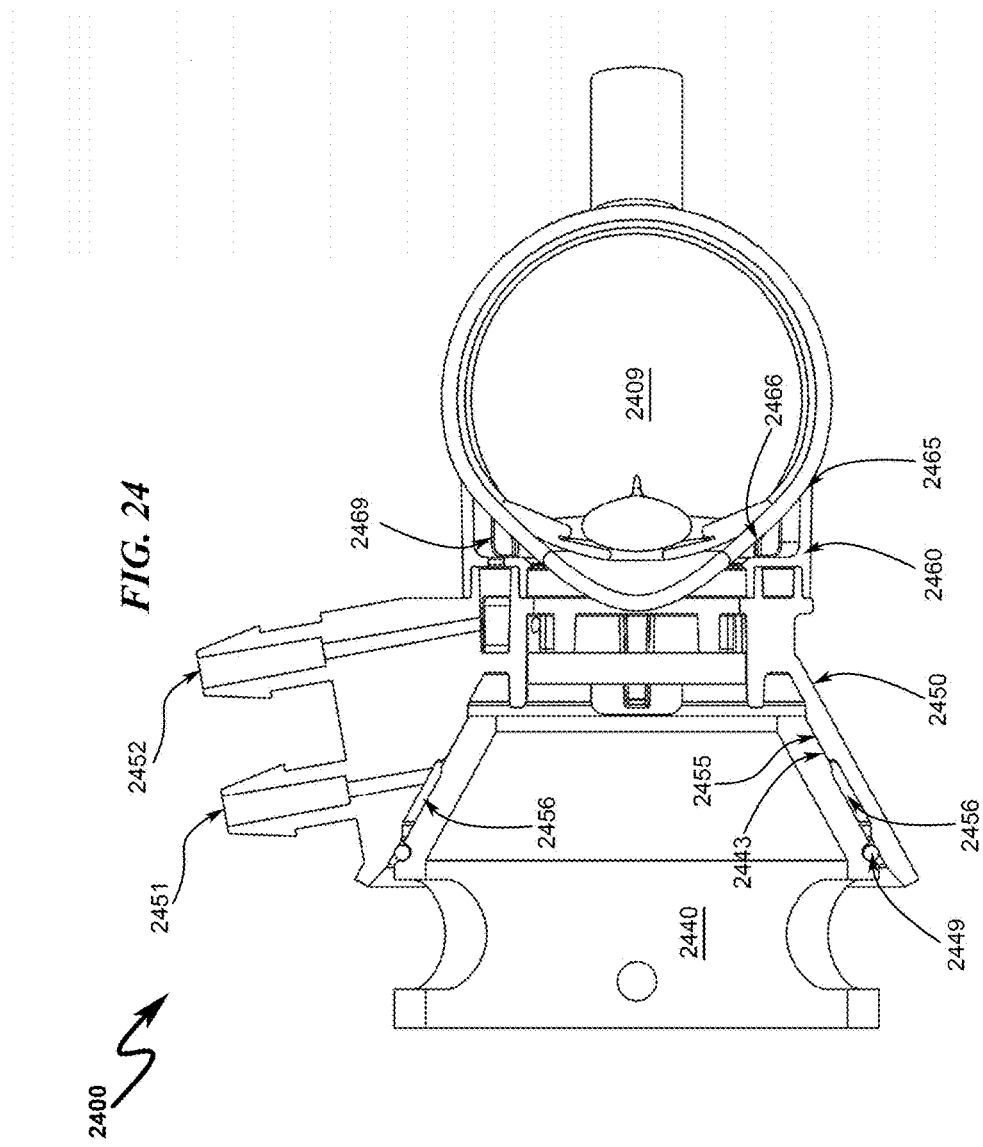
FIG. 24 illustrates a top section detail view of a preferred exemplary invention embodiment depicting typical mating between OWR, OPI, OSR, and PES.

Assembly views depicting a preferred invention LPI optical path are depicted in FIG. 17 (1700)-FIG. 24 (2400). These views depict several features of the preferred invention embodiment including the optical window retainer (OWR) (1740) (and associated vacuum sealing gasket (VSG) (1749) that mates with the ocular patient interface (OPI) (1750)), ocular patient interface (OPI) (1750) (including docking vacuum port (DVP) (1951), suction vacuum port (SVP) (1952), liquid injection port (LIP) (1953), and liquid interface window (LIW) (1759)), ocular suction ring (OSR) (1760), and a typical patient eye surface (PES) (1709).

Exemplary VSP (2500)-(2900)

Figure 25:
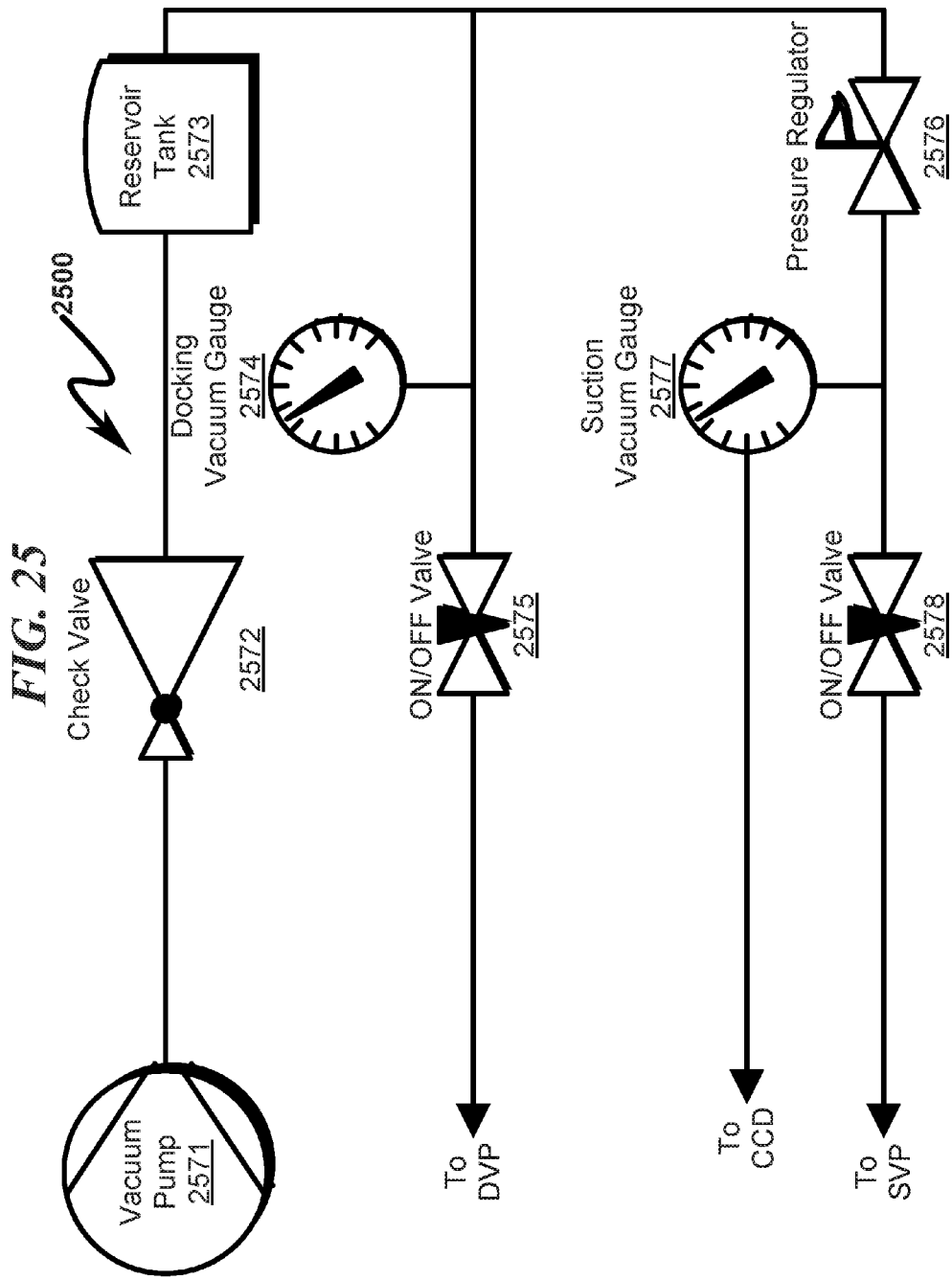
FIG. 25 illustrates a schematic depicting an exemplary VSP implementation useful in many preferred invention embodiments.
Figure 29:
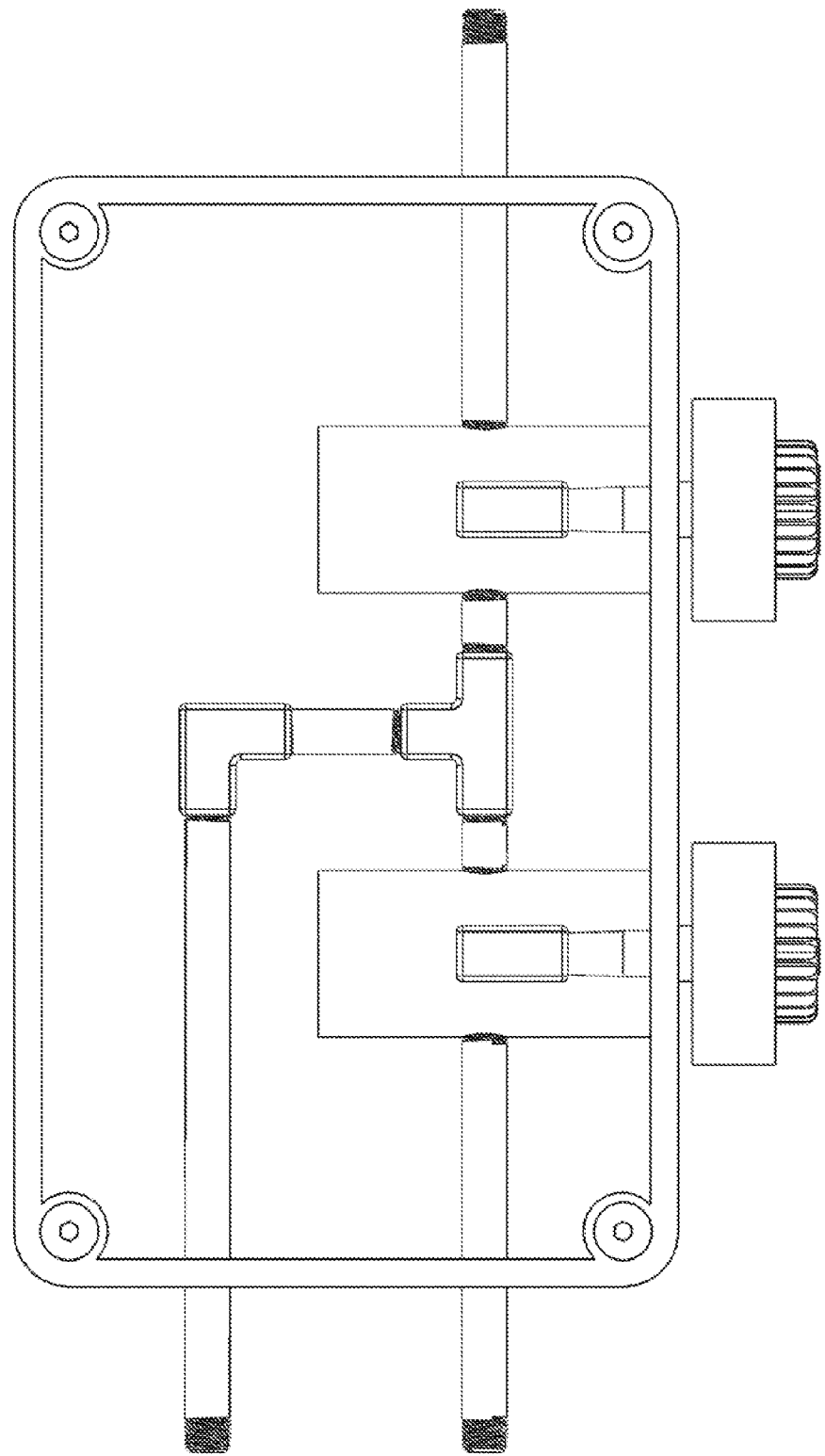
FIG. 29 illustrates a top view of a preferred exemplary VSP control fixture (with cover removed) useful in many preferred invention embodiments.
Figure 30:
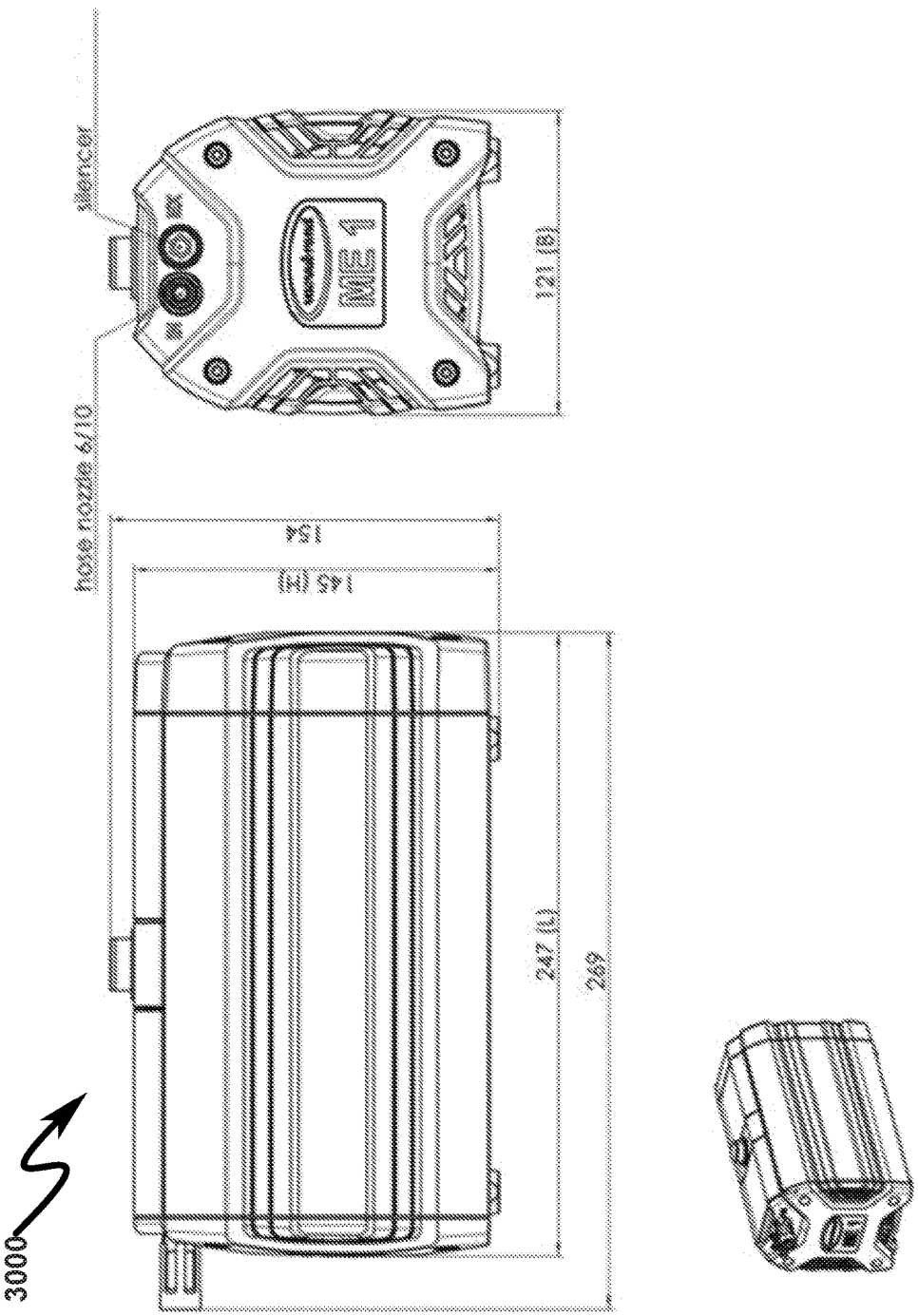
FIG. 30 illustrates a typical physical configuration of a vacuum pump suitable for use with the present invention.

Preferred exemplary embodiments of the vacuum suction pump (VSP) are depicted in FIG. 25 (2500)-FIG. 29 (2900).

FIG. 25 (2500) depicts a general schematic of the VSP. The VSP generally comprises a vacuum pump (2571) producing a vacuum source that is fed through a check valve (2572) connected to a vacuum reservoir (2573). The vacuum reservoir (2573) is monitored by a docking vacuum gauge (DVG) (2574) that supplies an ON/OFF valve (2575) that supplies vacuum to the DVP that affects mating between the OWR and the OPI.

The vacuum reservoir (2573) also supplies a pressure/vacuum regulator (2576) that supplies regulated vacuum monitored by a suction vacuum gauge (SVG) (2577) and which feeds an ON/OFF valve (2578) that supplies vacuum to the SVP that affects mating between the OSR and the PES.

As generally depicted in other drawings, the DVP (2451) feeds a vacuum docking void (VDV) (2456) between the conical mating surface (CMS) (2455) on the OPI (2450) and a corresponding vacuum mating surface (VMS) (2443) on the OWR (2440). Thus, when vacuum is provided to the DVP (2451) by the VSP, mating is activated between the OWR (2440) and the OPI (2450).

Similarly, the OPI (2450) contains a SVP vacuum port (2452) that connects with the OSR (2460) and allows a patient eye vacuum chamber (EVC) (2469) in the OSR (2460) to vacuum mate the OSR (2460) to the PES (2409) when vacuum is applied to the SVP (2452). The SVG in some configurations may be monitored by the CCD to ensure that suction pressure applied to the PES is maintained within acceptable limits.

Figure 26:
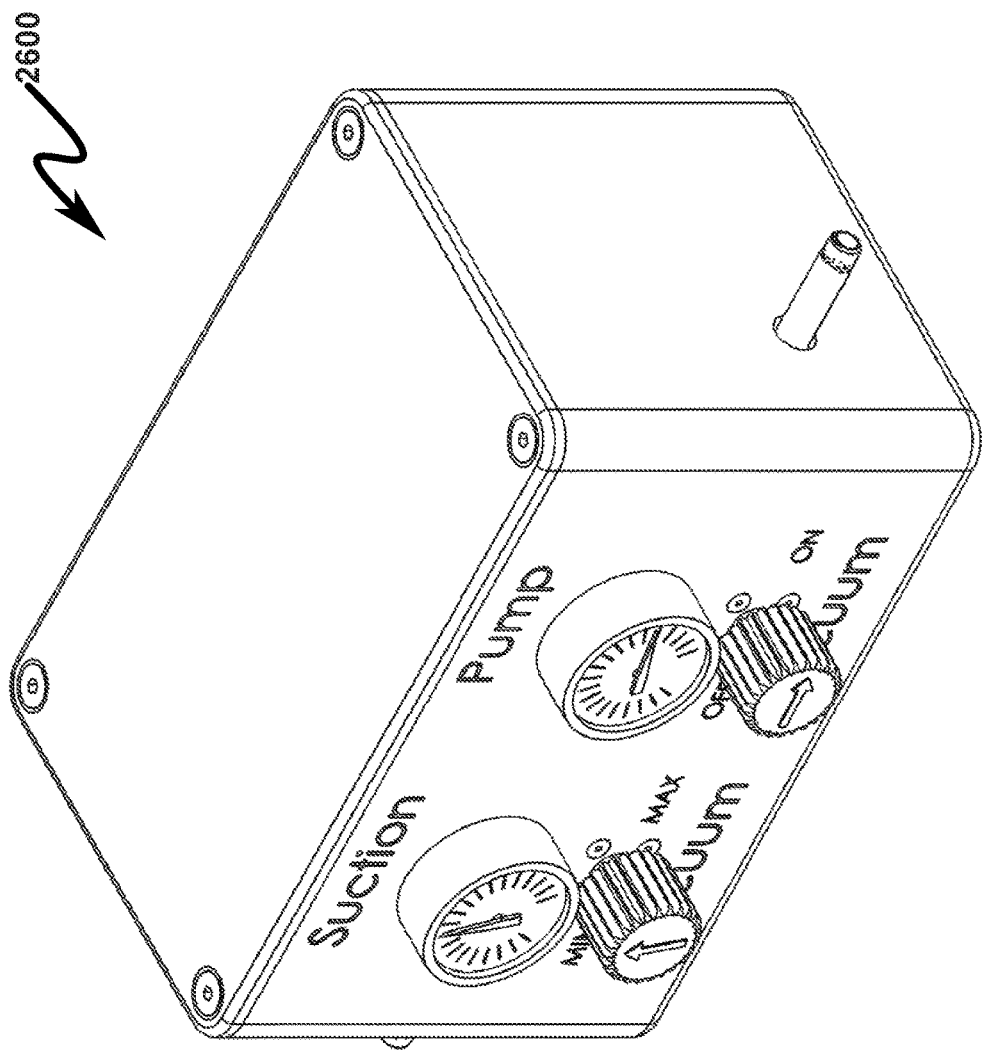
FIG. 26 illustrates a top right front perspective view of a preferred exemplary VSP control fixture useful in many preferred invention embodiments.
Figure 27:
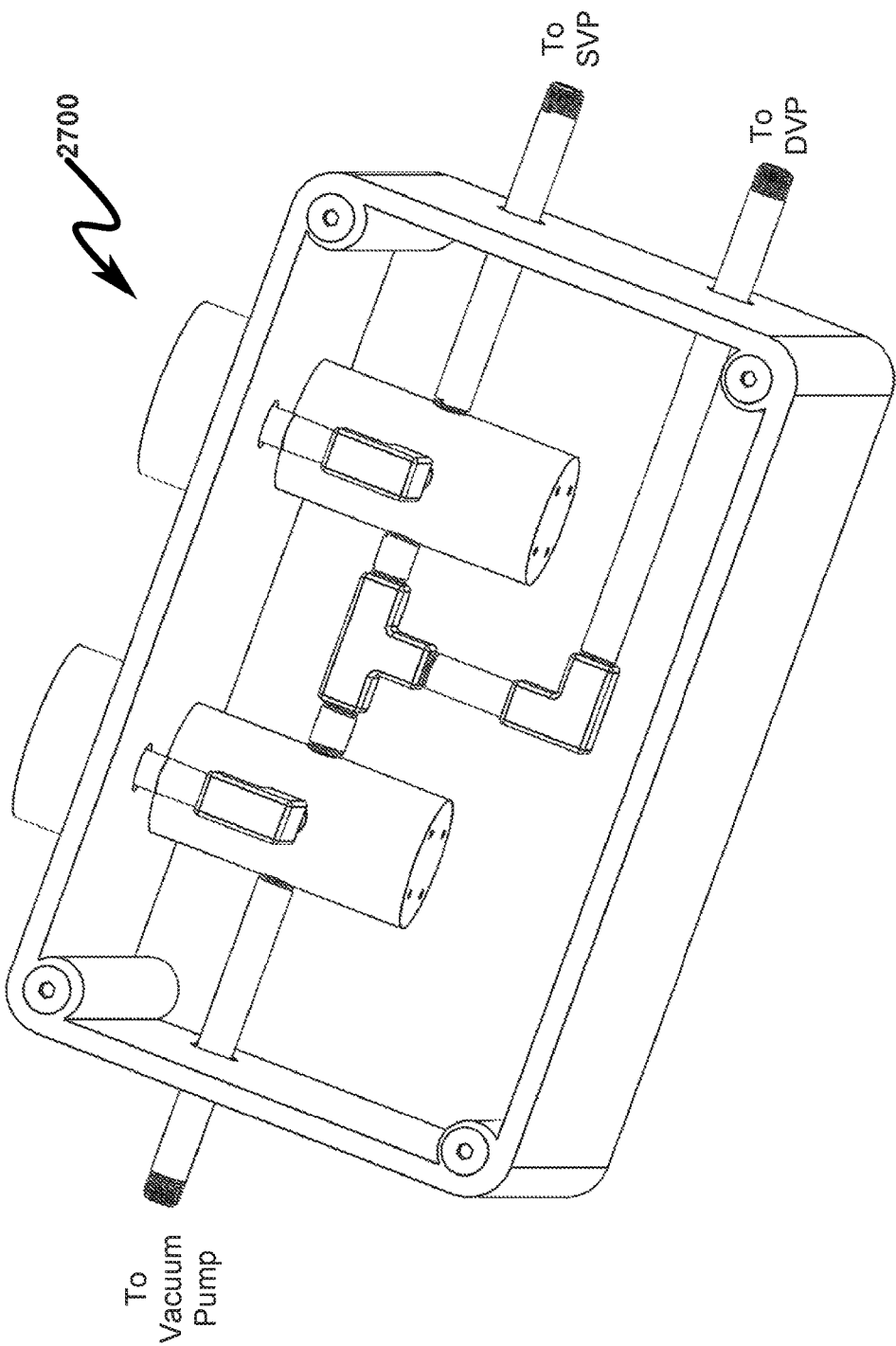
FIG. 27 illustrates a top left rear perspective view of a preferred exemplary VSP control fixture (with cover removed) useful in many preferred invention embodiments.
Figure 28:
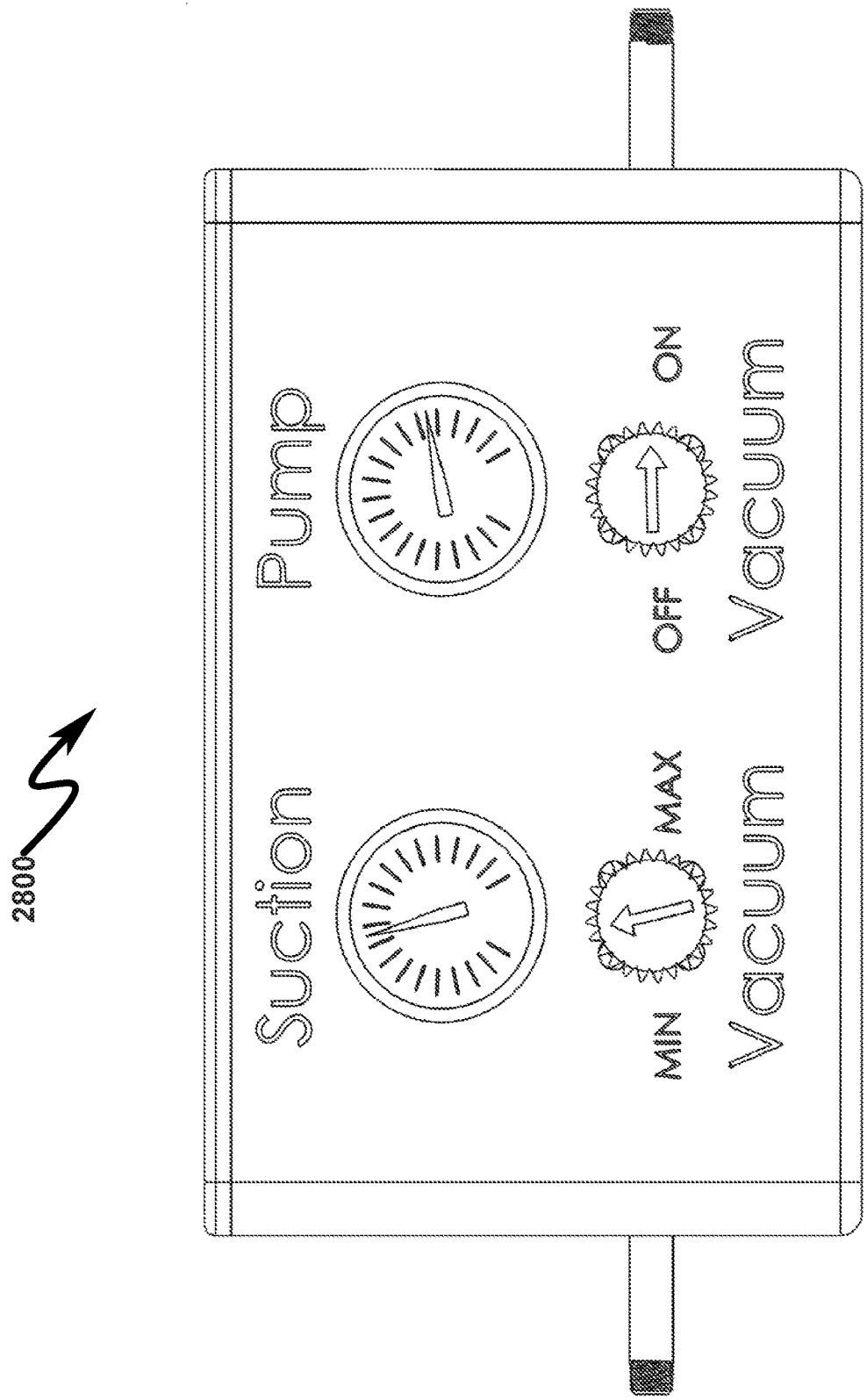
FIG. 28 illustrates a front view of a preferred exemplary VSP control fixture useful in many preferred invention embodiments.

FIG. 26 (2600)-FIG. 29 (2900) depict several views of a control box useful in implementing much of the functionality of the FIG. 25 (2500) schematic. This vacuum control system may be augmented with automated vacuum pressure measurement by the CCD as well as a variety of manual/automatic vacuum bleed-off valves depending on application context and degree of computerized automation.

Exemplary Vacuum Pump (3000)-(3200)

While many vacuum pumps may be suitable for use in implementing the present invention, VACUUBRAND® Model ME1 is a preferred vacuum source in many preferred invention embodiments. Typical vacuum performance characteristics from a suitable vacuum pump in this application are summarized in the following table:

| Vacuum Pump Parameter | Value |
|---|---|
| Number of heads/stages | 1 |
| Maximum pumping speed at 50/60 Hz | 0.7/0.85 m³/h |
| | 0.4/0.5 CFM |
| Ultimate vacuum (absolute) | 100 mbar |
| | 75 torr |
| Ambient temperature range (operaton) | 10-40° C. |
| Ambient temperature range (storage) | −10-60° C. |
| Maximum back pressure (absolute) | 1.1 bar |
| Rated motor speed at 50/60 Hz | 1500/1800 rpm |
| Rated motor power | 0.04 kW |
| Degree of protection | IP 40 |
| Noise level at 50 Hz | 45 dBA |

-continued

| Vacuum Pump Parameter | Value |
| --- | --- |
| Dimensions (L × W × H) | 247 × 121 × 145 mm |
| Weight | 5.0 kg |
| Vacuum regulation | Via vacuum regulator valve (ME1 part number 696842) |

A typical physical configuration of a vacuum pump suitable for use with the present invention is depicted in FIG. 29 (2900).

Figure 31:
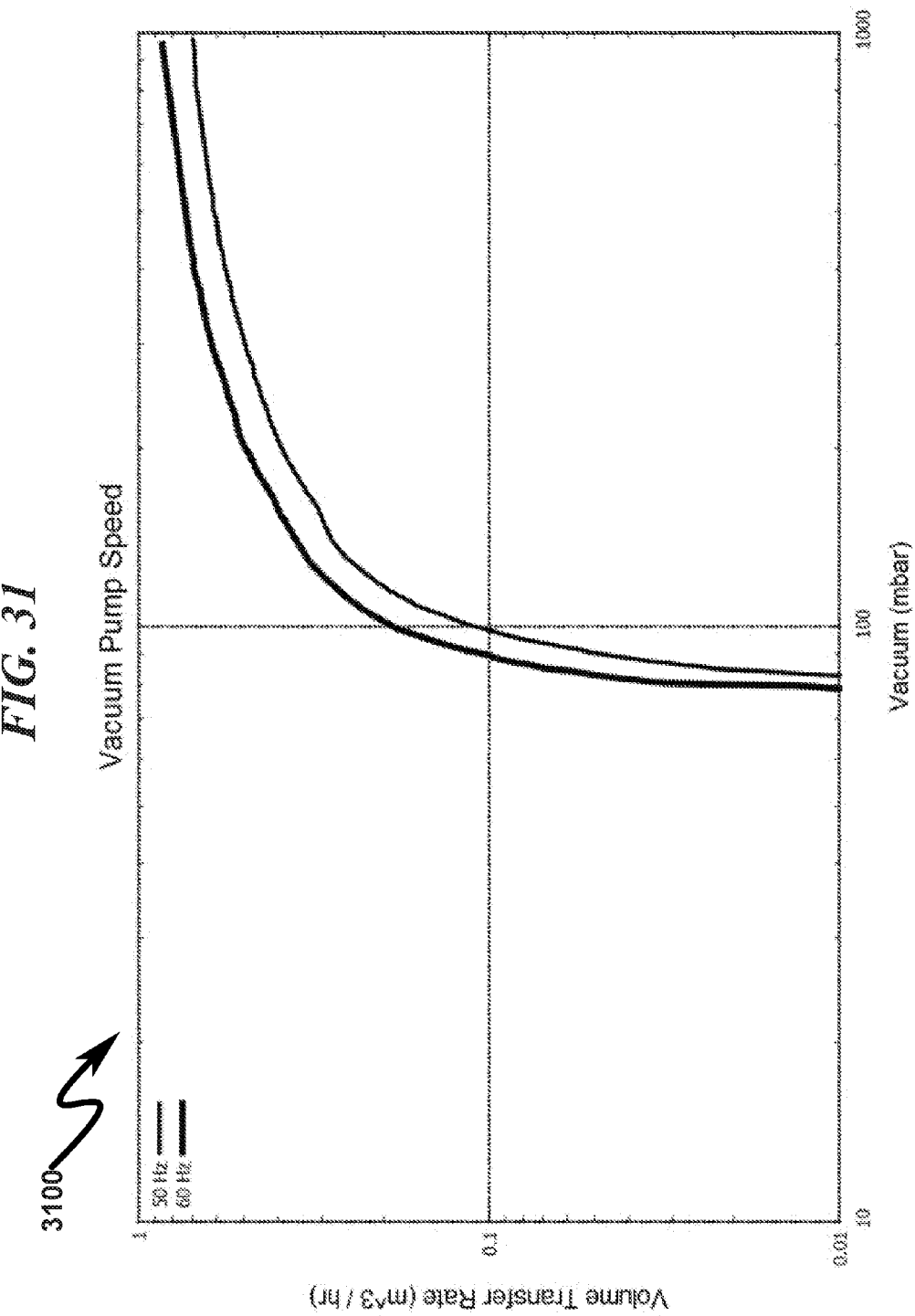
FIG. 31 illustrates typical vacuum pump performance characteristics that are suitable for implementing the present invention.
Figure 32:
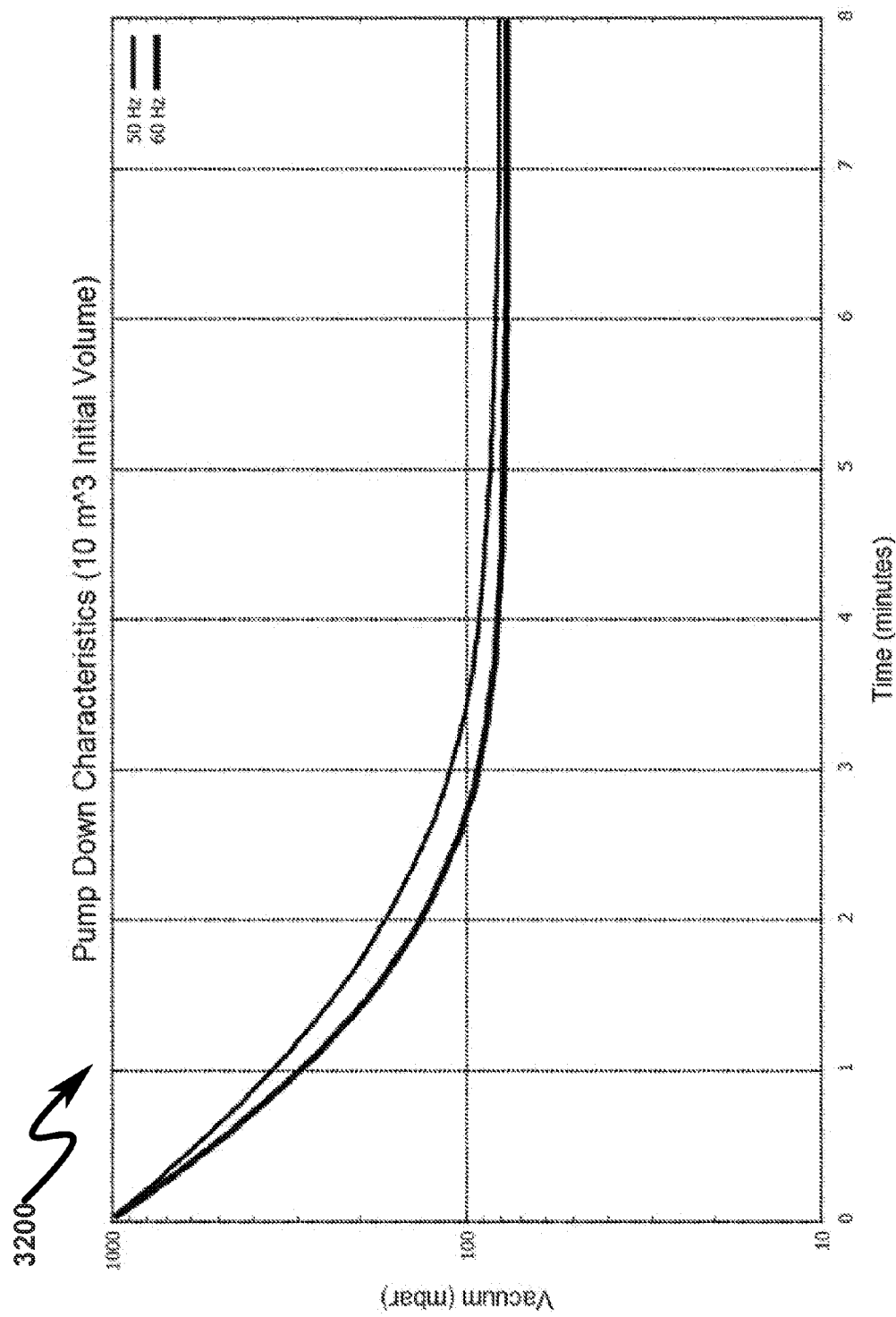
FIG. 32 illustrates typical vacuum pump performance characteristics that are suitable for implementing the present invention.

FIG. 31 (3100)-FIG. 32 (3200) depict typical vacuum pump performance characteristics that are suitable for implementing the present invention.

Exemplary Laser Objective Bracket (LOB) (3300)-(4800)

Figure 33:
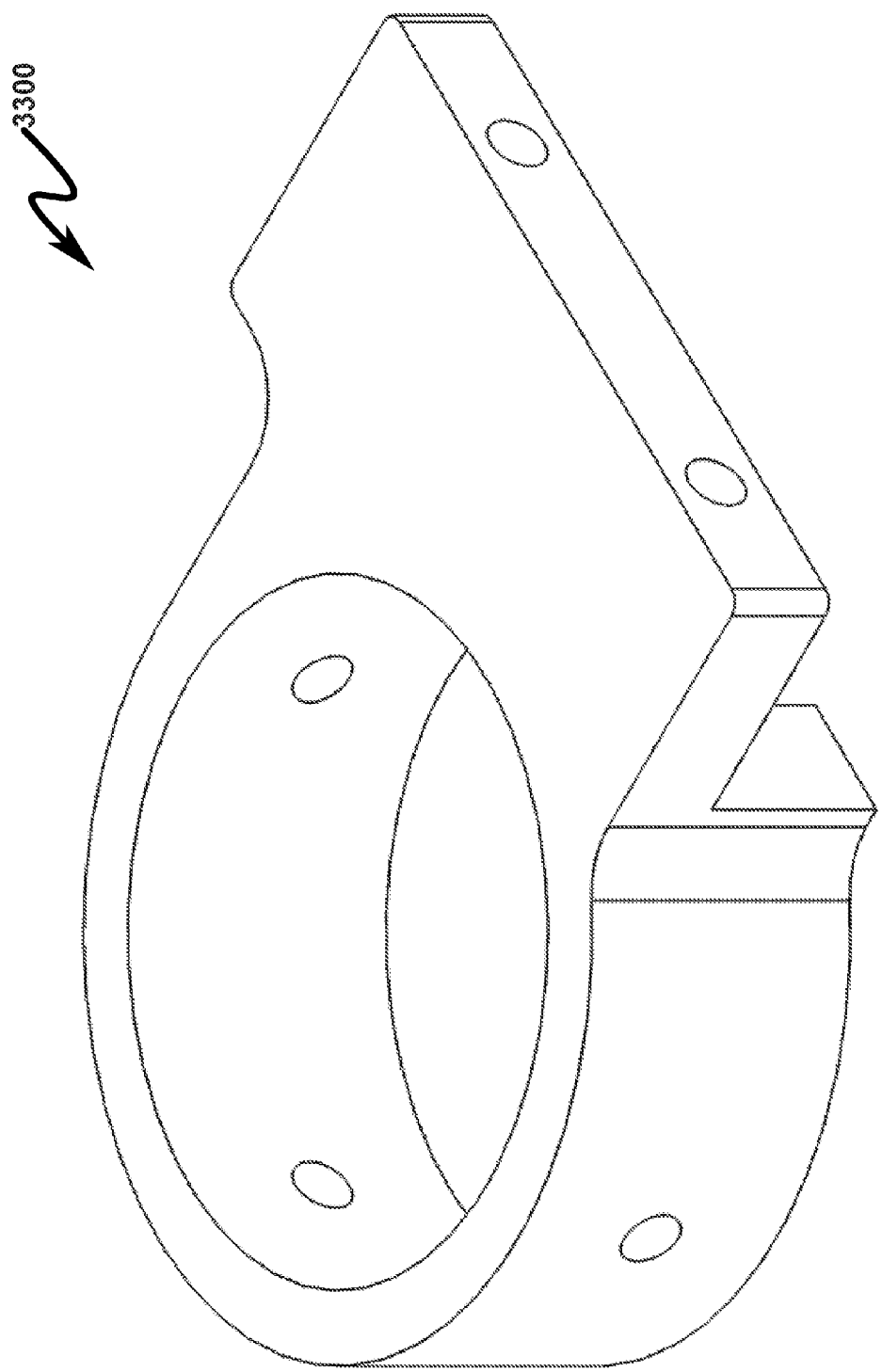
FIG. 33 illustrates a top right front perspective view of a preferred exemplary laser objective bracket (LOB) embodiment useful in some invention configurations.
Figure 34:
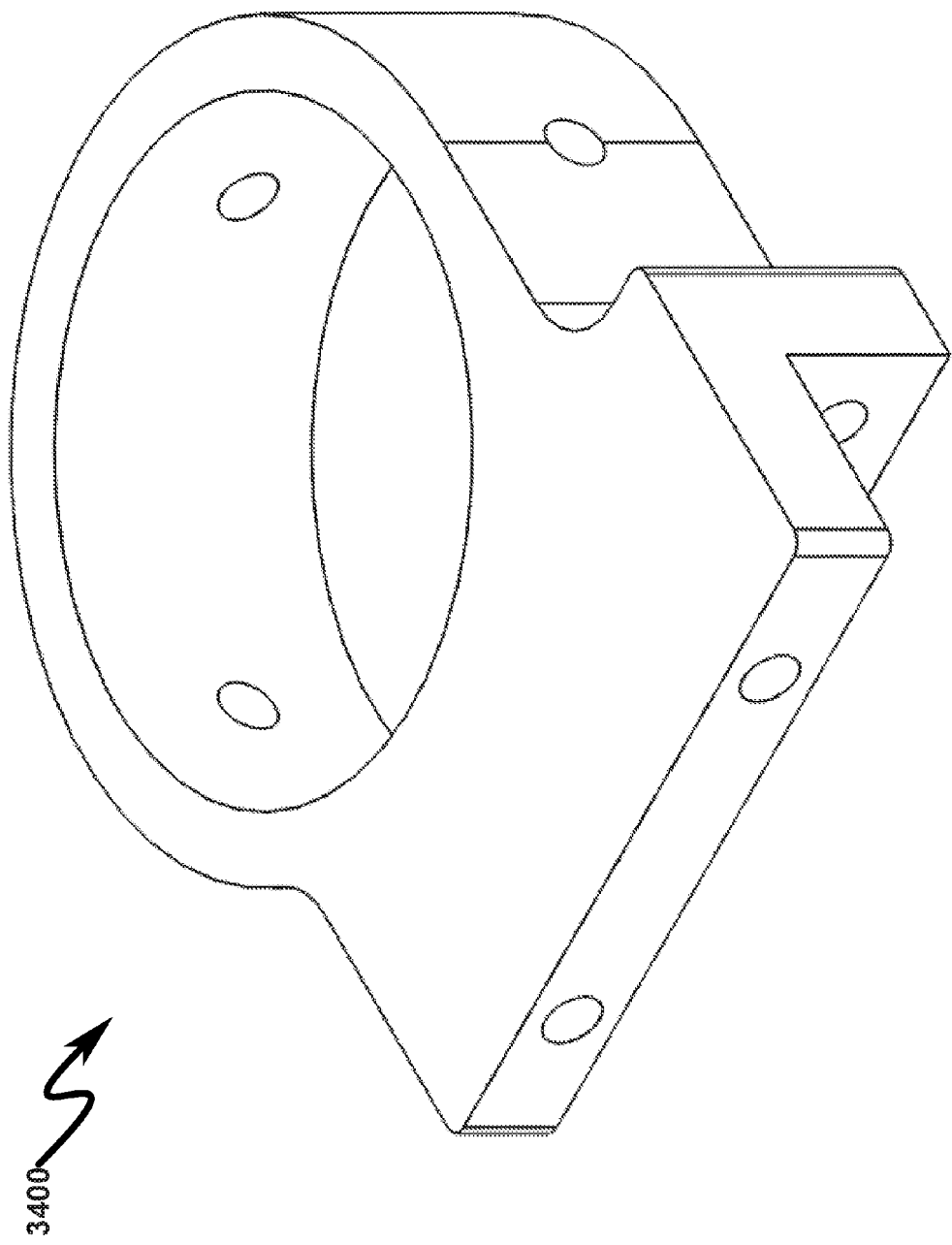
FIG. 34 illustrates a top right rear perspective view of a preferred exemplary laser objective bracket (LOB) embodiment useful in some invention configurations.
Figure 35:
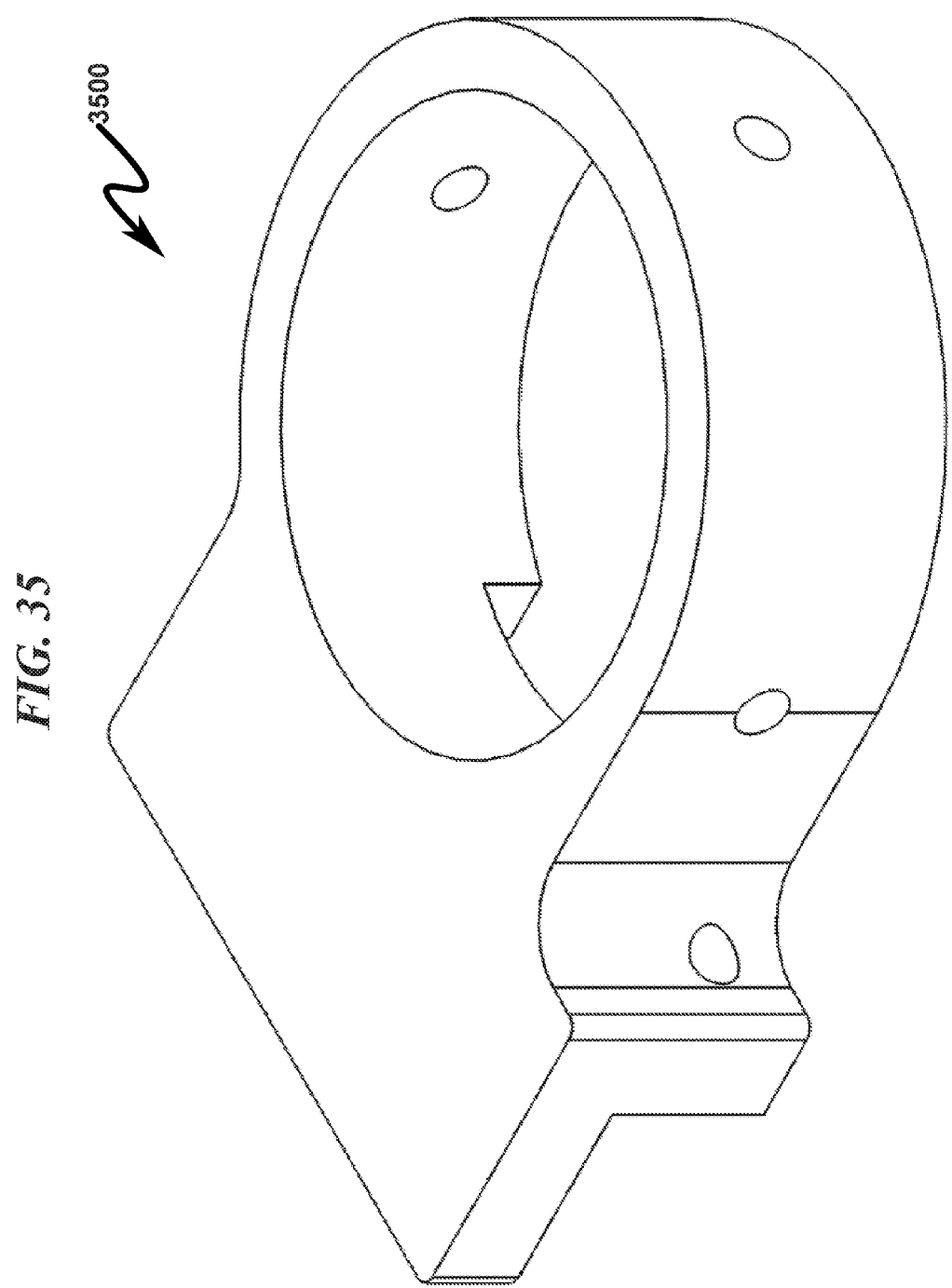
FIG. 35 illustrates a top left rear perspective view of a preferred exemplary laser objective bracket (LOB) embodiment useful in some invention configurations.
Figure 36:
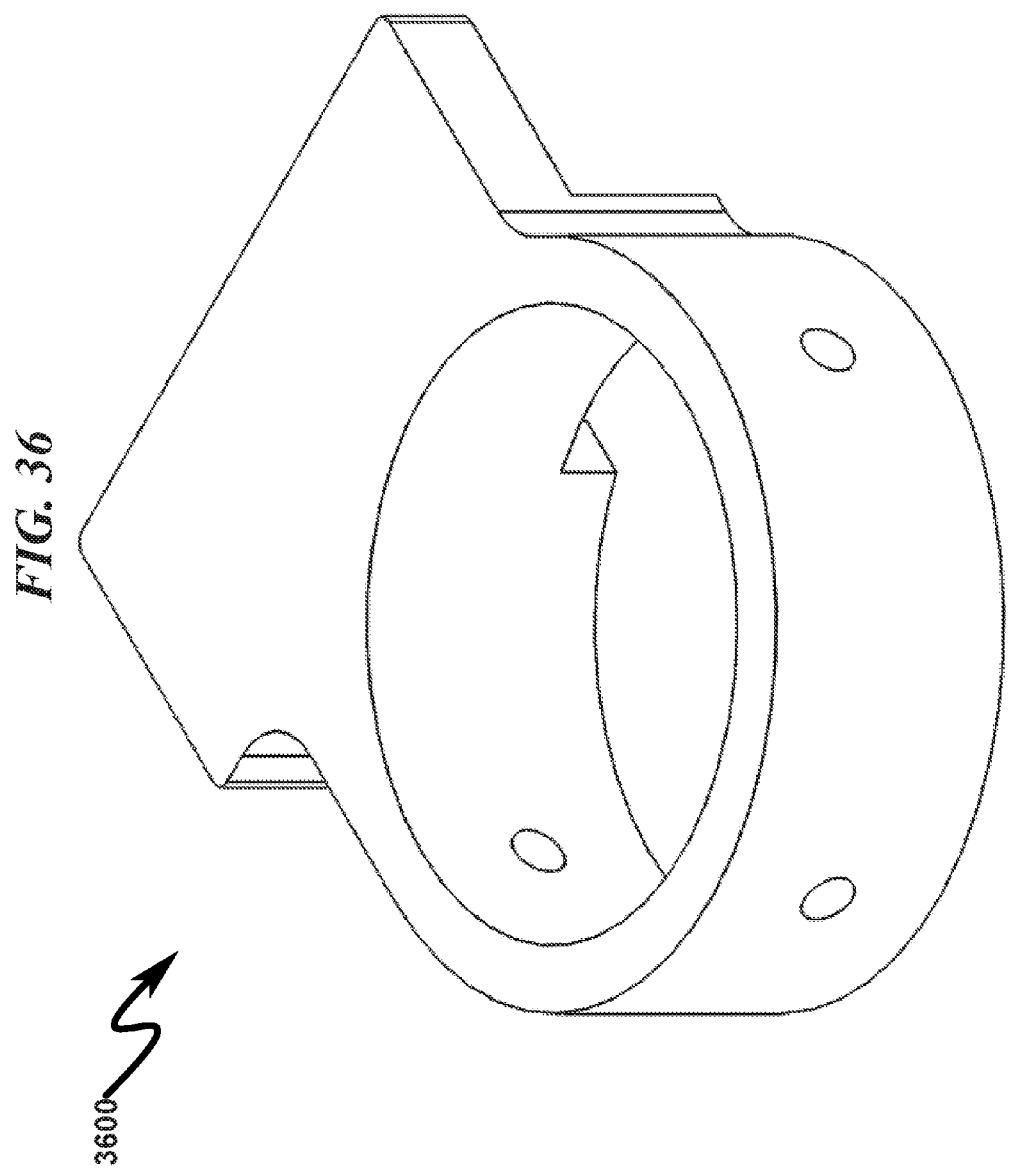
FIG. 36 illustrates a top left front perspective view of a preferred exemplary laser objective bracket (LOB) embodiment useful in some invention configurations.
Figure 37:
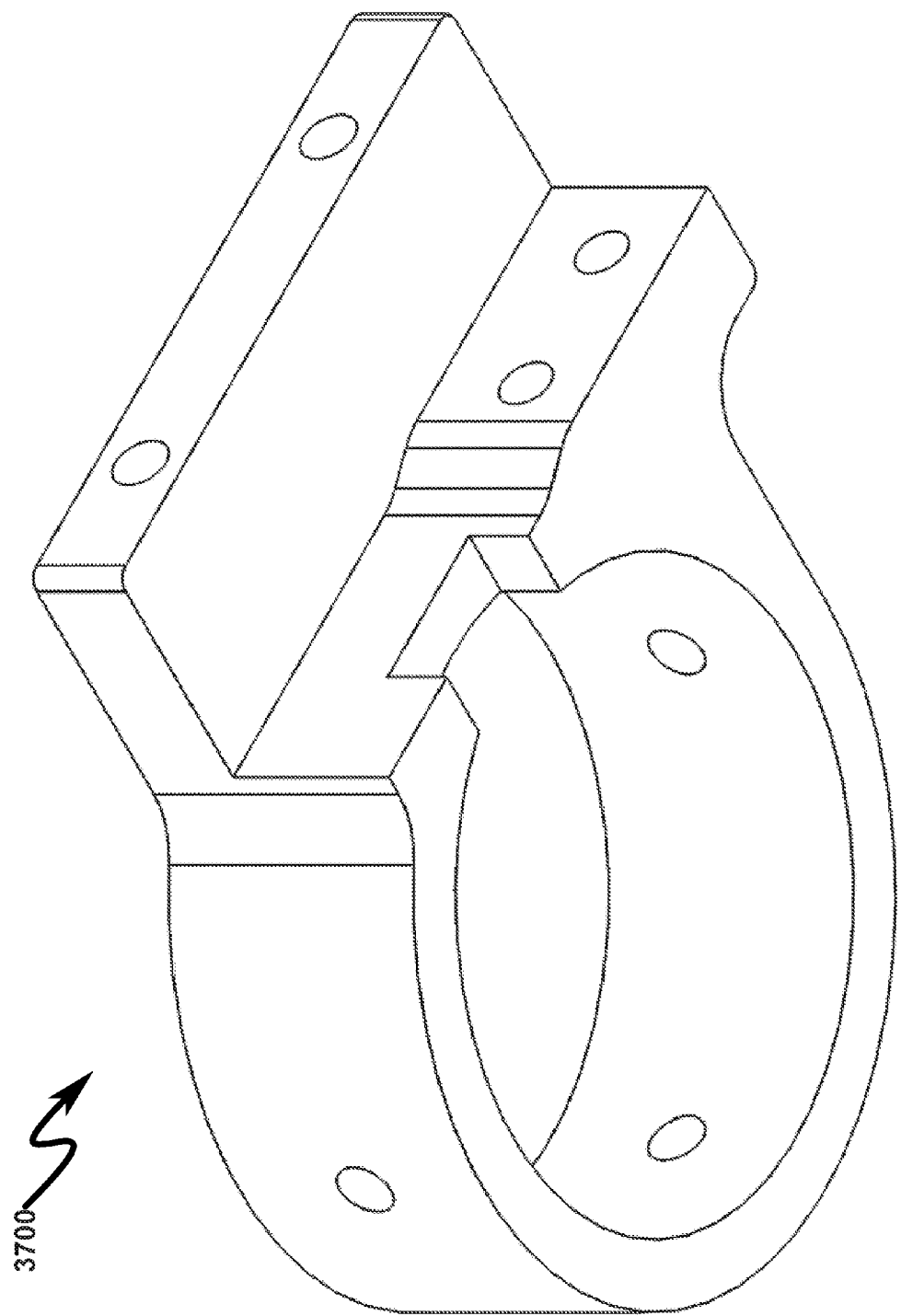
FIG. 37 illustrates a bottom right front perspective view of a preferred exemplary laser objective bracket (LOB) embodiment useful in some invention configurations.
Figure 38:
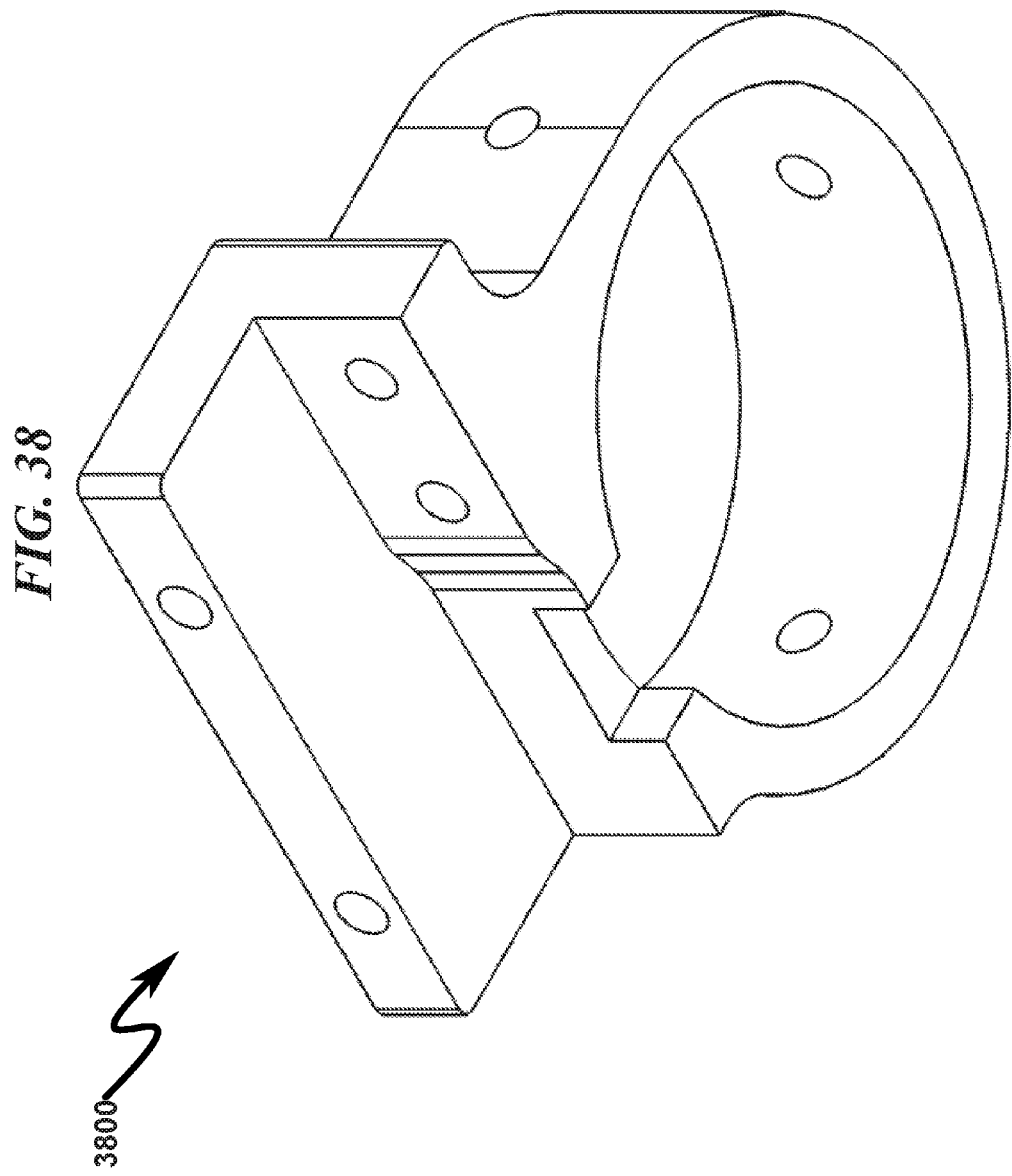
FIG. 38 illustrates a bottom right rear perspective view of a preferred exemplary laser objective bracket (LOB) embodiment useful in some invention configurations.
Figure 39:
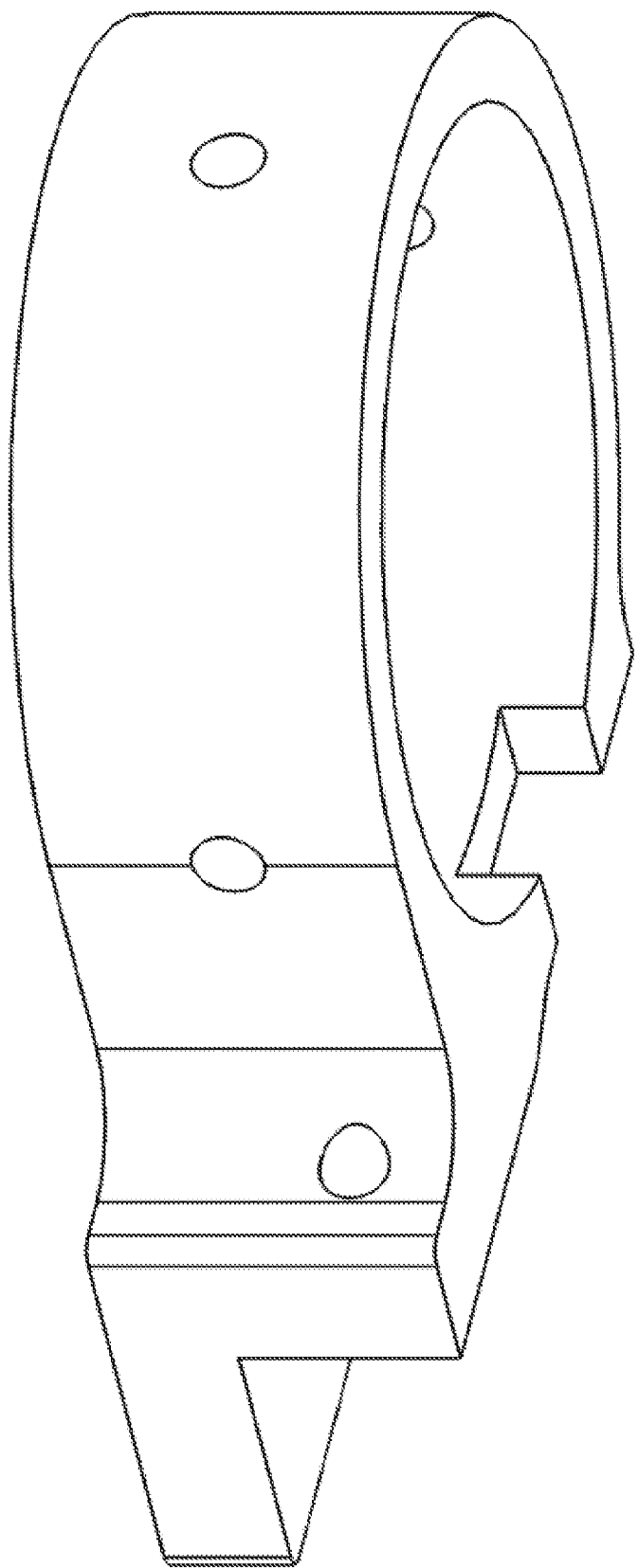
FIG. 39 illustrates a bottom left rear perspective view of a preferred exemplary laser objective bracket (LOB) embodiment useful in some invention configurations.
Figure 40:
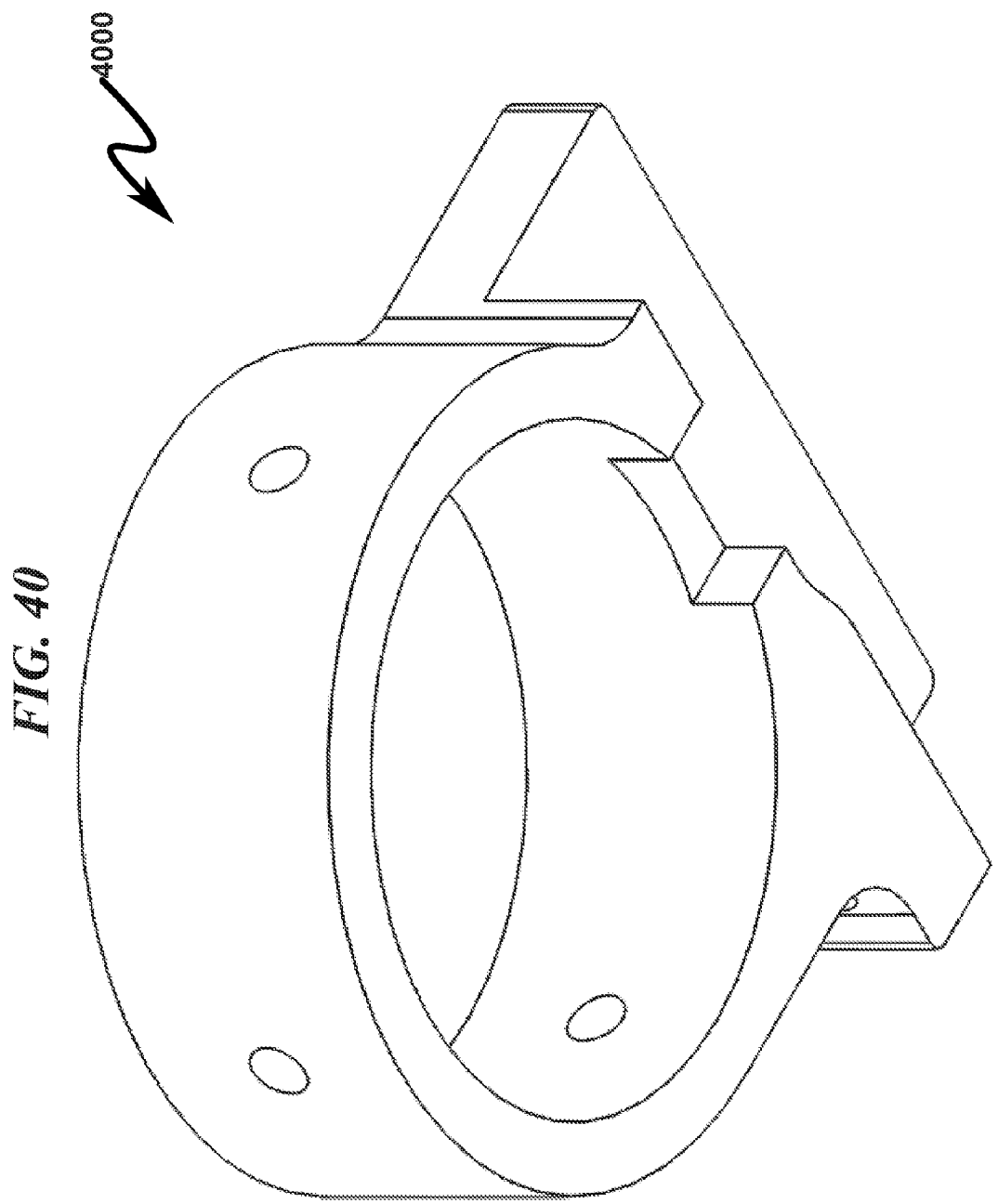
FIG. 40 illustrates a bottom left front perspective view of a preferred exemplary laser objective bracket (LOB) embodiment useful in some invention configurations.
Figure 41:
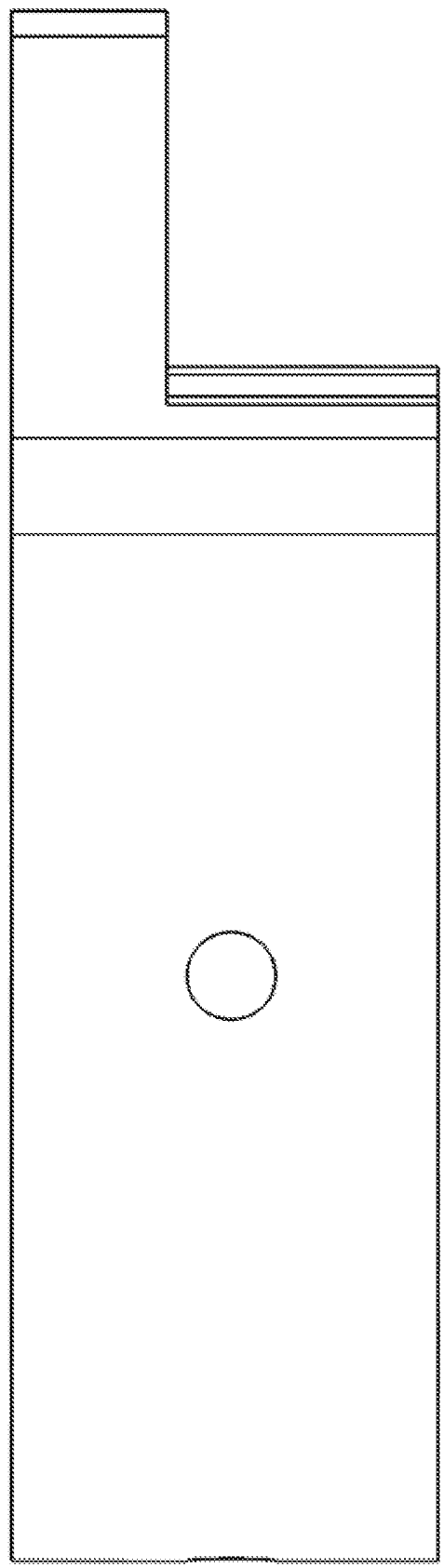
FIG. 41 illustrates a front view of a preferred exemplary laser objective bracket (LOB) embodiment useful in some invention configurations.
Figure 42:
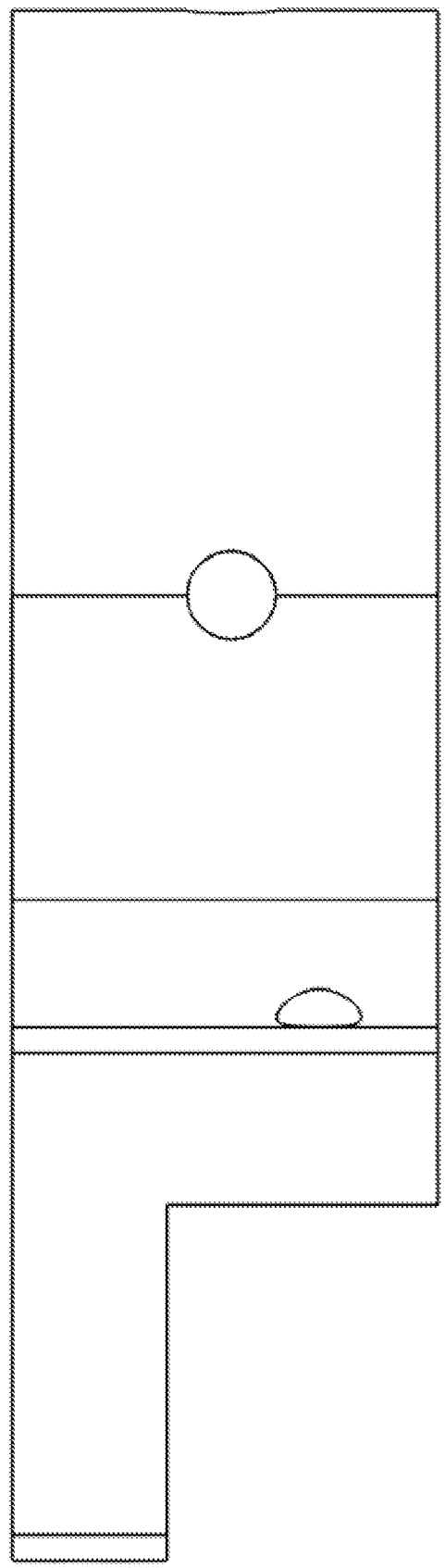
FIG. 42 illustrates a rear view of a preferred exemplary laser objective bracket (LOB) embodiment useful in some invention configurations.
Figure 43:
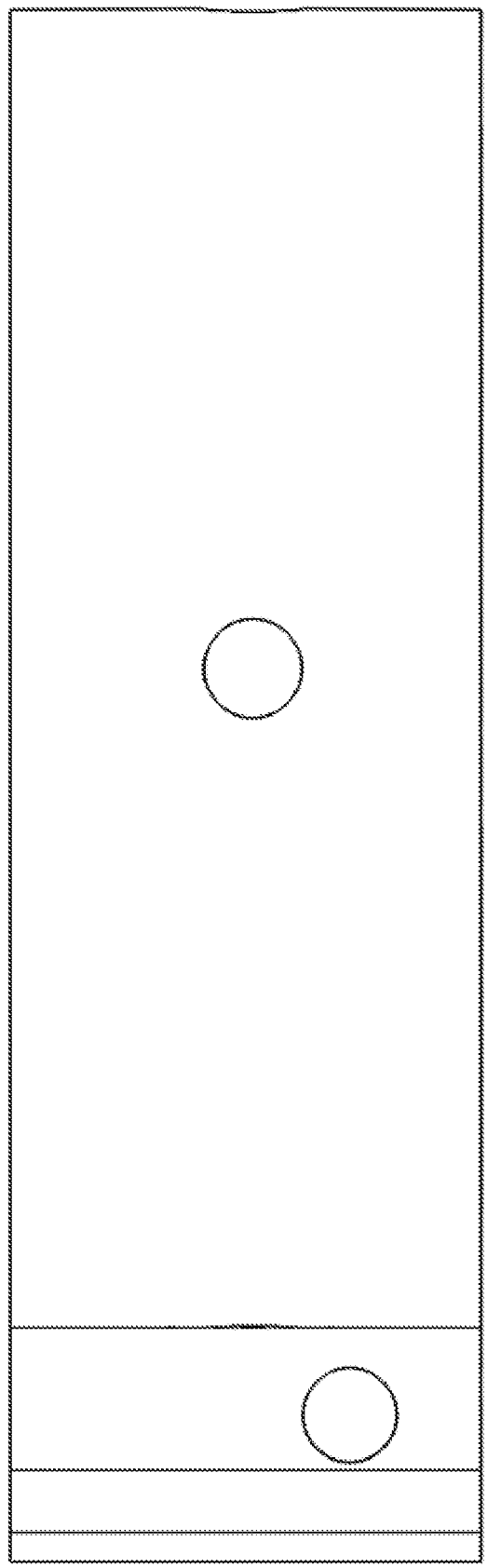
FIG. 43 illustrates a left view of a preferred exemplary laser objective bracket (LOB) embodiment useful in some invention configurations.
Figure 44:
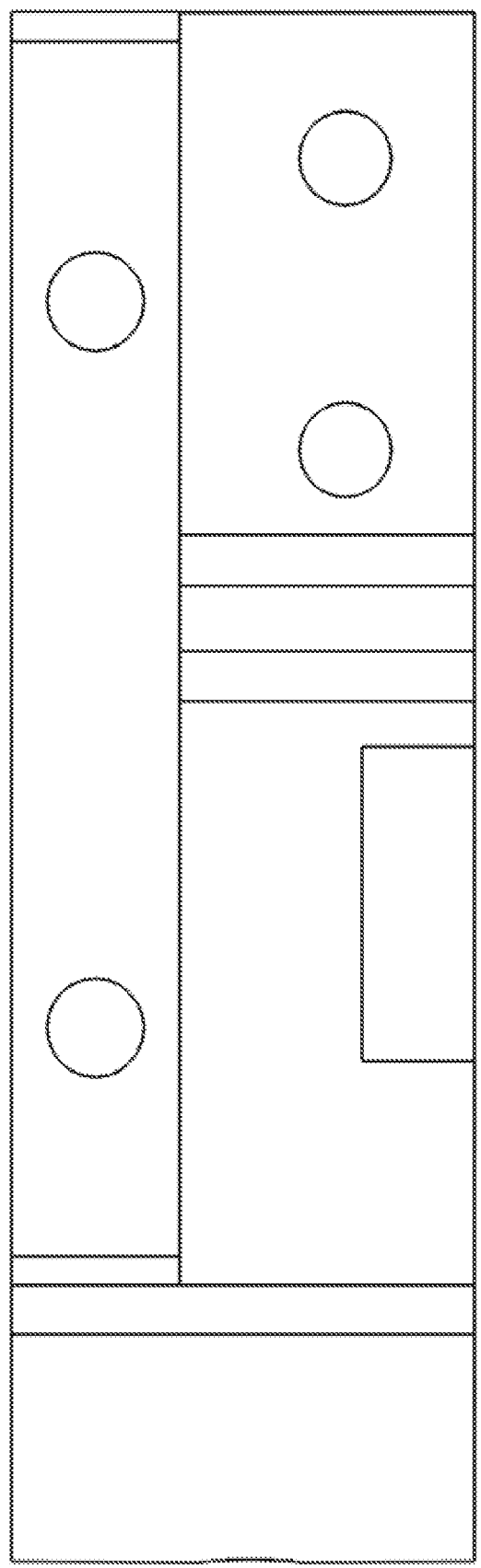
FIG. 44 illustrates a right view of a preferred exemplary laser objective bracket (LOB) embodiment useful in some invention configurations.
Figure 45:
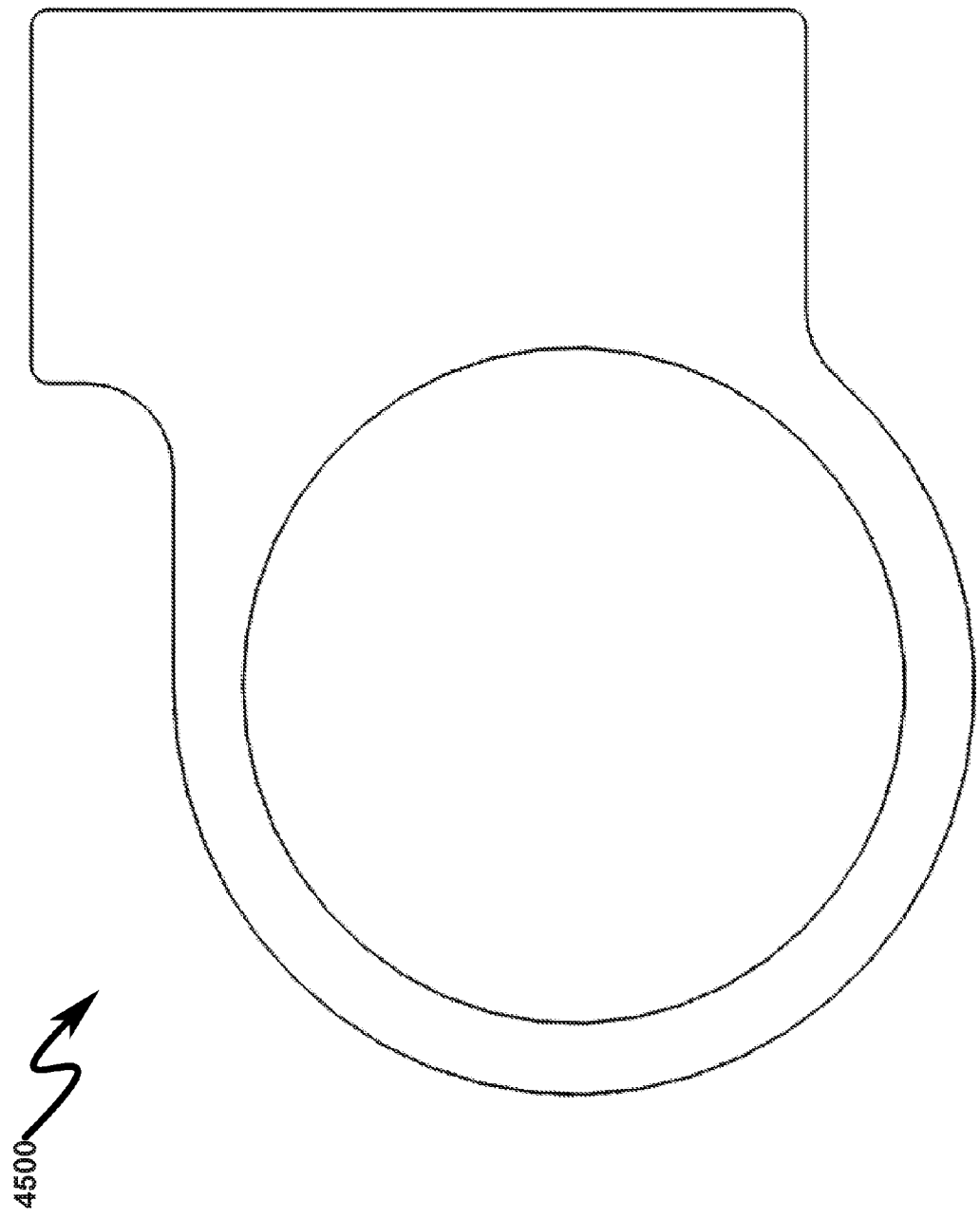
FIG. 45 illustrates a top view of a preferred exemplary laser objective bracket (LOB) embodiment useful in some invention configurations.
Figure 46:
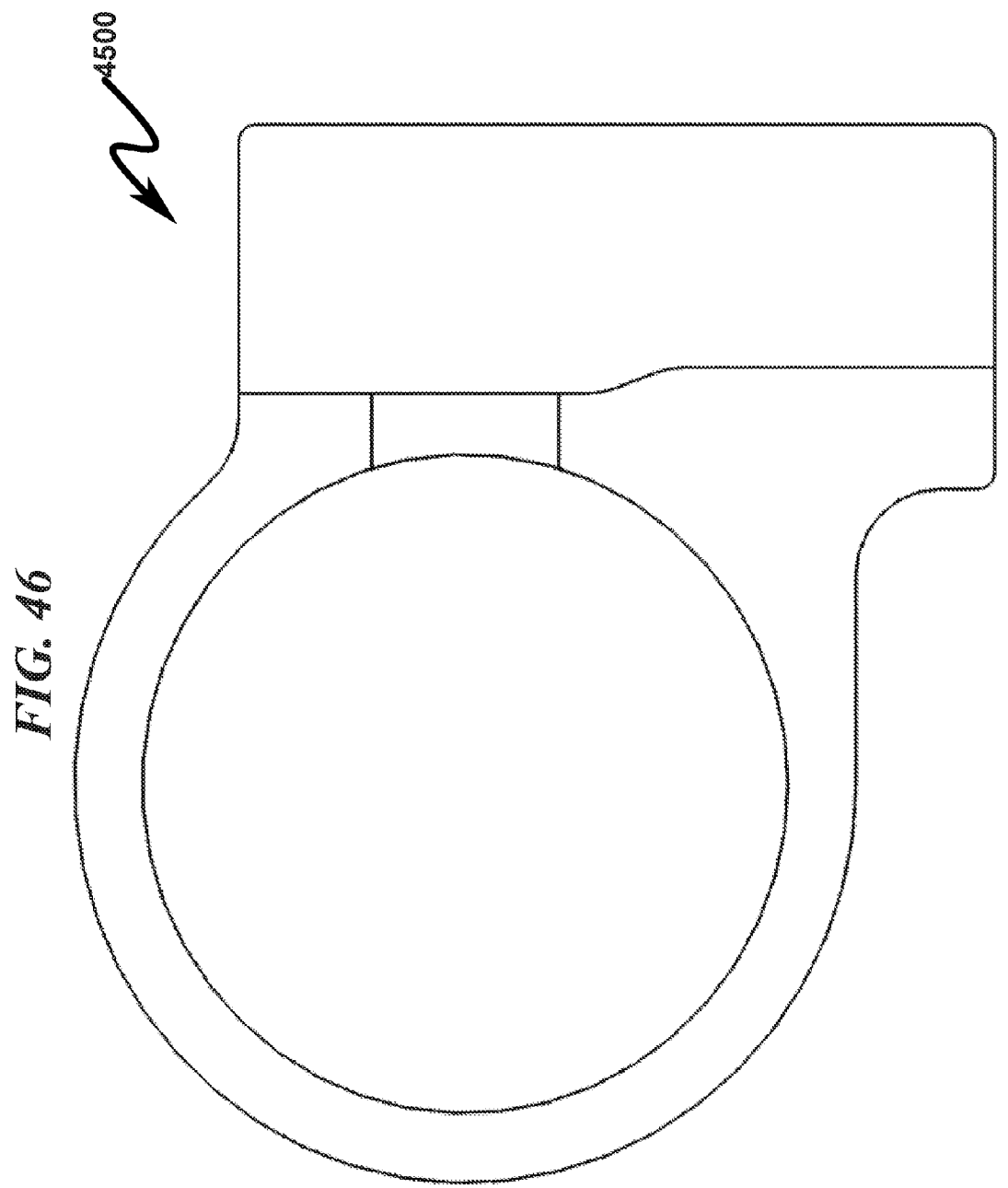
FIG. 46 illustrates a bottom view of a preferred exemplary laser objective bracket (LOB) embodiment useful in some invention configurations.
Figure 47:
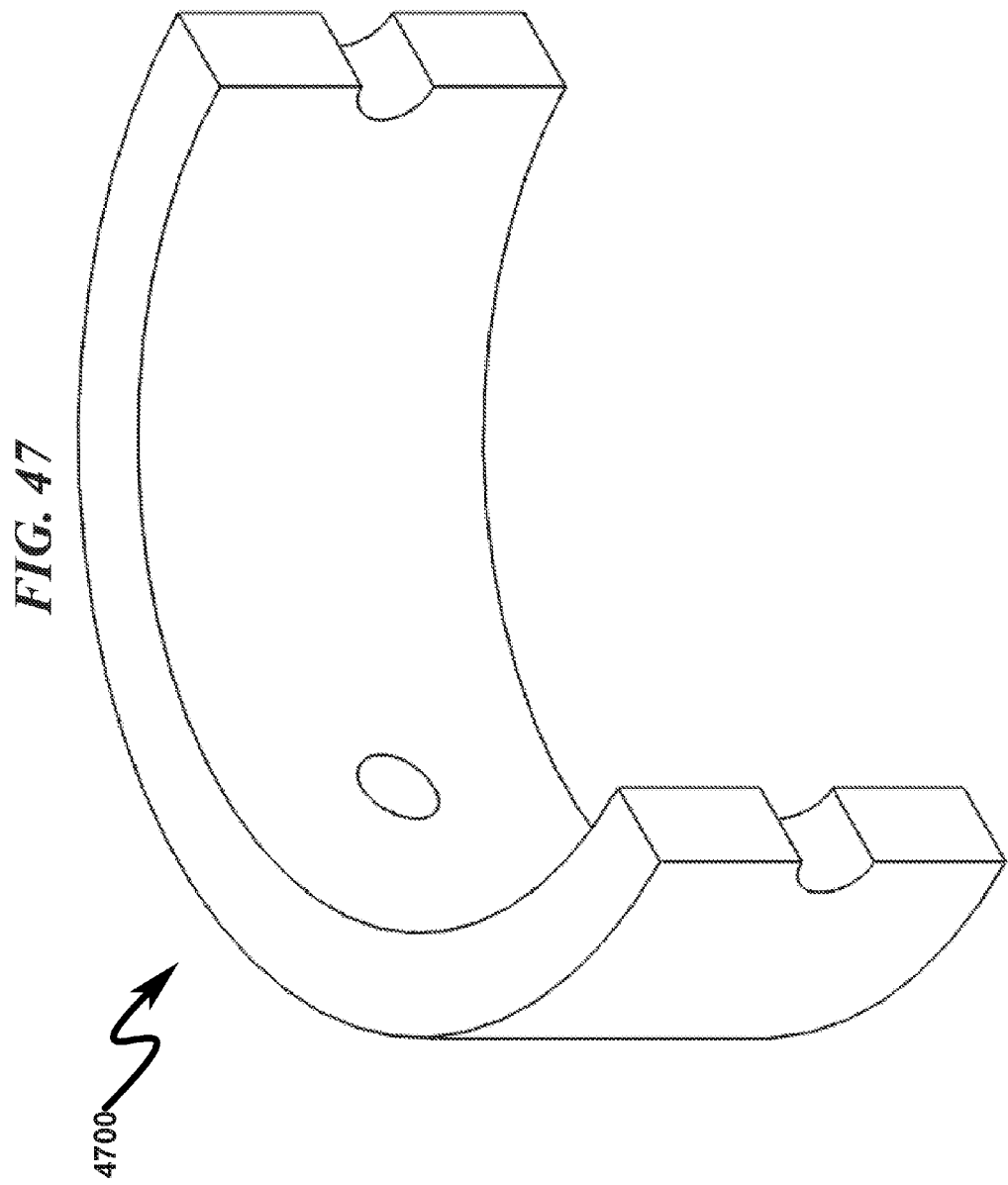
FIG. 47 illustrates a right section perspective view of a preferred exemplary laser objective bracket (LOB) embodiment useful in some invention configurations.
Figure 48:
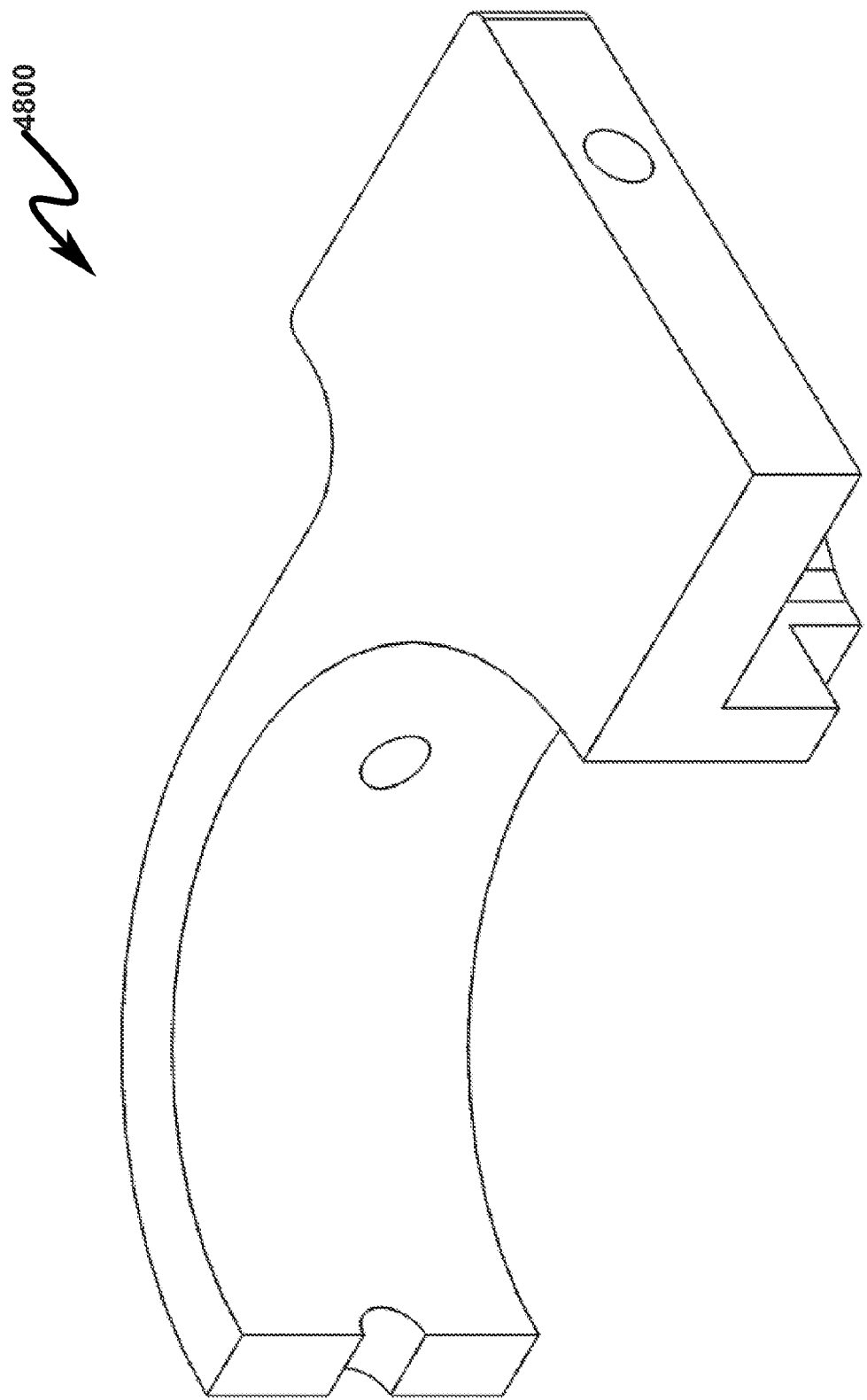
FIG. 48 illustrates a front section perspective view of a preferred exemplary laser objective bracket (LOB) embodiment useful in some invention configurations.

A preferred exemplary embodiment of a typical laser objective bracket (LOB) is generally depicted in the detail views presented in FIG. 33 (3300)-FIG. 48 (4800).

Exemplary Ocular Force Sensor (OFS) (4900)-(6400)

Figure 49:
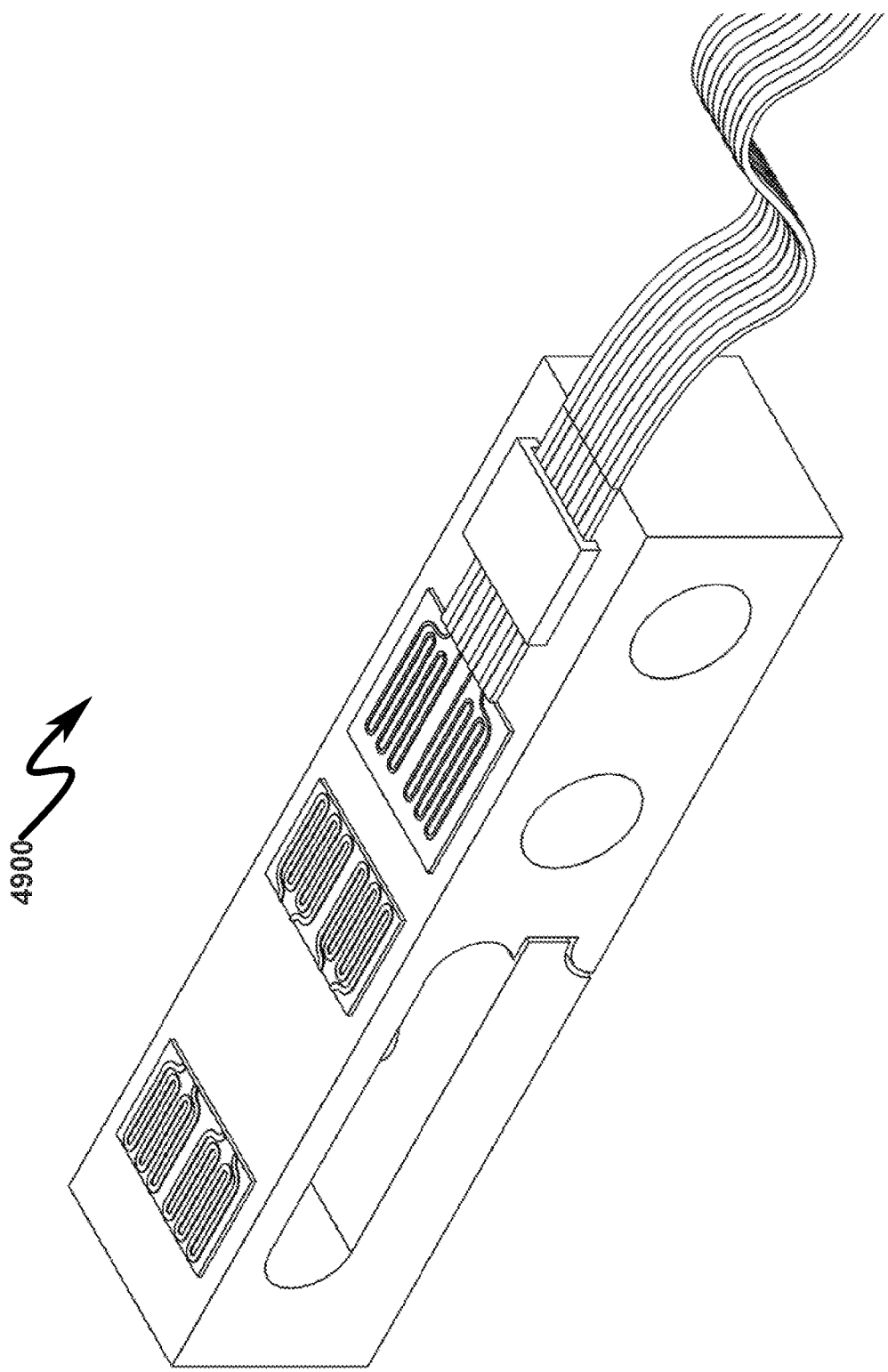
FIG. 49 illustrates a top right front perspective view of a preferred exemplary ocular force sensor (OFS) embodiment useful in some invention configurations.
Figure 50:
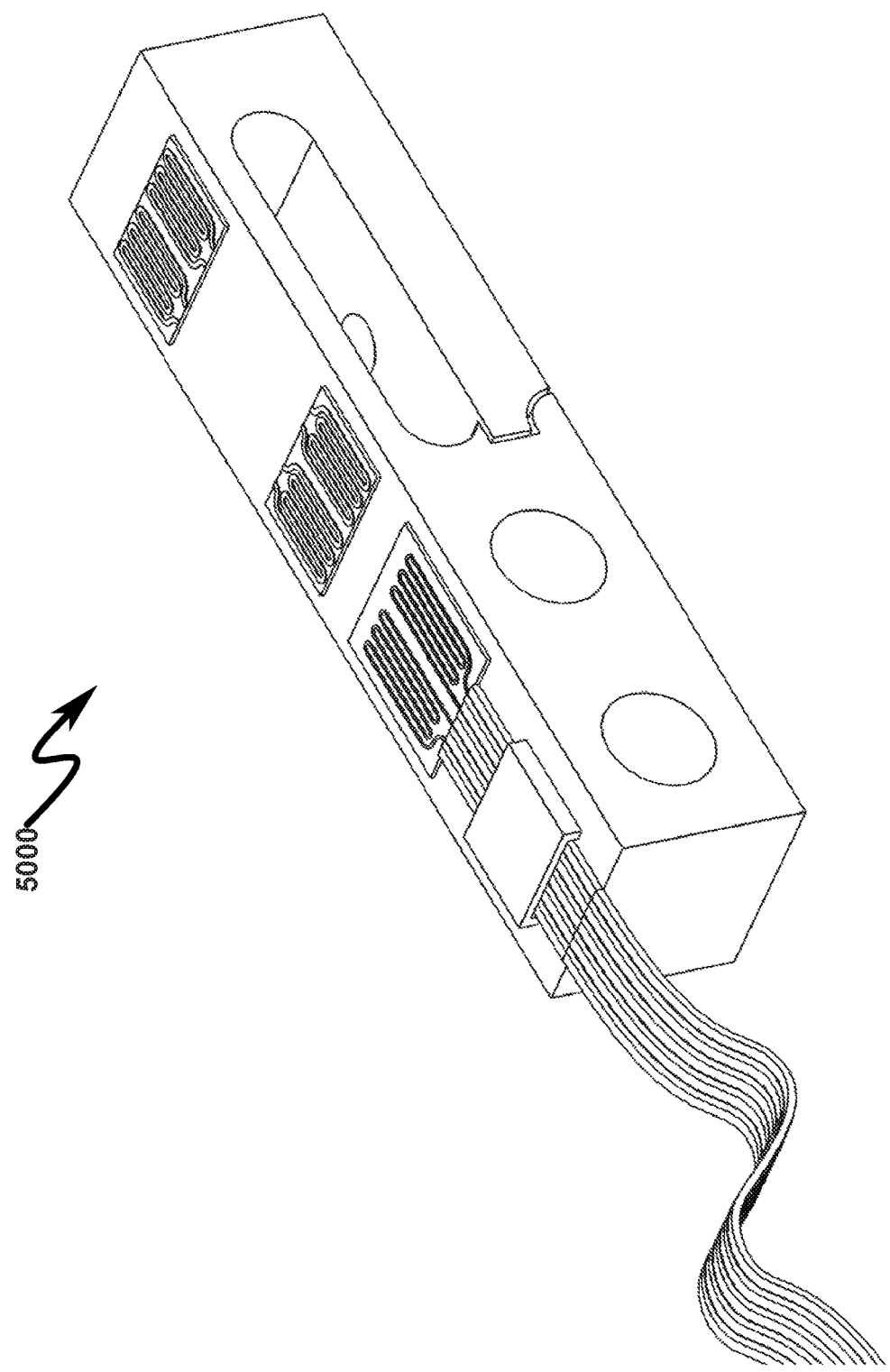
FIG. 50 illustrates a top right rear perspective view of a preferred exemplary ocular force sensor (OFS) embodiment useful in some invention configurations.
Figure 51:
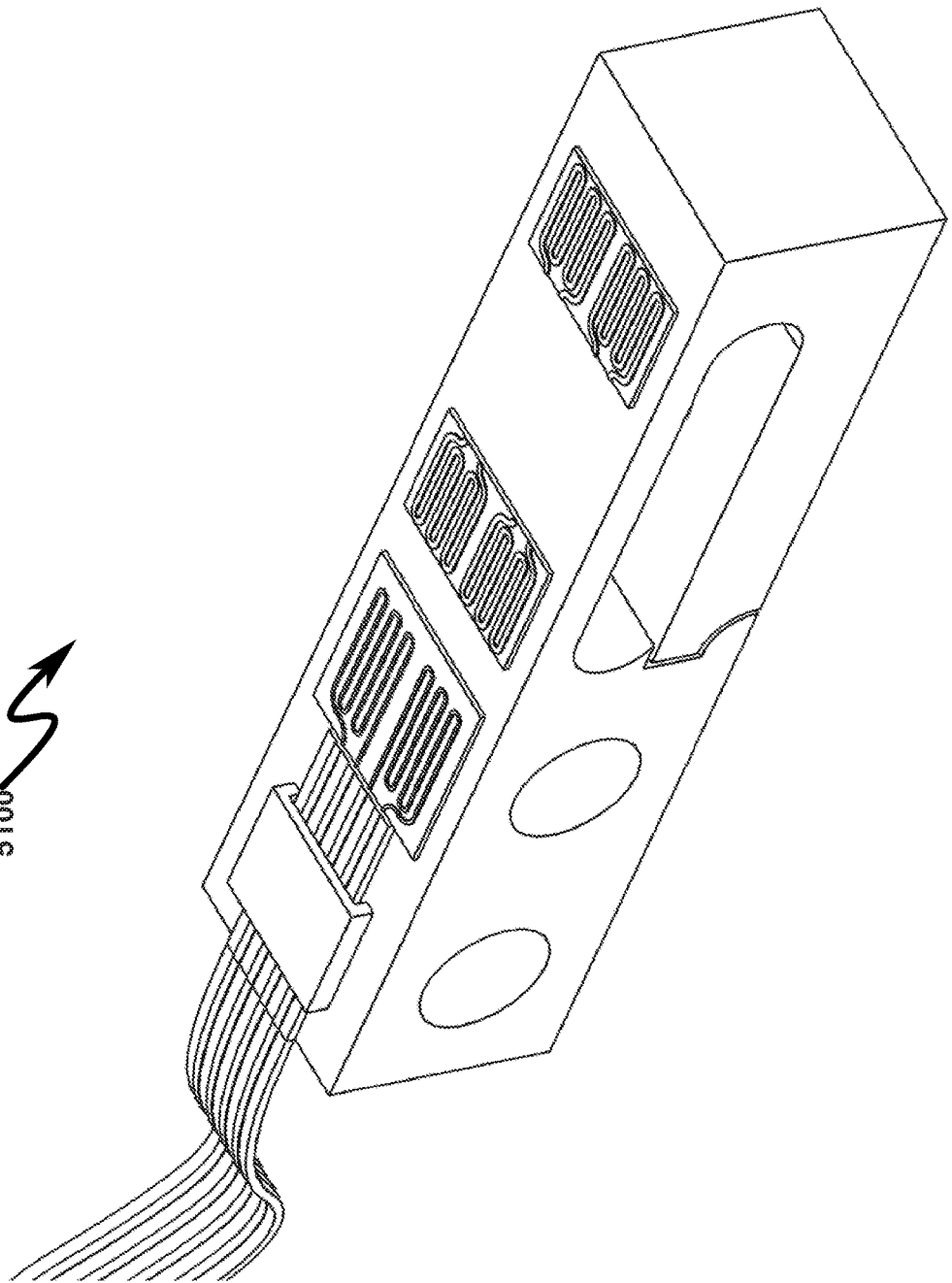
FIG. 51 illustrates a top left rear perspective view of a preferred exemplary ocular force sensor (OFS) embodiment useful in some invention configurations.
Figure 52:
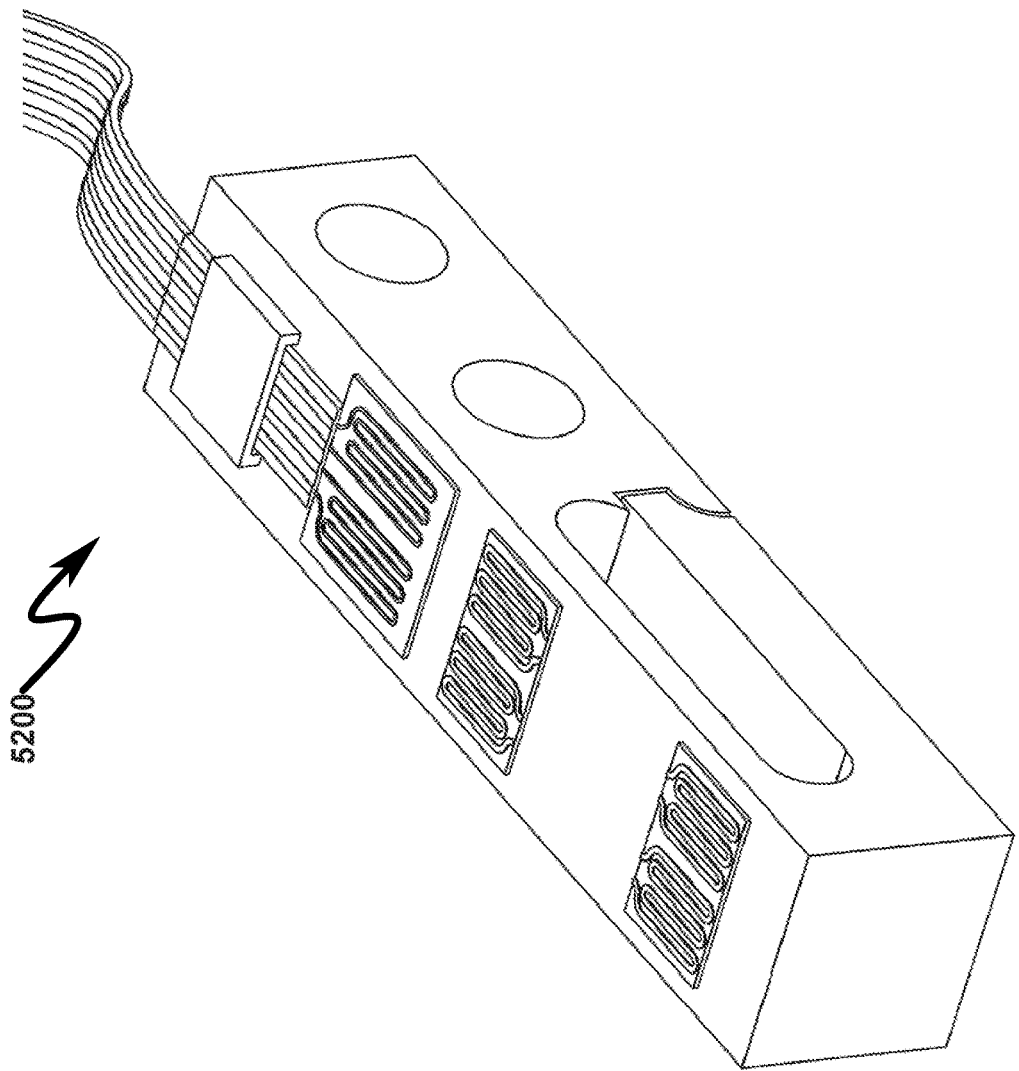
FIG. 52 illustrates a top left front perspective view of a preferred exemplary ocular force sensor (OFS) embodiment useful in some invention configurations.
Figure 53:
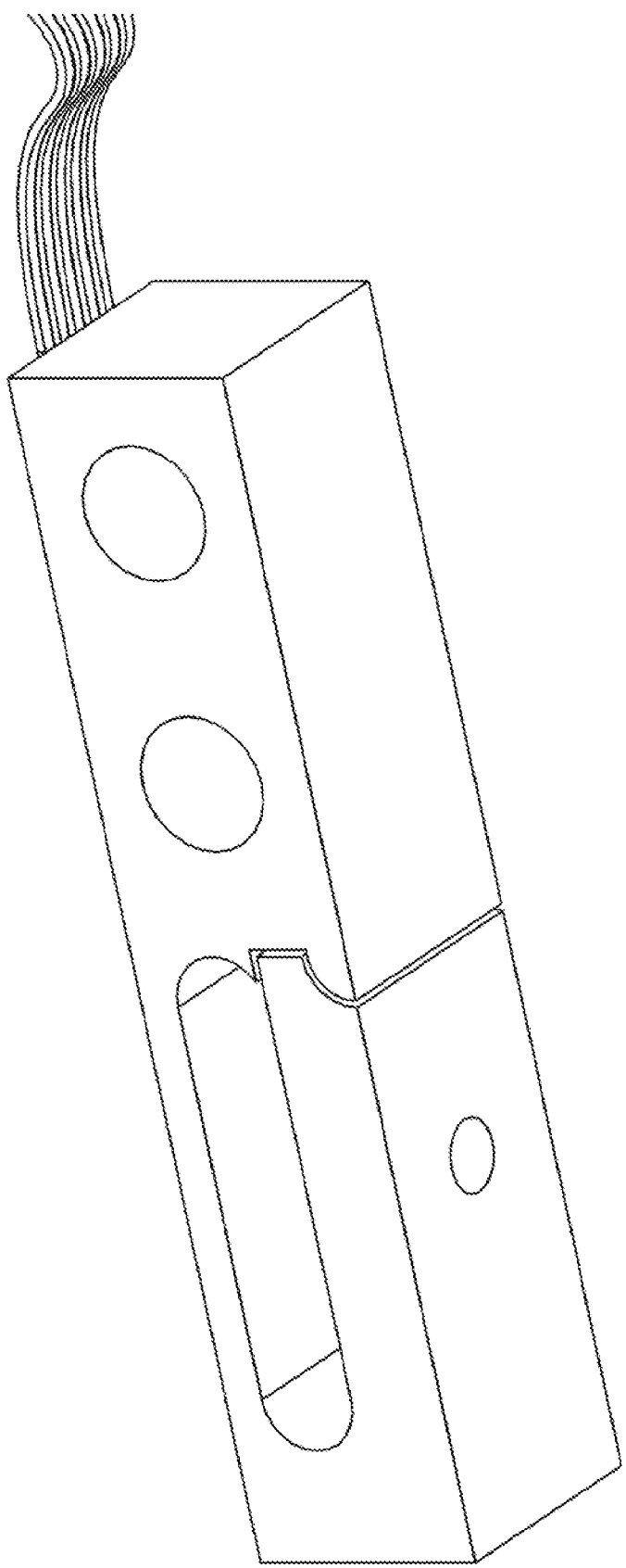
FIG. 53 illustrates a bottom right front perspective view of a preferred exemplary ocular force sensor (OFS) embodiment useful in some invention configurations.
Figure 54:
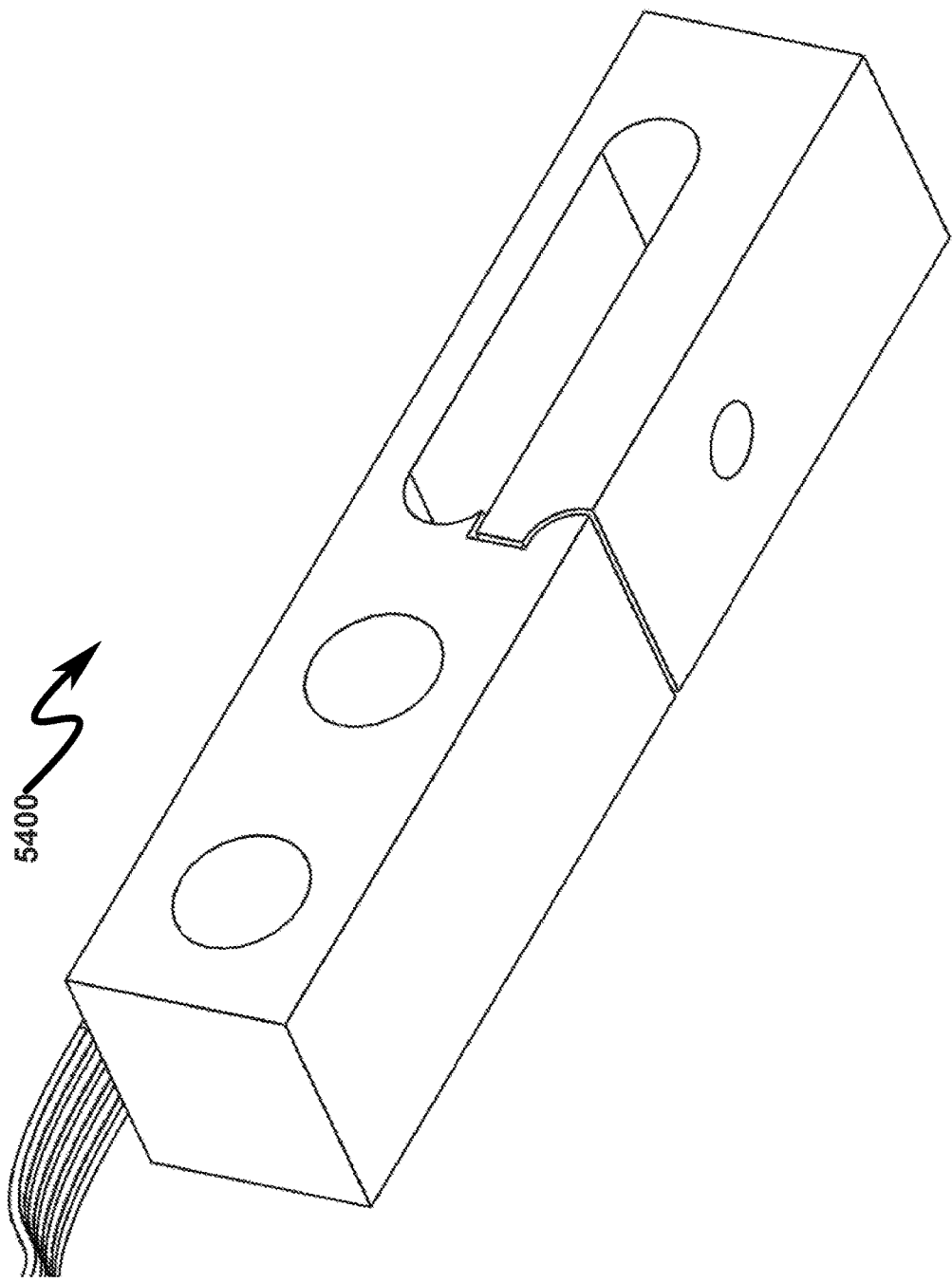
FIG. 54 illustrates a bottom right rear perspective view of a preferred exemplary ocular force sensor (OFS) embodiment useful in some invention configurations.
Figure 55:
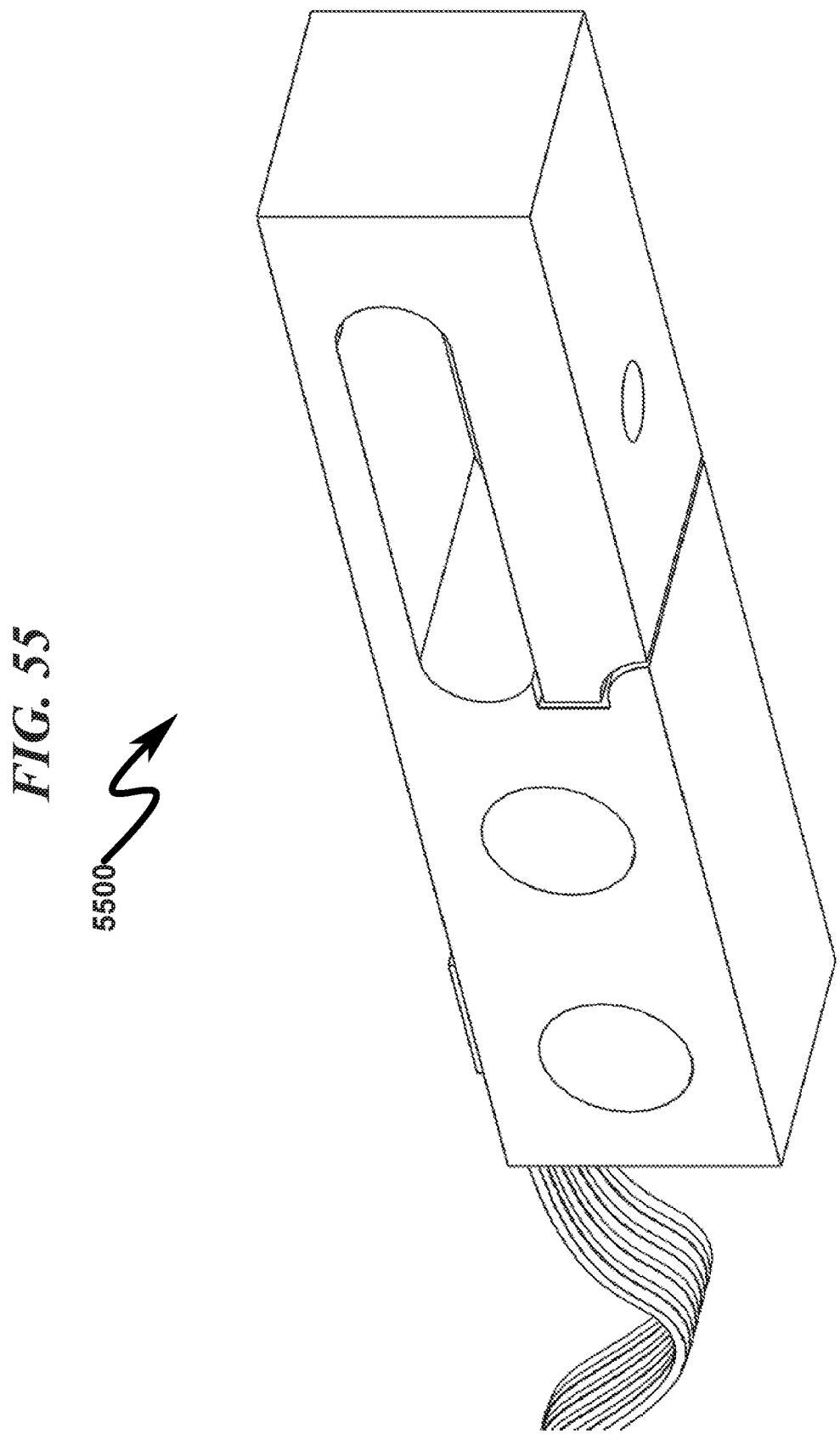
FIG. 55 illustrates a bottom left rear perspective view of a preferred exemplary ocular force sensor (OFS) embodiment useful in some invention configurations.
Figure 56:
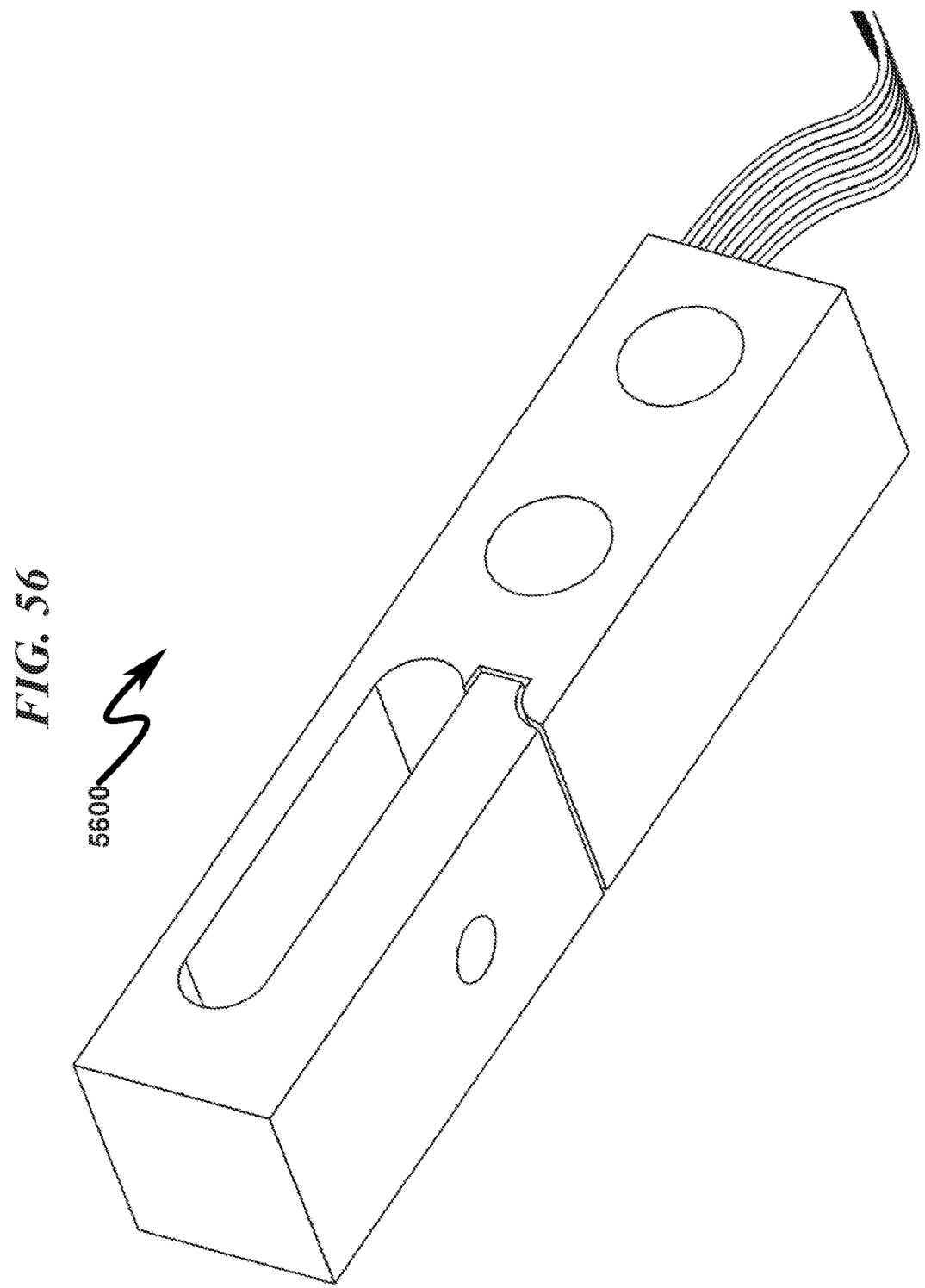
FIG. 56 illustrates a bottom left front perspective view of a preferred exemplary ocular force sensor (OFS) embodiment useful in some invention configurations.
Figure 57:
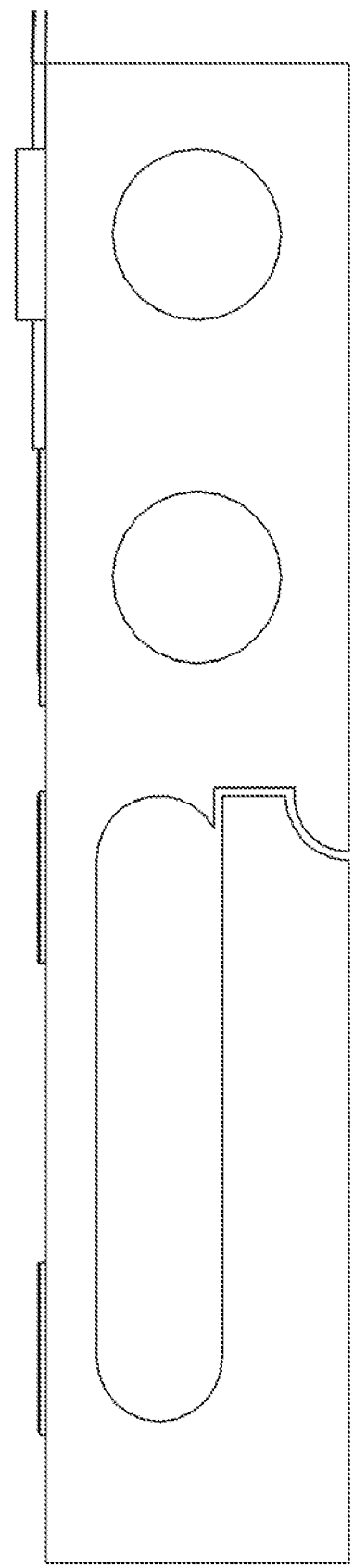
FIG. 57 illustrates a front view of a preferred exemplary ocular force sensor (OFS) embodiment useful in some invention configurations.
Figure 58:
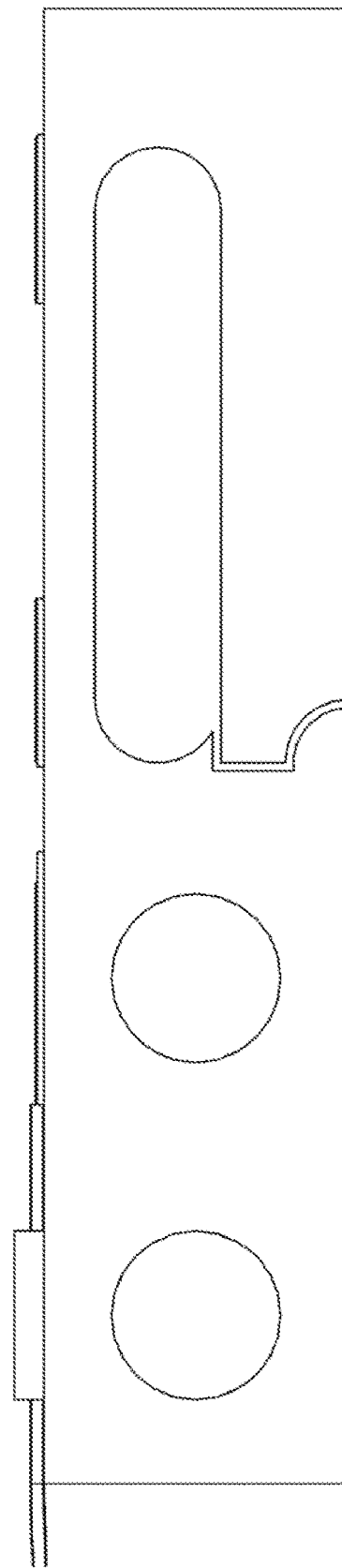
FIG. 58 illustrates a rear view of a preferred exemplary ocular force sensor (OFS) embodiment useful in some invention configurations.
Figure 59:
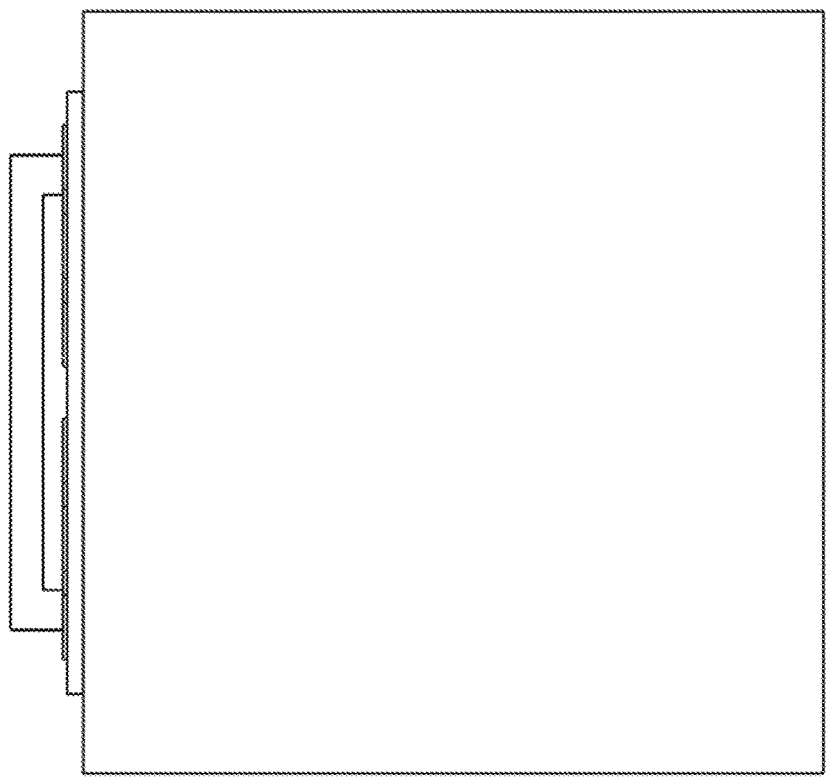
FIG. 59 illustrates a left view of a preferred exemplary ocular force sensor (OFS) embodiment useful in some invention configurations.
Figure 60:
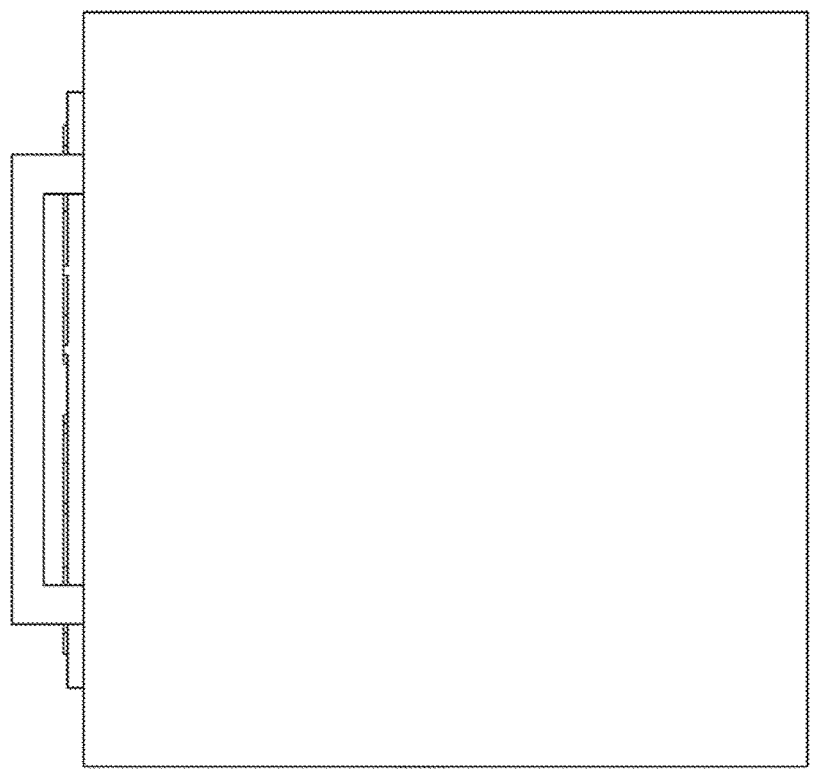
FIG. 60 illustrates a right view of a preferred exemplary ocular force sensor (OFS) embodiment useful in some invention configurations.
Figure 61:
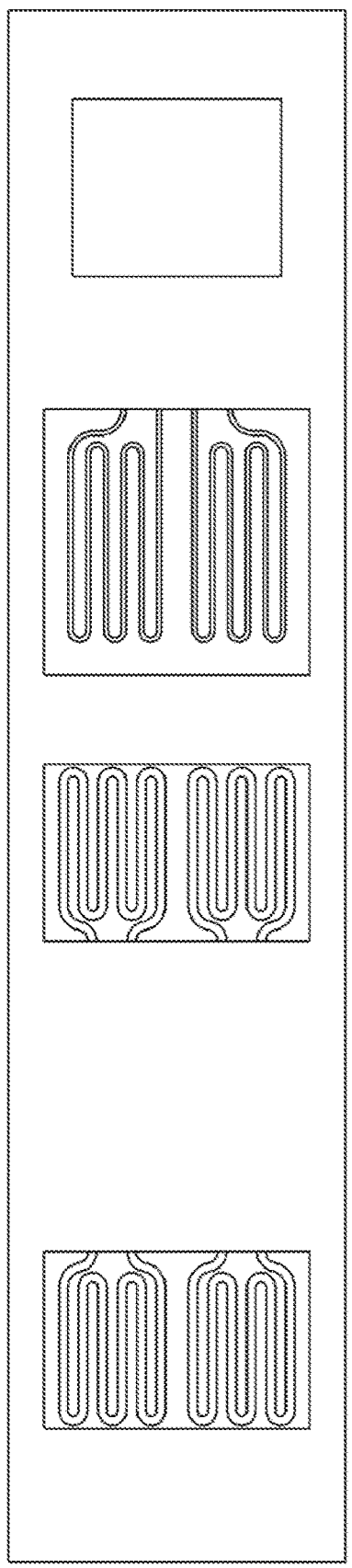
FIG. 61 illustrates a top view of a preferred exemplary ocular force sensor (OFS) embodiment useful in some invention configurations.
Figure 62:
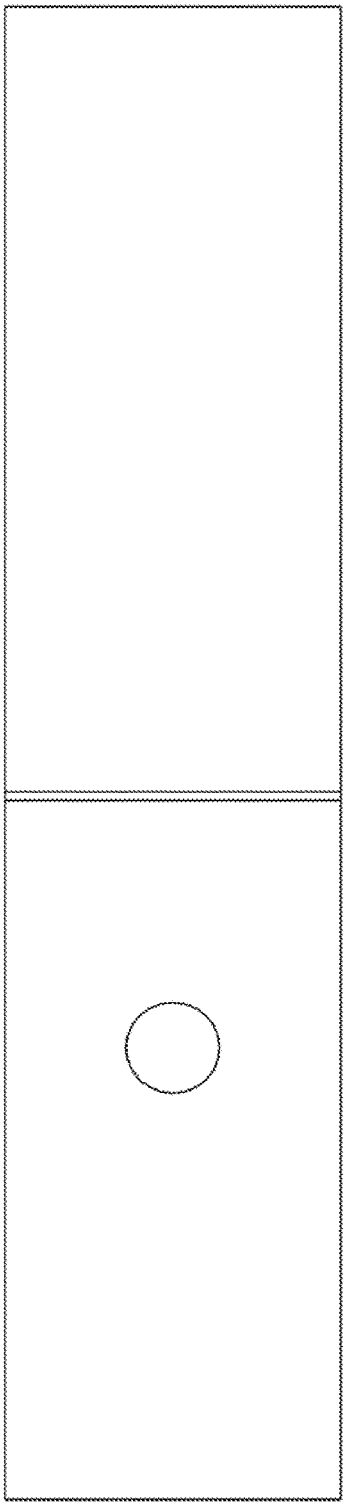
FIG. 62 illustrates a bottom view of a preferred exemplary ocular force sensor (OFS) embodiment useful in some invention configurations.
Figure 63:
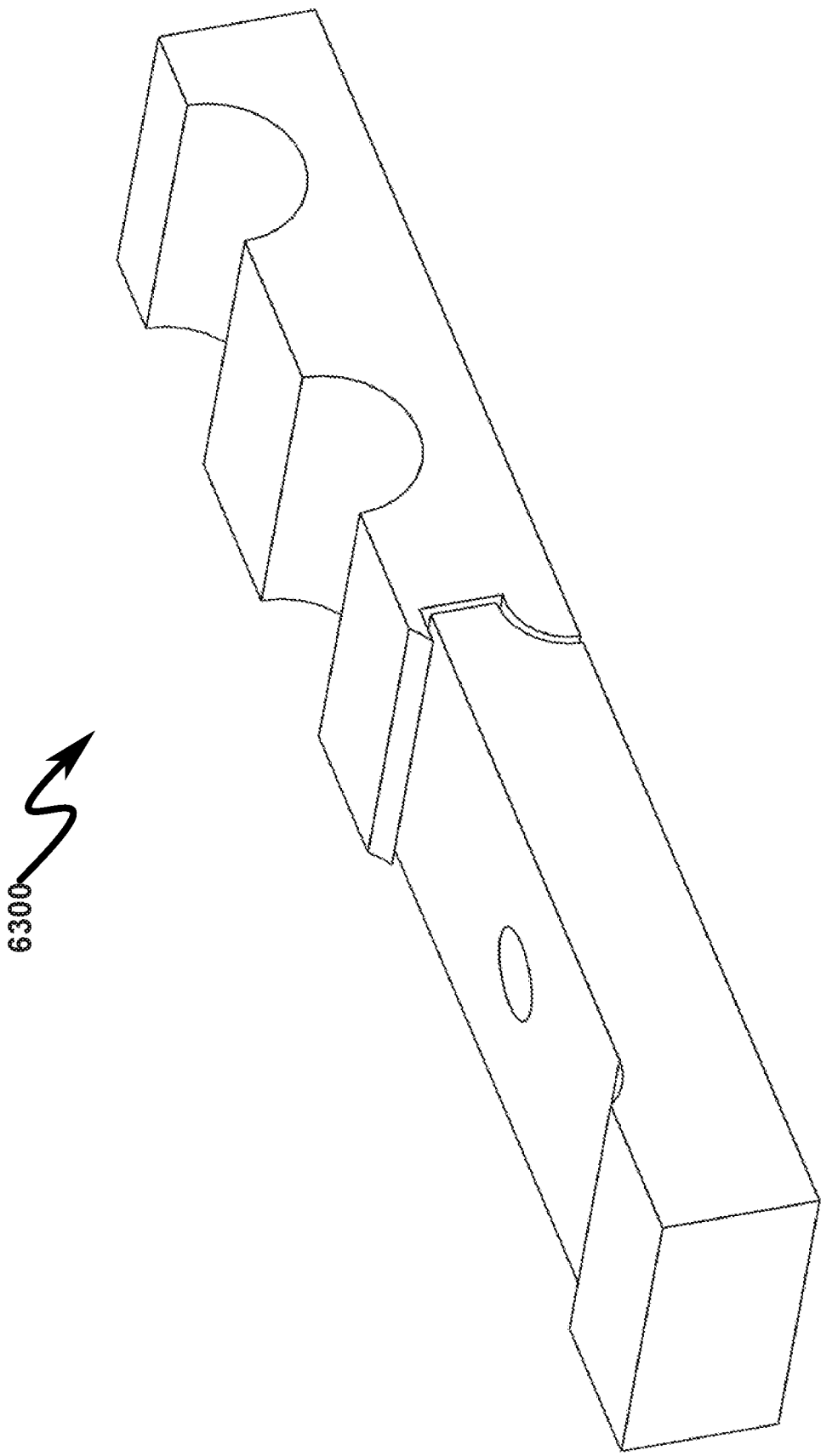
FIG. 63 illustrates a right section perspective view of a preferred exemplary ocular force sensor (OFS) embodiment useful in some invention configurations.
Figure 64:
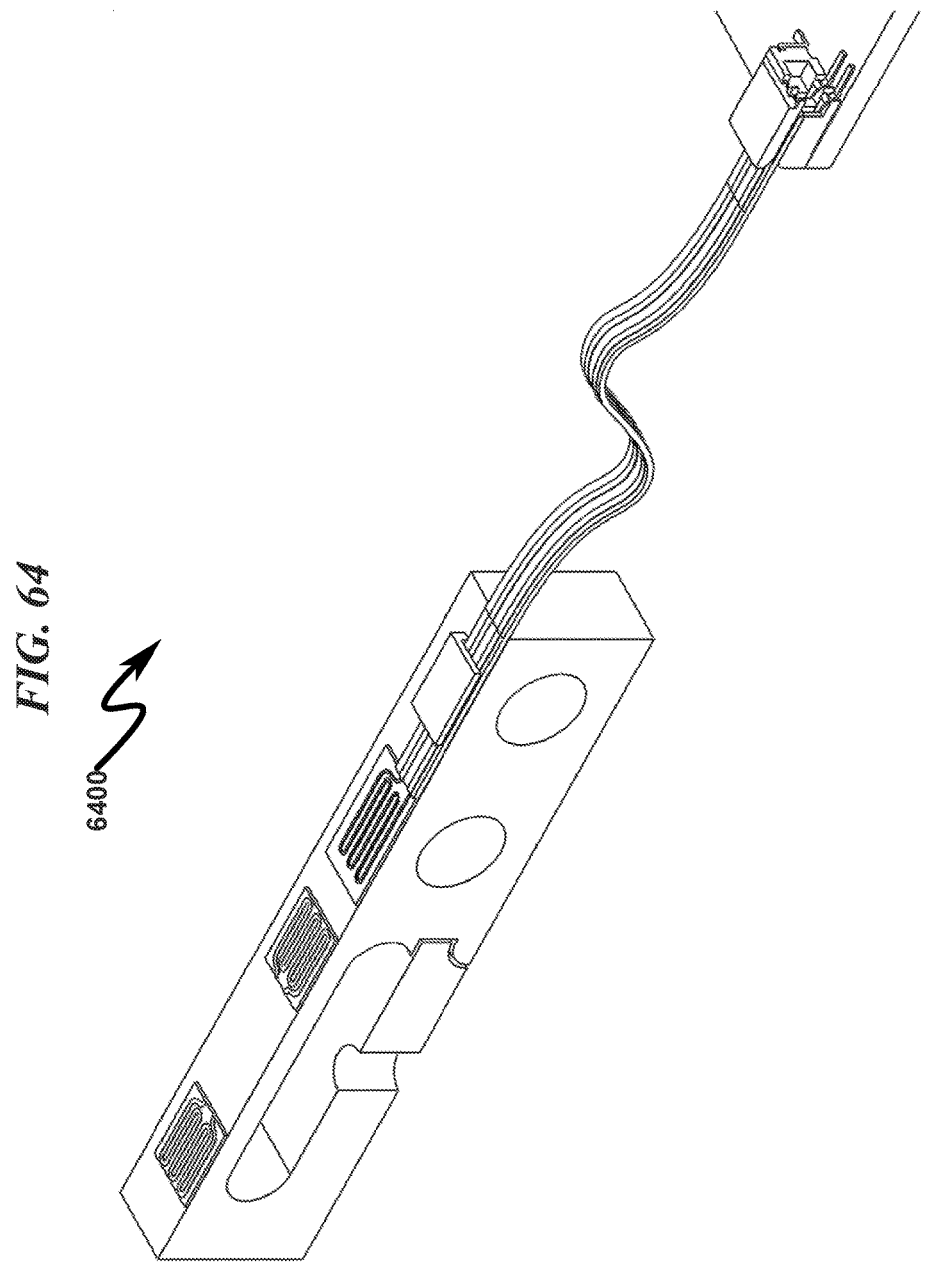
FIG. 64 illustrates a top section perspective view of a preferred exemplary ocular force sensor (OFS) embodiment useful in some invention configurations.

A preferred exemplary embodiment of a typical ocular force sensor (OFS) is generally depicted in the detail views presented in FIG. 49 (4900)-FIG. 64 (6400). Sensor electronics connecting to the CCD is not depicted in these diagrams. The pressure sensor depicted operates by deflecting a portion of the sensor body in response to torque applied by the LOB. Sensors on the OFS detect this torsional application of force and respond by sending differential analog signals to the sensor electronics for conversion to digital and transmission to the CCD.

While many ocular force sensors (OFS) may be used to implement the invention, many preferred exemplary invention embodiments may utilize a FUTEK ADVANCED SENSOR TECHNOLOGY, INC. (10 Thomas, Irvine Calif. 92618-2702—futek@futek.com/www.futek.com) Model LSM200 (FSH00064) pressure sensor. The model LSM200 is a Beam Load Cell (BLS) that offers a slim design with an side mounting feature making it ideal for use as the OFS in many present invention embodiments. Utilized in both Tension and Compression, this particular BLS has a length of 1.75", width of 0.38" and a height of 0.36". The LSM200 is configured in 2024 Aluminum (10 lb) and it has a 2" Molex flexible 4 conductor type (1 mm pitch) cable.

Typical specifications for a suitable OFS in the present invention application context are as follows:

| | |
| --- | --- |
| Rated Output (RO) | 2.3 mV/V nominal |
| Capacity (lb/N) | 10/44.5 |
| Safe overload | 100% of RO |
| Zero balance | ±5% of RO |
| Excitation (VDC or VAC) | 18 MAX |
| Bridge resistance | 1000 Ω nominal |
| Nonlinearity | ±0.2% of RO |
| Hysteresis | ±0.2% of RO |
| Nonrepeatability | ±0.1% of RO |
| Temperature shift zero | ±0.03% of RO [0.05% of RO/° C.] |
| Temperature shift span | ±0.03% of LOAD [0.05% of LOAD/° C.] |
| Compensated temperature | 60 to 160° F. [−50 to 93° C.] |
| Weight | 3 oz [85 g] |
| Material | aluminum |
| Deflection | 0.01 [0.25 mm] nominal |
| Cable | MOLEX flex cable type A, 1 mm pitch, 4 conductor, 2-in [50.8 mm] long |

Exemplary Optical Separator Bracket (OSB) (6500)-(8000)

Figure 65:
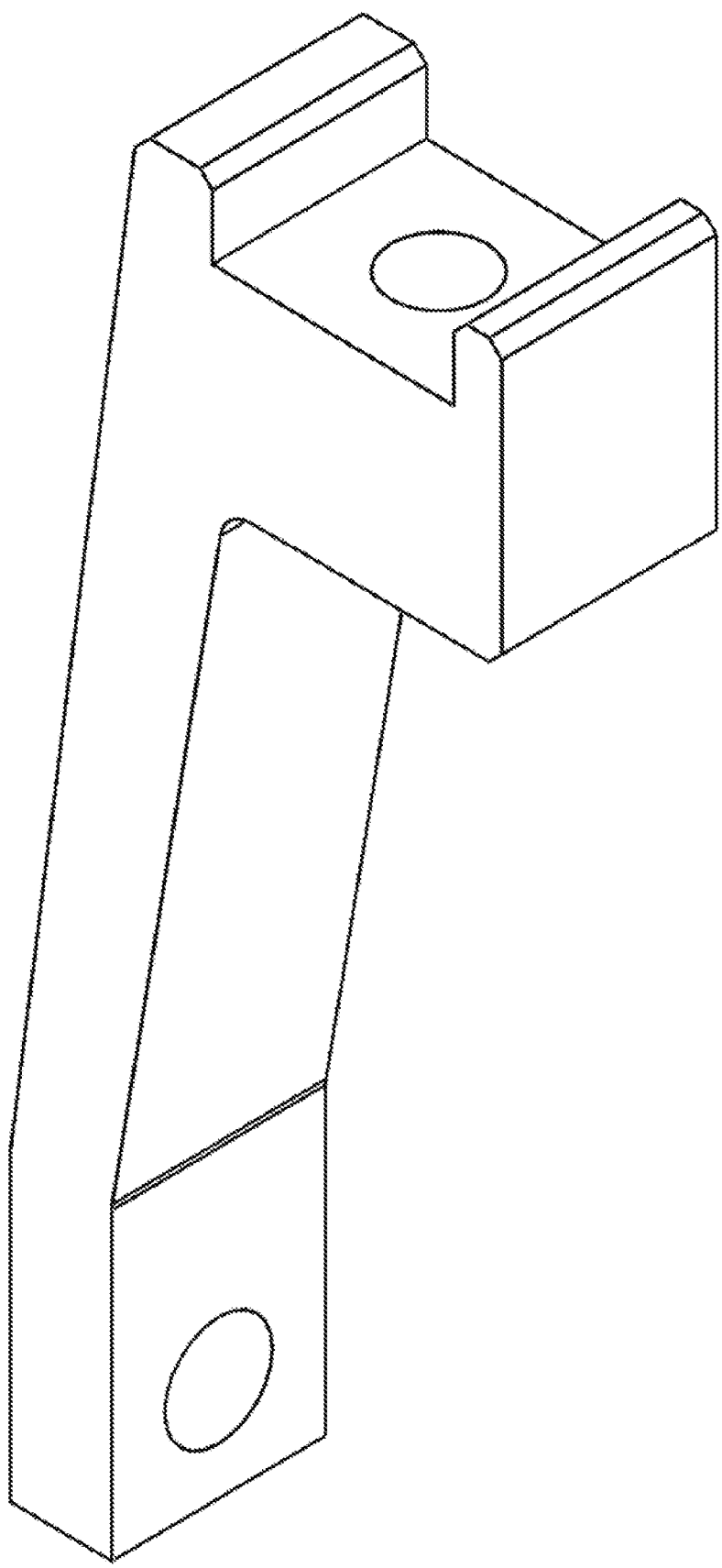
FIG. 65 illustrates a top right front perspective view of a preferred exemplary optical separator bracket (OSB) embodiment useful in some invention configurations.
Figure 66:
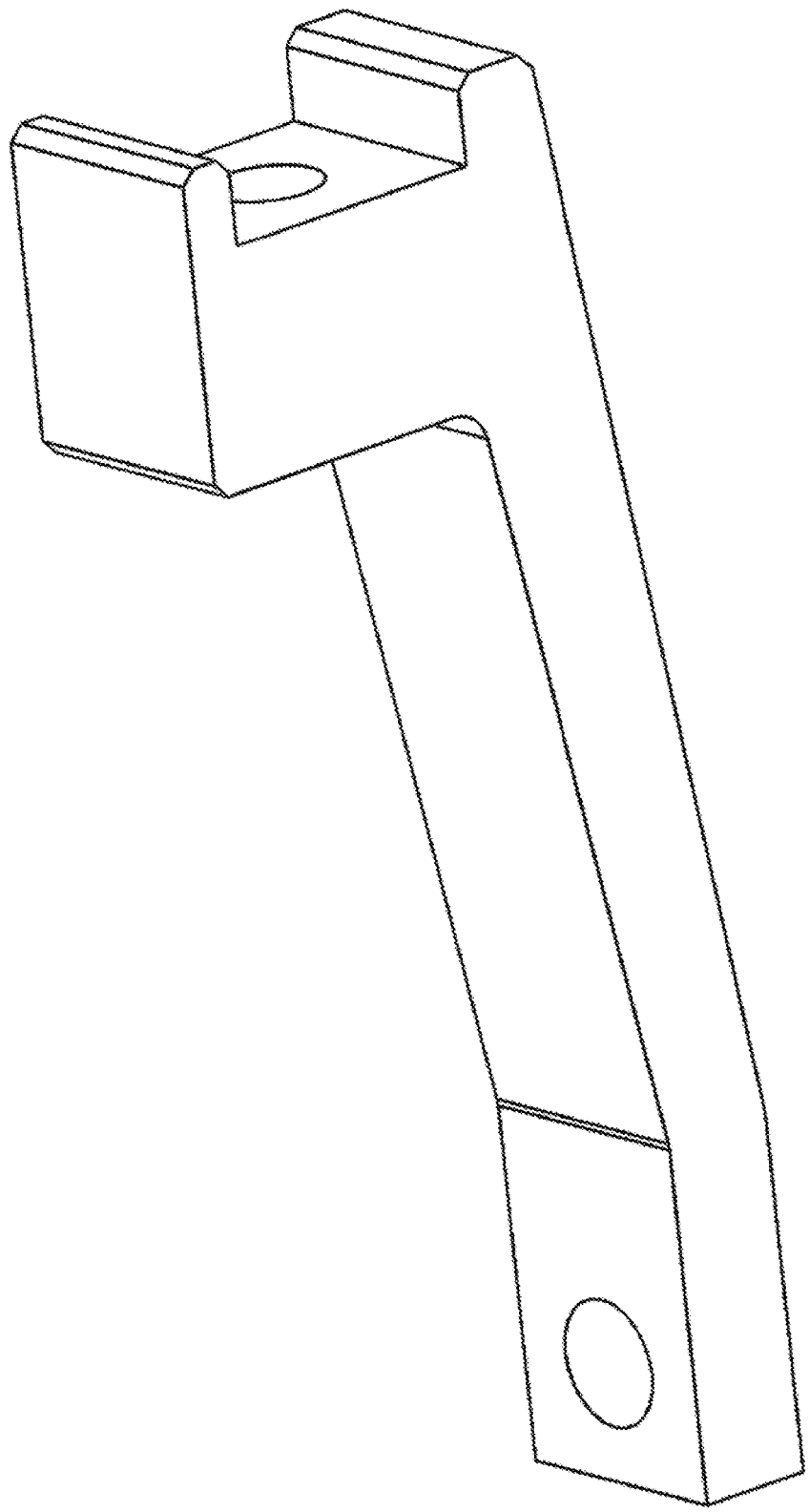
FIG. 66 illustrates a top right rear perspective view of a preferred exemplary optical separator bracket (OSB) embodiment useful in some invention configurations.
Figure 67:
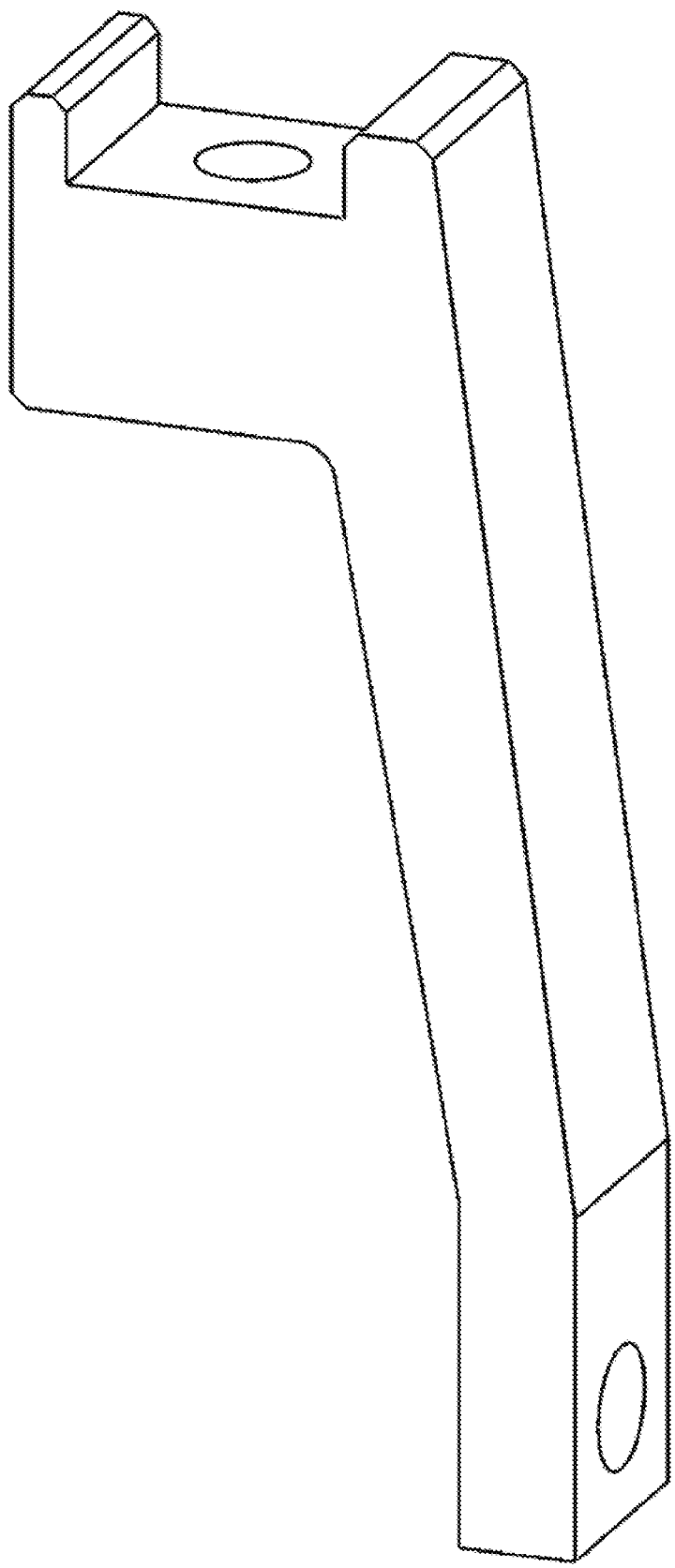
FIG. 67 illustrates a top left rear perspective view of a preferred exemplary optical separator bracket (OSB) embodiment useful in some invention configurations.
Figure 68:
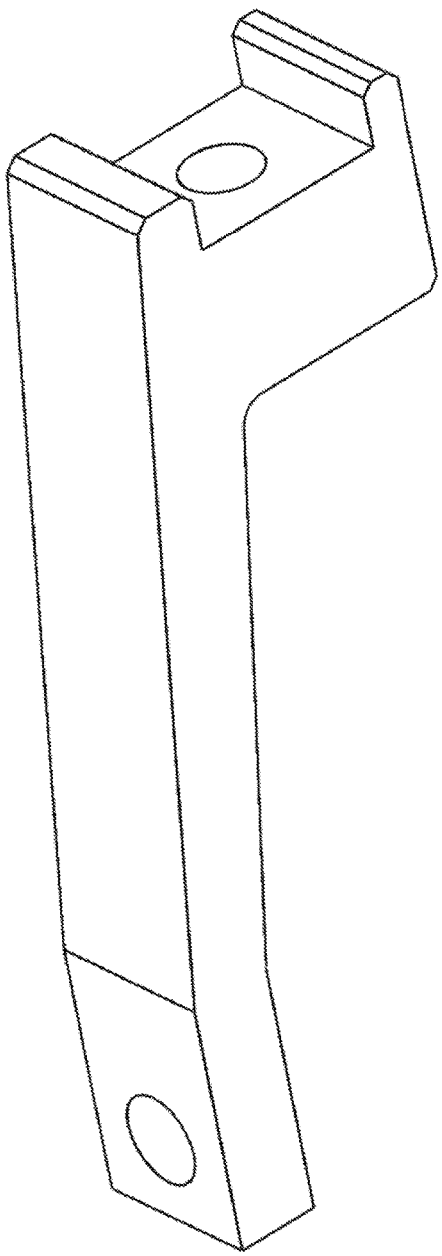
FIG. 68 illustrates a top left front perspective view of a preferred exemplary optical separator bracket (OSB) embodiment useful in some invention configurations.
Figure 69:
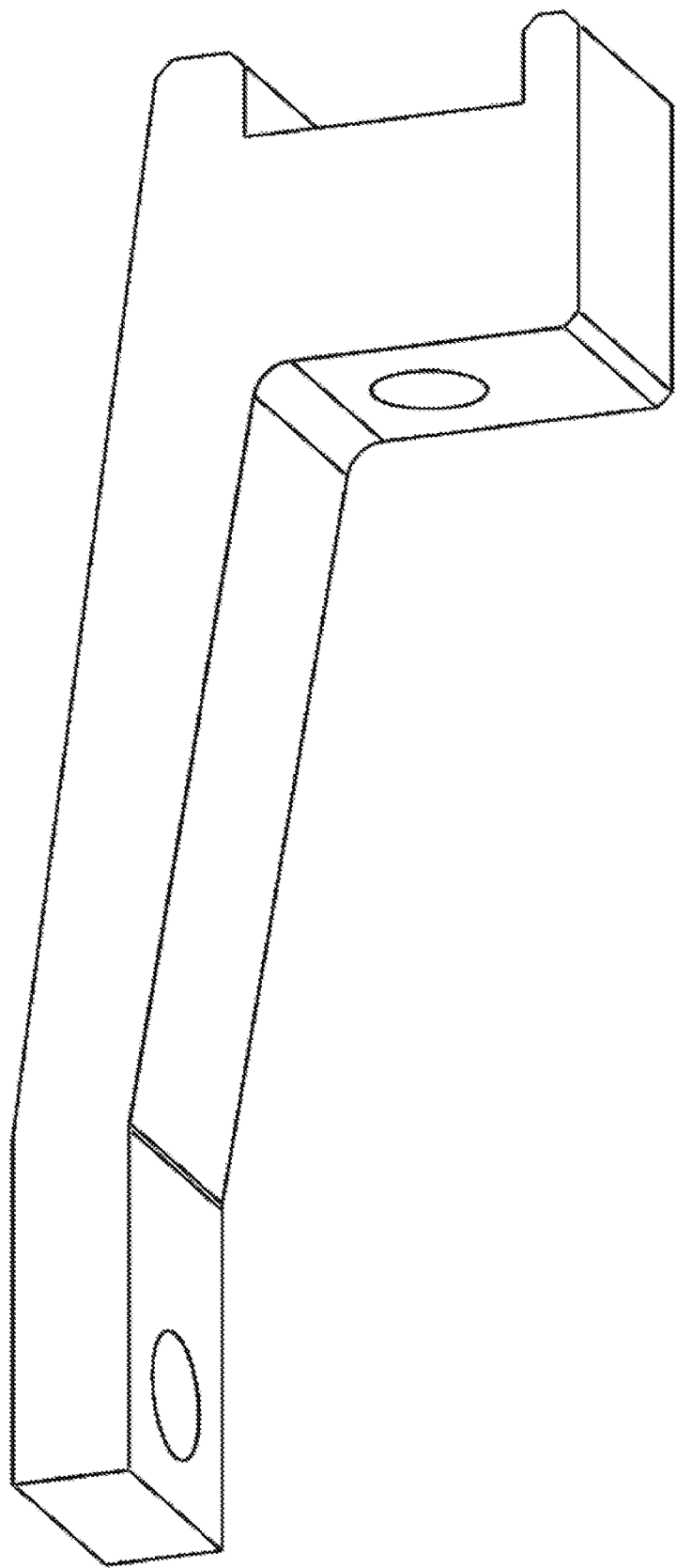
FIG. 69 illustrates a bottom right front perspective view of a preferred exemplary optical separator bracket (OSB) embodiment useful in some invention configurations.
Figure 70:
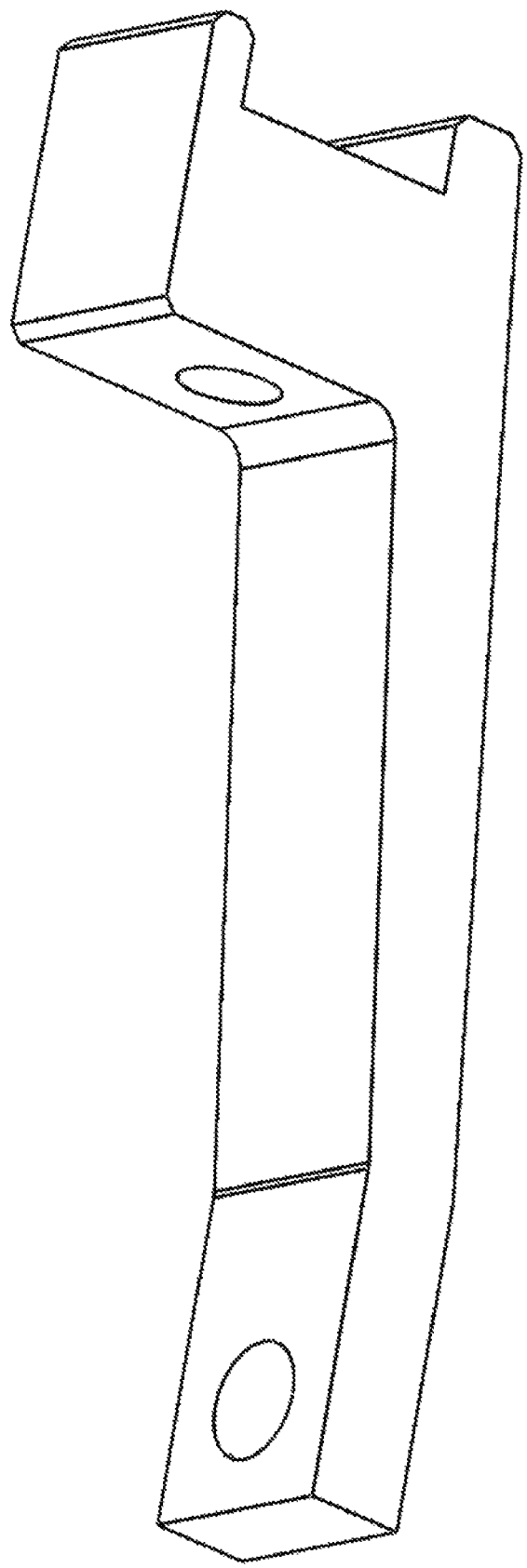
FIG. 70 illustrates a bottom right rear perspective view of a preferred exemplary optical separator bracket (OSB) embodiment useful in some invention configurations.
Figure 71:
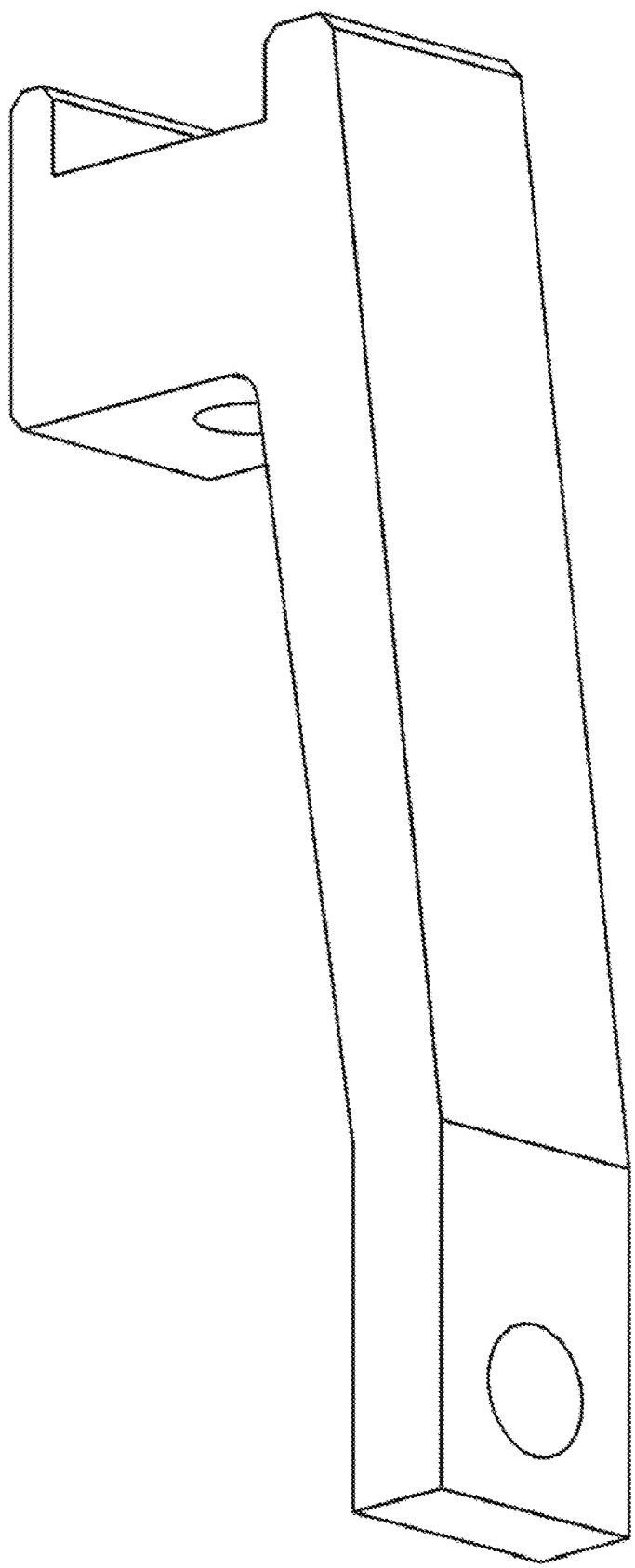
FIG. 71 illustrates a bottom left rear perspective view of a preferred exemplary optical separator bracket (OSB) embodiment useful in some invention configurations.
Figure 72:
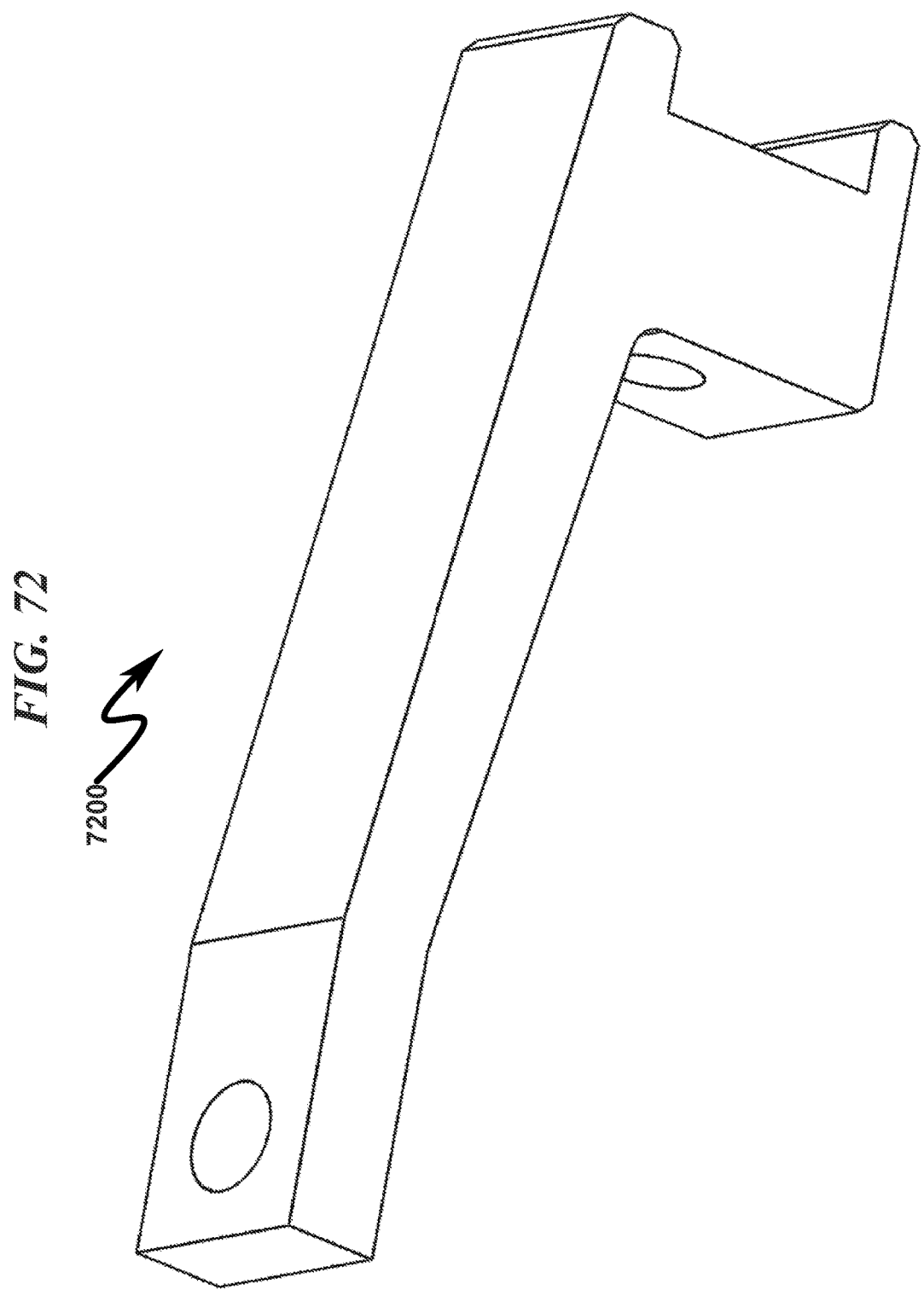
FIG. 72 illustrates a bottom left front perspective view of a preferred exemplary optical, separator bracket (OSB) embodiment useful in some invention configurations.
Figure 73:
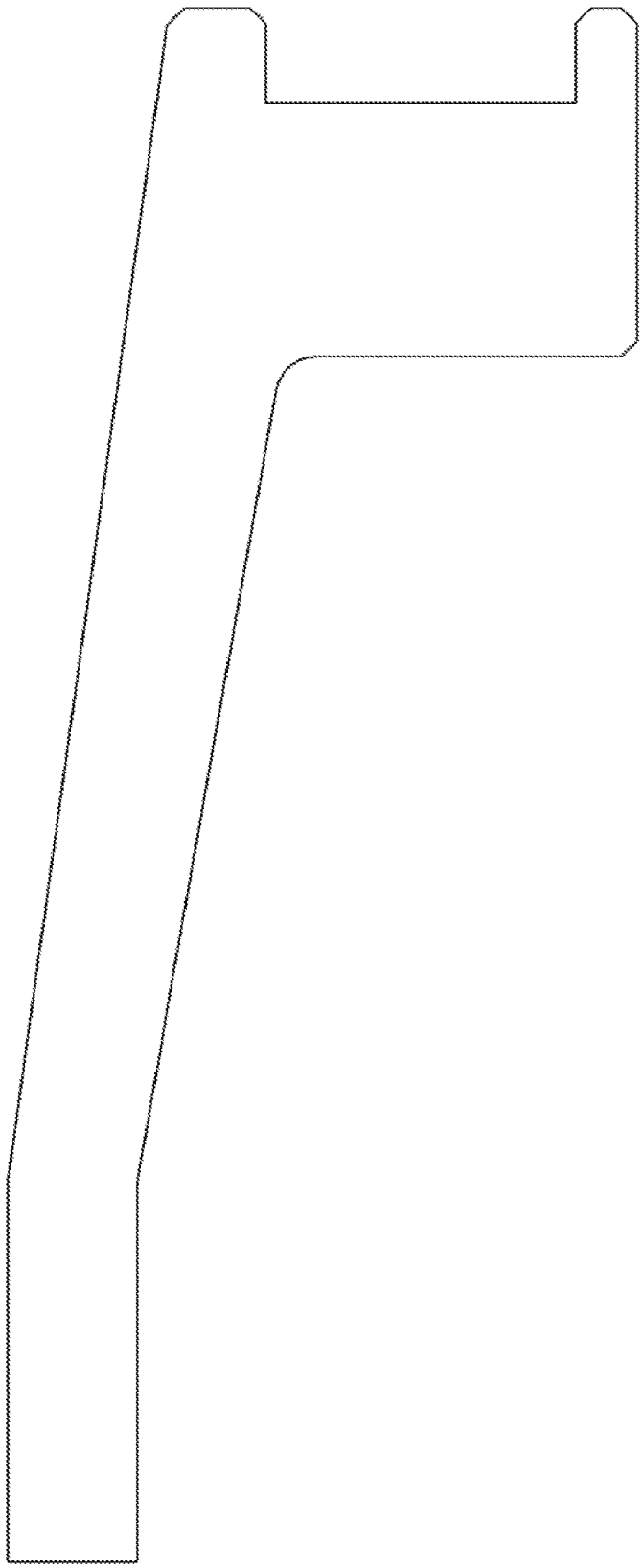
FIG. 73 illustrates a front view of a preferred exemplary optical separator bracket (OSB) embodiment useful in some invention configurations.
Figure 74:
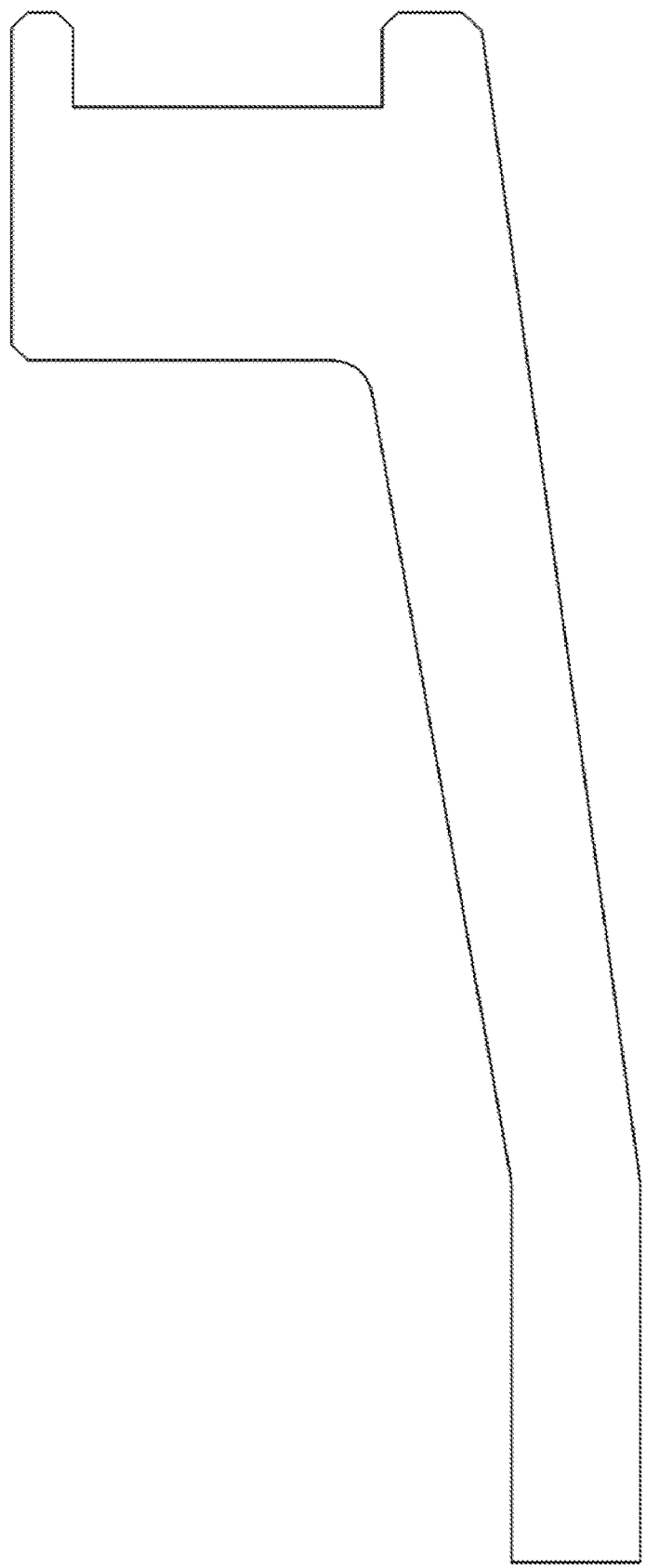
FIG. 74 illustrates a rear view of a preferred exemplary optical separator bracket (OSB) embodiment useful in some invention configurations.
Figure 75:
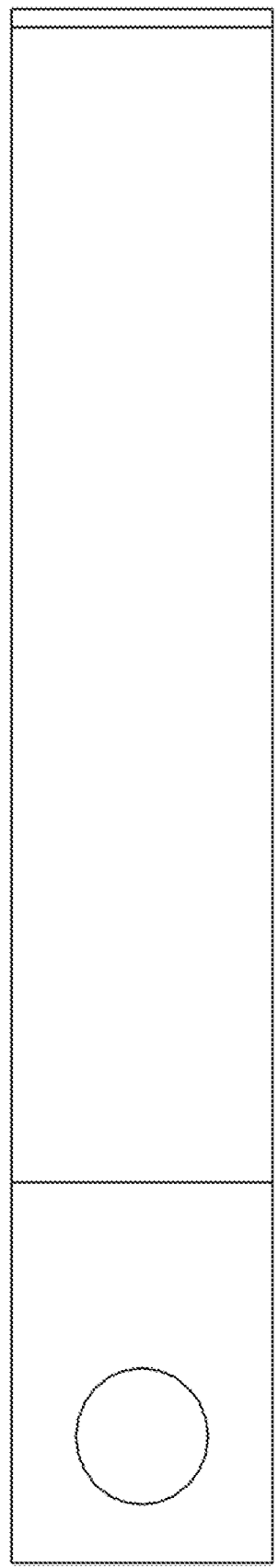
FIG. 75 illustrates a left view of a preferred exemplary optical separator bracket (OSB) embodiment useful in some invention configurations.
Figure 76:
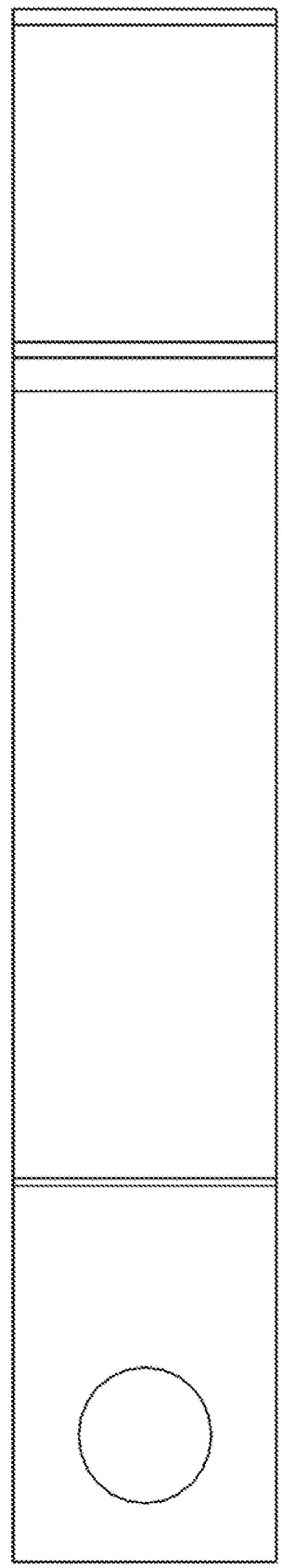
FIG. 76 illustrates a right view of a preferred exemplary optical separator bracket (OSB) embodiment useful in some invention configurations.
Figure 77:
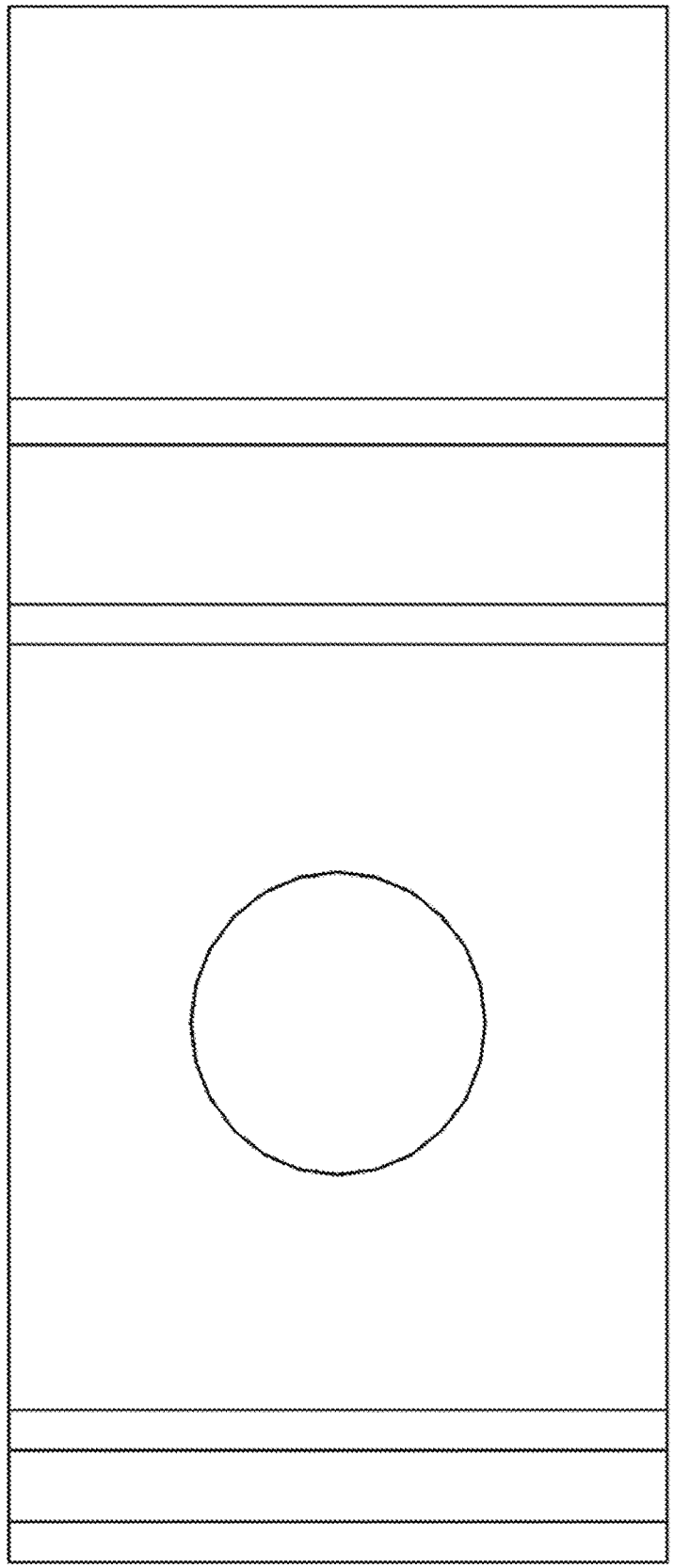
FIG. 77 illustrates a top view of a preferred exemplary optical separator bracket (OSB) embodiment useful in some invention configurations.
Figure 78:
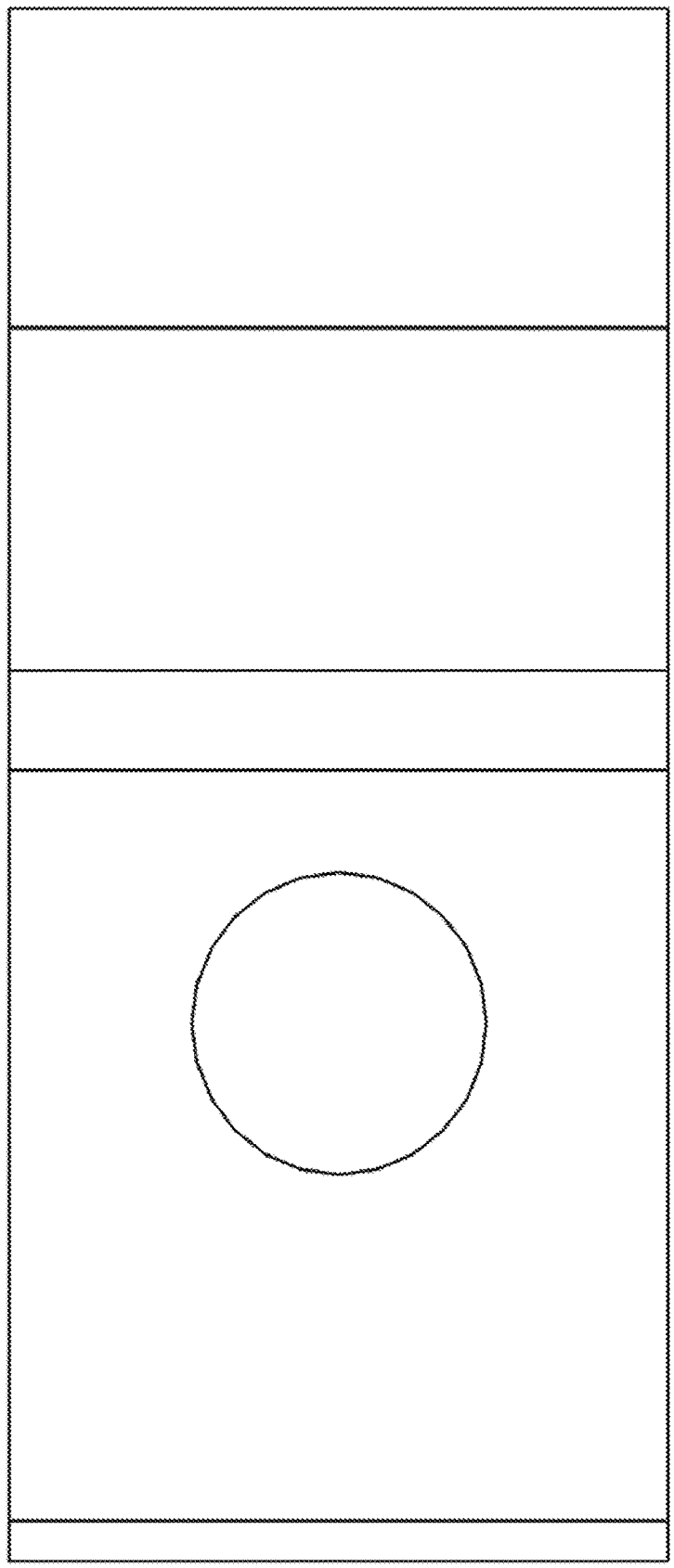
FIG. 78 illustrates a bottom view of a preferred exemplary optical separator bracket (OSB) embodiment useful in some invention configurations.
Figure 79:
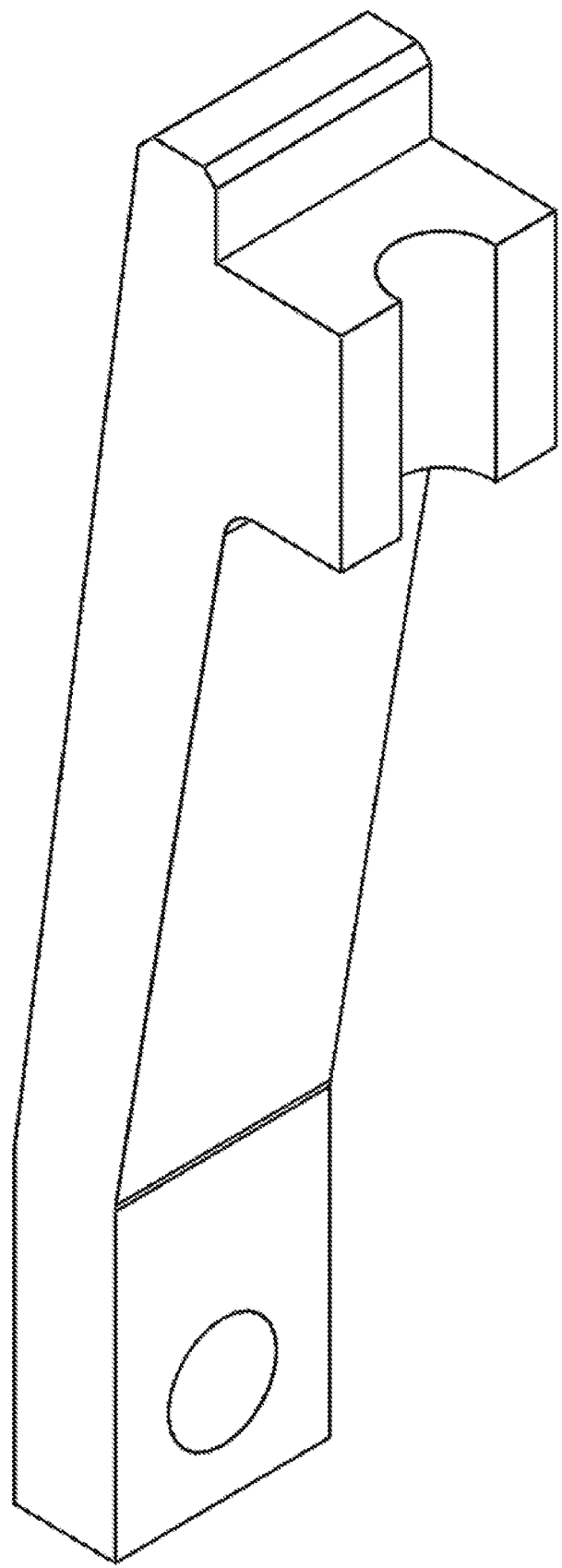
FIG. 79 illustrates a right section perspective view of a preferred exemplary optical separator bracket (OSB) embodiment useful in some invention configurations.
Figure 80:
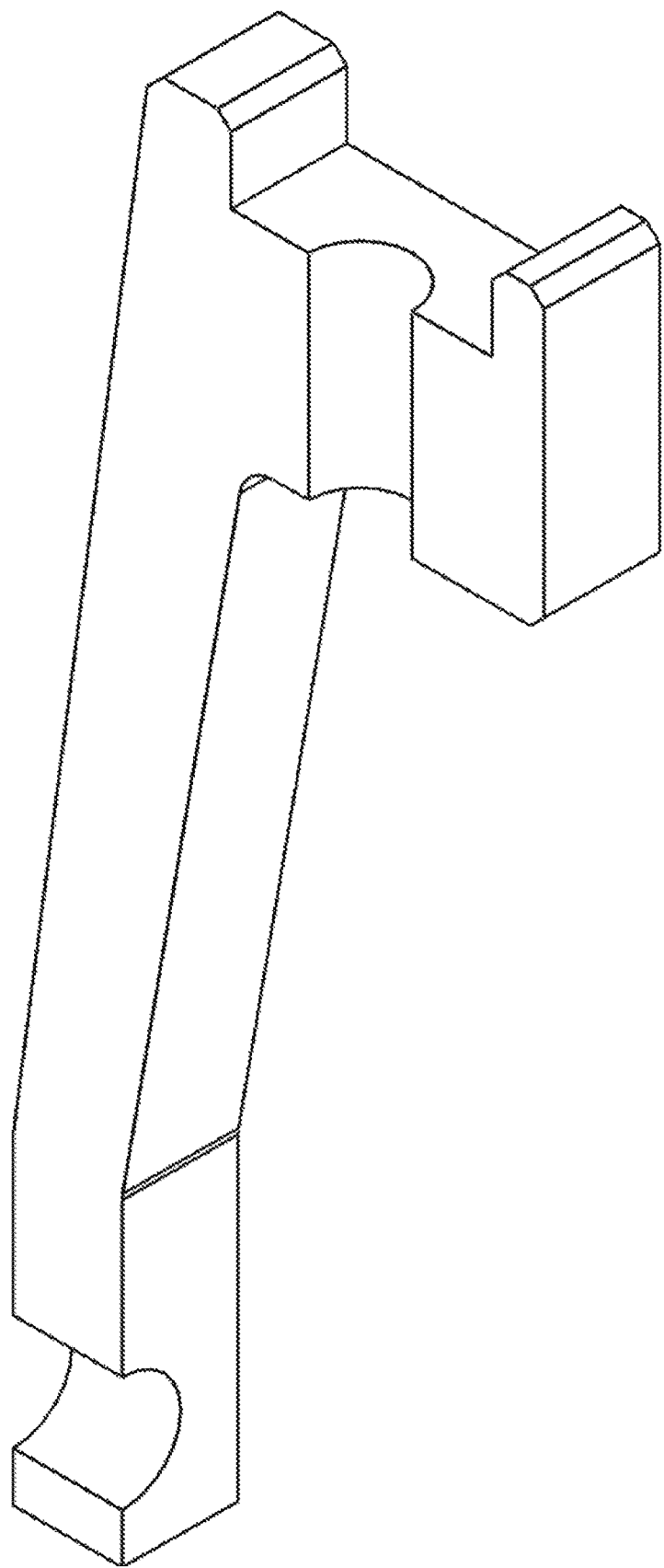
FIG. 80 illustrates a front section perspective view of a preferred exemplary optical separator bracket (OSB) embodiment useful in some invention configurations.

A preferred exemplary embodiment of a typical optical separator bracket (OSB) is generally depicted in the detail views presented in FIG. 65 (6500)-FIG. 80 (8000).

Exemplary Optical Window Retainer (OWR) (8100)-(9600)

Figure 81:
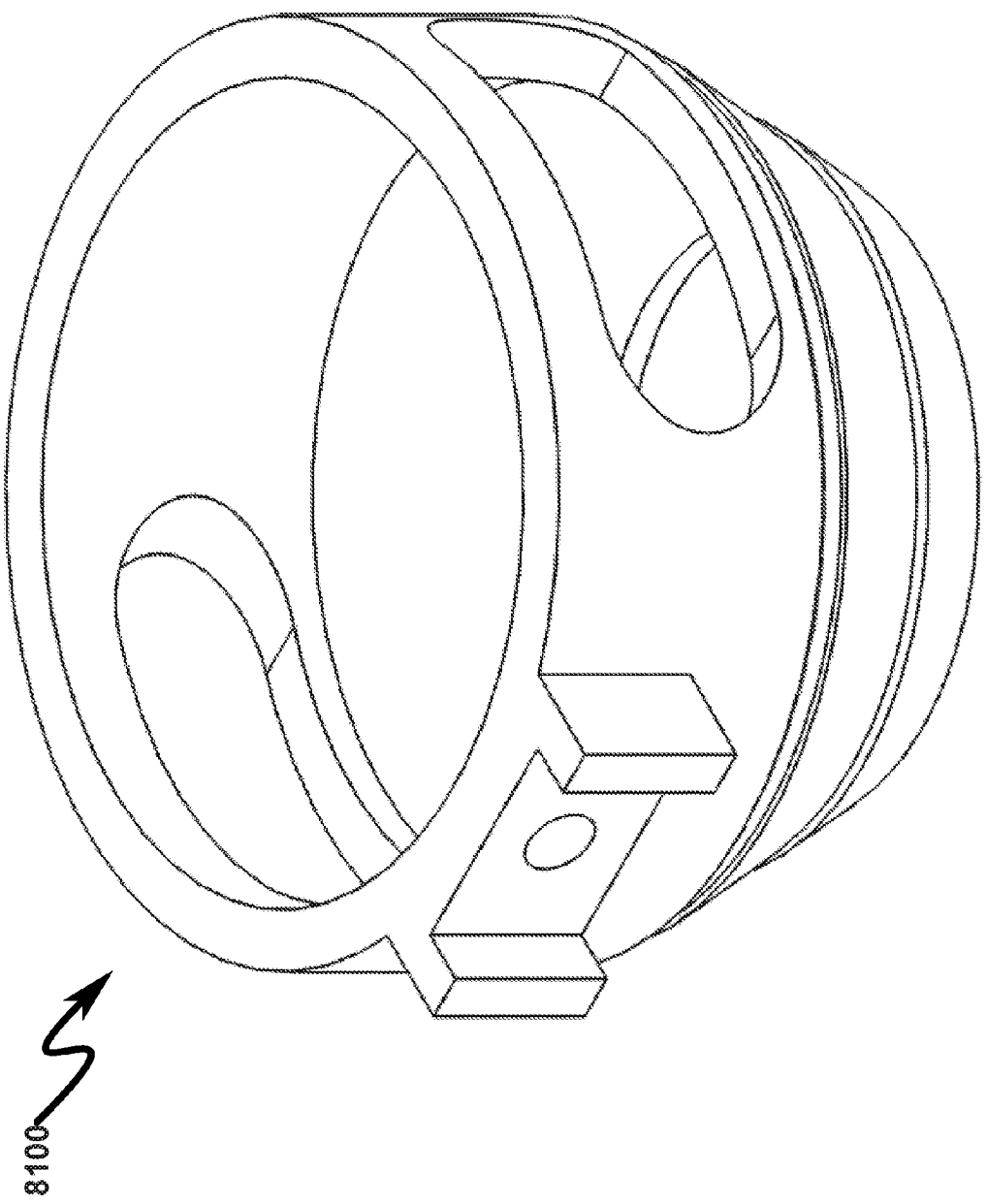
FIG. 81 illustrates a top right front perspective view of a preferred exemplary optical window retainer (OWR) embodiment useful in some invention configurations.
Figure 82:
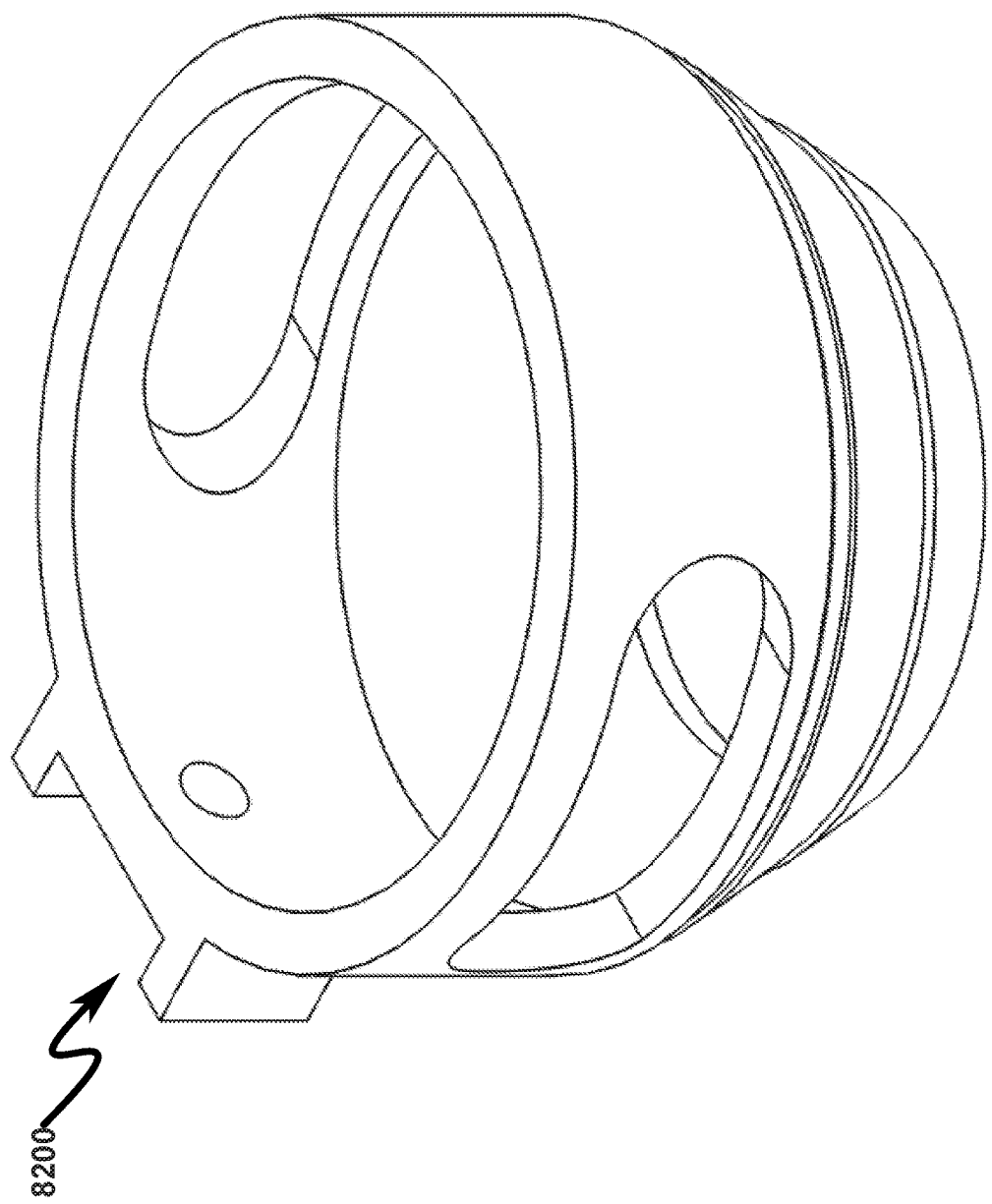
FIG. 82 illustrates a top right rear perspective view of a preferred exemplary optical window retainer (OWR) embodiment useful in some invention configurations.
Figure 83:
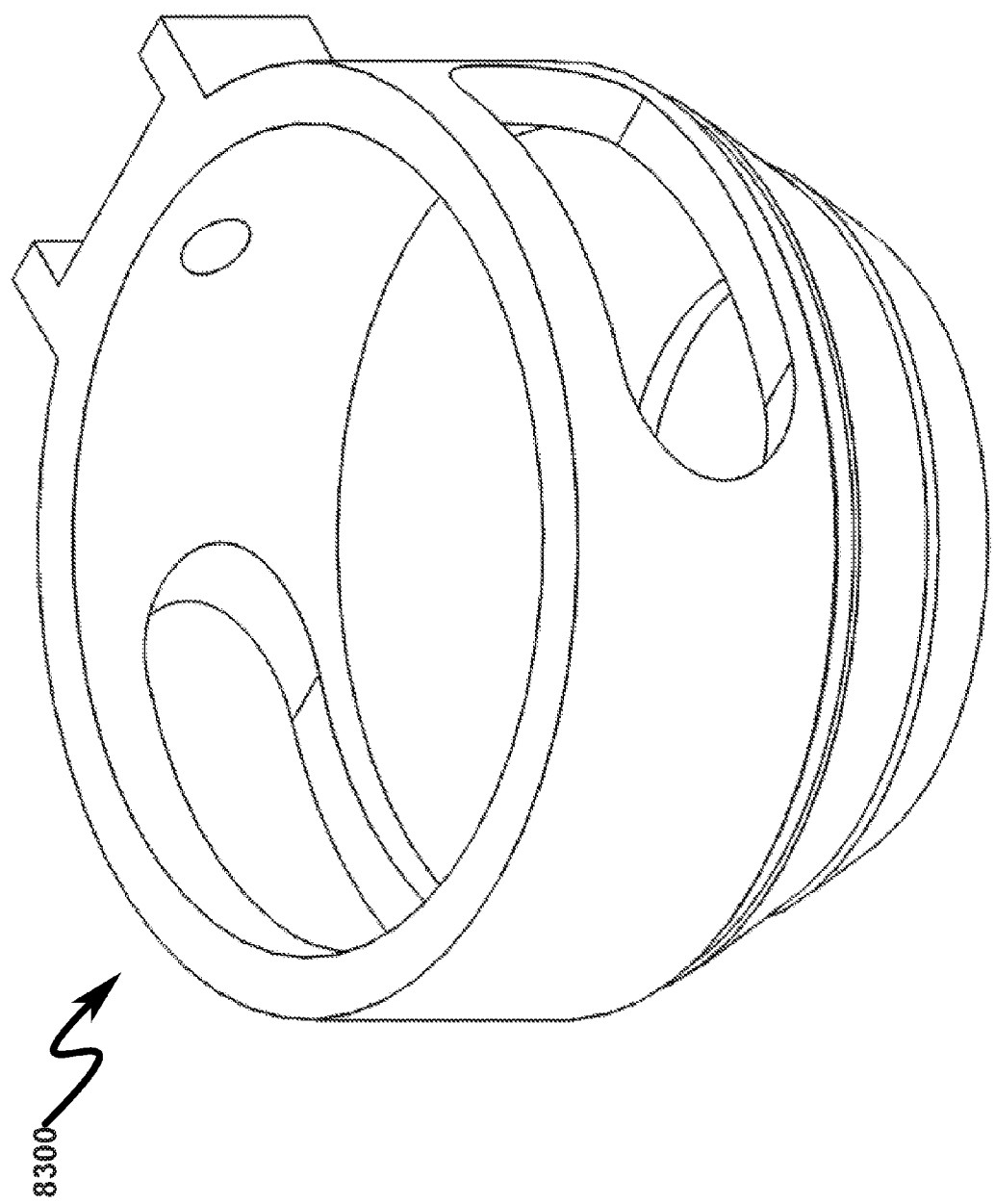
FIG. 83 illustrates a top left rear perspective view of a preferred exemplary optical window retainer (OWR) embodiment useful in some invention configurations.
Figure 84:
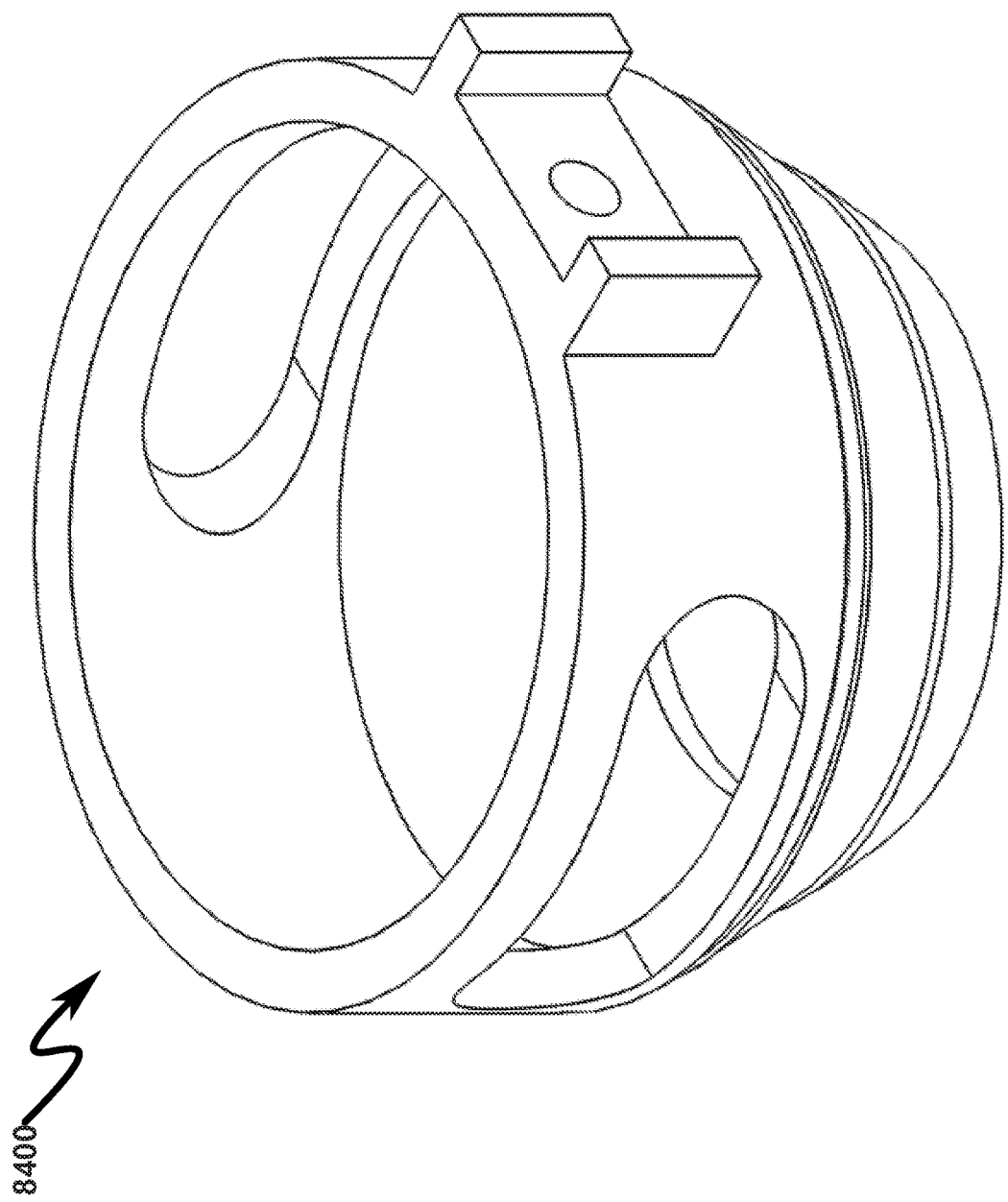
FIG. 84 illustrates a top left front perspective view of a preferred exemplary optical window retainer (OWR) embodiment useful in some invention configurations.
Figure 85:
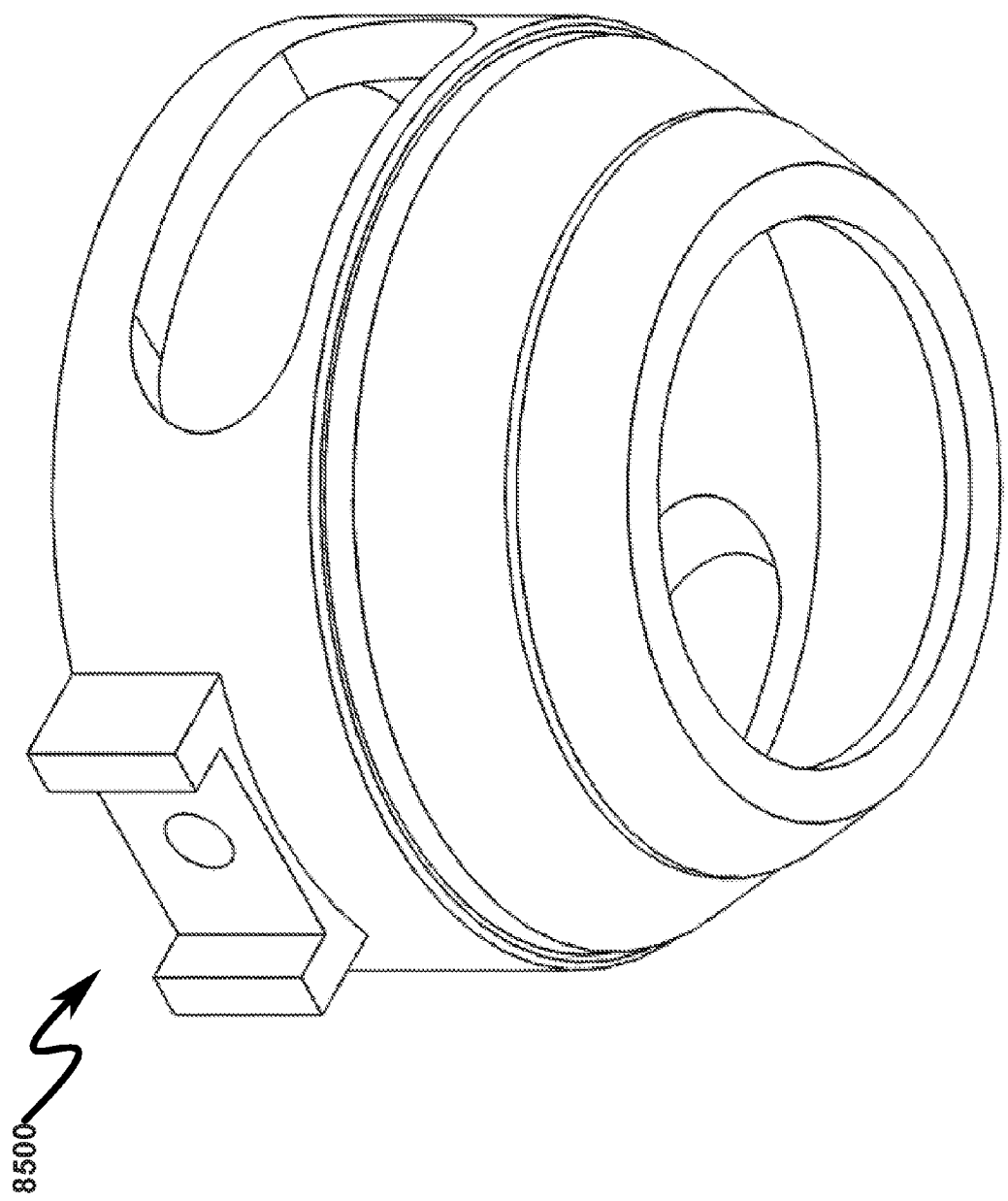
FIG. 85 illustrates a bottom right front perspective view of a preferred exemplary optical window retainer (OWR) embodiment useful in some invention configurations.
Figure 86:
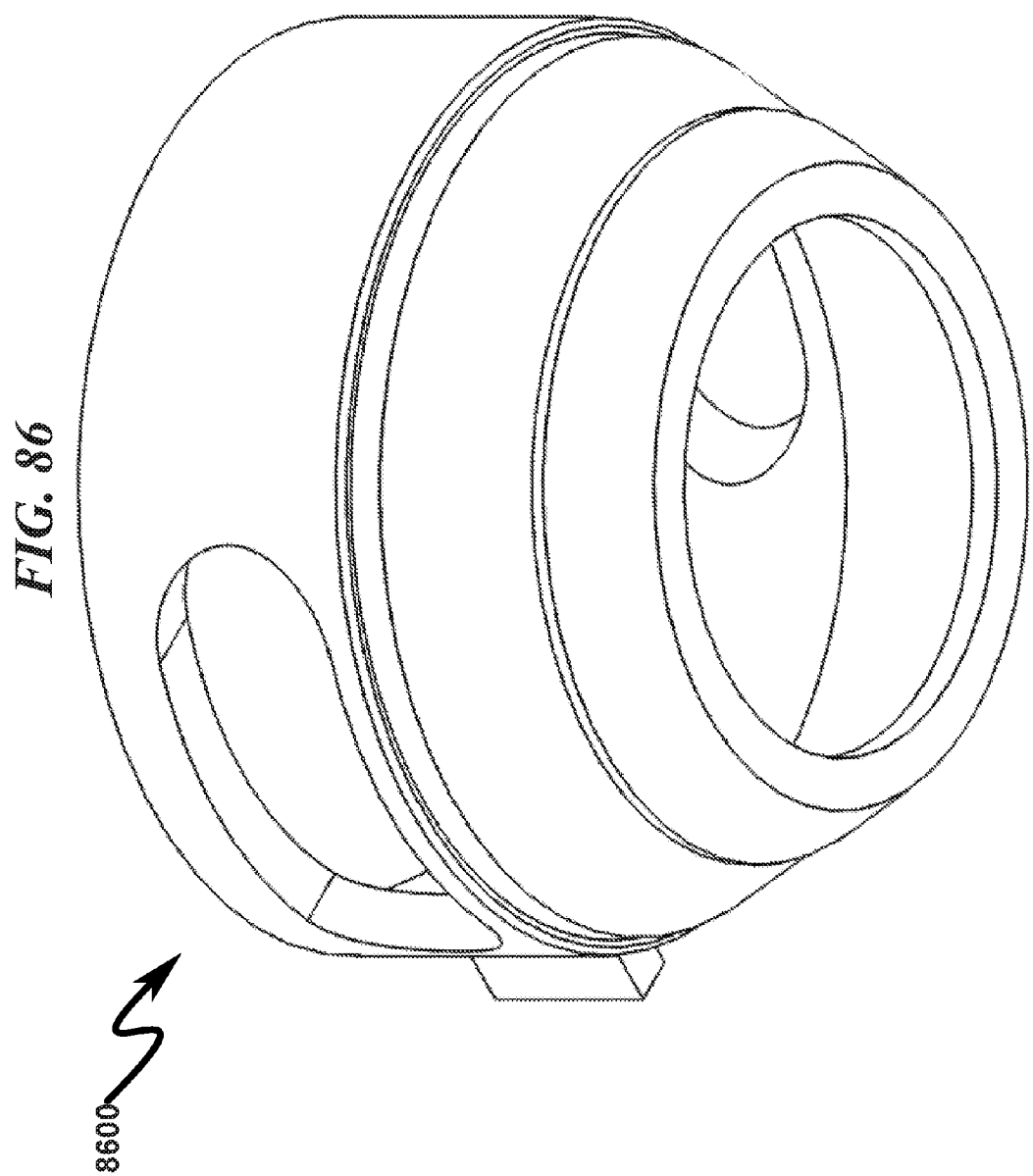
FIG. 86 illustrates a bottom right rear perspective view of a preferred exemplary optical window retainer (OWR) embodiment useful in some invention configurations.
Figure 87:
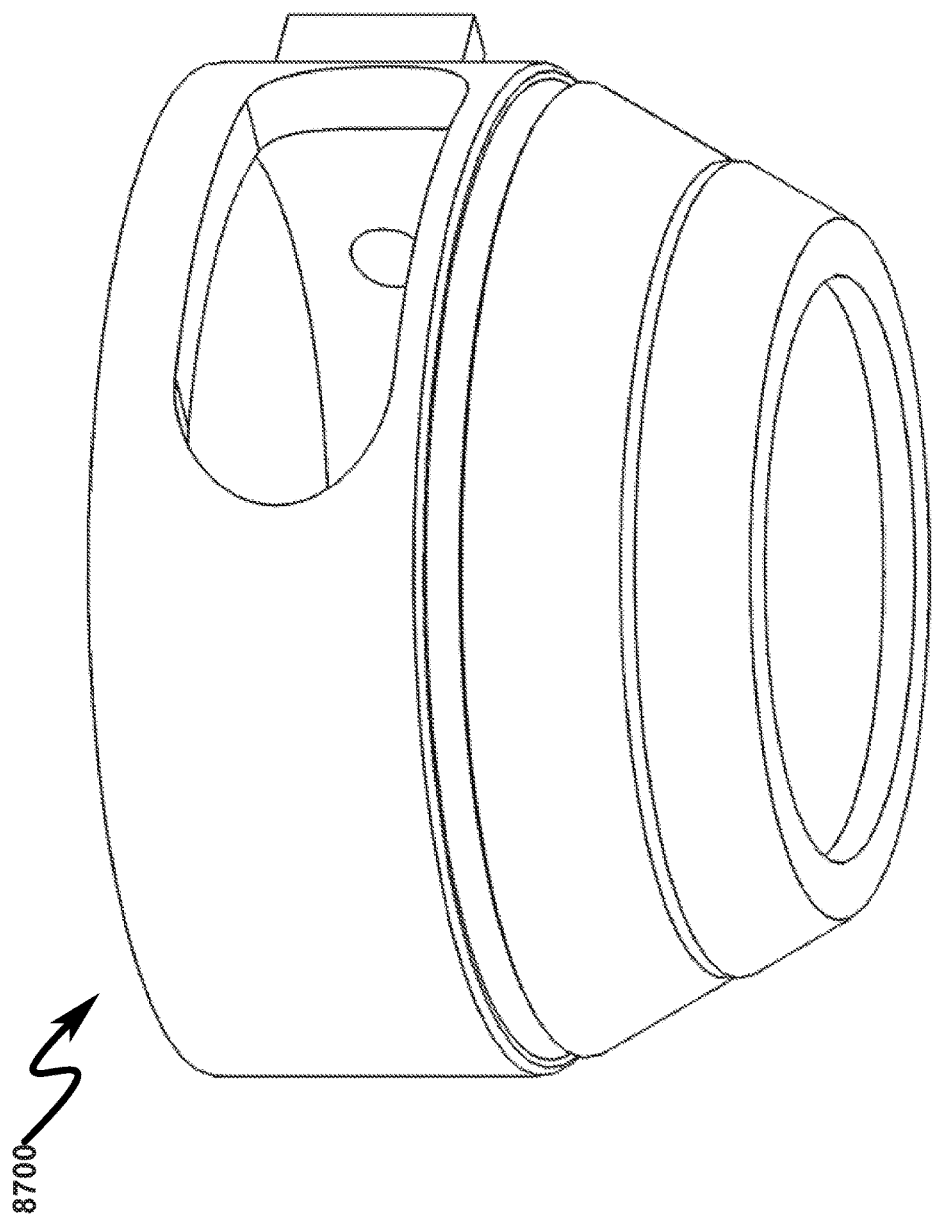
FIG. 87 illustrates a bottom left rear perspective view of a preferred exemplary optical window retainer (OWR) embodiment useful in some invention configurations.
Figure 88:
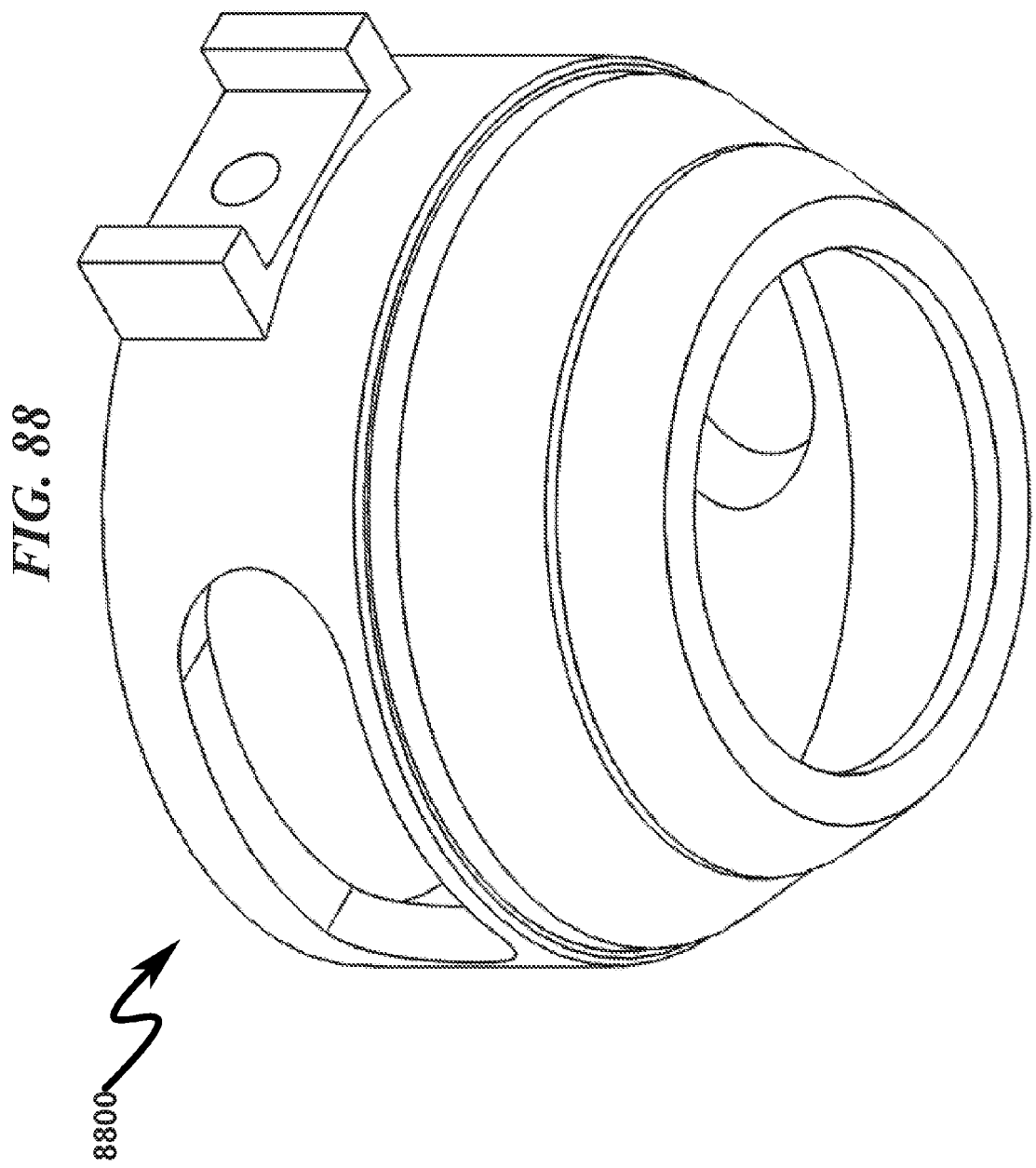
FIG. 88 illustrates a bottom left front perspective view of a preferred exemplary optical window retainer (OWR) embodiment useful in some invention configurations.
Figure 89:
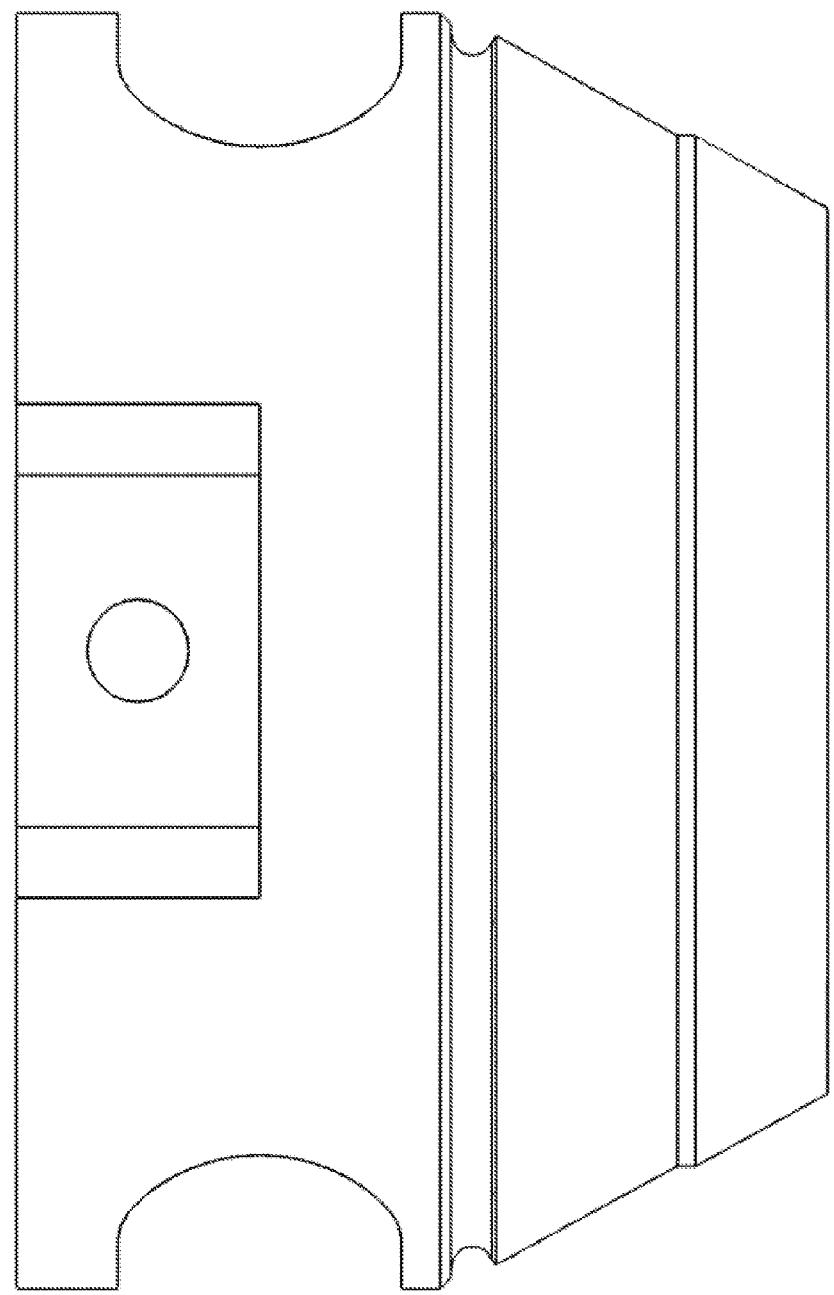
FIG. 89 illustrates a front view of a preferred exemplary optical window retainer (OWR) embodiment useful in some invention configurations.
Figure 90:
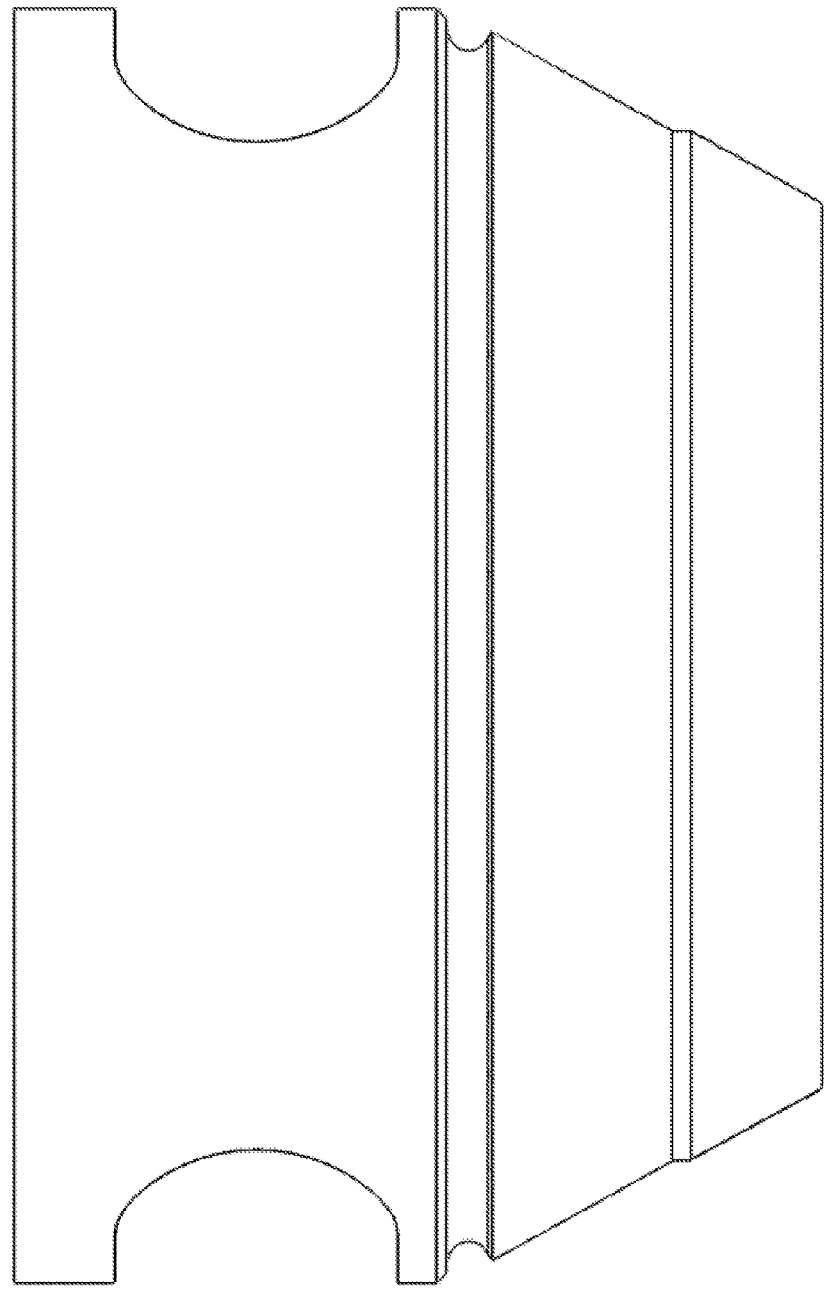
FIG. 90 illustrates a rear view of a preferred exemplary optical window retainer (OWR) embodiment useful in some invention configurations.
Figure 91:
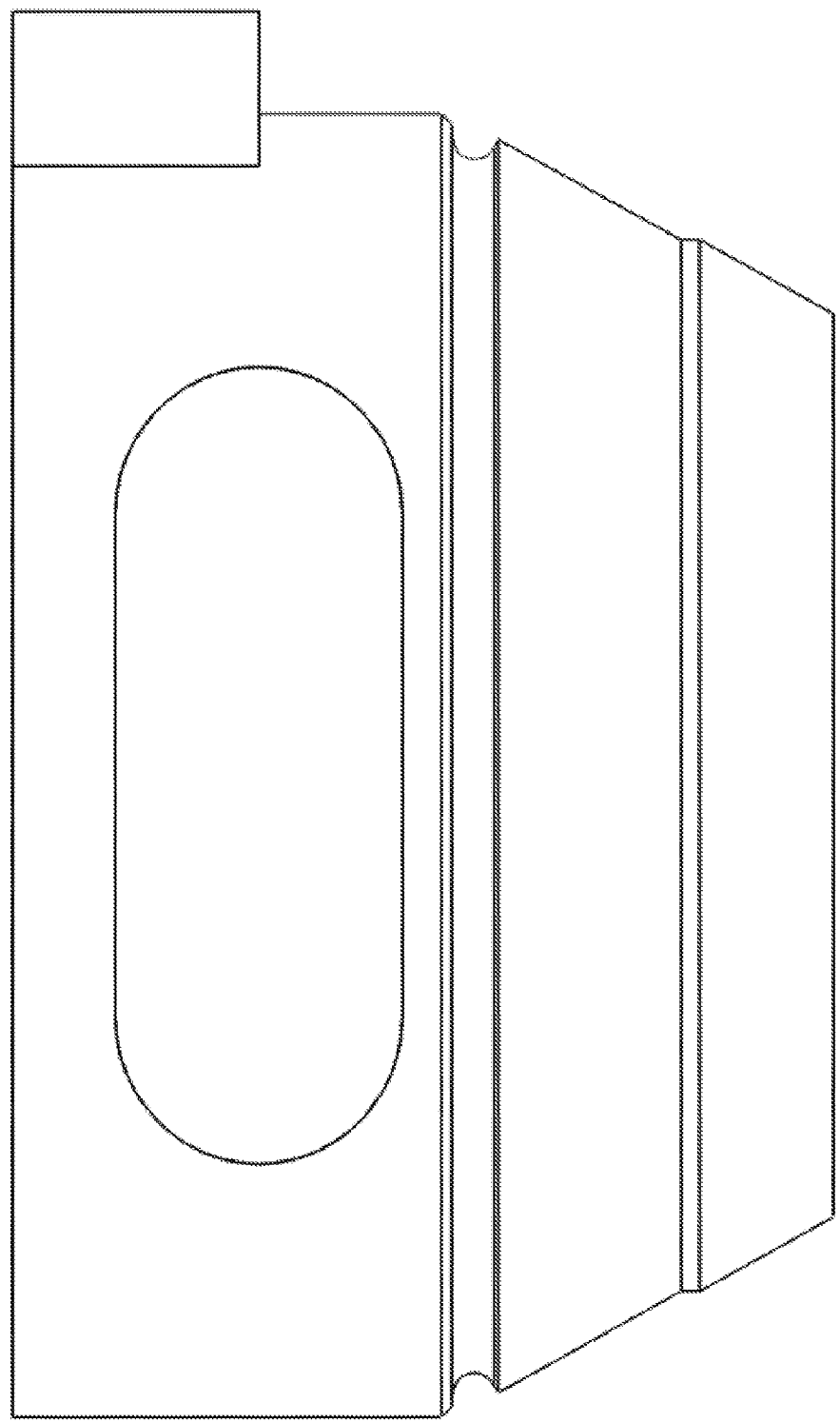
FIG. 91 illustrates a left view of a preferred exemplary optical window retainer (OWR) embodiment useful in some invention configurations.
Figure 92:
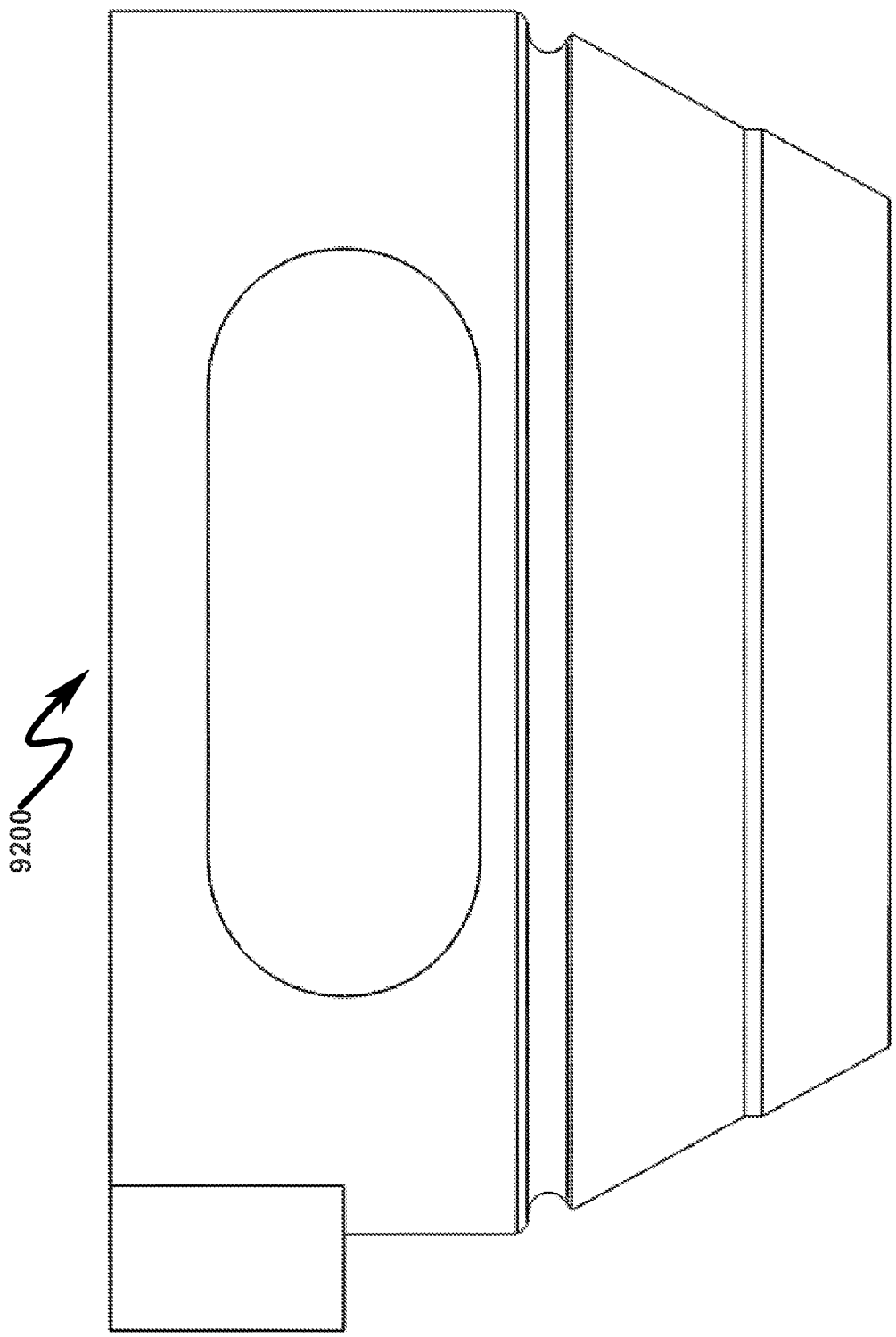
FIG. 92 illustrates a right view of a preferred exemplary optical window retainer (OWR) embodiment useful in some invention configurations.
Figure 93:
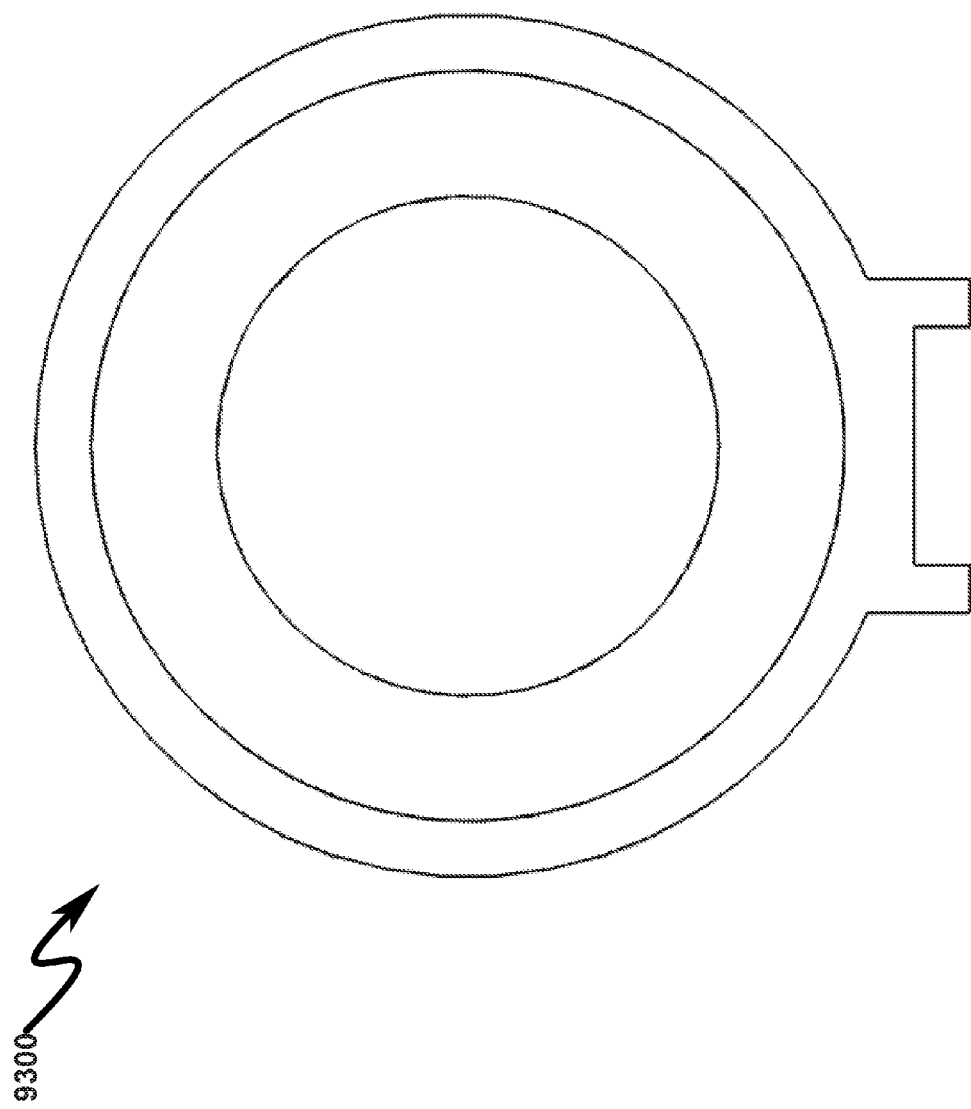
FIG. 93 illustrates a top view of a preferred exemplary optical window retainer (OWR) embodiment useful in some invention configurations.
Figure 94:
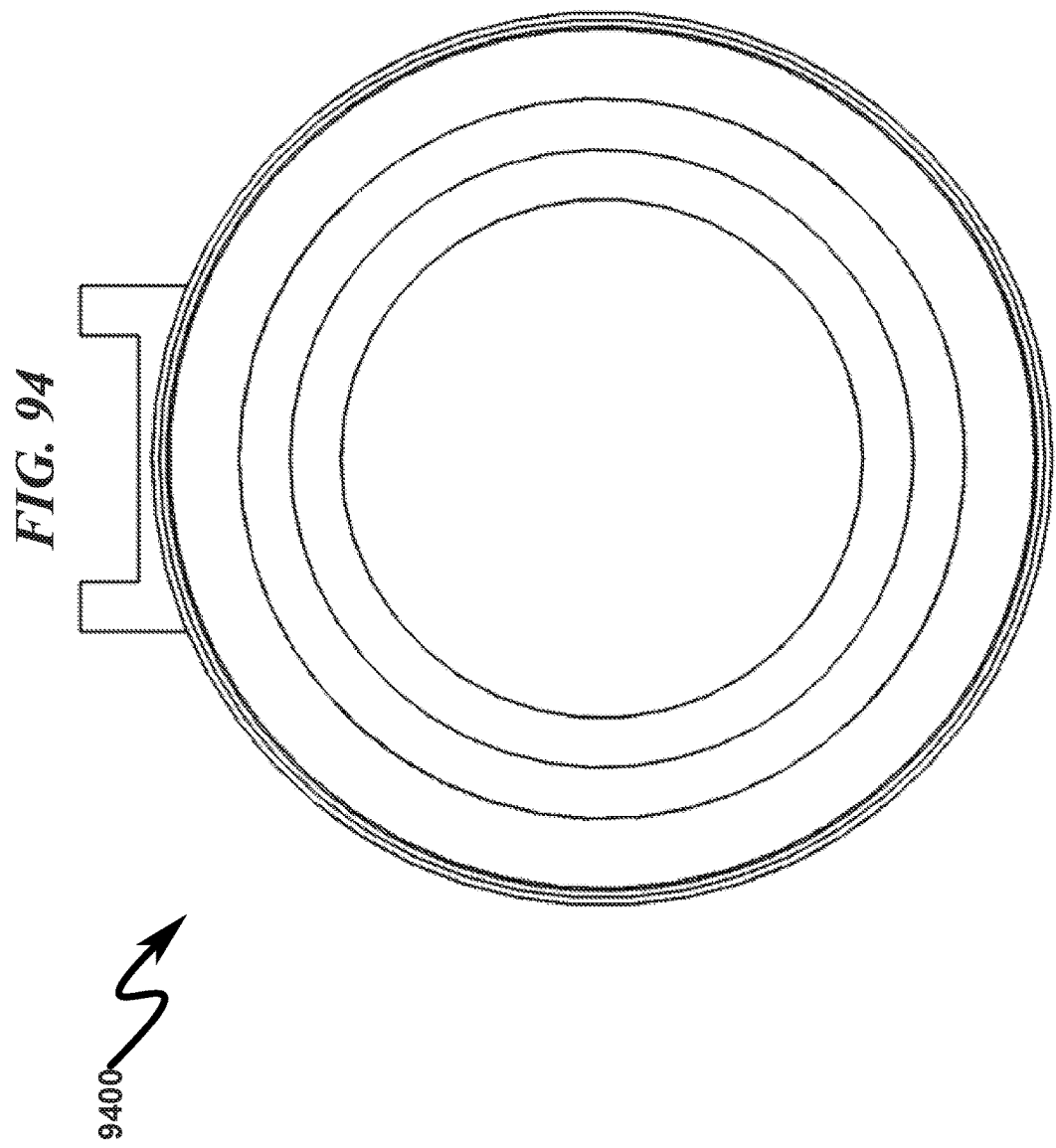
FIG. 94 illustrates a bottom view of a preferred exemplary optical window retainer (OWR) embodiment useful in some invention configurations.
Figure 95:
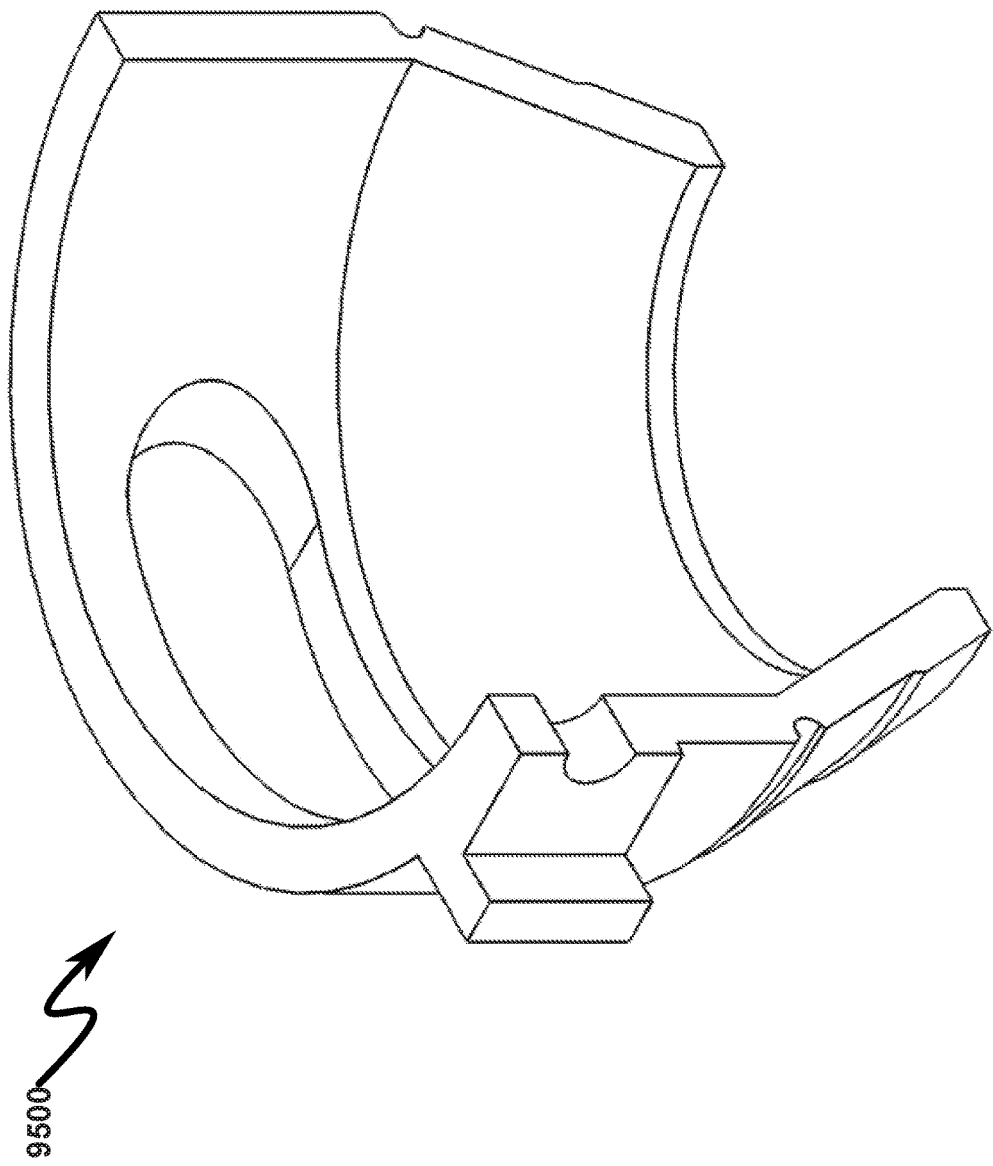
FIG. 95 illustrates a right section perspective view of a preferred exemplary optical window retainer (OWR) embodiment useful in some invention configurations.
Figure 96:
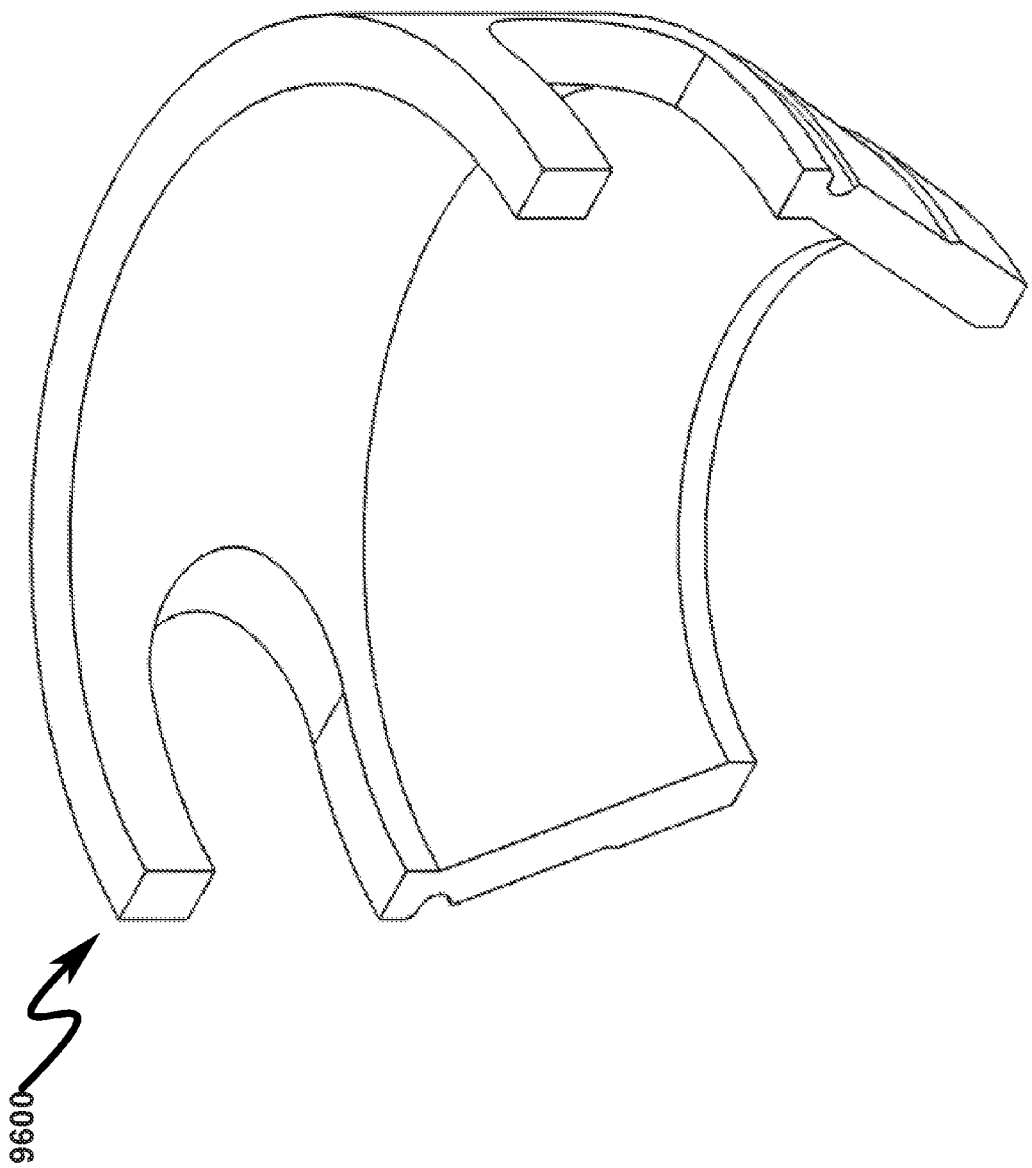
FIG. 96 illustrates a top section perspective view of a preferred exemplary optical window retainer (OWR) embodiment useful in some invention configurations.

A preferred exemplary embodiment of a typical optical window retainer (OWR) is generally depicted in the detail views presented in FIG. 81 (8100)-FIG. 96 (9600).

Exemplary Ocular Patient Interface (OPI) (9700)-(11200)

Figure 97:
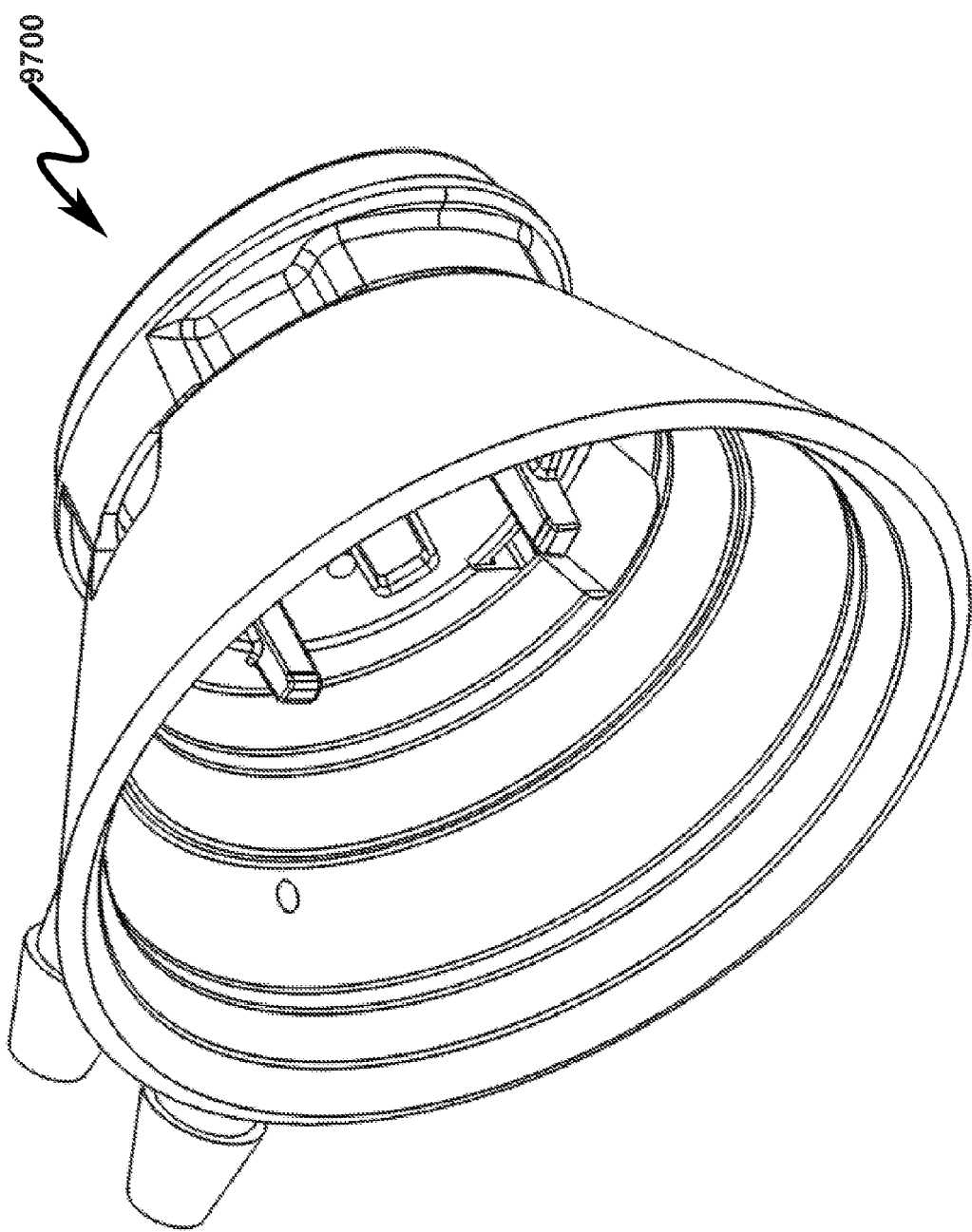
FIG. 97 illustrates a top right front perspective view of a preferred exemplary ocular patient interface (OPI) embodiment useful in some invention configurations.
Figure 98:
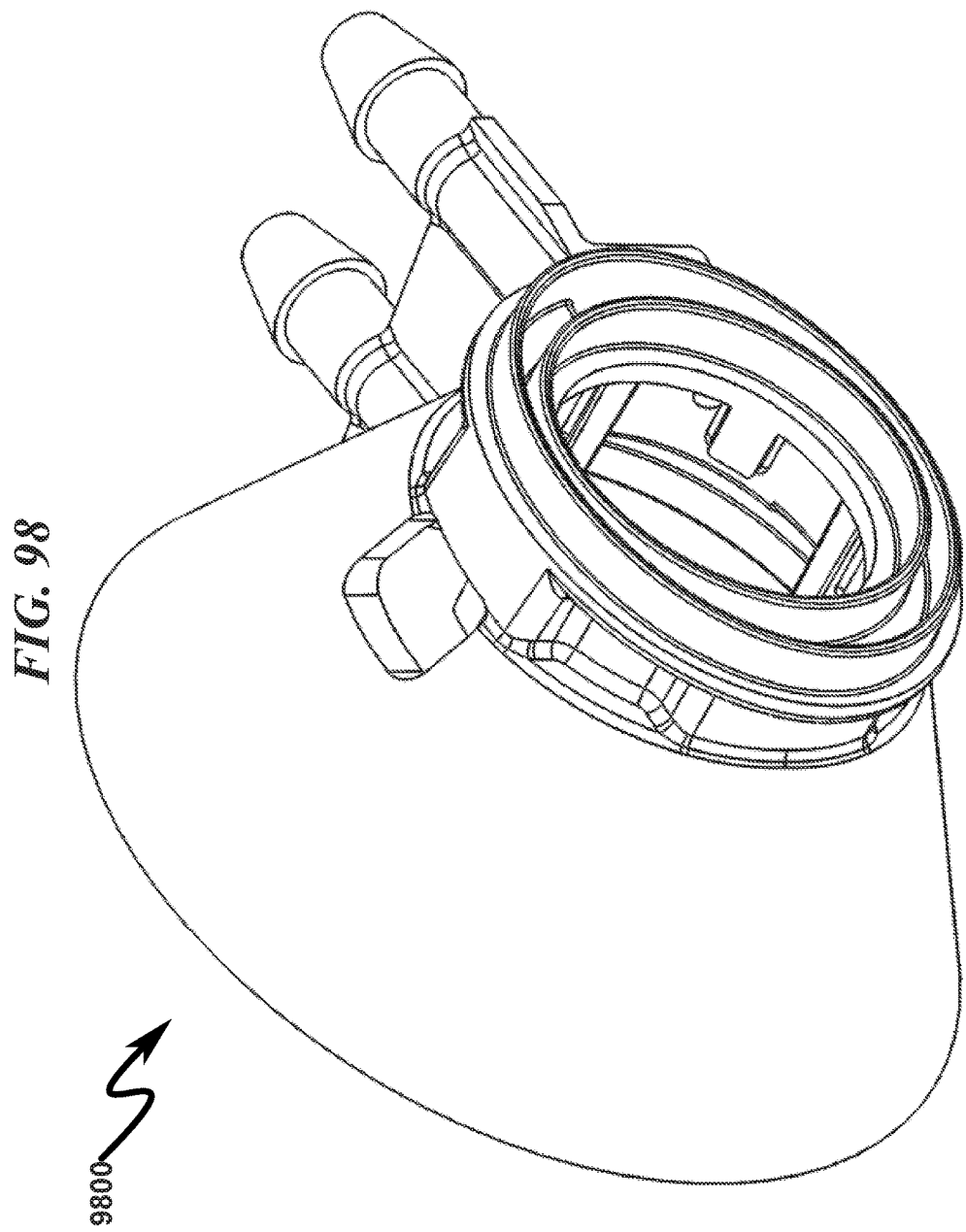
FIG. 98 illustrates a top right rear perspective view of a preferred exemplary ocular patient interface (OPI) embodiment useful in some invention configurations.
Figure 99:
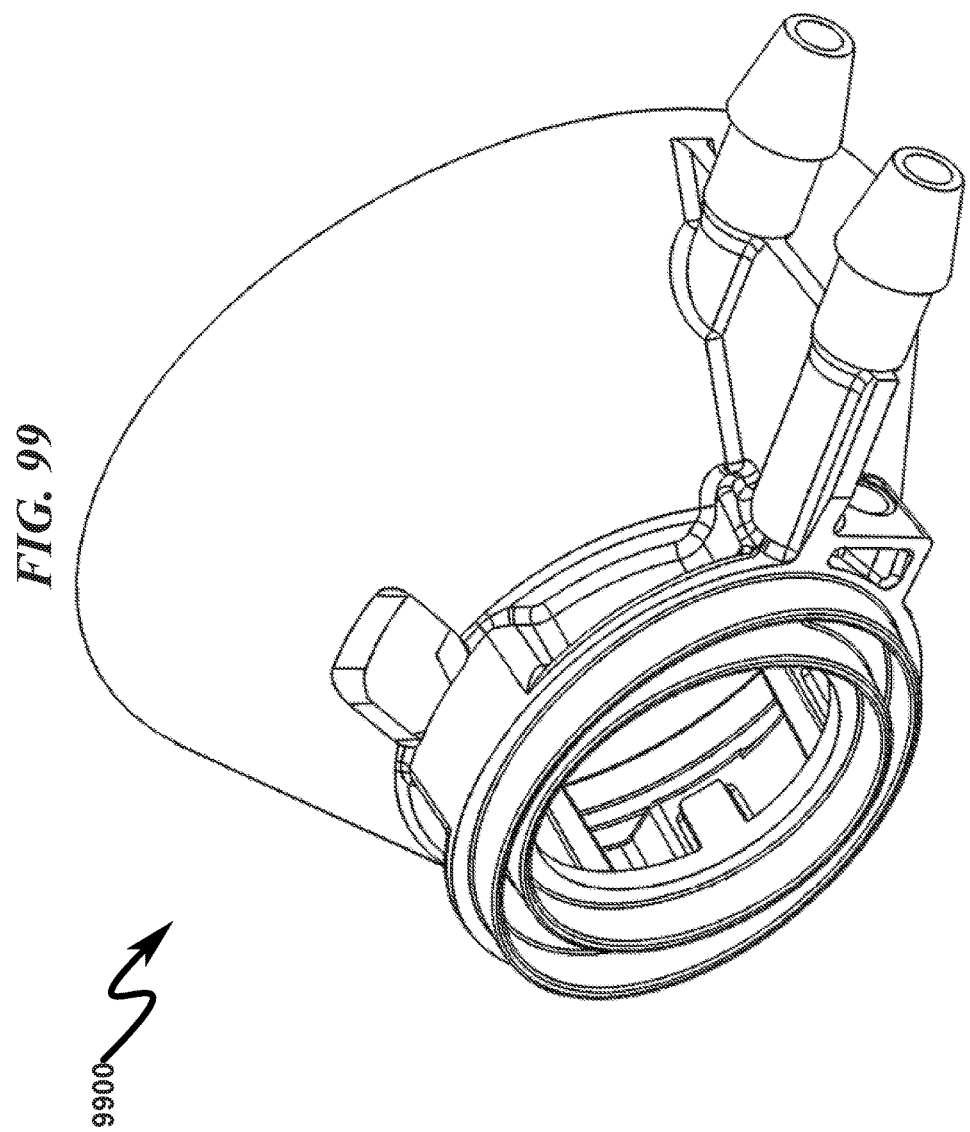
FIG. 99 illustrates a top left rear perspective view of a preferred exemplary ocular patient interface (OPI) embodiment useful in some invention configurations.
Figure 100:
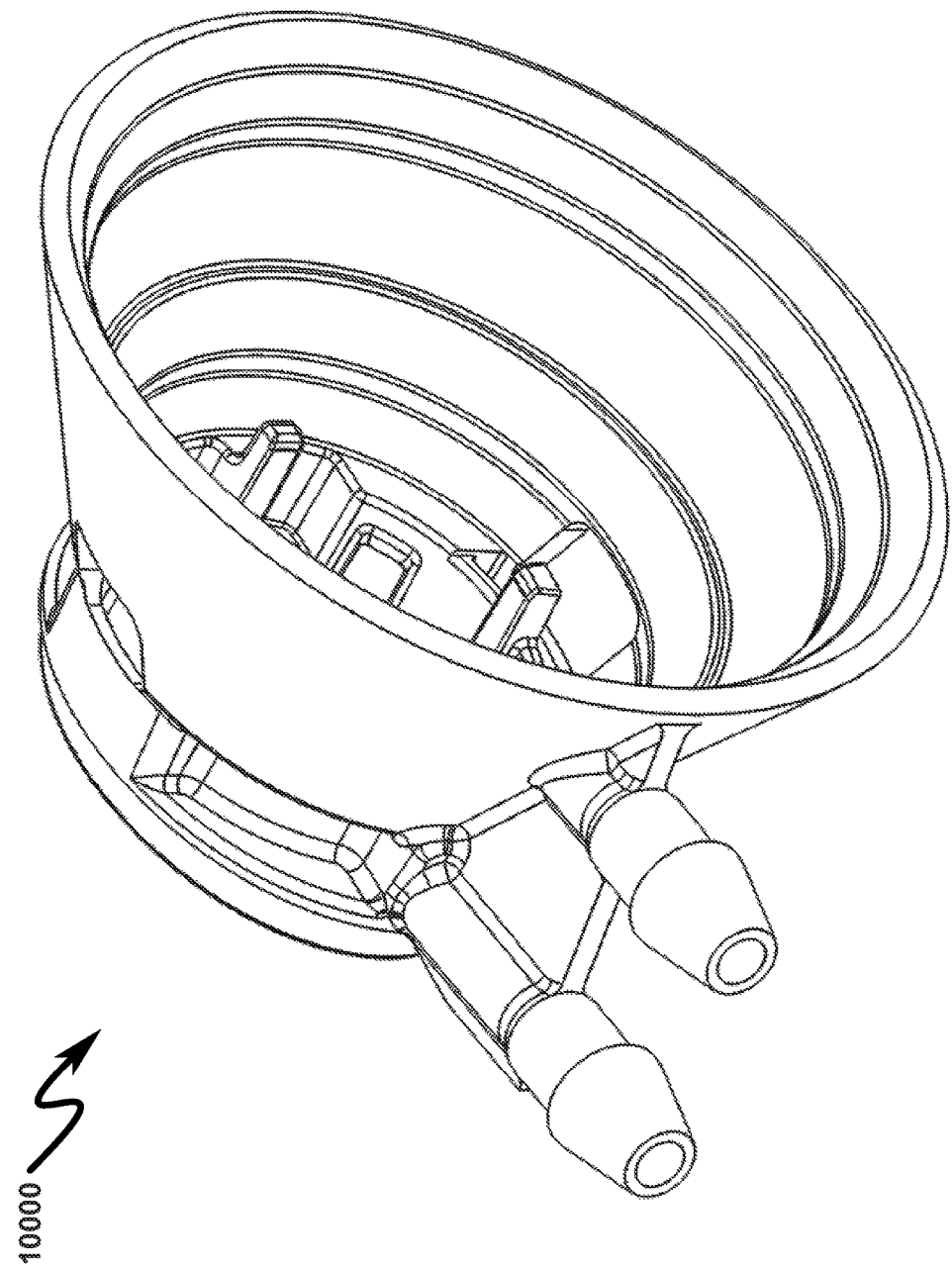
FIG. 100 illustrates a top left front perspective view of a preferred exemplary ocular patient interface (OPI) embodiment useful in some invention configurations.
Figure 101:
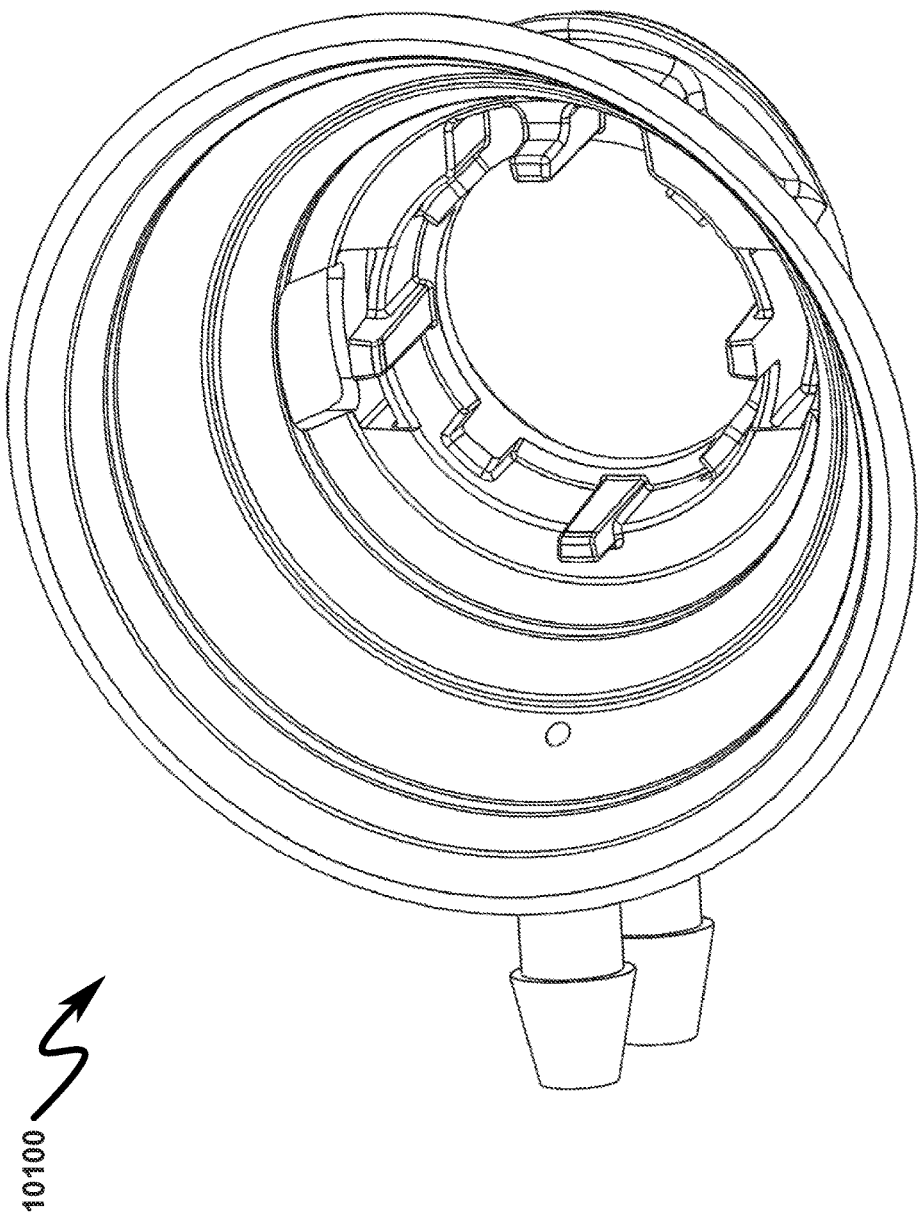
FIG. 101 illustrates a bottom right front perspective view of a preferred exemplary ocular patient interface (OPI) embodiment useful in some invention configurations.
Figure 102:
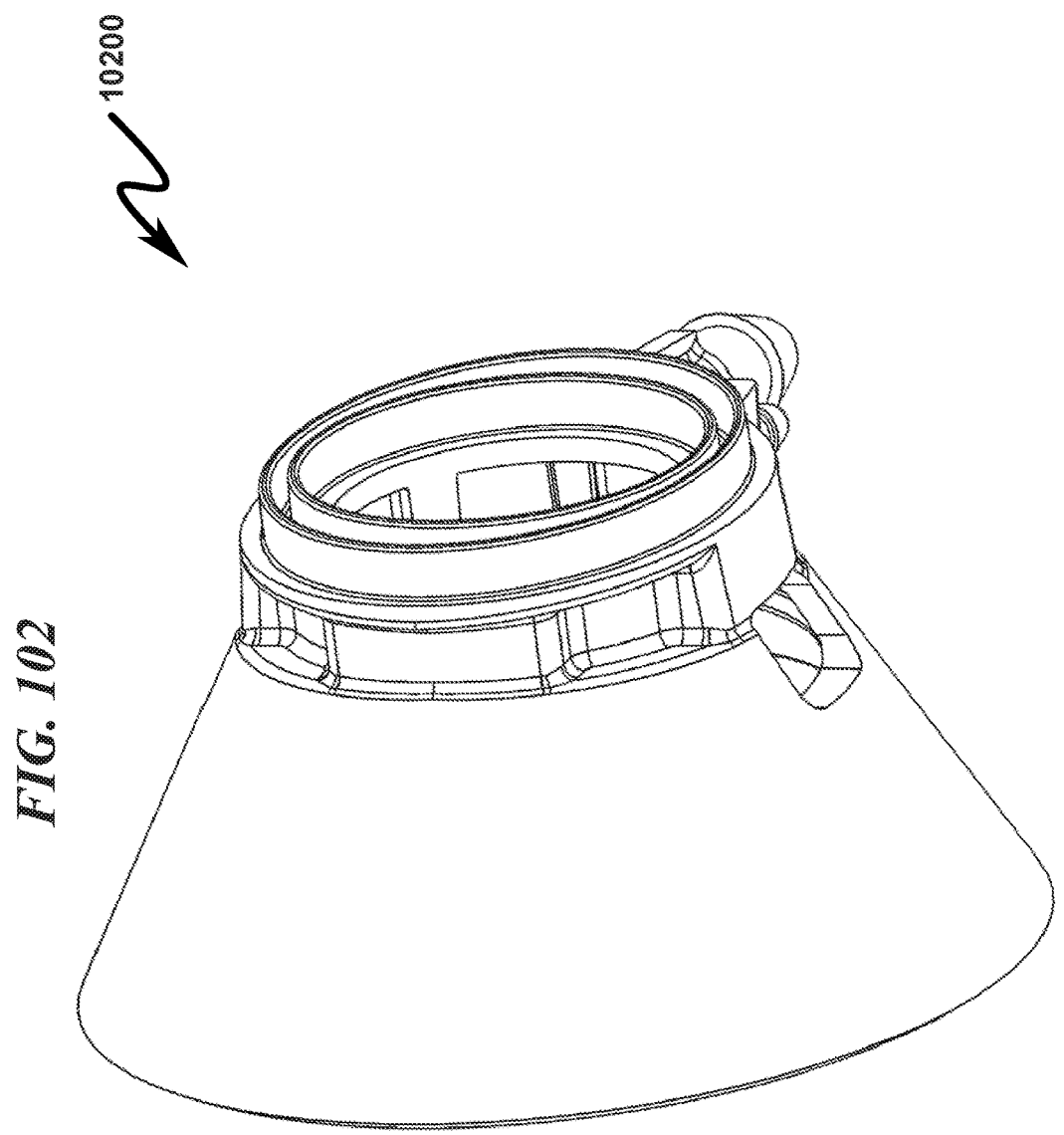
FIG. 102 illustrates a bottom right rear perspective view of a preferred exemplary ocular patient interface (OPI) embodiment useful in some invention configurations.
Figure 103:
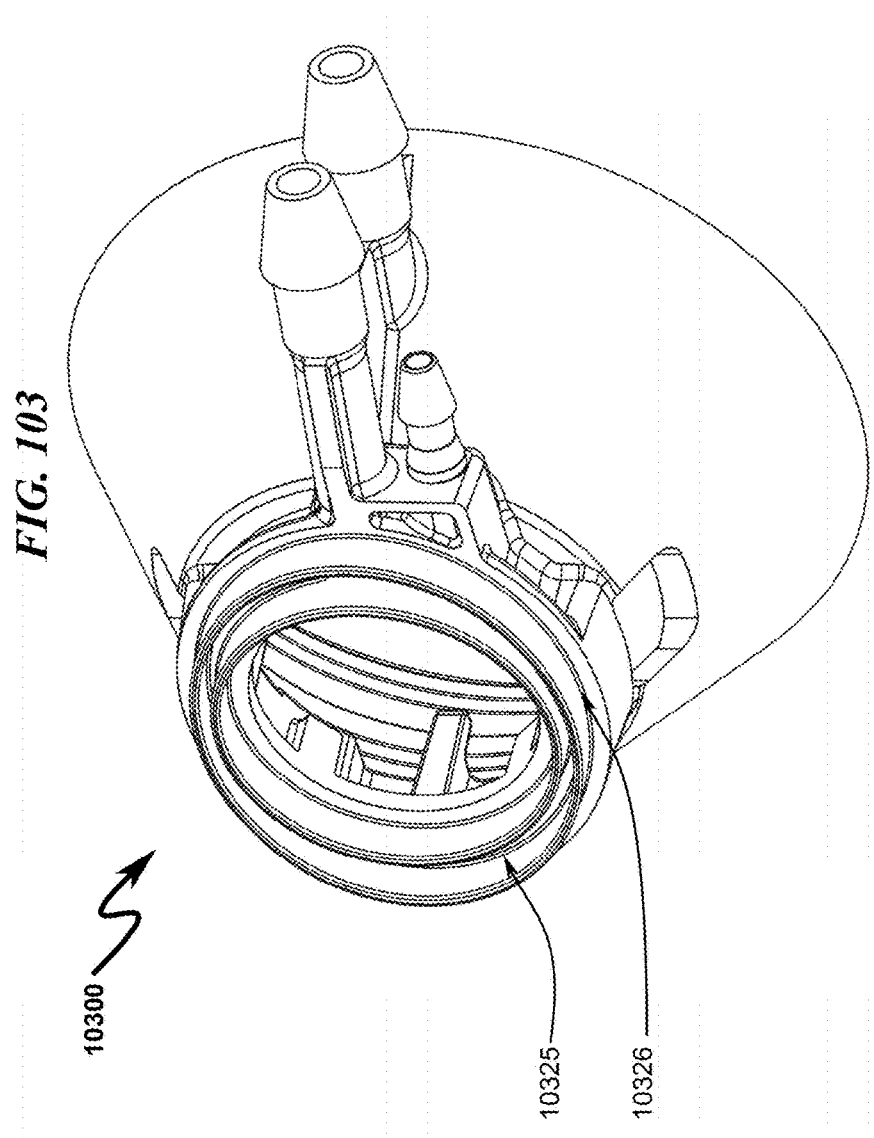
FIG. 103 illustrates a bottom left rear perspective view of a preferred exemplary ocular patient interface (OPI) embodiment useful in some invention configurations.
Figure 105:
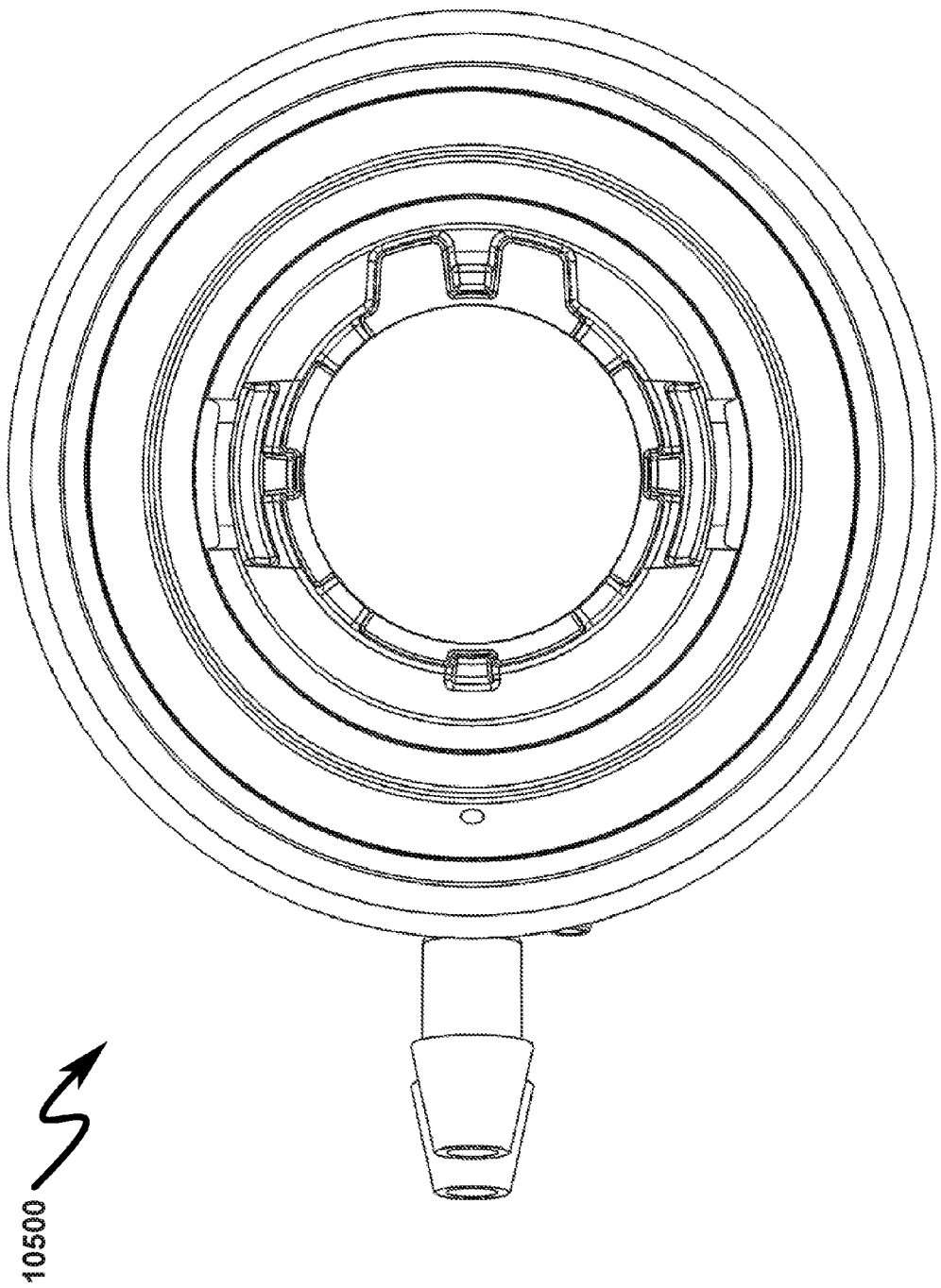
FIG. 105 illustrates a front view of a preferred exemplary ocular patient interface (OPI) embodiment useful in some invention configurations.
Figure 106:
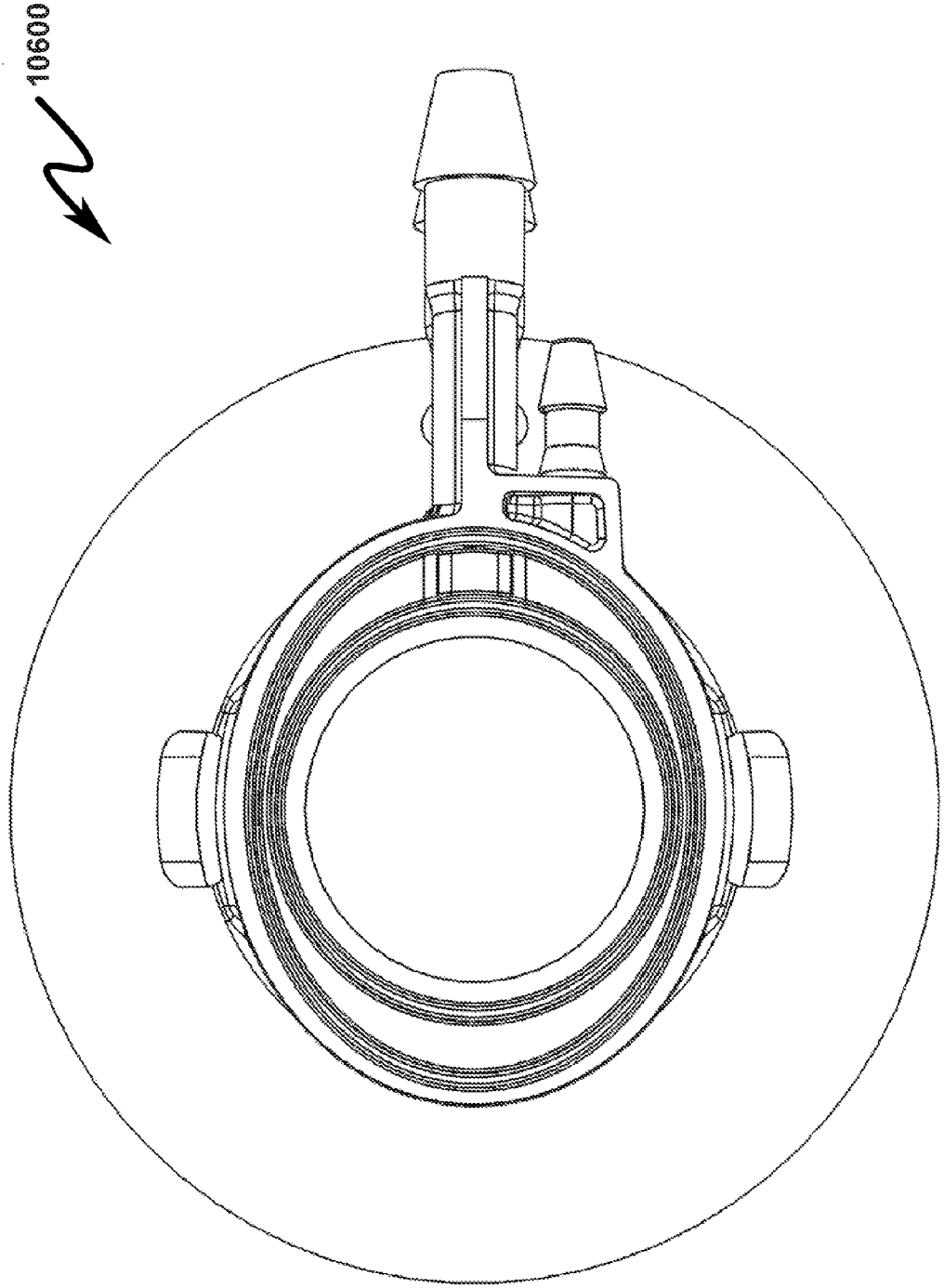
FIG. 106 illustrates a rear view of a preferred exemplary ocular patient interface (OPI) embodiment useful in some invention configurations.
Figure 107:
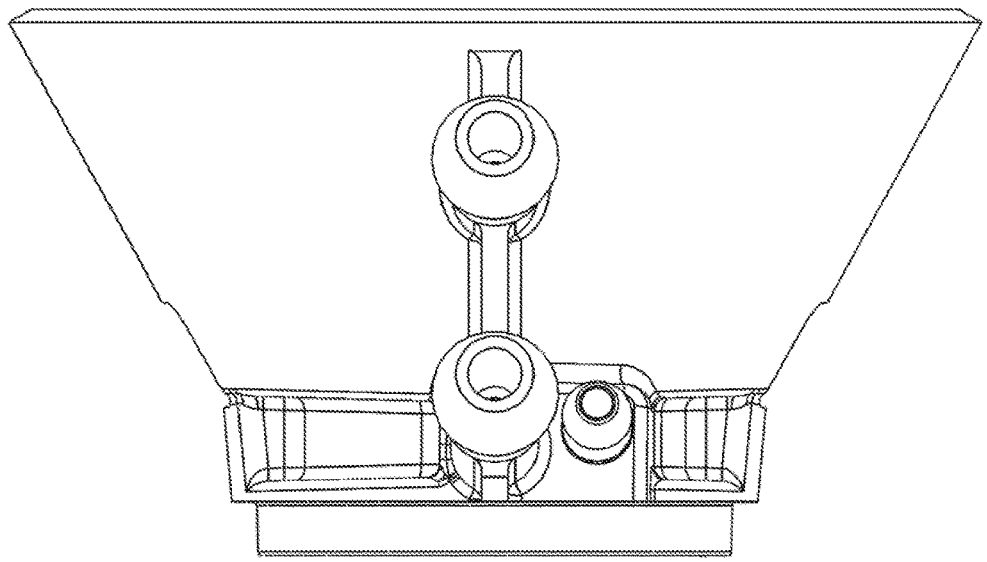
FIG. 107 illustrates a left view of a preferred exemplary ocular patient interface (OPI) embodiment useful in some invention configurations.
Figure 108:
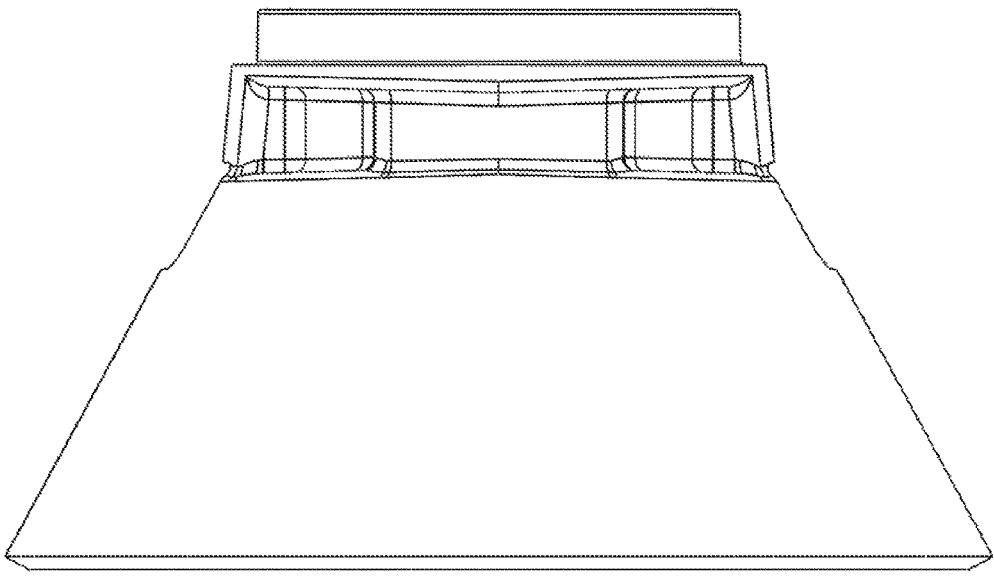
FIG. 108 illustrates a right view of a preferred exemplary ocular patient interface (OPI) embodiment useful in some invention configurations.
Figure 109:
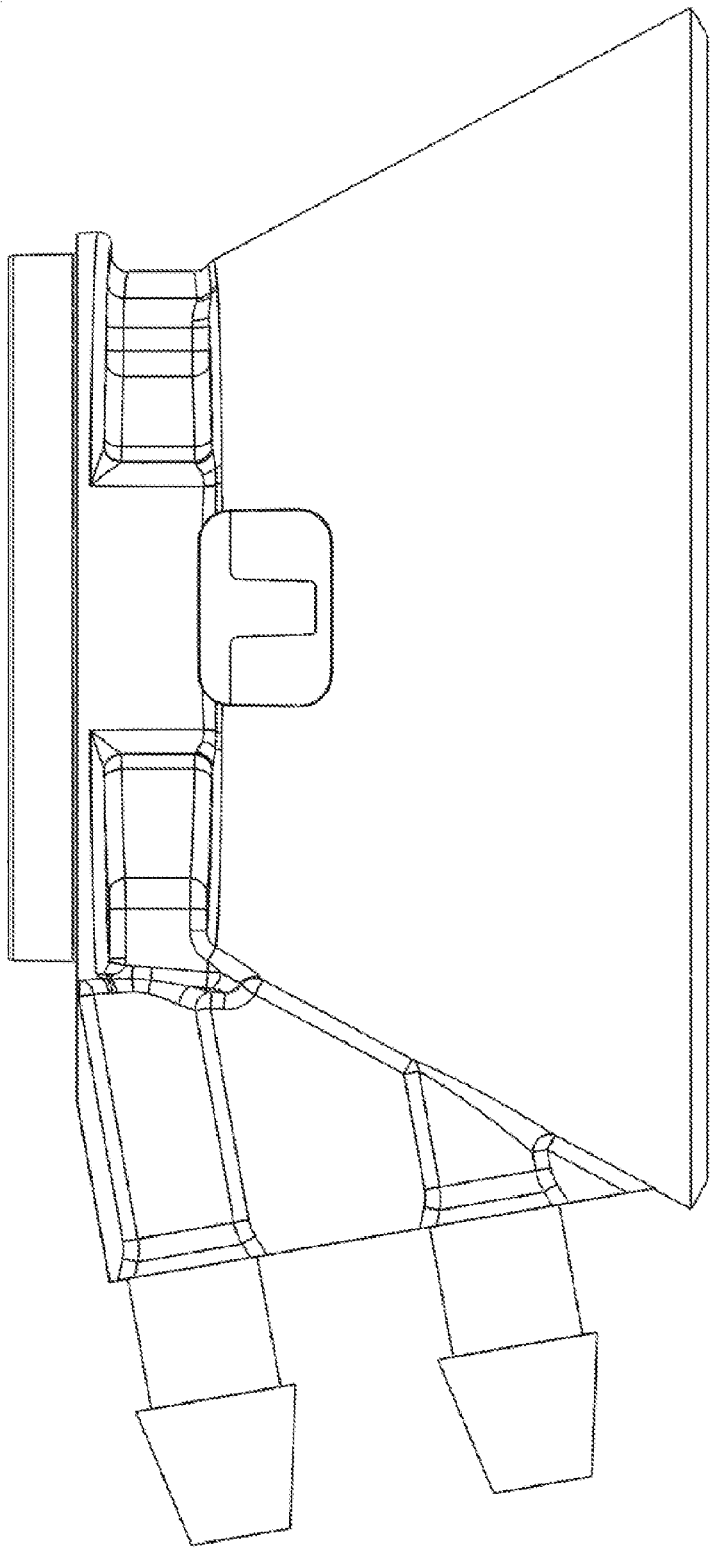
FIG. 109 illustrates a top view of a preferred exemplary ocular patient interface (OPI) embodiment useful in some invention configurations.
Figure 110:
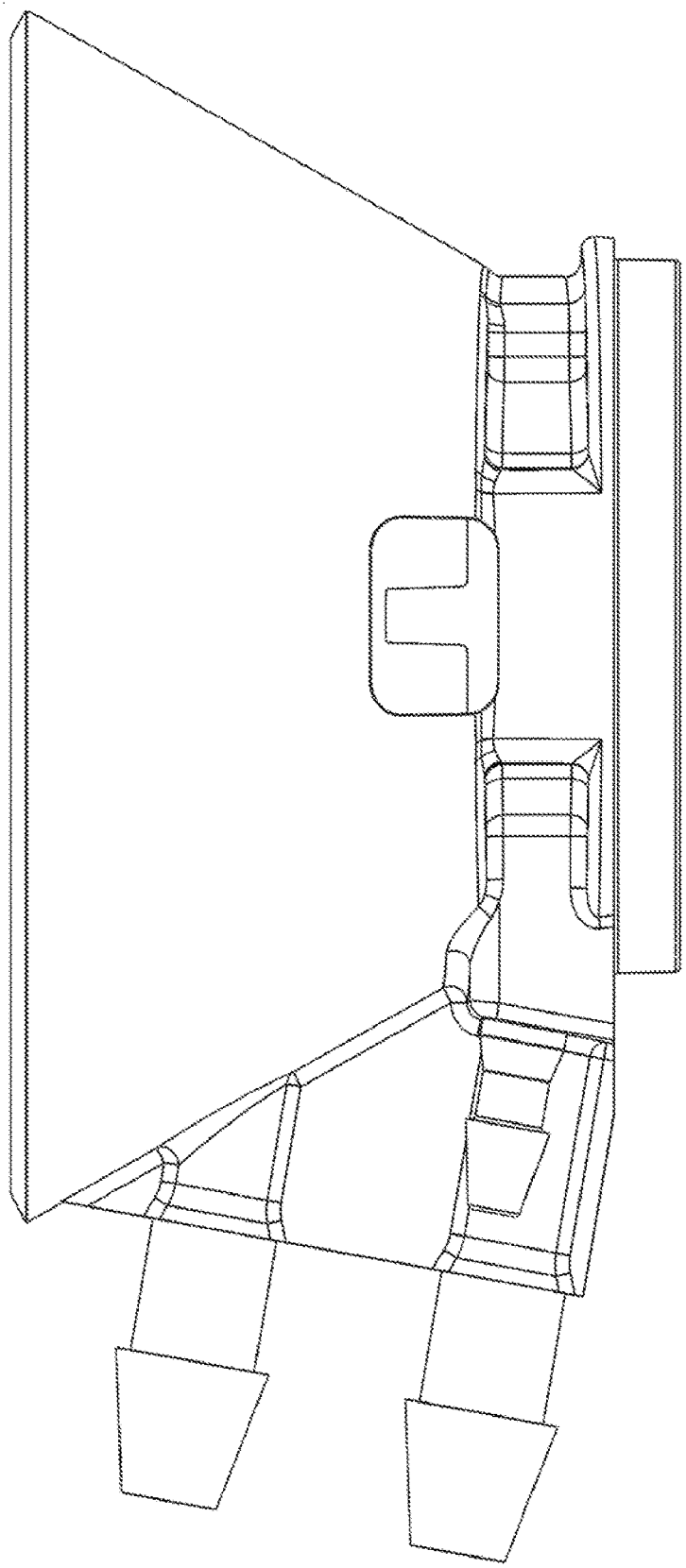
FIG. 110 illustrates a bottom view of a preferred exemplary ocular patient interface (OPI) embodiment useful in some invention configurations.
Figure 111:
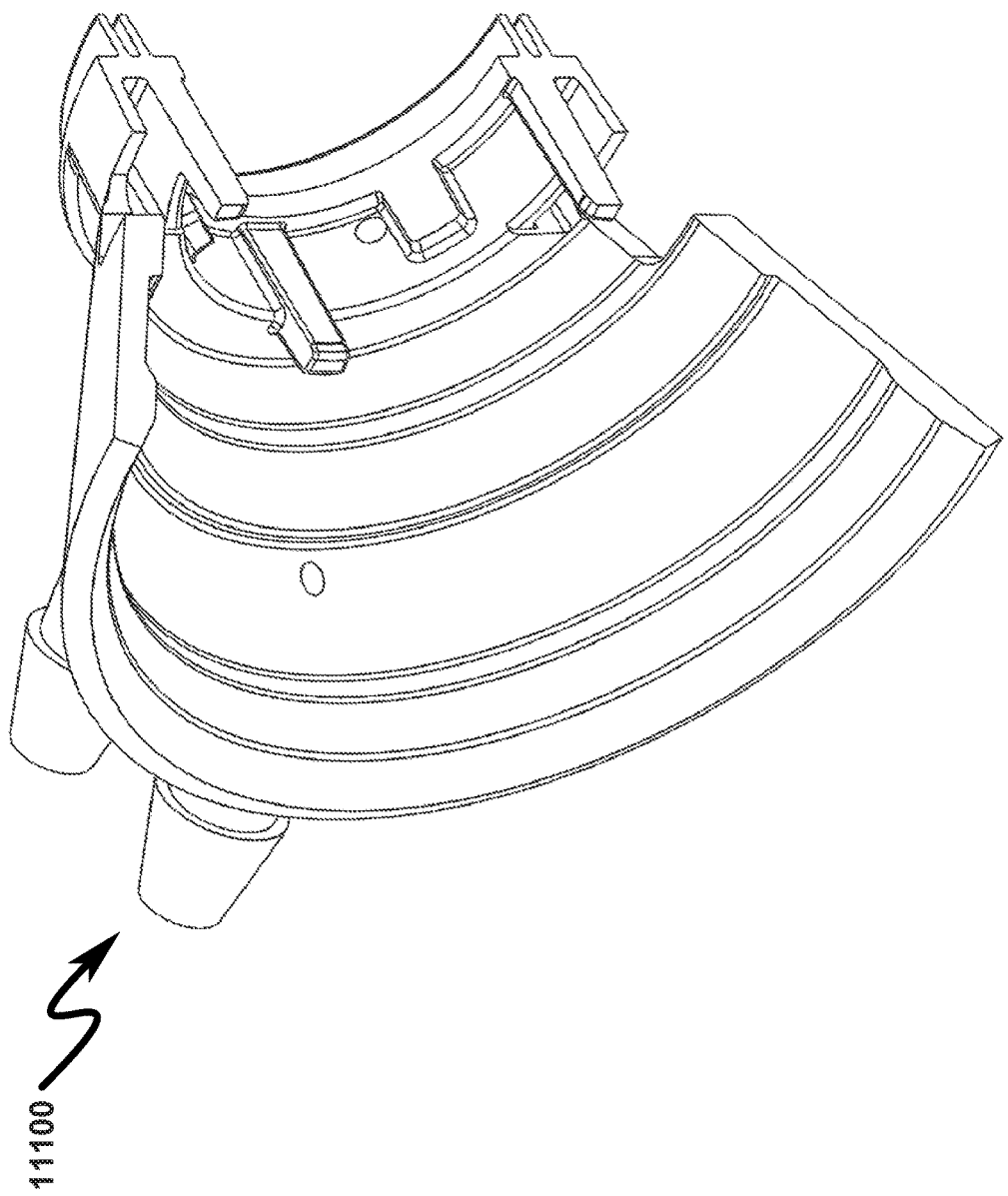
FIG. 111 illustrates a right section perspective view of a preferred exemplary ocular patient interface (OPI) embodiment useful in some invention configurations.
Figure 112:
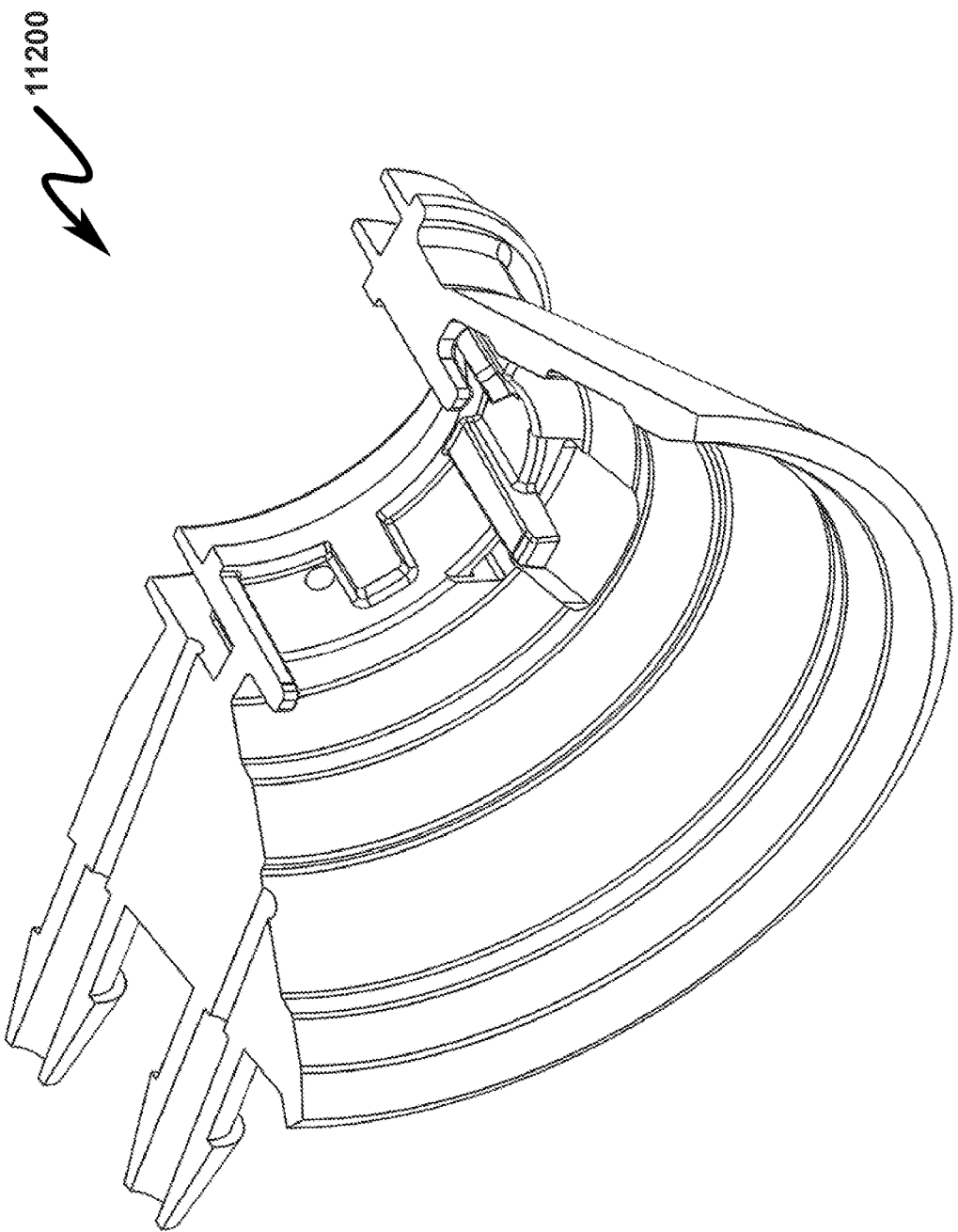
FIG. 112 illustrates a top section perspective view of a preferred exemplary ocular patient interface (OPI) embodiment useful in some invention configurations.

A preferred exemplary embodiment of a typical ocular patient interface (OPI) is generally depicted in the detail views presented in FIG. 97 (9700)-FIG. 112 (11200).

Exemplary Ocular Suction Ring (OSR) (11300)-(12800)

Figure 113:
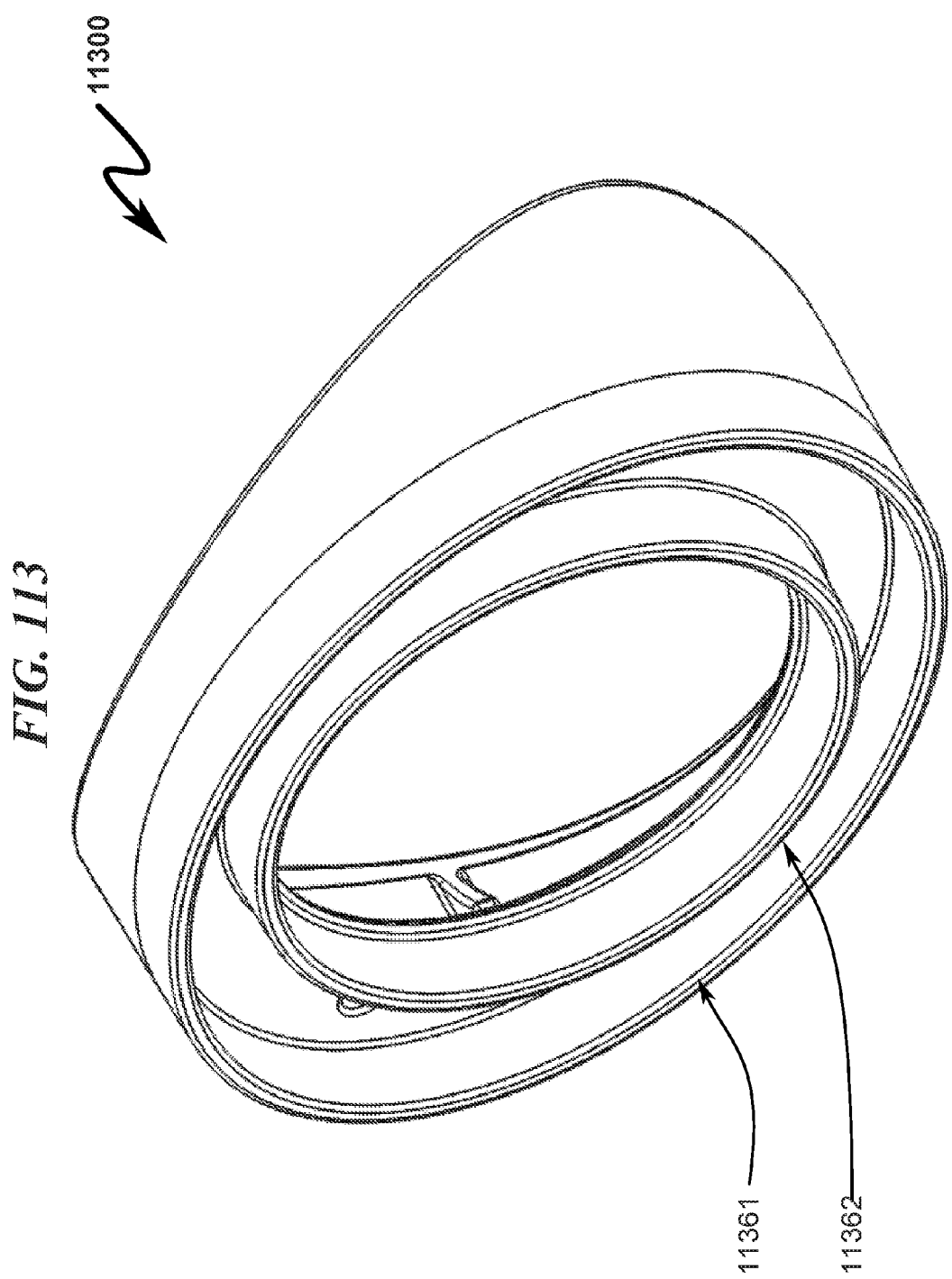
FIG. 113 illustrates a top right front perspective view of a preferred exemplary ocular suction ring (OSR) embodiment useful in some invention configurations.
Figure 114:
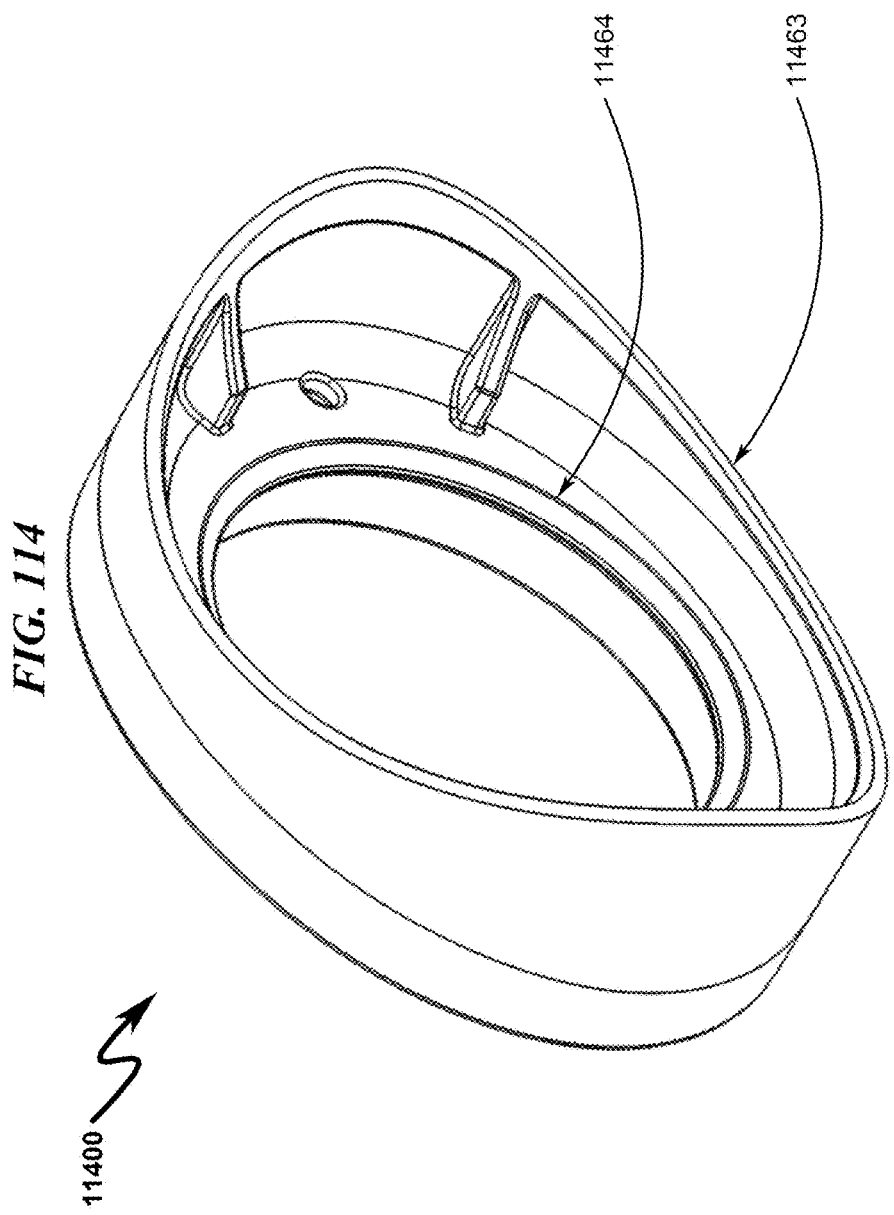
FIG. 114 illustrates a top right rear perspective view of a preferred exemplary ocular suction ring (OSR) embodiment useful in some invention configurations.
Figure 115:
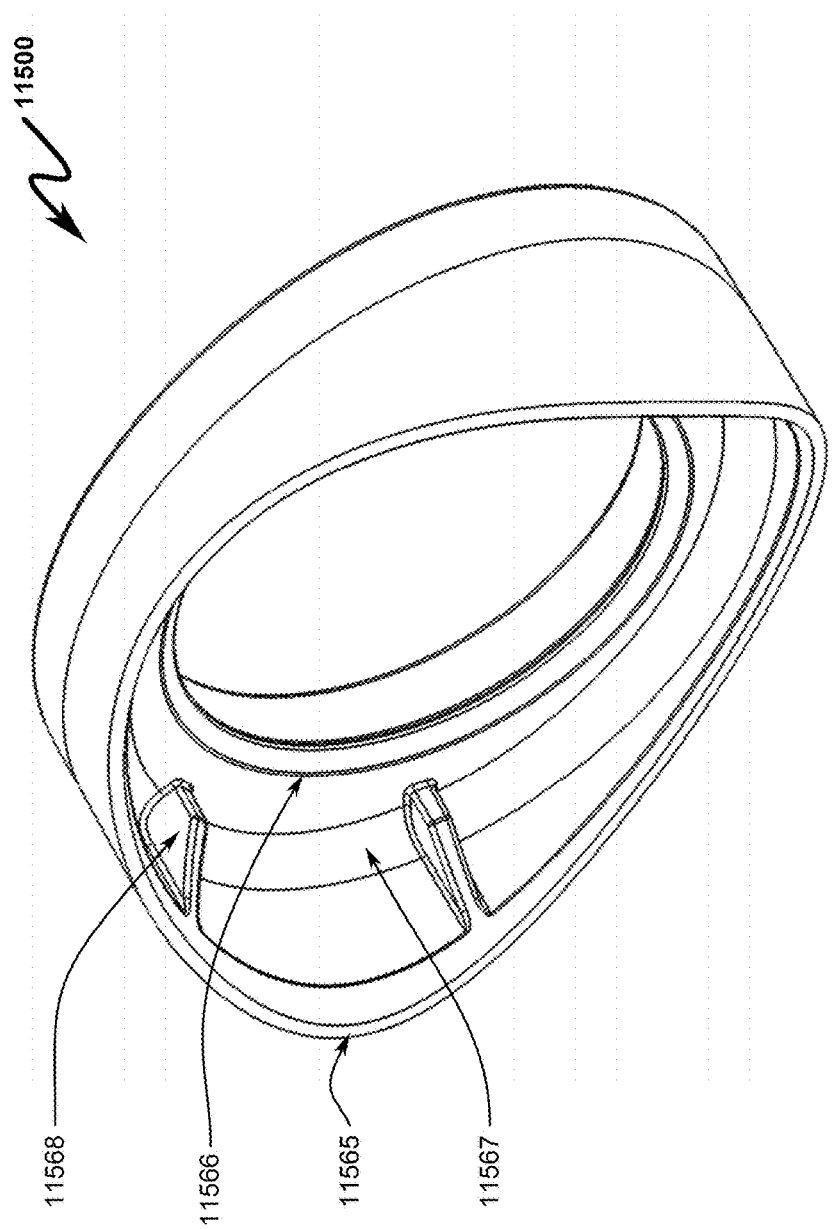
FIG. 115 illustrates a top left rear perspective view of a preferred exemplary ocular suction ring (OSR) embodiment useful in some invention configurations.
Figure 116:
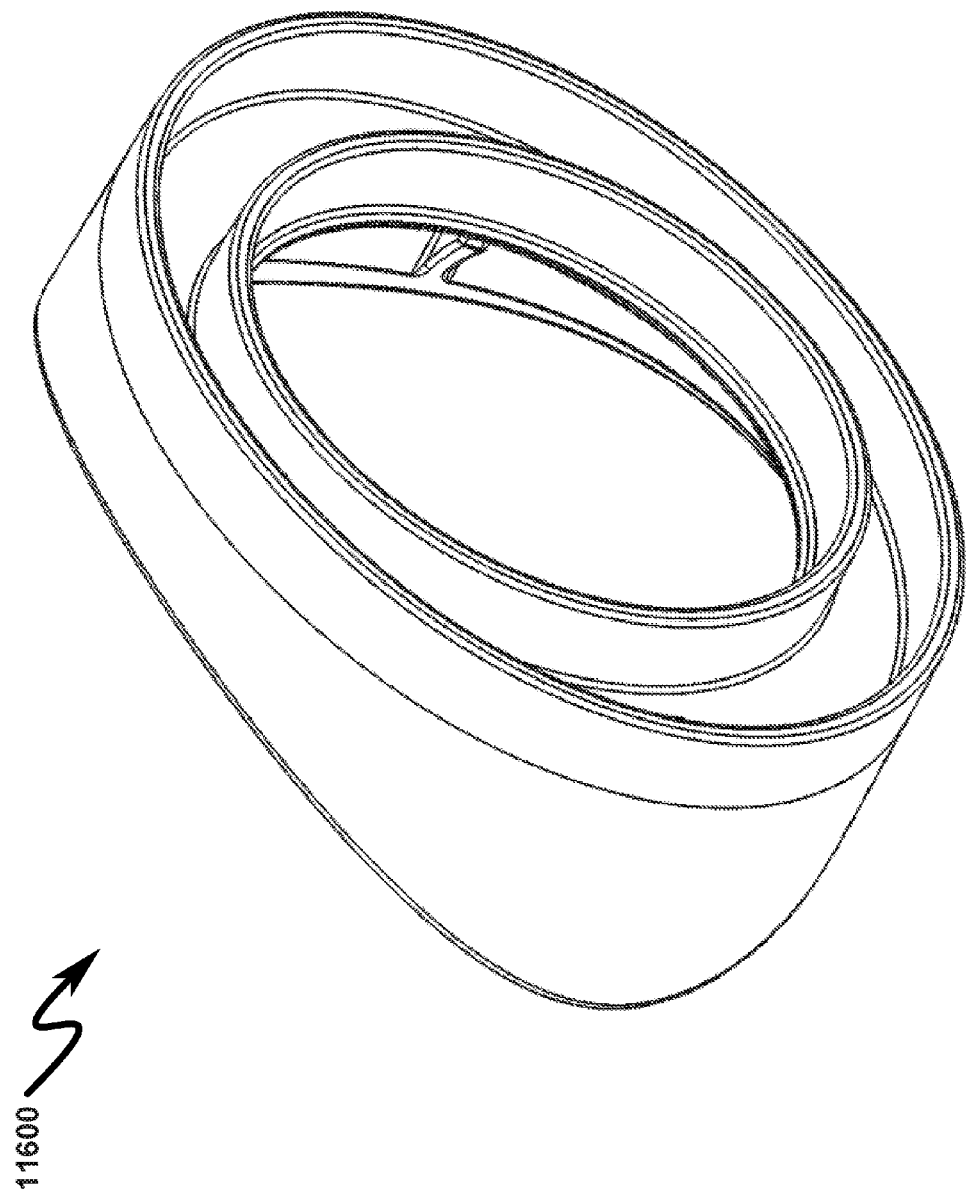
FIG. 116 illustrates a top left front perspective view of a preferred exemplary ocular suction ring (OSR) embodiment useful in some invention configurations.
Figure 117:
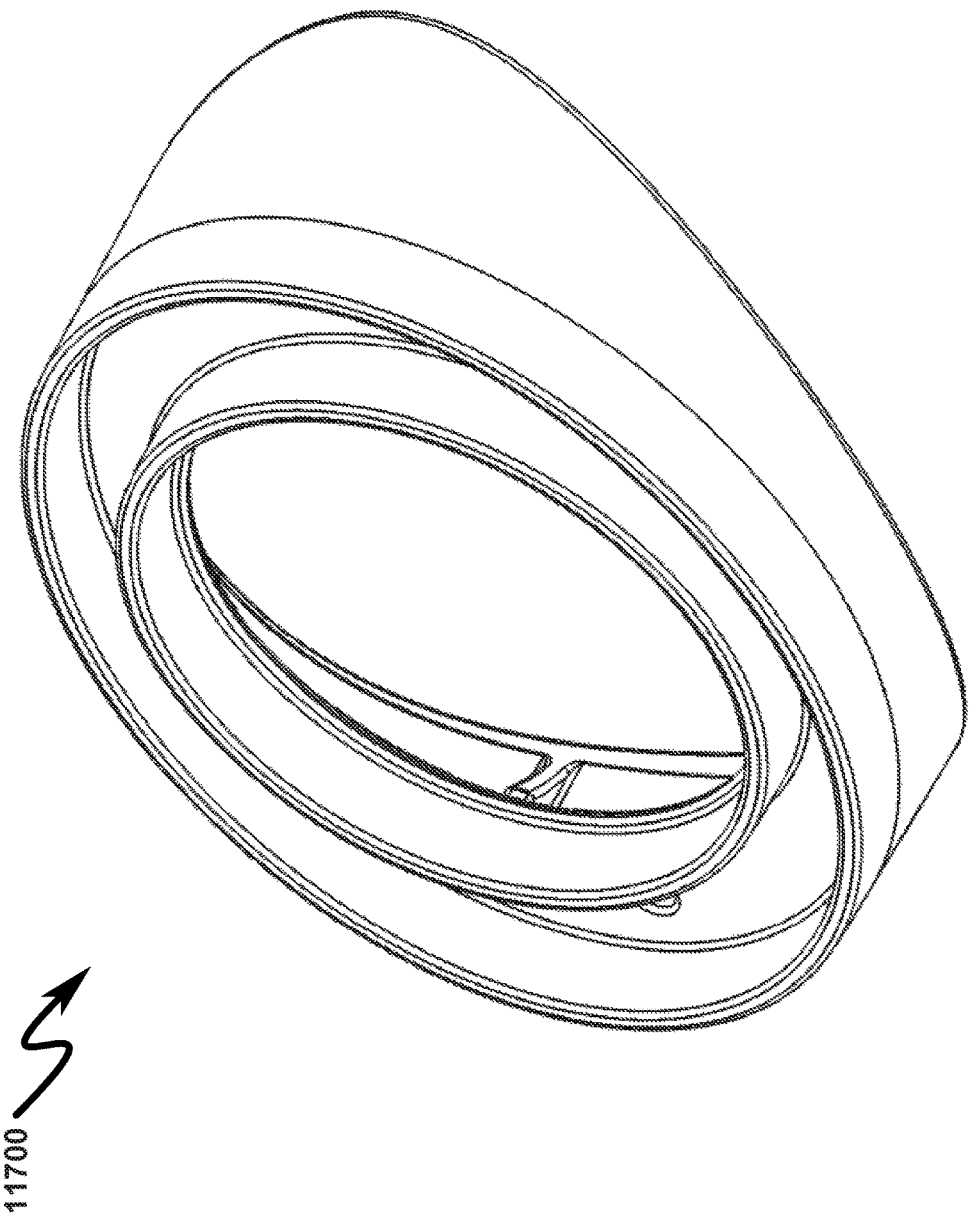
FIG. 117 illustrates a bottom right front perspective view of a preferred exemplary ocular suction ring (OSR) embodiment useful in some invention configurations.
Figure 118:
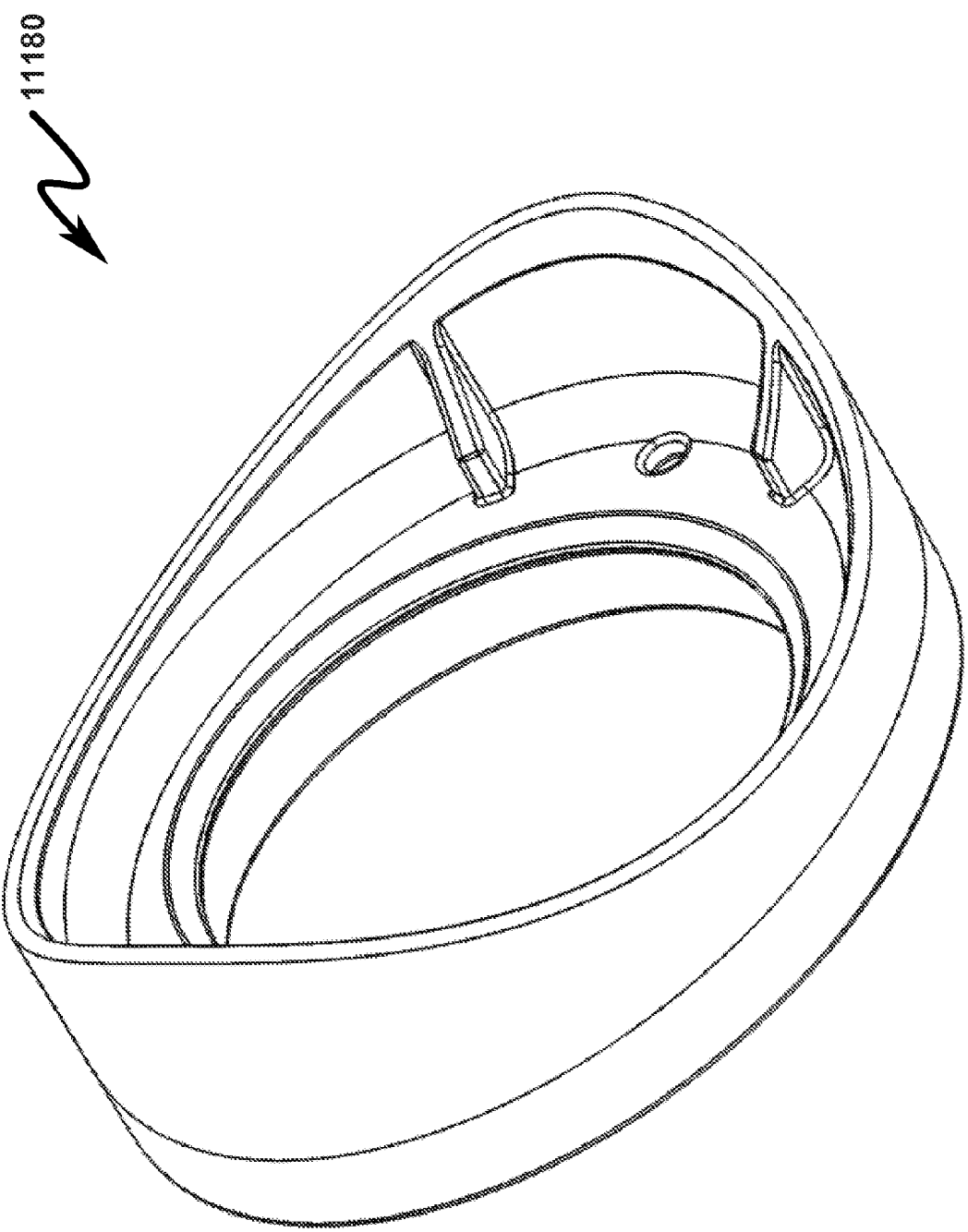
FIG. 118 illustrates a bottom right rear perspective view of a preferred exemplary ocular suction ring (OSR) embodiment useful in some invention configurations.
Figure 119:
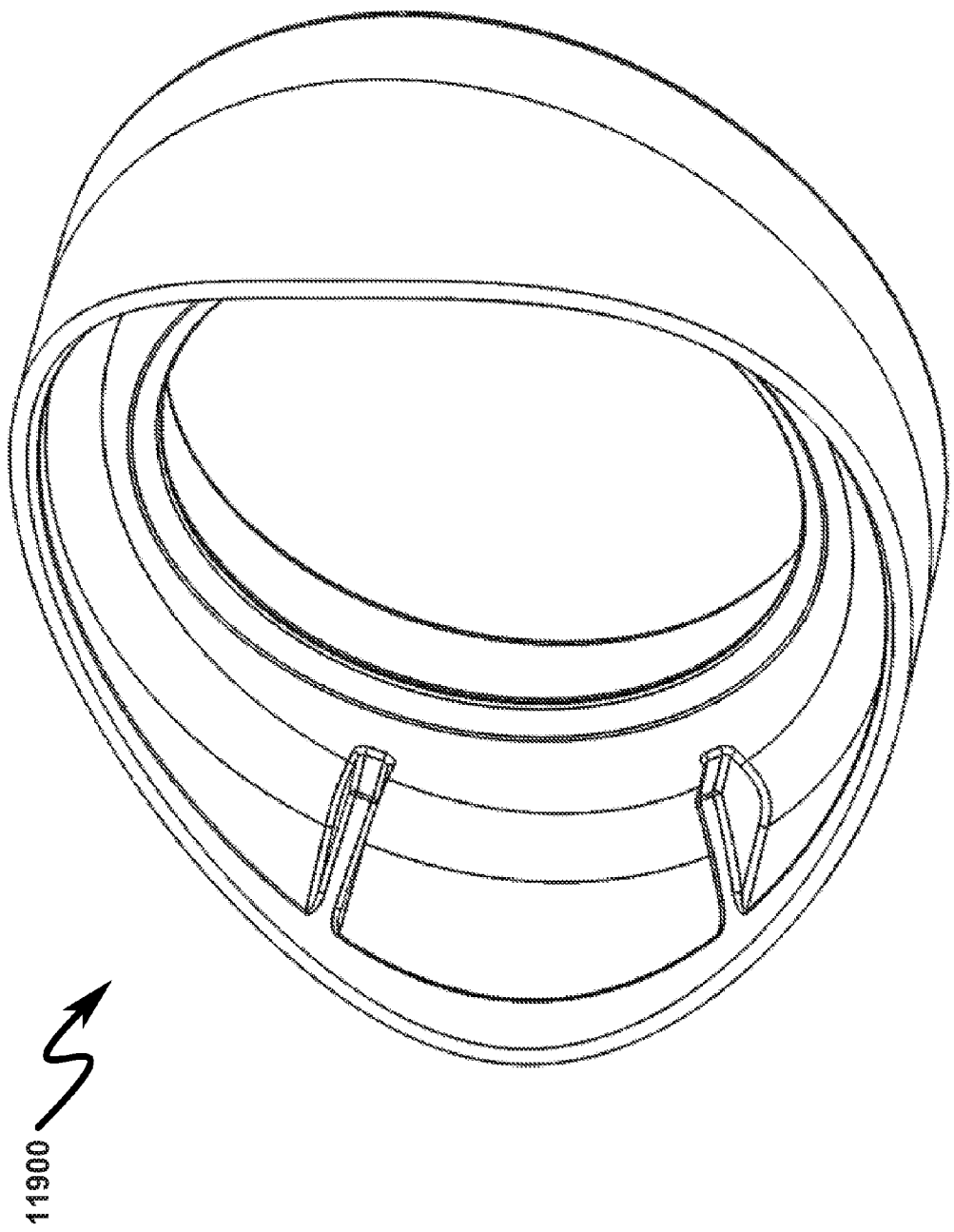
Figure 120:
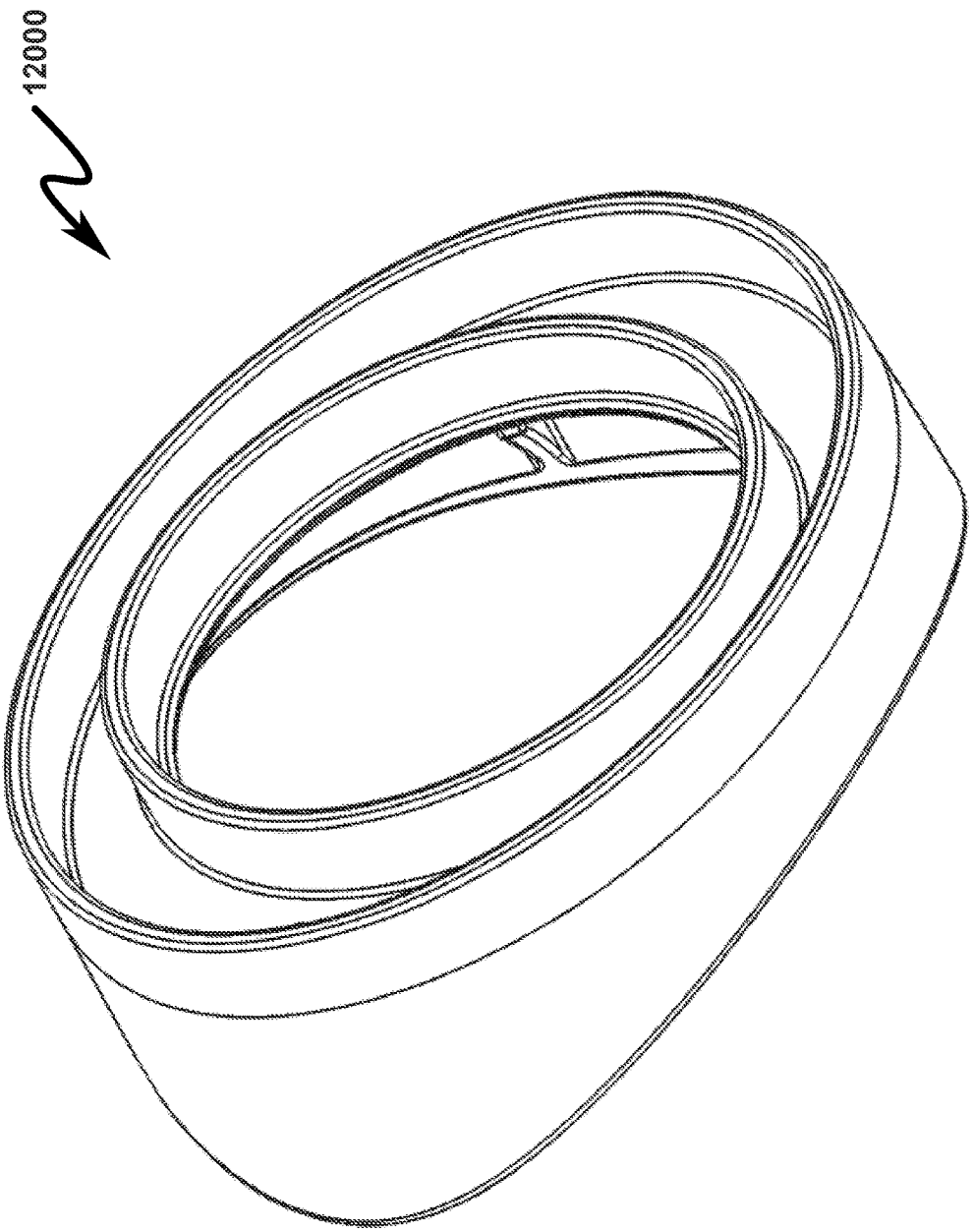
Figure 121:
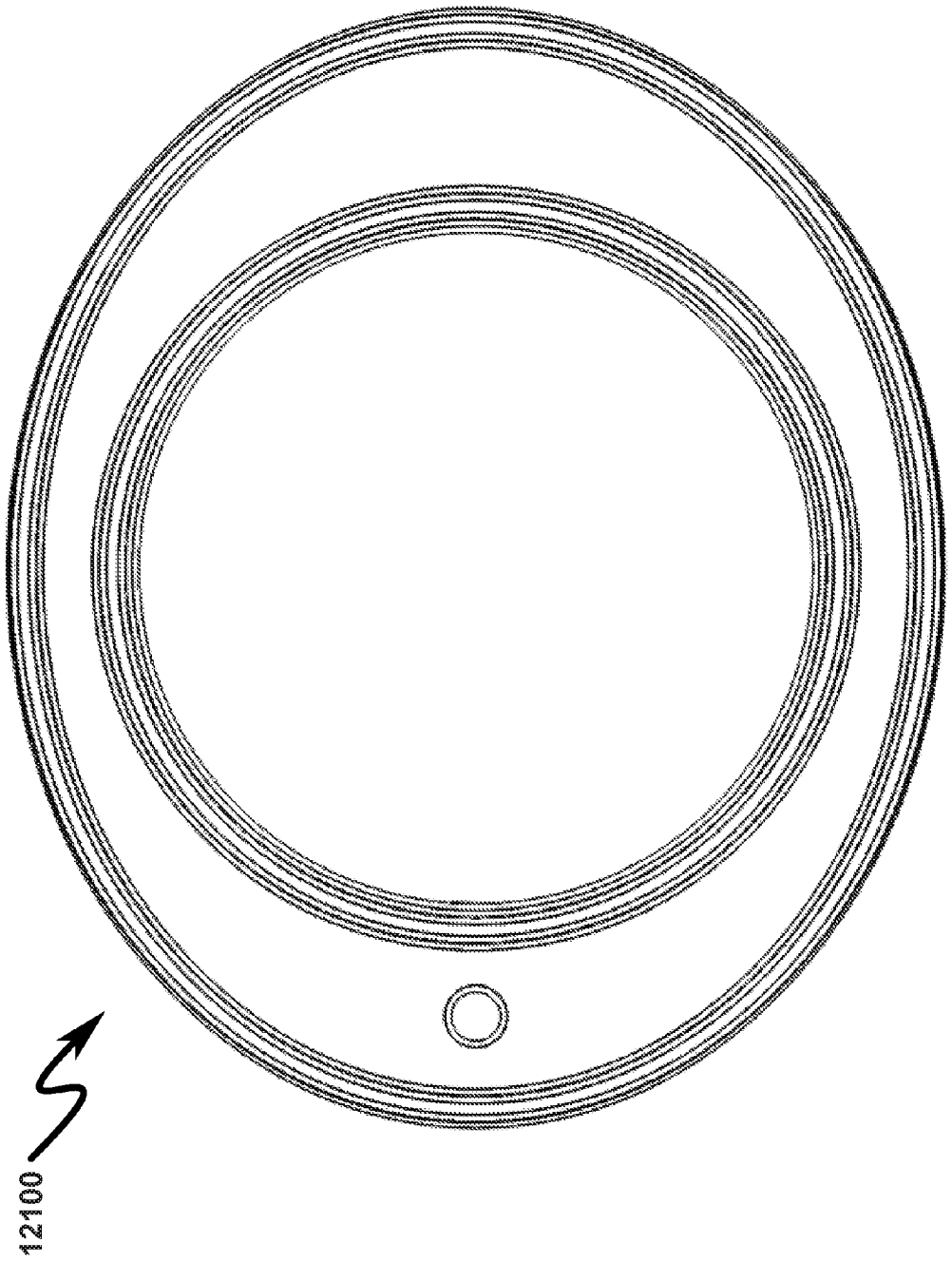
Figure 122:
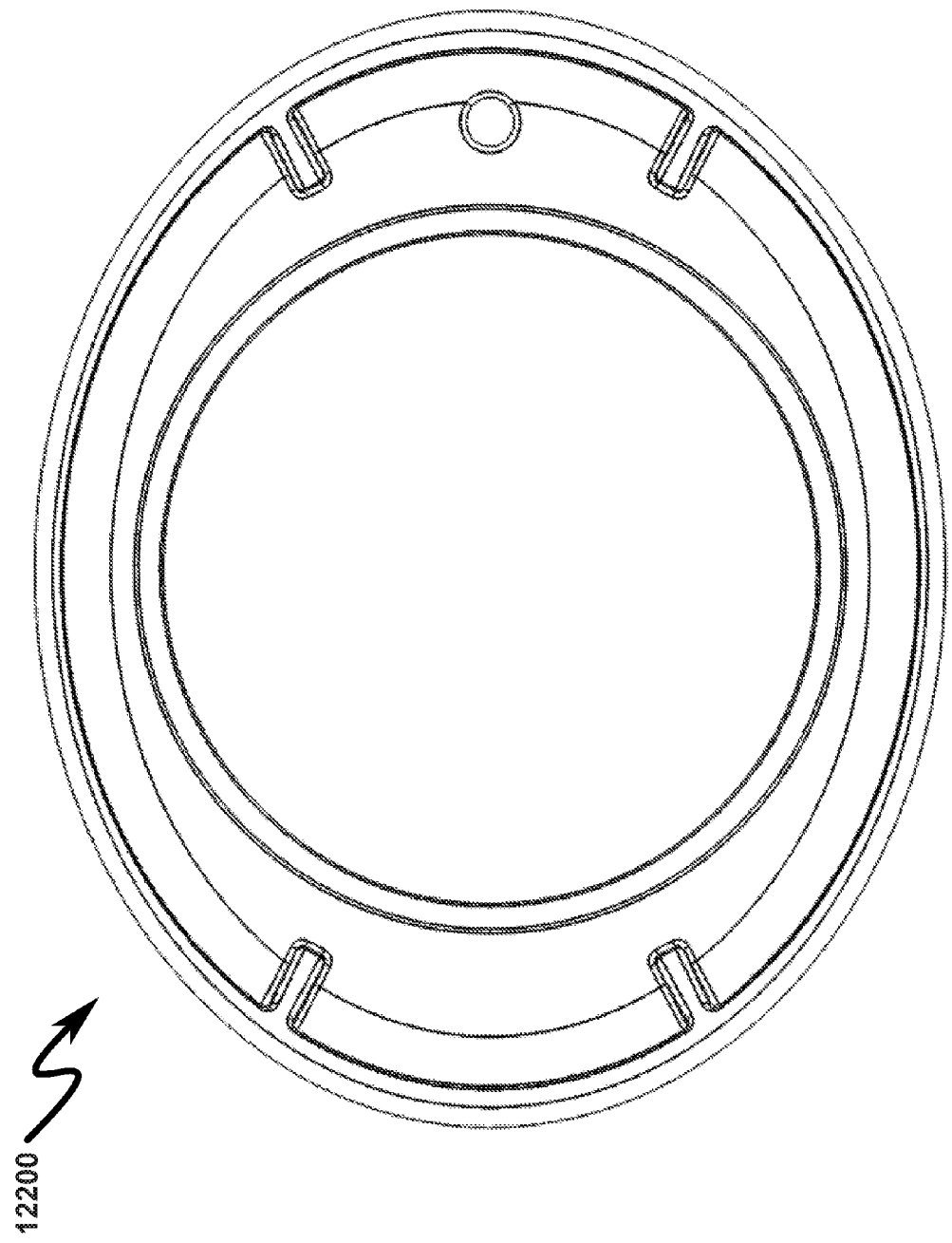
Figure 123:
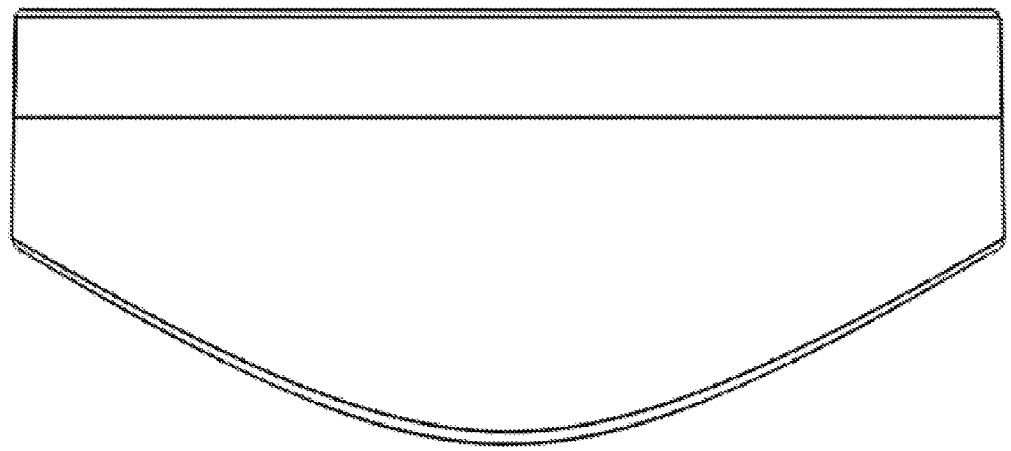
Figure 124:
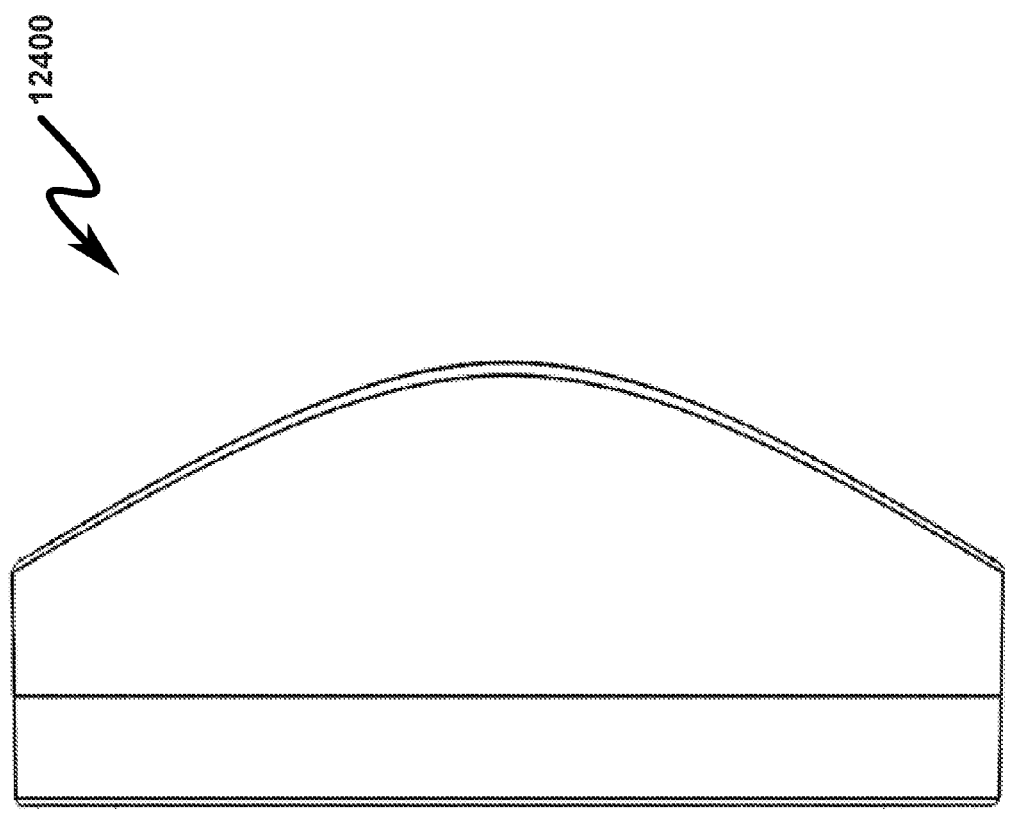
Figure 125:
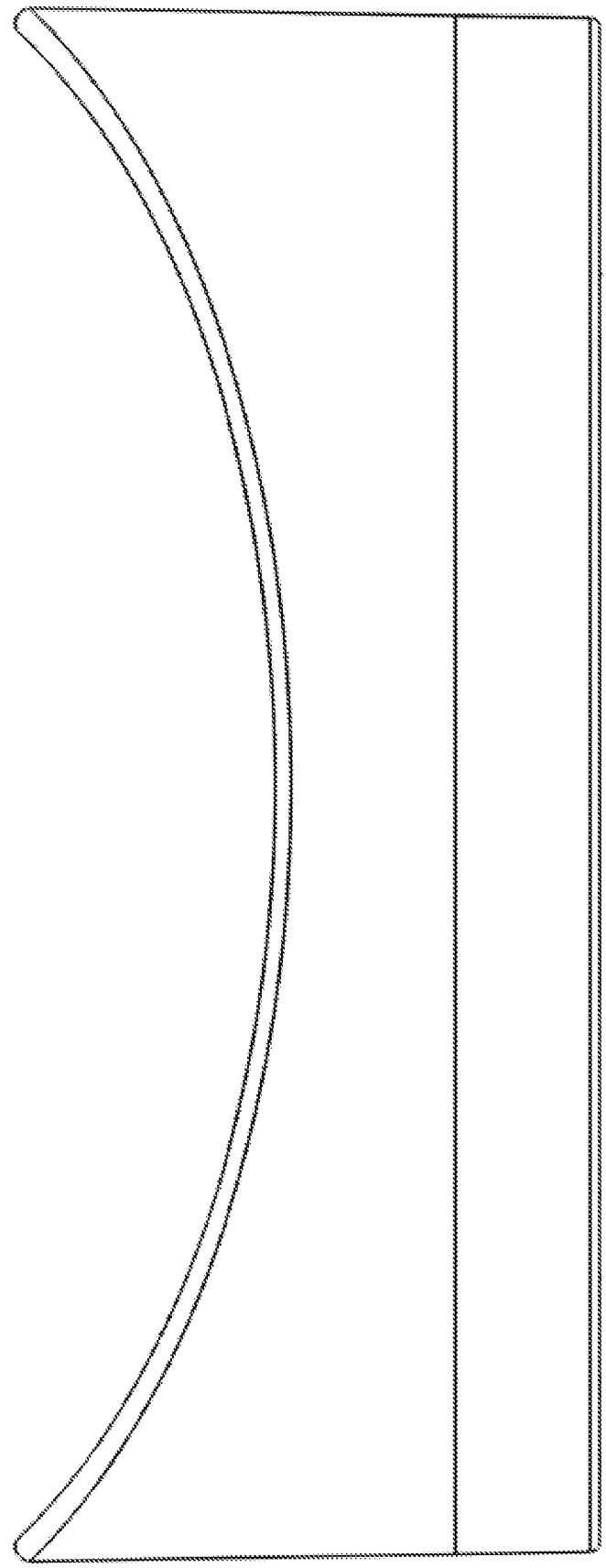
Figure 126:
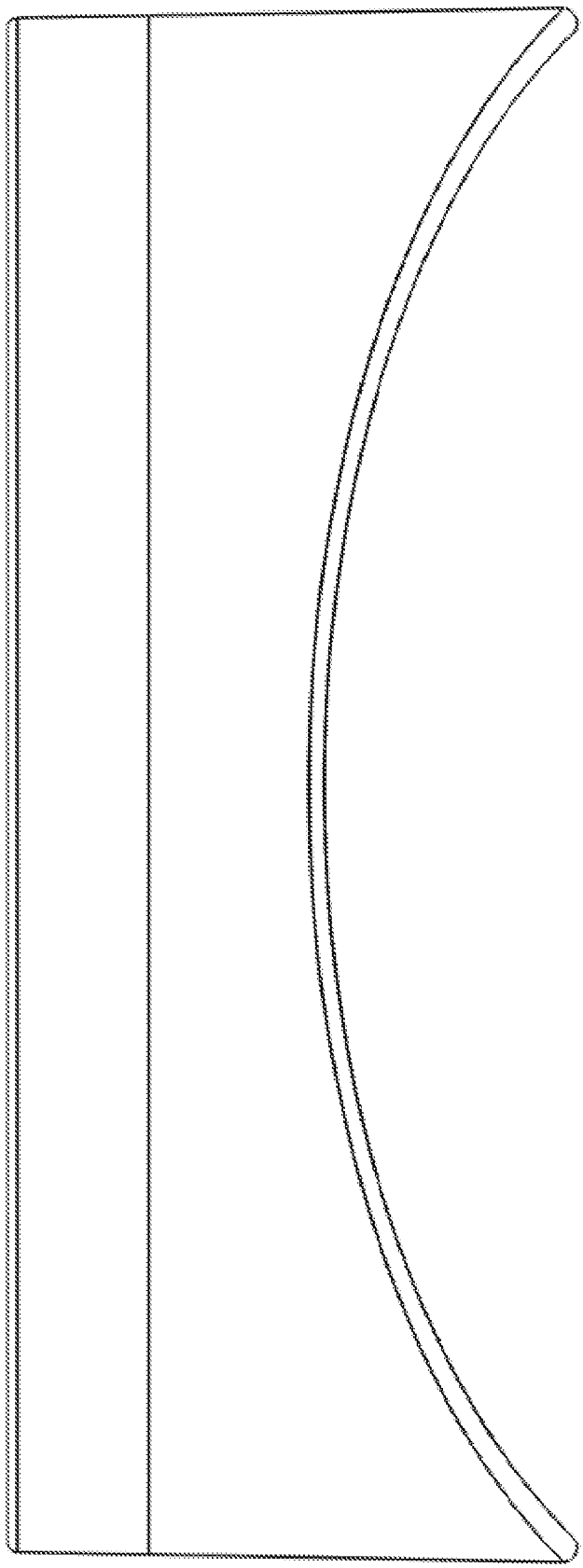
Figure 127:
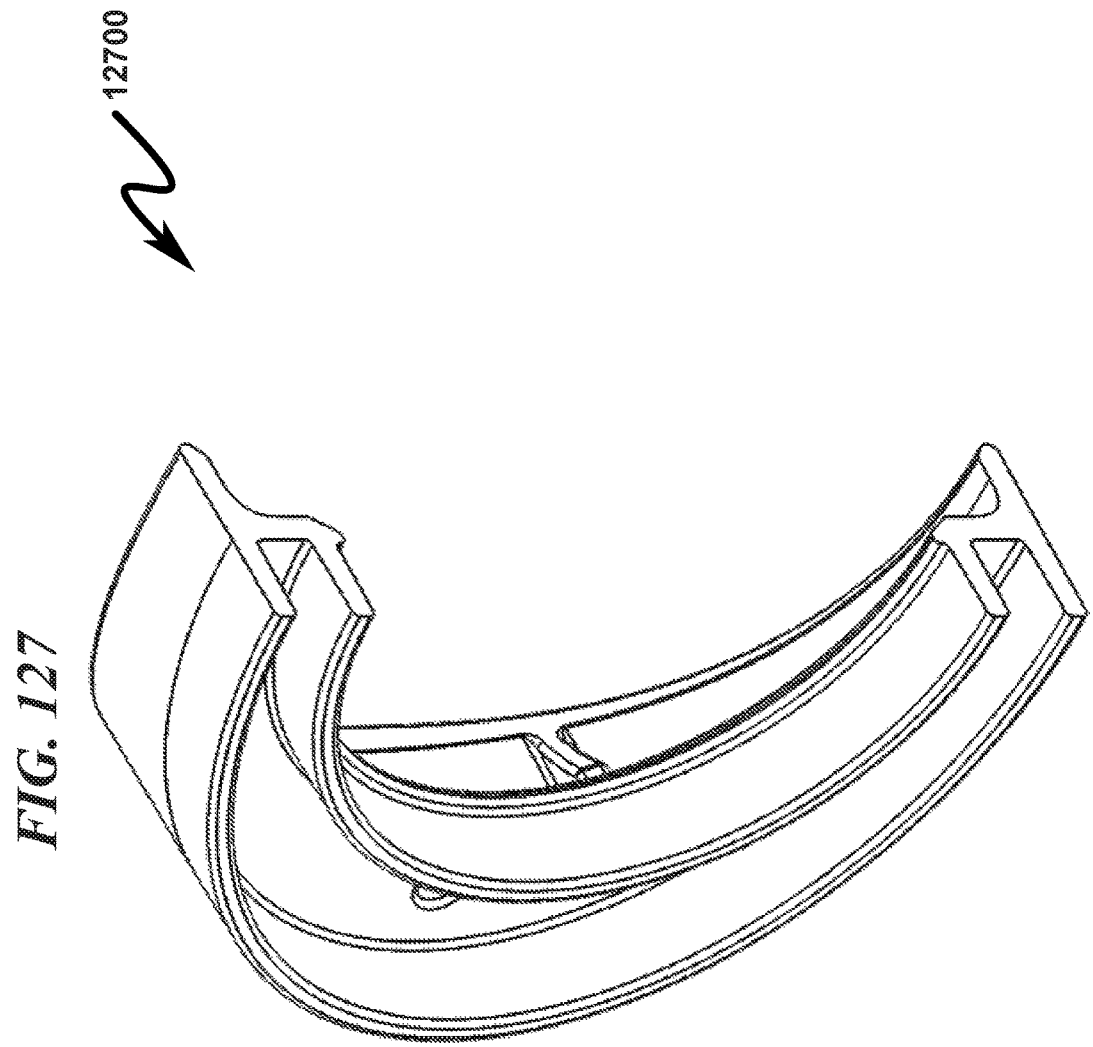

A preferred exemplary embodiment of a typical ocular suction ring (OSR) is generally depicted in the detail views presented in FIG. 113 (11300)-FIG. 128 (12800).

The OSR comprises a mating contact ring (MCR) (11361, 11362) configured to mate with a corresponding mating contact surface (MOS) (10325, 10326) on the OPI.

The OSR further comprises an outer contact ring (OCR) configured to mate with a patient eye surface (PES) and an inner contact ring (ICR) (11464) configured to mate with the PES. The total surface contact area of the OCR (11463) and ICR (11464) is larger than that of conventional LOI and as such reduces the surface pressure on the PES during ophthalmic laser treatment. This larger surface contact area reduces the chance of damage to the PES during the ophthalmic laser treatment process and drastically improves the comfort level of the patient during the treatment process.

The OCR forms an outer elliptical cylindrical tube (OET) having an outer ellipse major axis (OEJ) and an outer ellipse minor axis (OEN) that configure the OCR with an outer ellipse eccentricity (OEE) greater than zero. The ICR forms an inner elliptical cylindrical tube (IET) having an inner ellipse major axis (IEJ) and an inner ellipse minor axis (IEN) that configure the ICR with an inner ellipse eccentricity (IEE) greater than zero.

The OEJ is coincident with the IEJ and the OEN is coincident with the IEN.

The OET comprises an outer distal peripheral edge (ODE) (11565) that is longitudinally curved to conform to the PEE. The IET comprises an inner distal peripheral edge (IDE) (11566) that is longitudinally curved to conform to the PES;

The OCR and the ICR are joined together with a contact ring radius (CRR) (11567) to form a patient eye vacuum chamber (EVC) when the PES is simultaneously contacted with the ODE and the IDE.

A number of radial ribs (11568) may be incorporated between the ODE (11565) and the CRR (11567) to stabilize the ODE (11565) and provide uniform pressure across the PES without damaging the patient eye during treatment.

Preferred Embodiment System Summary

The present invention preferred exemplary system embodiment anticipates a wide variety of variations in the basic theme of construction, but can be generalized as an ophthalmic laser treatment system comprising:
  (a) ocular suction ring (OSR);
  (b) ocular patient interface (OPI);
  (c) optical window retainer (OWR);
  (d) optical separator bracket (OSB);
  (e) ocular force sensor (OFS);
  (f) laser objective bracket (LOB);
  (g) vacuum suction pump (VSP); and
  (h) computer control device (CCD);
  wherein:
  the OSR comprises a mating contact ring (MCR) configured to mate with a corresponding mating contact surface (MCS) on the OPI;
  the OSR further comprises an outer contact ring (OCR) configured to mate with a patient eye surface (PES);
  the OSR further comprises an inner contact ring (ICR) configured to mate with the PES;
  the OCR forms an outer elliptical cylindrical tube (OET) having an outer ellipse major axis (OEJ) and an outer ellipse minor axis (OEN) that configure the OCR with an outer ellipse eccentricity (OEE) greater than zero;
  the ICR forms an inner elliptical cylindrical tube (IET) having an inner ellipse major axis (IEJ) and an inner ellipse minor axis (IEN) that configure the ICR with an inner ellipse eccentricity (IEE) greater than zero;
  the OEJ is coincident with the IEJ;
  the OEN is coincident with the IEN;
  the OET comprises an outer distal peripheral edge (ODE) that is longitudinally curved to conform to the PES;
  the IET comprises an inner distal peripheral edge (IDE) that is longitudinally curved to conform to the PES;
  the OCR and the ICR are joined together with a contact ring radius (CRR) to form a patient eye vacuum chamber (EVC) when the PES is simultaneously contacted with the ODE and the IDE;
  the OPI comprises a conical mating surface (CMS) configured to mate with a corresponding vacuum mating surface (VMS) on the OWR and provide for a vacuum docking void (VDV) between the CMS and the VMS;
  the OPI is configured to dynamically mate to the OWR when vacuum is applied to the VDV;
  the OPI further comprises a docking vacuum port (DVP), a suction vacuum port (SVP), and a liquid injection port (LIP);
  the OPI is configured to retain a liquid interface window (LIW) concentric with the MCS;
  the VSP is configured to supply controlled differential vacuum to the DVP and the SVP;
  the DVP is connected to the VDV;
  the OWR is mechanically coupled to the OSB;
  the OSB is mechanically coupled to the OFS;
  the OFS is configured to sense pressure applied to the PES by the OSR via measurement of deflections of the OFS caused by application of mechanical force by the PES through the OSR, the OPI, the OWR, and the OSB;
  the LOB is configured to retain a laser radiation source (LRS);
  the LRS is configured to direct laser radiation through the OWR and the EVC to the PES; and
  the CCD is configured to control operation of the LRS, monitor pressure readings from the OFS, and monitor applied vacuum pressure to the PES by the VSP.

This general system summary may be augmented by the various elements described herein to produce a wide variety of invention embodiments consistent with this overall design description.

Preferred Embodiment Method Summary

The present invention preferred exemplary method embodiment anticipates a wide variety of variations in the basic theme of implementation, but can be generalized as an ophthalmic laser treatment method, the method operating in conjunction with an ophthalmic laser treatment system comprising:
  (a) ocular suction ring (OSR);
  (b) ocular patient interface (OPI);
  (c) optical window retainer (OWR);
  (d) optical separator bracket (OSB);
  (e) ocular force sensor (OFS);
  (f) laser objective bracket (LOB);
  (g) vacuum suction pump (VSP); and
  (h) computer control device (CCD);
  wherein:
  the OSR comprises a mating contact ring (MCR) configured to mate with a corresponding mating contact surface (MCS) on the OPI;
  the OSR further comprises an outer contact ring (OCR) configured to mate with a patient eye surface (PES);
  the OSR further comprises an inner contact ring (ICR) configured to mate with the PES;
  the OCR forms an outer elliptical cylindrical tube (OET) having an outer ellipse major axis (OEJ) and an outer ellipse minor axis (OEN) that configure the OCR with an outer ellipse eccentricity (OEE) greater than zero;
  the ICR forms an inner elliptical cylindrical tube (IET) having an inner ellipse major axis (IEJ) and an inner ellipse minor axis (IEN) that configure the ICR with an inner ellipse eccentricity (IEE) greater than zero;
  the OEJ is coincident with the IEJ;
  the OEN is coincident with the IEN;
  the OET comprises an outer distal peripheral edge (ODE) that is longitudinally curved to conform to the PES;
  the IET comprises an inner distal peripheral edge (IDE) that is longitudinally curved to conform to the PES;
  the OCR and the ICR are joined together with a contact ring radius (CRR) to form a patient eye vacuum chamber (EVC) when the PES is simultaneously contacted with the ODE and the IDE;
  the OPI comprises a conical mating surface (CMS) configured to mate with a corresponding vacuum mating surface (VMS) on the OWR and provide for a vacuum docking void (VDV) between the CMS and the VMS;
  the OPI is configured to dynamically mate to the OWR when vacuum is applied to the VDV;
  the OPI further comprises a docking vacuum port (DVP), a suction vacuum port (SVP), and a liquid injection port (LIP);
  the OPI is configured to retain a liquid interface window (LIW) concentric with the MCS;
  the VSP is configured to supply controlled differential vacuum to the DVP and the SVP;
  the DVP is connected to the VDV;
  the OWR is mechanically coupled to the OSB;

the OSB is mechanically coupled to the OFS;
the OFS is configured to sense pressure applied to the PES by the OSR via measurement of deflections of the OFS caused by application of mechanical force by the PES through the OSR, the OPI, the OWR, and the OSB;
the LOB is configured to retain a laser radiation source (LRS);
the LRS is configured to direct laser radiation through the OWR and the EVC to the PES; and
the CCD is configured to control operation of the LRS, monitor pressure readings from the OFS, and monitor applied vacuum pressure to the PES by the VSP;
wherein the method comprises the steps of:
(1) Connecting a suction tube to the OPI;
(2) Setting vacuum pressure on the VSP;
(3) Activating the VSP to vacuum mate the OSR to the PES;
(4) Positioning the LPI to mate the OSR onto the PES;
(5) Under control of the CCD, monitoring vacuum pressure to the PES by reading vacuum measurements obtained from a vacuum gauge connected to the VSP;
(6) Under control of the CCD, monitoring applied pressure to the PES by reading pressure measurements obtained by the OFS;
(7) Docking the OWR to the OPI;
(8) Activate a docking ring vacuum with the VSP;
(9) Injecting a balanced liquid solution (BLS) into the LIP of the OPI;
(10) Performing ophthalmic laser surgery with a laser radiation source (LRS) operated by the CCD and positioned by the LOB;
(11) Dejecting the BLS using the LIP of the OPI;
(12) Opening an OPI vacuum relief valve (OPI-VRV) in the VSP to disengage the OWR from the OPI;
(13) Opening an OSR vacuum relief valve (OSR-VRV) in the VSP to disengage the OSR from the PES;
(14) Undocking the OWR from the OPI; and
(15) Undocking the OSR from the PES.

One skilled in the art will recognize that these method steps may be augmented or rearranged without limiting the teachings of the present invention. This general method summary may be augmented by the various elements described herein to produce a wide variety of invention embodiments consistent with this overall design description.

System/Method Variations

The present invention anticipates a wide variety of variations in the basic theme of construction. The examples presented previously do not represent the entire scope of possible usages. They are meant to cite a few of the almost limitless possibilities.

This basic system and method may be augmented with a variety of ancillary embodiments, including but not limited to:

An embodiment wherein the OSR further comprises one or more radial ribs connecting the OCR and the CRR and configured to contact said PES.
An embodiment wherein the OSR further comprises four radial ribs connecting the OCR and the CRR and configured to contact said PES.
An embodiment wherein the OEJ has a length in the range from 20 mm to 25 mm.
An embodiment wherein the OEJ has a length of 23 mm.
An embodiment wherein the OEN has a length in the range from 17 mm to 21 mm.
An embodiment wherein the OEN has a length of 19 mm.
An embodiment wherein the VSP further comprises a vacuum regulator configured to limit suction force applied by the OSR to the PES.
An embodiment wherein the OPI further comprises a liquid overflow chamber (LOC) configured to accept fluid injected from the LIP that overflows coverage of the PES.
An embodiment wherein the OPI further comprises a liquid overflow port (LOP) configured to emit fluid injected from the LIP that overflows containment by the LOC.

One skilled in the art will recognize that other embodiments are possible based on combinations of elements taught within the above invention description. The present invention anticipates that any combination of the above embodiments and their individual elements may be constructed and be considered the scope of the disclosed invention.

Generalized Computer Usable Medium

In various alternate embodiments, the present invention may be implemented as a computer program product for use with a computerized computing system. Those skilled in the art will readily appreciate that programs defining the functions defined by the present invention can be written in any appropriate programming language and delivered to a computer in many forms, including but not limited to: (a) information permanently stored on non-writeable storage media (e.g., read-only memory devices such as ROMs or CD-ROM disks); (b) information alterably stored on writeable storage media (e.g., hard disks and USB thumb drives); and/or (c) information conveyed to a computer through communication media, such as a local area network, a telephone network, or a public network such as the Internet. When carrying computer readable instructions that implement the present invention methods, such computer readable media represent alternate embodiments of the present invention.

As generally illustrated herein, the present invention system embodiments can incorporate a variety of computer readable media that comprise computer usable medium having computer readable code means embodied therein. One skilled in the art will recognize that the software associated with the various processes described herein can be embodied in a wide variety of computer accessible media from which the software is loaded and activated. Pursuant to In re Beauregard, 35 USPQ2d 1383 (U.S. Pat. No. 5,710,578), the present invention anticipates and includes this type of computer readable media within the scope of the invention. Pursuant to In re Nuijten, 500 F.3d 1346 (Fed. Cir. 2007) (U.S. patent application Ser. No. 09/211,928), the present invention scope is limited to computer readable media wherein the media is both tangible and non-transitory.

CONCLUSION

An ophthalmic laser treatment system and method providing for a liquid optical interface (LOI) with a patient eye surface (PES) using an elliptical ocular suction ring (OSR) has been disclosed. A disposable ocular patient interface (OPI) provides for simultaneous differential vacuum mating of the PES, OSR, OPI, and an optical window retainer (OWR). The PES, OSR, OPI, and OWR form an enclosed volume in which liquid may be interjected to cover the PES during laser treatment. A vacuum suction pump (VSP) provides controlled vacuum to the OPI ensuring proper differential vacuum mating (DVM) between the PES, OSR, OPI, and OWR during laser treatment. The OWR connects to a laser objective bracket (LOB) via an ocular force sensor (OFS) and an optical separator bracket (OSB). The OFS senses applied pressure to the PES and provides data to a computerized control device (CCD) that limits applied pressure to the PES during laser treatment.

CLAIMS INTERPRETATION

The following rules apply when interpreting the CLAIMS of the present invention:
The CLAIM PREAMBLE should be considered as limiting the scope of the claimed invention.
"WHEREIN" clauses should be considered as limiting the scope of the claimed invention.
"WHEREBY" clauses should be considered as limiting the scope of the claimed invention.
"ADAPTED TO" clauses should be considered as limiting the scope of the claimed invention.
"ADAPTED FOR" clauses should be considered as limiting the scope of the claimed invention.
The term "MEANS" specifically invokes the means-plus-function claims limitation recited in 35 U.S.C. § 112(f); and such claim shall be construed to cover the corresponding structure, material, or acts described in the specification and equivalents thereof.
The phrase "MEANS FOR" specifically invokes the means-plus-function claims limitation recited in 35 U.S.C. § 112(f) and such claim shall be construed to cover the corresponding structure, material, or acts described in the specification and equivalents thereof.
The phrase "STEP FOR" specifically invokes the step-plus-function claims limitation recited in 35 U.S.C. § 112(f) and such claim shall be construed to cover the corresponding structure, material, or acts described in the specification and equivalents thereof.
The step-plus-function claims limitation recited in 35 U.S.C. § 112(f) shall be construed to cover the corresponding structure, material, or acts described in the specification and equivalents thereof ONLY for such claims including the phrases "MEANS FOR", "MEANS", or "STEP FOR".
The phrase "AND/OR" in the context of an expression "X and/or Y" should be interpreted to define the set of "(X and Y)" in union with the set "(X or Y)" as interpreted by Ex Parte Gross (USPTO Patent Trial and Appeal Board, Appeal 2011-004811, Ser. No. 11/565,411, ("'and/or' covers embodiments having element A alone, B alone, or elements A and B taken together").
The claims presented herein are to be interpreted in light of the specification and drawings presented herein with sufficiently narrow scope such as to not preempt any abstract idea.
The claims presented herein are to be interpreted in light of the specification and drawings presented herein with sufficiently narrow scope such as to not preclude every application of any idea.
The claims presented herein are to be interpreted in light of the specification and drawings presented herein with sufficiently narrow scope such as to preclude any basic mental process that could be performed entirely in the human mind.
The claims presented herein are to be interpreted in light of the specification and drawings presented herein with sufficiently narrow scope such as to preclude any process that could be performed entirely by human manual effort.

What is claimed is:
1. A liquid patient interface (LPI) system for use in ophthalmic laser surgery, said system comprising:
(a) ocular suction ring (OSR);
(b) ocular patient interface (OPI);
(c) optical window retainer (OWR);
(d) optical separator bracket (OSB);
(e) ocular force sensor (OFS);
(f) laser objective bracket (LOB);
(g) vacuum suction pump (VSP); and
(h) computer control device (CCD);
wherein:
said ocular suction ring (OSR) comprises a mating contact ring (MCR) configured to mate with a corresponding mating contact surface (MCS) on said ocular patient interface (OPI);
said ocular suction ring (OSR) further comprises an outer contact ring (OCR) configured to mate with a patient eye surface (PES);
said ocular suction ring (OSR) further comprises an inner contact ring (ICR) configured to mate with said patient eye surface (PES);
said outer contact ring (OCR) comprises an outer elliptical cylindrical tube (OET) having an outer ellipse major axis (OEJ) and an outer ellipse minor axis (OEN) that configure said outer contact ring (OCR) with an outer ellipse eccentricity (OEE) greater than zero;
said inner contact ring (ICR) comprises an inner elliptical cylindrical tube (IET) having an inner ellipse major axis (IEJ) and an inner ellipse minor axis (IEN) that configure said inner contact ring (ICR) with an inner ellipse eccentricity (IEE) greater than zero;
said outer ellipse major axis (OEJ) is coincident with said inner ellipse major axis (IEJ);
said outer ellipse minor axis (OEN) is coincident with said inner ellipse minor axis (IEN);
said outer elliptical cylindrical tube (OET) comprises an outer distal peripheral edge (ODE) that is longitudinally curved to conform to said patient eye surface (PES);
said inner elliptical cylindrical tube (IET) comprises an inner distal peripheral edge (IDE) that is longitudinally curved to conform to said patient eye surface (PES);
said outer contact ring (OCR) and said inner contact ring (ICR) are joined together with a contact ring radius (CRR) to form a patient eye vacuum chamber (EVC) configured to said patient eye surface (PES) when said outer distal peripheral edge (ODE) and said inner distal peripheral edge (IDE) simultaneously contact said patient eye surface (PES);
said ocular patient interface (OPI) comprises a conical mating surface (CMS) configured to mate with a corresponding vacuum mating surface (VMS) on said optical window retainer (OWR) and provide for a vacuum docking void (VDV) between said conical mating surface (CMS) and said vacuum mating surface (VMS);
said ocular patient interface (OPI) is configured to dynamically mate to said optical window retainer (OWR) when vacuum is applied to said vacuum docking void (VDV);
said ocular patient interface (OPI) further comprises a docking vacuum port (DVP), a suction vacuum port (SVP), and a liquid injection port (LIP);

said ocular patient interface (OPI) is configured to retain a liquid interface window (LIW) concentric with said mating contact surface (MCS);

said vacuum suction pump (VSP) is configured to supply controlled differential vacuum to said docking vacuum port (DVP) and said suction vacuum port (SVP);

said docking vacuum port (DVP) is connected to said vacuum docking void (VDV);

said optical window retainer (OWR) is mechanically coupled to said optical separator bracket (OSB);

said optical separator bracket (OSB) is mechanically coupled to said ocular force sensor (OFS);

said ocular force sensor (OFS) is configured to sense pressure applied to said patient eye surface (PES) by said ocular suction ring (OSR) via measurement of deflections of said ocular force sensor (OFS) caused by application of mechanical force by said patient eye surface (PES) through said ocular suction ring (OSR), said ocular patient interface (OPI), said optical window retainer (OWR), and said optical separator bracket (OSB);

said laser objective bracket (LOB) is configured to retain a laser radiation source (LRS);

said laser radiation source (LRS) is configured to direct laser radiation through said optical window retainer (OWR) and said patient eye vacuum chamber (EVC) to said patient eye surface (PES); and said computer control device (CCD) is configured to control operation of said laser radiation source (LRS), monitor pressure readings from said ocular force sensor (OFS), and monitor applied vacuum pressure to said patient eye surface (PES) by said vacuum suction pump (VSP).

2. The liquid patient interface (LPI) system of claim 1 wherein said ocular suction ring (OSR) further comprises one or more radial ribs connecting said outer contact ring (OCR) and said contact ring radius (CRR) and configured to contact said patient eye surface (PES).

3. The liquid patient interface (LPI) system of claim 1 wherein said ocular suction ring (OSR) further comprises four radial ribs connecting said outer contact ring (OCR) and said contact ring radius (CRR) and configured to contact said patient eye surface (PES).

4. The liquid patient interface (LPI) system of claim 1 wherein said outer ellipse major axis (OEJ) has a length in the range from 20 mm to 25 mm.

5. The liquid patient interface (LPI) system of claim 1 wherein said outer ellipse major axis (OEJ) has a length of 23 mm.

6. The liquid patient interface (LPI) system of claim 1 wherein said outer ellipse minor axis (OEN) has a length in the range from 17 mm to 21 mm.

7. The liquid patient interface (LPI) system of claim 1 wherein said outer ellipse minor axis (OEN) has a length of 19 mm.

8. The liquid patient interface (LPI) system of claim 1 wherein said vacuum suction pump (VSP) further comprises a vacuum regulator configured to limit suction force applied by said ocular suction ring (OSR) to said patient eye surface (PES).

9. The liquid patient interface (LPI) system of claim 1 wherein said ocular patient interface (OPI) further comprises a liquid overflow chamber (LOC) configured to accept fluid injected from said liquid injection port (LIP) that overflows coverage of said patient eye surface (PES).

10. The liquid patient interface (LPI) system of claim 1 wherein said ocular patient interface (OPI) further comprises a liquid overflow port (LOP) configured to emit fluid injected from said liquid injection port (LIP) that overflows containment by said liquid overflow chamber (LOC).

11. [Method Base 1] An ophthalmic laser treatment method, said method operating a liquid patient interface (LPI) system comprising:
 (a) ocular suction ring (OSR);
 (b) ocular patient interface (OPI);
 (c) optical window retainer (OWR);
 (d) optical separator bracket (OSB);
 (e) ocular force sensor (OFS);
 (f) laser objective bracket (LOB);
 (g) vacuum suction pump (VSP); and
 (h) computer control device (CCD);
wherein:
said ocular suction ring (OSR) comprises a mating contact ring (MCR) configured to mate with a corresponding mating contact surface (MCS) on said ocular patient interface (OPI);

said ocular suction ring (OSR) further comprises an outer contact ring (OCR) configured to mate with a patient eye surface (PES);

said ocular suction ring (OSR) further comprises an inner contact ring (ICR) configured to mate with said patient eye surface (PES);

said outer contact ring (OCR) comprises an outer elliptical cylindrical tube (OET) having an outer ellipse major axis (OEJ) and an outer ellipse minor axis (OEN) that configure said outer contact ring (OCR) with an outer ellipse eccentricity (OEE) greater than zero;

said inner contact ring (ICR) comprises an inner elliptical cylindrical tube (IET) having an inner ellipse major axis (IEJ) and an inner ellipse minor axis (IEN) that configure said inner contact ring (ICR) with an inner ellipse eccentricity (IEE) greater than zero;

said outer ellipse major axis (OEJ) is coincident with said inner ellipse major axis (IEJ);

said outer ellipse minor axis (OEN) is coincident with said inner ellipse minor axis (IEN);

said outer elliptical cylindrical tube (OET) comprises an outer distal peripheral edge (ODE) that is longitudinally curved to conform to said patient eye surface (PES);

said inner elliptical cylindrical tube (IET) comprises an inner distal peripheral edge (IDE) that is longitudinally curved to conform to said patient eye surface (PES);

said outer contact ring (OCR) and said inner contact ring (ICR) are joined together with a contact ring radius (CRR) to form a patient eye vacuum chamber (EVC) configured to said patient eye surface (PES) when said patient eye surface (PES) is contacted simultaneously with said outer distal peripheral edge (ODE) and said inner distal peripheral edge (IDE);

said ocular patient interface (OPI) comprises a conical mating surface (CMS) configured to mate with a corresponding vacuum mating surface (VMS) on said optical window retainer (OWR) and provide for a vacuum docking void (VDV) between said conical mating surface (CMS) and said vacuum mating surface (VMS);

said ocular patient interface (OPI) is configured to dynamically mate to said optical window retainer (OWR) when vacuum is applied to said vacuum docking void (VDV);

said ocular patient interface (OPI) further comprises a docking vacuum port (DVP), a suction vacuum port (SVP), and a liquid injection port (LIP);

said ocular patient interface (OPI) is configured to retain a liquid interface window (LIW) concentric with said mating contact surface (MCS);

said vacuum suction pump (VSP) is configured to supply controlled differential vacuum to said docking vacuum port (DVP) and said suction vacuum port (SVP);

said docking vacuum port (DVP) is connected to said vacuum docking void (VDV);

said optical window retainer (OWR) is mechanically coupled to said optical separator bracket (OSB);

said optical separator bracket (OSB) is mechanically coupled to said ocular force sensor (OFS);

said ocular force sensor (OFS) is configured to sense pressure applied to said patient eye surface (PES) by said ocular suction ring (OSR) via measurement of deflections of said ocular force sensor (OFS) caused by application of mechanical force by said patient eye surface (PES) through said ocular suction ring (OSR), said ocular patient interface (OPI), said optical window retainer (OWR), and said optical separator bracket (OSB);

said laser objective bracket (LOB) is configured to retain a laser radiation source (LRS);

said laser radiation source (LRS) is configured to direct laser radiation through said optical window retainer (OWR) and said patient eye vacuum chamber (EVC) to said patient eye surface (PES); and said computer control device (CCD) is configured to control operation of said laser radiation source (LRS), monitor pressure readings from said ocular force sensor (OFS), and monitor and control applied vacuum pressure to said patient eye surface (PES) by said vacuum suction pump (VSP);

wherein said method comprises the steps of:

(1) Connecting said vacuum suction pump (VSP) to said ocular patient interface (OPI);

(2) Setting differential vacuum pressures on said vacuum suction pump (VSP);

(3) Positioning said liquid patient interface (LPI) to mate said ocular suction ring (OSR) onto said patient eye surface (PES);

(4) Activating said vacuum suction pump (VSP) to vacuum mate said ocular suction ring (OSR) to said patient eye surface (PES);

(5) Under control of said computer control device (CCD), monitoring vacuum pressure to said patient eye surface (PES) by reading vacuum measurements obtained from a vacuum gauge connected to said vacuum suction pump (VSP);

(6) Under control of said computer control device (CCD), monitoring applied pressure to said patient eye surface (PES) by reading pressure measurements obtained by said ocular force sensor (OFS);

(7) Docking said optical window retainer (OWR) to said ocular patient interface (OPI);

(8) Activate a docking ring vacuum with said vacuum suction pump (VSP);

(9) Injecting a balanced liquid solution (BLS) into said liquid injection port (LIP) of said ocular patient interface (OPI);

(10) Performing ophthalmic laser surgery with a laser radiation source (LRS) operated by said computer control device (CCD) and positioned by said laser objective bracket (LOB);

(11) Dejecting said balanced liquid solution (BLS) using said liquid injection port (LIP) of said ocular patient interface (OPI);

(12) Undocking said optical window retainer (OWR) from said ocular patient interface (OPI); and

(13) Undocking said ocular suction ring (OSR) from said patient eye surface (PES).

12. The ophthalmic laser treatment method of claim 11 wherein said ocular suction ring (OSR) further comprises one or more radial ribs connecting said outer contact ring (OCR) and said contact ring radius (CRR) and configured to contact said patient eye surface (PES).

13. The ophthalmic laser treatment method of claim 11 wherein said ocular suction ring (OSR) further comprises four radial ribs connecting said outer contact ring (OCR) and said contact ring radius (CRR) and configured to contact said patient eye surface (PES).

14. The ophthalmic laser treatment method of claim 11 wherein said outer ellipse major axis (OEJ) has a length in the range from 20 mm to 25 mm.

15. The ophthalmic laser treatment method of claim 11 wherein said outer ellipse major axis (OEJ) has a length of 23 mm.

16. The ophthalmic laser treatment method of claim 11 wherein said outer ellipse minor axis (OEN) has a length in the range from 17 mm to 21 mm.

17. The ophthalmic laser treatment method of claim 11 wherein said outer ellipse minor axis (OEN) has a length of 19 mm.

18. The ophthalmic laser treatment method of claim 11 wherein said vacuum suction pump (VSP) further comprises a vacuum regulator configured to limit suction force applied by said ocular suction ring (OSR) to said patient eye surface (PES).

19. The ophthalmic laser treatment method of claim 11 wherein said ocular patient interface (OPI) further comprises a liquid overflow chamber (LOC) configured to accept fluid injected from said liquid injection port (LIP) that overflows coverage of said patient eye surface (PES).

20. The ophthalmic laser treatment method of claim 11 wherein said ocular patient interface (OPI) further comprises a liquid overflow port (LOP) configured to emit fluid injected from said liquid injection port (LIP) that overflows containment by said liquid overflow chamber (LOC).

21. [Code Base 1] A tangible non-transitory computer usable medium having computer-readable program code means embodied thereon comprising an ophthalmic laser treatment method, said method operating a liquid patient interface (LPI) system comprising:

(a) ocular suction ring (OSR);
(b) ocular patient interface (OPI);
(c) optical window retainer (OWR);
(d) optical separator bracket (OSB);
(e) ocular force sensor (OFS);
(f) laser objective bracket (LOB);
(g) vacuum suction pump (VSP); and
(h) computer control device (CCD);

wherein:

said ocular suction ring (OSR) comprises a mating contact ring (MCR) configured to mate with a corresponding mating contact surface (MCS) on said ocular patient interface (OPI);

said ocular suction ring (OSR) further comprises an outer contact ring (OCR) configured to mate with a patient eye surface (PES);

said ocular suction ring (OSR) further comprises an inner contact ring (ICR) configured to mate with said patient eye surface (PES);

said outer contact ring (OCR) comprises an outer elliptical cylindrical tube (OET) having an outer ellipse major axis (OEJ) and an outer ellipse minor axis (OEN) that configure said outer contact ring (OCR) with an outer ellipse eccentricity (OEE) greater than zero;
said inner tact ring (ICR) comprises an inner elliptical cylindrical tube (IET) having an inner ellipse major axis (IEJ) and an inner ellipse minor axis (IEN) that configure said inner contact ring (ICR) with an inner ellipse eccentricity (IEE) greater than zero;
said outer ellipse major axis (OEJ) is coincident with said inner ellipse major axis (IEJ);
said outer ellipse minor axis (OEN) is coincident with said inner ellipse minor axis (IEN);
said outer elliptical cylindrical tube (OET) comprises an outer distal peripheral edge (ODE) that is longitudinally curved to conform to said patient eye surface (PES);
said inner elliptical cylindrical tube (IET) comprises an inner distal peripheral edge (IDE) that is longitudinally curved to conform to said patient eye surface (PES);
said outer contact ring (OCR) and said inner contact ring (ICR) are joined together with a contact ring radius (CRR) to form a patient eye vacuum chamber (EVC) configured to said patient eye surface (PES) when said patient eye surface (PES) is contacted simultaneously with said outer distal peripheral edge (ODE) and said inner distal peripheral edge (IDE);
said ocular patient interface (OPI) comprises a conical mating surface (CMS) configured to mate with a corresponding vacuum mating surface (VMS) on said optical window retainer (OWR) and provide for a vacuum docking void (VDV) between said conical mating surface (CMS) and said vacuum mating surface (VMS);
said ocular patient interface (OPI) is configured to dynamically mate to said optical window retainer (OWR) when vacuum is applied to said vacuum docking void (VDV);
said ocular patient interface (OPI) further comprises a docking vacuum port (DVP), a suction vacuum port (SVP), and a liquid injection port (LIP);
said ocular patient interface (OPI) is configured to retain a liquid interface window (LIW) concentric with said mating contact surface (MCS);
said vacuum suction pump (VSP) is configured to supply controlled differential vacuum to said docking vacuum port (DVP) and said suction vacuum port (SVP);
said docking vacuum port (DVP) is connected to said vacuum docking void (VDV);
said optical window retainer (OWR) is mechanically coupled to said optical separator bracket (OSB);
said optical separator bracket (OSB) is mechanically coupled to said ocular force sensor (OFS);
said ocular force sensor (OFS) is configured to sense pressure applied to said patient eye surface (PES) by said ocular suction ring (OSR) via measurement of deflections of said ocular force sensor (OFS) caused by application of mechanical force by said patient eye surface (PES) through said ocular suction ring (OSR), said ocular patient interface (OPI), said optical window retainer (OWR), and said optical separator bracket (OSB);
said laser objective bracket (LOB) is configured to retain a laser radiation source (LRS);
said laser radiation source (LRS) is configured to direct laser radiation through said optical window retainer (OWR) and said patient eye vacuum chamber (EVC) to said patient eye surface (PES); and said computer control device (CCD) is configured to control operation of said laser radiation source (LRS), monitor pressure readings from said ocular force sensor (ORS), and monitor and control applied vacuum pressure to said patient eye surface (PES) by said vacuum suction pump (VSP);
wherein said method comprises the steps of:
(1) Connecting said vacuum suction pump (VSP) to said docking vacuum port (DVP) and said suction vacuum port (SVP) of said ocular patient interface (OPI);
(2) Setting differential vacuum pressures on said vacuum suction pump (VSP);
(3) Positioning said liquid patient interface (LPI) to mate said ocular suction ring (OSR) onto said patient eye surface (PES);
(4) Activating said vacuum suction pump (VSP) to vacuum mate said ocular suction ring (OSR) to said patient eye surface (PES);
(5) Under control of said computer control device (CCD), monitoring vacuum pressure to said patient eye surface (PES) by reading vacuum measurements obtained from a vacuum gauge connected to said vacuum suction pump (VSP);
(6) Under control of said computer control device (CCD), monitoring applied pressure to said patient eye surface (PES) by reading pressure measurements obtained by said ocular force sensor (OFS);
(7) Docking said optical window retainer (OWR) to said ocular patient interface (OPI);
(8) Activate a docking ring vacuum with said vacuum suction pump (VSP);
(9) Injecting a balanced liquid solution (BLS) into said liquid injection port (LIP) of said ocular patient interface (OPI);
(10) Performing ophthalmic laser surgery with a laser radiation source (LRS) operated by said computer control device (CCD) and positioned by said laser objective bracket (LOB);
(11) Dejecting said balanced liquid solution (BLS) using said liquid injection port (LIP) of said ocular patient interface (OPI);
(12) Undocking said optical window retainer (OWR) from said ocular patient interface (OPI); and
(13) Undocking said ocular suction ring (OSR) from said patient eye surface (PES).

22. The computer usable medium of claim 21 wherein said ocular suction ring (OSR) further comprises one or more radial ribs connecting said outer contact ring (OCR) and said contact ring radius (CRR) and configured to contact said patient eye surface (PES).

23. The computer usable medium of claim 21 wherein said ocular suction ring (OSR) further comprises four radial ribs connecting said outer contact ring (OCR) and said contact ring radius (CRR) and configured to contact said patient eye surface (PES).

24. The computer usable medium of claim 21 wherein said outer ellipse major axis (OEJ) has a length in the range from 20 mm to 25 mm.

25. The computer usable medium of claim 21 wherein said outer ellipse major axis (OEJ) has a length of 23 mm.

26. The computer usable medium of claim 21 wherein said outer ellipse minor axis (OEN) has a length in the range from 17 mm to 21 mm.

27. The computer usable medium of claim 21 wherein said outer ellipse minor axis (OEN) has a length of 19 mm.

28. The computer usable medium of claim 21 wherein said vacuum suction pump (VSP) further comprises a vacuum regulator configured to limit suction force applied by said ocular suction ring (OSR) to said patient eye surface (PES).

29. The computer usable medium of claim 21 wherein said ocular patient interface (OPI) further comprises a liquid overflow chamber (LOC) configured to accept fluid injected from said liquid injection port (LIP) that overflows coverage of said patient eye surface (PES).

30. The computer usable medium of claim 21 wherein said ocular patient interface (OPI) further comprises a liquid overflow port (LOP) configured to emit fluid injected from said liquid injection port (LIP) that overflows containment by said liquid overflow chamber (LOC).

* * * * *